(12) United States Patent
West et al.

(10) Patent No.: US 9,732,128 B2
(45) Date of Patent: Aug. 15, 2017

(54) METHODS OF MODIFYING TRANSCRIPTIONAL REGULATORY NETWORKS IN STEM CELLS

(75) Inventors: Michael D. West, Mill Valley, CA (US); Karen B. Chapman, Mill Valley, CA (US)

(73) Assignee: BioTime, Inc., Alameda, CA (US)

( * ) Notice: Subject to any disclaimer, the term of this patent is extended or adjusted under 35 U.S.C. 154(b) by 270 days.

(21) Appl. No.: 13/279,123

(22) Filed: Oct. 21, 2011

(65) Prior Publication Data

US 2012/0129262 A1 May 24, 2012

Related U.S. Application Data

(60) Provisional application No. 61/415,244, filed on Nov. 18, 2010, provisional application No. 61/406,064, filed on Oct. 22, 2010.

(51) Int. Cl.
| | |
|---|---|
| *C12N 5/00* | (2006.01) |
| *C12N 5/02* | (2006.01) |
| *A01N 63/00* | (2006.01) |
| *C07K 14/47* | (2006.01) |
| *C12N 5/074* | (2010.01) |

(52) U.S. Cl.
CPC ........ *C07K 14/4702* (2013.01); *C12N 5/0696* (2013.01); *C12N 2501/602* (2013.01); *C12N 2501/603* (2013.01)

(58) Field of Classification Search
None
See application file for complete search history.

(56) References Cited

U.S. PATENT DOCUMENTS

| | | | |
|---|---|---|---|
| 7,033,831 B2 | 4/2006 | Fisk et al. | |
| 7,510,870 B2 * | 3/2009 | Oh | 435/325 |
| 2002/0001842 A1 | 1/2002 | Chapman et al. | |
| 2002/0142397 A1 | 10/2002 | Collas et al. | |
| 2003/0046722 A1 | 3/2003 | Collas et al. | |
| 2004/0014210 A1 * | 1/2004 | Jessell et al. | 435/368 |
| 2004/0199935 A1 | 10/2004 | Chapman et al. | |
| 2005/0014258 A1 | 1/2005 | Collas et al. | |
| 2005/0074880 A1 * | 4/2005 | Sang et al. | 435/455 |
| 2006/0212952 A1 | 9/2006 | Collas et al. | |
| 2006/0246446 A1 * | 11/2006 | Evans et al. | 435/6 |
| 2006/0251642 A1 * | 11/2006 | Wolffe et al. | 424/94.65 |
| 2007/0259423 A1 | 11/2007 | Odorico et al. | |
| 2008/0070303 A1 | 3/2008 | West et al. | |
| 2009/0047263 A1 * | 2/2009 | Yamanaka et al. | 424/93.21 |
| 2009/0263896 A1 * | 10/2009 | Kelly et al. | 435/366 |
| 2009/0280096 A1 * | 11/2009 | Kubo et al. | 424/93.7 |
| 2010/0167404 A1 | 7/2010 | West et al. | |
| 2010/0184033 A1 | 7/2010 | West et al. | |

FOREIGN PATENT DOCUMENTS

| | | |
|---|---|---|
| WO | WO 01/00650 | 1/2001 |
| WO | WO 2007/019398 | 2/2007 |
| WO | WO 2009101407 A2 * | 8/2009 |
| WO | 2010033906 | 3/2010 |
| WO | 2011103343 | 8/2011 |

OTHER PUBLICATIONS

Takahashi et al. Induction of Pluripotent Stem Cells from Adult Human Fibroblasts by Defined Factors. Cell, 2007. 131:861-872.*
Darlington et al. Expression of RESP18 in Peptidergic and Catecholaminerigic Neurons. The Journal of Histochemistry & Cytochemistry, 1997. 45(9):1265-1277.*
Gonzales et al, Distribution patterns of estrogen receptor alpha and beta in the human cortex and hippocampus during development and adulthood. J Comp Neurol. 2007. 503(6): 790-802.*
"Comparable" downloaded from http://www.merriam-webster.com/dictionary/comparable on Mar. 6, 2014.*
Brugmann et al. Induction and Specification of the Vertebrate Ectodermal Placodes: precursors of the cranial sensory organs. Biology of the Cell, 2005. 97(5): 303-315.*
Graham et al. SOX2 Functions to Maintain Neural Progenitor Identity. Neuron 2003. 39:749-765.*
Sansom et al. The Level of the Transcription Factor PAX6 is Essential for Controlling the Balance between Neural Stem Cell Self-Renewal and Neurogenesis. PLOS Genetics, 2009.*
Negorev et al. Sp100 as a Potent Tumor Suppressor: Accelerated Senescence and Rapid Malignant Transformation of Human Fibroblasts through Modulation of an Embryonic Stem Cell Program, (2010) Cancer Research 70:9991.
Niwa et al., "Quantative expression of Oct-3/4 defines differentiation, dedifferentiation or self-renewal of ES cells" Nature Genetics (2000) vol. 24, pp. 372-378.

* cited by examiner

*Primary Examiner* — Christopher M Babic
*Assistant Examiner* — Kimberly A Aron
(74) *Attorney, Agent, or Firm* — Jennifer Fleischer

(57) ABSTRACT

The vast differentiation potential of human embryonic and induced pluripotent stem cells, including their potential to cascade through all of the somatic cell lineages and to display the complete transcriptional regulatory network of human biology, has generated interest in deriving scalable, purified, and identified cell types and methods of discovering the precise structure of the human regulatory network. However, the innate capacity of pluripotent cells to display all these lineages is not necessarily reflected during their culture in vitro. The clonal isolation and propagation of progenitors greatly facilitates the generation of highly purified and identified formulations for research and therapeutic purposes. Nevertheless, other cell types have yet to be isolated and propagated from normal cells and methods of isolating said novel cell types as well as methods for introducing perturbations into the transcriptional regulatory network in order to construct a computer model of the entire human transcriptional regulatory network would greatly benefit basic research as well as manufacturing technology for cell-based therapies.

5 Claims, 6 Drawing Sheets

METHODS OF MODIFYING TRANSCRIPTIONAL REGULATORY NETWORKS IN STEM CELLS

CROSS REFERENCE TO RELATED APPLICATIONS

This application claims the benefit under 35 U.S.C. §119(e) to U.S. Provisional Patent Application Ser. No. 61/406,064, filed Oct. 22, 2010 and U.S. Provisional Patent Application Ser. No. 61/415,244, filed Nov. 18, 2010. The entirety of each of these applications is incorporated herein by reference.

INTRODUCTION

The comprehensive differentiation potential of human pluripotent stem cells such as human embryonic stem (hES) and human induced pluripotent stem (hiPS) cells opens new opportunities in research and cell-based therapy. Their potential to cascade through all of the somatic cell lineages and to display all of the transcriptional pathways of development has generated interest in the use of these cells to map the precise structure of the human transcriptional regulatory network and to generate cell-based therapies for a potential wide array of disorders. However, many in vitro differentiation technologies yield only partially purified cell formulations that may pose the risk of ectopic tissue formation at engraftment sites. Embryoid bodies, or other similar differentiation modalities in vitro contain dozens or hundreds of discrete cell types in a mixture. The clonal isolation and propagation of progenitors greatly facilitates the generation of highly purified and identified formulations for research and therapeutic purposes (see, e.g., West et al, 2008. *Regen. Med.* 3(3): 287-308; U.S. patent application Ser. No. 11/604,047, filed on Nov. 21, 2006 (US Patent Pub. No. 2008/0070303) and Ser. No. 12/504,630, filed on Jul. 16, 2009 (US Patent Pub. No. 2010/0184033), all of which are incorporated herein by reference). Nevertheless, other cell types have yet to be isolated and propagated from normal pluripotent and multipotent cells. Thus, methods of isolating such novel cell types, as well as methods for introducing perturbations into the transcriptional regulatory network in stem cells in order to construct a computer model of the entire human transcriptional regulatory network, would greatly benefit basic research as well as manufacturing technology for cell-based therapies.

SUMMARY

We have demonstrated that the long initial telomere length of hES cells, together with the robust proliferative capacity of primitive hES-derived progenitor cell types facilitates the industrial expansion and characterization of >140 diverse and scalable clonal lineages with diverse site and temporal-specific homeobox gene expression (West et al, 2008. *Regen. Med.* 3(3): 287-308; see also U.S. patent application Ser. No. 11/604,047, filed on Nov. 21, 2006 (US Patent Pub. No. 2008/0070303); U.S. patent application Ser. No. 12/504,630, filed on Jul. 16, 2009 (US Patent Pub. No. 2010/0184033); PCT Patent application serial no. PCT/US2011/037969, filed on May 25, 2011 titled "Improved Methods of Screening Embryonic Progenitor Cell Lines"; and U.S. Provisional application 61/496,436, filed on Jun. 13, 2011 titled "Methods and Compositions for Producing Endothelial Progenitor Cells From Pluripotent Stem Cells", each of which is incorporated herein by reference). We describe a technology to generate such novel and scalable cell lines through the exogenous or endogenous up or down-regulation of the activity of transcriptional regulators. Such exogenously or endogenously-introduced modifications to the activity of transcriptional regulators may include transcription factors constitutively expressed in pluripotent stem cells such as hES cells or somatic cells reprogrammed to pluripotency such as hiPS cells. Such transcriptional regulators can be introduced in a manner that allows the precise regulation of the level and timing of their expression including but not limited to the use of an inducible promoter driving the expression or inhibition of expression of a number of transcription factors. The exogenously-administered transcriptional regulators with precise control of level and timing of expression are introduced in pluripotent stem cells which also have inducible levels of expression of a gene capable of forcing cell proliferation (cell cycle driver). Also described herein are computer algorithms useful in assembling a computer model of the transcriptional regulatory network of human and other animal species.

DETAILED DESCRIPTION OF THE INVENTION

Abbreviations

Figure 1:
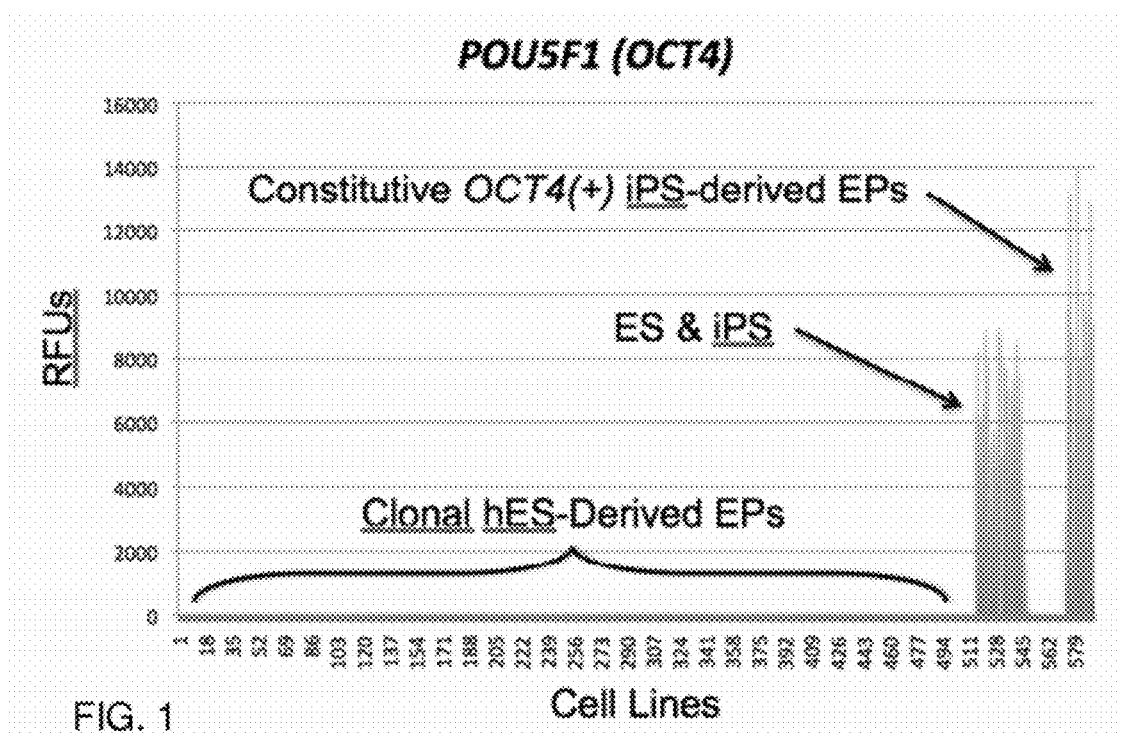
FIG. 1: Constitutive expression of the transcription factor OCT4 in clonal iPS-derived progenitorprogenitor cell lines compared to normal hES-derived diverse clonal progenitor-progenitors and normal hES cells.

AFP—Alpha fetoprotein
BMP—Bone Morphogenic Protein
BRL—Buffalo rat liver
BSA—Bovine serum albumin
CD—Cluster Designation
cGMP—Current Good Manufacturing Processes
CNS—Central Nervous System
DMEM—Dulbecco's modified Eagle's medium
DMSO—Dimethyl sulphoxide DPBS—Dulbecco's Phosphate Buffered Saline
EBs—Embryoid bodies
EC—Embryonal carcinoma
EC—Cells Embryonal carcinoma cells; hEC cells are human embryonal carcinoma cells
ECAPCs—Embryonic cutaneous adipocyte progenitor cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells
EP Cells—Embryonic progenitor cells are cells derived from primordial stem cells that are more differentiated than primordial stem cells, in that they no longer display markers such as SSEA4, TRA1-60 or TRA-1-81 seropositivity in the case of the human species, but have not fully differentiated. Embryonic progenitor cells correspond to the embryonic stages as opposed to the postnatal stage of development.
ES Cells—Embryonic stem cells; hES cells are human ES cells
FACS—Fluorescence activated cell sorting
FBS—Fetal bovine serum
FCS—Fetal calf serum
FGF—Fibroblast Growth Factor
GFP—Green Fluorescent Protein
GMP—Good Manufacturing Practices
hED—Cells Human embryo-derived cells
hEG Cells—Human embryonic germ cells are stem cells derived from the primordial germ cells of fetal tissue.
hEP Cells—Human embryonic progenitor cells are embryonic progenitor cells from the human species.
hiPS Cells—Human induced pluripotent stem cells.
HSE—Human skin equivalents are mixtures of cells and biological or synthetic matrices manufactured for testing purposes or for therapeutic application in promoting wound repair.
HUVEC—Human umbilical vein endothelial cell
ICM—Inner cell mass of the mammalian blastocyst-stage embryo.
iPS cells—Induced pluripotent stem cells.
LOH—Loss of Heterozygosity
MEM—Minimal essential medium
miRNA—Micro RNA
MSC—Mesenchymal Stem Cell
NT—Nuclear Transfer
PBS—Phosphate buffered saline
PEGDA—Polyethylene glycol diacrylate
PS fibroblasts—Pre-scarring fibroblasts are fibroblasts derived from the skin of early gestational skin or derived from ED cells that display a prenatal pattern of gene expression in that they promote the rapid healing of dermal wounds without scar formation.
RA—Retinoic acid
RFU—Relative Fluorescence Units
SCNT—Somatic Cell Nuclear Transfer
SFM—Serum-Free Medium
SPF—Specific Pathogen-Free
SV40—Simian Virus 40
Tag—Large T-antigen
T-EDTA—Trypsin EDTA

DEFINITIONS

The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte. Such techniques include the use of cytoplasm such as EC cell-derived cytoplasm that is enriched in factors such as OCT4, LIN28, SOX2, NANOG, KLF4, and modifications that decrease the expression of SP100 (see U.S. application Nos. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006.

The term "blastomere/morula cells" refers to blastomere or morula cells in a mammalian embryo or blastomere or morula cells cultured in vitro with or without additional cells including differentiated derivatives of those cells.

The term "cell expressing gene X", "gene X is expressed in a cell" (or cell population), or equivalents thereof, means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "clonal" or alternatively "monoclonal" refers to a population of cells obtained the expansion of a single cell into a population of cells all derived from that original single cells and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "differentiated cells" when used in reference to cells made by methods of this invention from pluripotent stem cells refer to cells having reduced potential to differentiate when compared to the parent pluripotent stem cells. The differentiated cells of this invention comprise cells that could differentiate further (i.e., they may not be terminally differentiated).

The term "direct differentiation" refers to process of differentiating: blastomere cells, morula cells, ICM cells, ED cells, or somatic cells reprogrammed to an undifferentiated state (such as in the process of making iPS cells but before such cells have been purified in an undifferentiated state) directly without the intermediate state of propagating isolated undifferentiated stem cells such as hES cells as undifferentiated cell lines. A nonlimiting example of direct differentiation would be the culture of an intact human blastocyst into culture and the derivation of ED cells without the generation of a human ES cell line as was described (Bongso et al, 1994. Human Reproduction 9:2110).

The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The ES cells may be derived from fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, have a more flattened appearance in culture and typically do not contribute to germ line differentiation, and are therefore called "ES-like cells." It is commonly believed that human ES cells are in reality "ES-like", however, in this application we will use the term ES cells to refer to both ES and ES-like cell lines.

The term "histotypic culture" refers to cultured cells that are aggregated to create a three-dimensional structure with tissue-like cell density such as occurs in the culture of some cells over a layer of agar or such as occurs when cells are cultured in three dimensions in a collagen gel, sponge, or other polymers such as are commonly used in tissue engineering.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and 5,843,780 to Thomson, incorporated herein by reference). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application Nos. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells.

The term "iPS cells" or "human iPS cells" refers to cells with properties similar to ES cells or hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. Application Ser. No. 09/736,268 filed on Dec. 15, 2000; U.S. application Ser. No. 10/831,599, filed Apr. 23, 2004; and U.S. Patent Publication 20020142397 (application Ser. No. 10/015,824, entitled "Methods for Altering Cell Fate"); U.S. Patent Publication 20050014258 (application Ser. No. 10/910,156, entitled "Methods for Altering Cell Fate"); U.S. Patent Publication 20030046722 (application Ser. No. 10/032,191, entitled "Methods for cloning mammals using reprogrammed donor chromatin or donor cells"); and U.S. Patent Publication 20060212952 (application Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "organotypic culture" refers to cultured cells that are aggregated to create a three-dimensional structure with tissue-like cell density such as occurs in the culture of some cells over a layer of agar, cultured as teratomas in an animal, otherwise grown in a three dimensional culture system but wherein said aggregated cells contain cells of different cell lineages, such as, by way of nonlimiting examples, the combination of epidermal keratinocytes and dermal fibroblasts, or the combination of parenchymal cells with their corresponding tissue stroma, or epithelial cells with mesenchymal cells.

The term "pluripotent stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "pluripotent stem cell not derived from a human embryo" (and grammatical equivalents thereof) refers to human plutipotent stem cells whose derivation does not require the destruction of a human embryo at any point during the derivation process, where a human embryo includes any human ovum after fertilisation, any non-fertilised human ovum into which the cell nucleus from a mature human cell has been transplanted, and any non-fertilised human ovum whose division and further development have been stimulated by parthenogenesis. Any of the methods and compositions described herein that employ or are drawn to any human pluripotent stem cells (e.g., hES cells, hED cells, hiPS cells, hEG cells, hEC, and the like) include embodiments in which the human pluripotent stem cells are not derived from a human embryo.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Primordial stem cells may be genetically modified or not genetically modified. Genetically modified cells may include markers such as fluorescent proteins to facilitate their identification in vitro or in vivo.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the present invention include methods of generating an isolated progenitor cell line by modulating the activity of a transcriptional regulator in a pluripotent stem cell; and inducing the differentiation of said pluripotent stem cell in vitro to generate a progenitor cell line. In certain embodiments, the activity of the transcriptional regulator is increased, where in some instances the transcriptional regulator is selected from: OCT4, SOX2, KLF4, NANOG, MYC, or the gene LIN28, or downregulated in some instances with genes such as SP100 and combinations thereof. Such transcriptional modulators may be introduced in any convenient manner, e.g., via exogenous expression from an expression vector (constitutive expression vector, inducible expression vector, retroviral vector, lentiviral vector, transient expression vector, and the like) or as a protein factor. In certain embodiments, the method further includes the modulation by up or down-regulating the levels of transcription factors or other factors that modify chromatin structure in pluripotent stem cells, or in somatic cells that are subsequently reprogrammed to pluripotency such as iPS cells, wherein said modified pluripotent cells may be used to generate clonal, oligoclonal, or polyclonal progenitor cell lines dependent on the introduced factor or factors. In certain embodiments, the method further includes increasing cell division in the derivatives of pluripotent stem cells, e.g., by providing a cell cycle regulator that overcomes cell cycle inhibition in the pluripotent stem cell (p53, SV40 T-antigen, adenovirus proteins E1A and E1B, papillomavirus proteins E6 and/or E7, CDK4, for example). The isolated progenitor cell lines produced according to aspects of the present invention have unique gene expression and developmental capabilities, including constitutively expressing one or more transcriptional regulator (or transcription factor), including but not limited to OCT4 and LHX3. Any convenient pluripotent stem cell may be employed in the methods, e.g., embryonic stem cells (ES cells), induced pluripotent stem cells (iPS cells), embryo-derived cells (ED cells), embryonic germ cells (EG cells), embryonal carcinoma cells (EC cells), pluripotent stem cell not derived from a human embryo, and the like.

Aspects of the invention also include isolated progenitor cell lines produced by the methods described herein. Exemplary progenitor cell lines include, but are not limited to, 14SKEL7X, 14SKEL18X, 14SKEL12Z, 14SKEL14Z, 14SKEL15Z, 14SKEL20Z, 14SKEL24Z, 14PEND2X, 14PEND11X, 14PEND12X, 14PEND14X, 14PEND20X, 14PEND23X, 14PEND24X, 14SMOO2X, 14SMOO8X, and 14PEND17Z with the specific gene expression profiles described herein.

Methods

In addition to the methods described below, methods that find use in the production and use of the cell lines described herein can be found in the following: U.S. Patent Publication 2008/0070303, entitled "Methods to accelerate the isolation of novel cell strains from pluripotent stem cells and cells obtained thereby"; U.S. patent application Ser. No. 12/504,630, filed on Jul. 16, 2009 (US Patent Pub. No. 2010/0184033) entitled "Methods to accelerate the isolation of novel cell strains from pluripotent stem cells and cells obtained thereby"; and PCT Application PCT/US2006/013519, filed on Apr. 11, 2006, entitled "NOVEL USES OF CELLS WITH PRENATAL PATTERNS OF GENE EXPRESSION"; PCT Application Serial No. PCT/US2006/030632, filed on Aug. 3, 2006, entitled "Improved Methods of Reprogramming Animal Somatic Cells"; U.S. application Ser. No. 11/989,988, filed on Aug. 3, 2006, entitled "Methods of Reprogramming Animal Somatic Cells"; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; U.S. Patent Publication 2002/0142397 (application. Ser. No. 10/015,824, entitled "Methods for Altering Cell Fate"); U.S. Patent Publication 2005/0014258 (application Ser. No. 10/910,156, entitled "Methods for Altering Cell Fate"); U.S. Patent Publication 2003/0046722 (application Ser. No. 10/032,191, entitled "Methods for cloning mammals using reprogrammed donor chromatin or donor cells"); U.S. Patent Publication 2006/0212952 (application Ser. No. 11/439,788, entitled "Methods for cloning mammals using reprogrammed donor chromatin or donor cells"; U.S. Patent Publication 2009/0068742 entitled "Nuclear Reprogramming Factor"; U.S. Patent Publication 2009/0047263 entitled "Nuclear reprogramming factor and induced pluripotent stem cells"; U.S. Patent Publication 2009/0191159 entitled "Multipotent/pluripotent cells and methods"; U.S. Patent Publication 2008/0280362 entitled "Methods for reprogramming somatic cells"; U.S. Patent Publication 2008/0233610 entitled "Somatic cell reprogramming"; U.S. Provisional application 61/492,329 filed on Jun. 1, 2011 entitled "Embryonic Stem Cell and Embryonic Progenitor-Associated Molecules Useful in the Management of Cancer and Cellular Reprogramming"; and Negorev et al., Cancer Research (2010) vol. 70(23) pp. 9991-10001, entitled "Sp100 as a Potent Tumor Suppressor: Accelerated Senescence and Rapid Malignant Transformation of Human Fibroblasts through Modulation of an Embryonic Stem Cell Program"; each of which is incorporated by reference herein in its entirety.

Methods for the Perturbation of One or More Transcriptional Regulators.

We use the term "transcriptional regulator" to refer to a molecule directly modifying the transcriptional complex in the regulatory regions of a given gene. Therefore, for the purposes of this application, transcription factors or factors that modify chromatin in association with transcription factor complexes such as but not limited to kinases, phosphatases, acetylases, deacetylases, methylases, and demethylases that modify histones are "transcriptional regulators" as defined herein. However, growth factors that bind to cell surface receptors stimulating cell signaling pathways that indirectly modulate transcription complexes are not considered "transcriptional regulators" for the purposes of this application. Pluripotent cells can respond to diverse inductive stimuli, including growth factors and cytokines, to ultimately modulate transcriptional regulators and consequently the differentiated state of the cell. Said inductive stimuli may be utilized to promote the differentiation of pluripotent stem cells into clonal, oligoclonal, or polyclonal lineages of progenitor cell lines as previously described (West et al, 2008. Regen. Med. 3(3): 287-308; see also U.S. patent application Ser. No. 11/604,047, filed on Nov. 21, 2006 (US Patent Pub. No. 2008/0070303) and Ser. No. 12/504,630, filed on Jul. 16, 2009 (US Patent Pub. No. 2010/0184033), incorporated herein by reference). Such transcriptional regulators are important in determining the differentiated fate of a cell and include transcription factors, which are generally nuclear or cytoplasmic and can either be constitutively expressed within the cell or be expressed in an inducible manner. Transcription factor proteins bind specific sequences found in the promoter regions of genes (target genes) whose expression they then regulate by either increasing or decreasing the transcription of that gene into RNA (e.g., mRNA). These binding sequences are generally 6-10 base pairs in length and are occasionally found in multiple copies within the promoter regions of target genes.

Although the transcription factor protein-DNA interaction is sequence-specific, the binding site for one given transcription factor may vary by several base pairs within different target genes. Therefore when we describe the specific DNA binding sequence for a transcription factor we refer to the non-variable part of the binding sequence, that is, the transcription factor consensus sequence. For example, the AP-1 transcription factor made up of Fos and Jun proteins binds to the TGACTCA consensus sequence. In comparison, the consensus sequence for the Smad transcription factor family which mediate TGF-β, activin and BMP induced changes in gene expression, is CAGACA.

I. Starting Cell Types

The cell types used in the present invention may include any animal cell type, where the animal is generally a vertebrate, e.g., a mammal, reptile, bird, amphibian, fish, etc. In some embodiments, the animal is a primate, e.g., a human. By way of nonlimiting example, hES cells, somatic cells reprogrammed to pluripotency such as hiPS, or human somatic cells may be used wherein said hES, hiPS, or somatic cells are genetically modified to constitutively express or up or down-regulate a transcriptional regulator or combination of transcriptional regulators as described below. The pluripotent stem cells may result from the reprogramming of a somatic cell that is genetically modified to constitutively overexpress a transcription factor. The constitutive expression may be accomplished by a number of means well-known in the art, including but not limited to stable transfection or retroviral or lentiviral infection. In addition, the transcriptional regulator may be introduced in a manner such that it is transiently expressed or transiently present as a protein, or in the case of somatic cells, the cells, when genetically modified to regulate the expression of a transcriptional regulator, may subsequently be reprogrammed or transdifferentiated such as to an iPS cell line. In these embodiments, the transcriptional regulator modifies the gene expression pattern of the iPS-derived cell types, such as clonal or oligoclonal progenitor cell lines with a prenatal pattern of gene expression.

II. Transcriptional Regulators

The transcriptional regulators of the present invention include transcription factors and chromatin-modifying molecules. The transcription factors of the present invention include those encoded in the human genome as well as homologs and orthologs from other species. Human transcription factors include the following: Apoptosis antagonizing transcription factor (AATF), also known as (aka) CHE1, DED, CHE-1 ACCESSION NUMBER NM_012138.3; activity-dependent neuroprotector homeobox (ADNP), transcript variant 1, aka ADNP1, KIAA0784 ACCESSION NUMBER NM_015339.2; activity-dependent neuroprotector homeobox (ADNP), transcript variant 2, aka ADNP1, KIAA0784 ACCESSION NUMBER NM_181442.1; ADNP homeobox 2 (ADNP2), aka KIAA0863, ZNF508, ACCESSION NUMBER NM_014913.2; AE binding protein 1 (AEBP1), aka FLJ33612, ACLP, ACCESSION NUMBER NM_001129.3; AF4/FMR2 family, member 1 (AFF1), aka MLLT2, MGC134969, AF4-MLL, MLL/AF4, PBM1, AF4, AF-4, ACCESSION NUMBER NM_005935.1; AF4/FMR2 family, member 4 (AFF4), aka AF5Q31, MGC75036, MCEF, ACCESSION NUMBER NM_014423.3; aryl hydrocarbon receptor (AHR), ACCESSION NUMBER NM_001621.3; autoimmune regulator (autoimmune polyendocrinopathy candidiasis ectodermal dystrophy) (AIRE), transcript variant AIRE-1, aka PGA1, APECED, AIRE1, APSI, APS1 ACCESSION NUMBER NM_000383.1; autoimmune regulator (AIRE), transcript variant AIRE-2, aka PGA1, APECED, AIRE1, APSI, APS1 ACCESSION NUMBER NM_000658.1; aristaless-like homeobox 3 (ALX3), aka MGC138212, MGC141988 ACCESSION NUMBER NM_006492.2; aristaless-like homeobox 4 (ALX4), aka KIAA1788, PFM2, FPP, PFM1, PFM ACCESSION NUMBER NM_021926.2; ankyrin repeat domain 30A (ANKRD30A), accession number XM_001131823.1; ankyrin repeat domain 30A (ANKRD30A), accession number XM_001131823.1; androgen receptor (AR), transcript variant 2, aka DHTR, SMAX1, TFM, HUMARA, AIS, NR3C4, KD, SBMA, ACCESSION NUMBER NM_001011645.1; androgen receptor (AR), transcript variant 2, aka DHTR, SMAX1, TFM, HUMARA, AIS, NR3C4, KD, SBMA, ACCESSION NUMBER NM_001011645.1; androgen receptor (dihydrotestosterone receptor, testicular feminization, spinal and bulbar muscular atrophy, Kennedy disease) (AR), transcript variant 1, aka DHTR, SMAX1, TFM, HUMARA, AIS, NR3C4, KD, SBMA, ACCESSION NUMBER NM_000044.2; arginine-fifty homeobox (ARGFX), ACCESSION NUMBER NM_001012659.1; AT rich interactive domain 3A (BRIGHT-like) (ARID3A), aka E2FBP1, DRIL3, BRIGHT, DRILL ACCESSION NUMBER NM_005224.2; AT rich interactive domain 4A (RBP1-like) (ARID4A), transcript variant 3, aka RBP1, RBP-1, RBBP1, ACCESSION NUMBER NM_023001.2; AT rich interactive domain 4A (RBP1-like) (ARID4A), transcript variant 2, aka RBP1, RBP-1, RBBP1, ACCESSION NUMBER NM_023000.2; AT rich interactive domain 4A (RBP1-like) (ARID4A), transcript variant 1, aka RBP1, RBP-1, RBBP1, ACCESSION NUMBER NM_002892.3; aryl hydrocarbon receptor nuclear translocator (ARNT), transcript variant 1, aka HIF-1beta, HIF1BETA, TANGO, HIF1B, ACCESSION NUMBER NM_001668.2; aryl hydrocarbon receptor nuclear translocator (ARNT), transcript variant 2, aka HIF-1beta, HIF1BETA, TANGO, HIF1B, ACCESSION NUMBER NM_178426.1; aryl-hydrocarbon receptor nuclear translocator 2 (ARNT2), aka KIAA0307, ACCESSION NUMBER NM_014862.3; aryl hydrocarbon receptor nuclear translocator-like (ARNTL), transcript variant 2, aka MOP3, BMAL1, BMAL1c, TIC, PASD3, MGC47515, JAP3, ACCESSION NUMBER NM_001030272.1; aryl hydrocarbon receptor nuclear translocator-like (ARNTL), transcript variant 3, aka MOP3, BMAL1, BMAL1c, TIC, PASD3, MGC47515, JAP3, ACCESSION NUMBER NM_001030273.1; aryl hydrocarbon receptor nuclear translocator-like 2 (ARNTL2), aka PASD9, CLIF, BMAL2, MOP9, MGC149671, MGC149672, ACCESSION NUMBER NM_020183.3; aristaless related homeobox (ARX), aka MRX43, MRX29, MRX32, MRXS1, ISSX, MRX38, PRTS, MRX54, MRX36, MRX33, ACCESSION NUMBER NM_139058.1; achaete-scute complex homolog 1 (Drosophila) (ASCL1), aka MASH1, ASH1, HASH1, ACCESSION NUMBER NM_004316.2; achaete-scute complex homolog 2 (Drosophila) (ASCL2), aka ASH2, MASH2, HASH2, ACCESSION NUMBER NM_005170.2; activating transcription factor 1 (ATF1), aka TREB36, FUS/ATF-1, EWS-ATF1, ACCESSION NUMBER NM_005171.3; activating transcription factor 2 (ATF2), aka MGC111558, CRE-BP1, CREB2, TREB7, HB16, ACCESSION NUMBER NM_001880.2; activating transcription factor 3 (ATF3), transcript variant 3, ACCESSION NUMBER NM_001030287.2; activating transcription factor 3 (ATF3), transcript variant 4, ACCESSION NUMBER NM_001040619.1; activating transcription factor 3 (ATF3), transcript variant 4, ACCESSION NUMBER NM_001040619.1; activating transcription factor 4 (tax-responsive enhancer element B67) (ATF4), transcript variant 1, aka TXREB, TAXREB67, CREB2, CREB-2, ACCESSION NUMBER NM_001675.2; activating transcription factor 4 (tax-responsive enhancer element B67) (ATF4), transcript variant 1, aka TXREB, TAXREB67, CREB2, CREB-2, ACCESSION NUMBER NM_001675.2; activating transcription factor 4 (tax-responsive enhancer element B67) (ATF4), transcript variant 2, aka TXREB, TAXREB67, CREB2, CREB-2 ACCESSION NUMBER NM_182810.1; activating transcription factor 5 (ATF5), aka ATFX, FLJ34666, HMFN0395, ACCESSION NUMBER NM_012068.3; activating transcription factor 6 (ATF6), ACCESSION NUMBER NM_007348.2; activating transcription factor 7 (ATF7), aka MGC57182, ATFA, ACCESSION NUMBER NM_006856.1; atonal homolog 1 (Drosophila) (ATOH1), aka MATH-1, ATH1, HATH1, ACCESSION NUMBER NM_005172.1; alpha thalassemia/mental retardation syndrome X-linked (RAD54 homolog, S. cerevisiae) (ATRX), transcript variant 3, aka XNP, ZNF-HX, MRXHF1, XH2, ATR2, SFM1, SHS, MRXS3, RAD54L, RAD54, MGC2094, ACCESSION NUMBER NM_138271.1; alpha thalassemia/mental retardation syndrome X-linked (RAD54 homolog, S. cerevisiae) (ATRX), transcript variant 1, aka XNP, ZNF-HX, MRXHF1, XH2, ATR2, SFM1, SHS, MRXS3, RAD54L, RAD54, MGC2094, ACCESSION NUMBER NM_000489.3; alpha thalassemia/mental retardation syndrome X-linked (RAD54 homolog, S. cerevisiae) (ATRX), transcript variant 1, aka XNP, ZNF-HX, MRXHF1, XH2, ATR2, SFM1, SHS, MRXS3, RAD54L, RAD54, MGC2094, ACCESSION NUMBER NM_000489.2; BTB and CNC homology 1, basic leucine zipper transcription factor 1 (BACH1), transcript variant 3, aka ACCESSION NUMBER NM_001011545.1; BTB and CNC homology 1, basic leucine zipper transcription factor 1 (BACH1), transcript variant 3, ACCESSION NUMBER NM_001011545.1; BTB and CNC homology 1, basic leucine zipper transcription factor 1 (BACH1), transcript variant 1, ACCESSION NUMBER NM_206866.1; BTB and CNC homology 1, basic leucine zipper transcription factor 2 (BACH2), ACCESSION NUMBER NM_021813.1; BTB and CNC homology 1, basic leucine zipper transcription factor 2 (BACH2), ACCESSION NUMBER NM_021813.1; bagpipe homeobox homolog 1 (*Drosophila*) (BAPX1), aka NKX3B, NKX3-2, MGC138171, NKX3.2, ACCESSION NUMBER NM_001189.2; BarH-like homeobox 1 (BARHL1), ACCESSION NUMBER NM_020064.2; BarH-like homeobox 2 (BARHL2), ACCESSION NUMBER NM_020063.1; BARX homeobox 1 (BARX1), ACCESSION NUMBER NM_021570.3; BARX homeobox 2 (BARX2), aka MGC133368, MGC133369, ACCESSION NUMBER NM_003658.4; basic leucine zipper transcription factor, ATF-like (BATF), aka B-ATF, BATF1, SFA-2, ACCESSION NUMBER NM_006399.2; basic leucine zipper transcription factor, ATF-like 2 (BATF2), aka MGC20410, ACCESSION NUMBER NM_138456.3; basic leucine zipper transcription factor, ATF-like 3 (BATF3), aka JUNDM1, BATF3, SNPT, ACCESSION NUMBER NM_018664.1; bromodomain adjacent to zinc finger domain, 1B (BAZ1B), transcript variant 1, aka WBSCR9, WBSCR10, WSTF, ACCESSION NUMBER NM_023005.2; B-cell CLL/lymphoma 3 (BCL3), aka D19537, BCL4, ACCESSION NUMBER NM_005178.2; B-cell CLL/lymphoma 6 (zinc finger protein 51) (BCL6), transcript variant 1, aka ZBTB27, ZNF51, LAZ3, BCL6A, BCL5, ACCESSION NUMBER NM_001706.2; B-cell CLL/lymphoma 6 (zinc finger protein 51) (BCL6), transcript variant 2, aka ZBTB27, ZNF51, LAZ3, BCL6A, BCL5, ACCESSION NUMBER NM_138931.1; basic helix-loop-helix domain containing, class B, 2 (BHLHB2), aka DEC1, STRA13, Stra14, SHARP-2, ACCESSION NUMBER NM_003670.1; basic helix-loop-helix domain containing, class B, 3 (BHLHB3), aka SHARP1, DEC2, SHARP-1, ACCESSION NUMBER NM_030762.1; basic leucine zipper nuclear factor 1 (BLZF1), aka GOLGIN-45, MGC22497, JEM1, JEM-1, JEM-1s, ACCESSION NUMBER NM_003666.2; basonuclin 1 (BNC1), aka BNC, HsT19447, BSN1, ACCESSION NUMBER NM_001717.2; basonuclin 1 (BNC1), aka BNC, HsT19447, BSN1, ACCESSION NUMBER NM_001717.2; bromodomain containing 8 (BRD8), transcript variant 3, aka SMAP, p120, SMAP2, ACCESSION NUMBER NM_183359.1; bromodomain containing 8 (BRD8), transcript variant 2, aka SMAP, p120, SMAP2, ACCESSION NUMBER NM_139199.1; BRF1 homolog, subunit of RNA polymerase III transcription initiation factor IIIB (*S. cerevisiae*) (BRF1), transcript variant 1, aka FLJ43034, TAF3C, TAFIII90, MGC105048, BRF, hBRF, TAF3B2, GTF3B, FLJ42674, TFIIIB90, TF3B90, ACCESSION NUMBER NM_001519.2; BRF1 homolog, subunit of RNA polymerase III transcription initiation factor IIIB (*S. cerevisiae*) (BRF1), transcript variant 1, akaFLJ43034, TAF3C, TAFIII90, MGC105048, BRF, hBRF, TAF3B2, GTF3B, FLJ42674, TFIIIB90, TF3B90, ACCESSION NUMBER NM_001519.2; BRF1 homolog, subunit of RNA polymerase III transcription initiation factor IIIB (*S. cerevisiae*) (BRF1), transcript variant 2, aka FLJ43034, TAF3C, TAFIII90, MGC105048, BRF, hBRF, TAF3B2, GTF3B, FLJ42674, TFIIIB90, TF3B90, ACCESSION NUMBER NM_145696.1; BTAF1 RNA polymerase II, B-TFIID transcription factor-associated, 170 kDa (Mot1 homolog, *S. cerevisiae*) (BTAF1), aka TAF172, KIAA0940, TAF(II)170, TAFII170, MOT1, MGC138406, ACCESSION NUMBER NM_003972.2; BTG family, member 2 (BTG2), aka PC3, TIS21, MGC126064, MGC126063, ACCESSION NUMBER NM_006763.2; BUD31 homolog (*S. cerevisiae*) (BUD31), aka MGC111202, YCR063W, EDG-2, EDG2, G10, ACCESSION NUMBER NM_003910.2; chromosome 11 open reading frame 9 (C11orf9), transcript variant 1, aka MGC10781, KIAA0954, ACCESSION NUMBER NM_013279.1; chromosome 21 open reading frame 66 (C21orf66), transcript variant 1, aka FLJ90561, GCFC, BM-020, ACCESSION NUMBER NM_016631.3; chromosome 21 open reading frame 66 (C21orf66), transcript variant 1, aka FLJ90561, GCFC, BM-020, ACCESSION NUMBER NM_016631.3; chromosome 21 open reading frame 66 (C21orf66), transcript variant 4, aka FLJ90561, GCFC, BM-020, ACCESSION NUMBER NM_058191.3; chromosome 21 open reading frame 66 (C21orf66), transcript variant 2, aka FLJ90561, GCFC, BM-020, ACCESSION NUMBER NM_013329.3; chromosome 2 open reading frame 3 (C2orf3), aka TCF9, GCF, DNABF, ACCESSION NUMBER NM_003203.3; chromosome 5 open reading frame 41 (C5orf41), aka DKFZp686G2059, DKFZp313F2319, ACCESSION NUMBER NM_153607.1; cartilage paired-class homeoprotein 1 (CART1), ACCESSION NUMBER NM_006982.1; core-binding factor, runt domain, alpha subunit 2, translocated to, 2 (CBFA2T2), transcript variant 2, aka MTGR1, EHT, ZMYND3, DKFZp313F2116, ACCESSION NUMBER NM_005093.3; core-binding factor, runt domain, alpha subunit 2, translocated to, 2 (CBFA2T2), transcript variant 2, aka MTGR1, EHT, ZMYND3, DKFZp313F2116, ACCESSION NUMBER NM_005093.3; core-binding factor, runt domain, alpha subunit 2, translocated to, 2 (CBFA2T2), transcript variant 3, aka MTGR1, EHT, ZMYND3, DKFZp313F2116, ACCESSION NUMBER NM_001032999.2; core-binding factor, runt domain, alpha subunit 2, translocated to, 3 (CBFA2T3), transcript variant 1, aka ZMYND4, MTGR2, MTG16, ETO2, ACCESSION NUMBER NM_005187.4; core-binding factor, runt domain, alpha subunit 2, translocated to, 3 (CBFA2T3), transcript variant 1, aka ZMYND4, MTGR2, MTG16, ETO2, ACCESSION NUMBER NM_005187.4; core-binding factor, runt domain, alpha subunit 2, translocated to, 3 (CBFA2T3), transcript variant 2, aka ZMYND4, MTGR2, MTG16, ETO2, ACCESSION NUMBER NM_175931.1; core-binding factor, beta subunit (CBFB), transcript variant 2, aka PEBP2B, ACCESSION NUMBER NM_001755.2; core-binding factor, beta subunit (CBFB), transcript variant 2, aka PEBP2B, ACCESSION NUMBER NM_001755.2; Cas-Br-M (murine) ecotropic retroviral transforming sequence (CBL), aka C-CBL, CBL2, RNF55, ACCESSION NUMBER NM_005188.2; CCR4 carbon catabolite repression 4-like (*S. cerevisiae*) (CCRN4L), aka CCR4L, MGC142060, MGC142054, MGC4120817, MGC78549, NOC, ACCESSION NUMBER NM_012118.2; caudal type homeobox 1 (CDX1), aka MGC116915, ACCESSION NUMBER NM_001804.2; caudal type homeobox 2 (CDX2), aka CDX3, CDX-3, ACCESSION NUMBER NM_001265.2; caudal type homeobox 4 (CDX4), ACCESSION NUMBER NM_005193.1; CCAAT/enhancer binding protein (C/EBP), alpha (CEBPA), aka CEBP, C/EBP-alpha, ACCESSION NUMBER NM_004364.2; CCAAT/enhancer binding protein (C/EBP), beta (CEBPB), aka CRP2, LAP, IL6 DBP, C/EBP-beta, TCF5, NF-IL6, MGC32080, ACCESSION NUMBER NM_005194.2; CCAAT/enhancer binding protein (C/EBP), delta (CEBPD), aka NF-IL6-beta, C/EBP-delta, CELF, CRP3, ACCESSION NUMBER NM_005195.3; CCAAT/enhancer binding protein (C/EBP), epsilon (CEBPE), aka C/EBP-epsilon, CRP1, ACCESSION NUMBER NM_001805.2; CCAAT/enhancer binding protein (C/EBP), gamma (CEBPG), aka GPE1BP, IG/EBP-1, ACCESSION NUMBER NM_001806.2; checkpoint suppressor 1 (CHES1), aka C14orf116, FOXN3, PRO1635, ACCESSION NUMBER NM_005197.2; ceh-10 homeodomain containing homolog (*C. elegans*) (CHX10), aka HOX10, MCOPCB3, MCOP2, RET1, ACCESSION NUMBER NM_182894.1; Cbp/p300-interacting transactivator, with Glu/Asp-rich carboxy-terminal domain, 1 (CITED1), aka MSG1, ACCESSION NUMBER NM_004143.2; Cbp/p300-interacting transactivator, with Glu/Asp-rich carboxy-terminal domain, 2 (CITED2), aka P35SRJ, MRG1, ACCESSION NUMBER NM_006079.3; clock homolog (mouse) (CLOCK), aka KIAA0334, ACCESSION NUMBER NM_004898.2; CCHC-type zinc finger, nucleic acid binding protein (CNBP), aka ZCCHC22, CNBP1, RNF163, PROMM, ZNF9, DM2, ACCESSION NUMBER NM_003418.1; CCR4-NOT transcription complex, subunit 7 (CNOT7), transcript variant 2, aka CAF1, hCAF-1, ACCESSION NUMBER NM_054026.2; CCR4-NOT transcription complex, subunit 7 (CNOT7), transcript variant 1, aka CAF1, hCAF-1, ACCESSION NUMBER NM_013354.5; CCR4-NOT transcription complex, subunit 7 (CNOT7), transcript variant 1, aka CAF1, hCAF-1, ACCESSION NUMBER NM_013354.5; CCR4-NOT transcription complex, subunit 8 (CNOT8), aka hCAF1, POP2, CAF1, CALIF, ACCESSION NUMBER NM_004779.4; cAMP responsive element binding protein 1 (CREB1), transcript variant A, aka MGC9284, CREB, ACCESSION NUMBER NM_004379.2; cAMP responsive element binding protein 3 (CREB3), aka LZIP, LUMAN, MGC15333, MGC19782, ACCESSION NUMBER NM_006368.4; cAMP responsive element binding protein 3-like 1 (CREB3L1), aka OASIS, ACCESSION NUMBER NM_052854.2; cAMP responsive element binding protein 3-like 2 (CREB3L2), aka BBF2H7, MGC131709, MGC71006, ACCESSION NUMBER NM_194071.2; cAMP responsive element binding protein 3-like 3 (CREB3L3), aka MGC126557, CREB-H, HYST1481, MGC126553, ACCESSION NUMBER NM_032607.1; cAMP responsive element binding protein 3-like 4 (CREB3L4), aka CREB4, ATCE1, JAL, hJAL, CREB3, AIBZIP, ACCESSION NUMBER NM_130898.2; cAMP responsive element binding protein 5 (CREB5), transcript variant 4, aka CRE-BPA, ACCESSION NUMBER NM_001011666.1; cAMP responsive element binding protein 5 (CREB5), transcript variant 2, aka CRE-BPA, ACCESSION NUMBER NM_004904.2; cAMP responsive element binding protein 5 (CREB5), transcript variant 1, aka CRE-BPA, ACCESSION NUMBER NM_182898.2; cAMP responsive element binding protein 5 (CREB5), transcript variant 1, aka CRE-BPA, ACCESSION NUMBER NM_182898.2; cAMP responsive element binding protein 5 (CREB5), transcript variant 3, aka CRE-BPA, ACCESSION NUMBER NM_182899.3; CREB binding protein (CREBBP), transcript variant 2, aka CBP, KAT3A, RTS, RSTS, ACCESSION NUMBER NM_001079846.1; CREB binding protein (CREBBP), transcript variant 1, aka CBP, KAT3A, RTS, RSTS, ACCESSION NUMBER NM_004380.2; cAMP responsive element binding protein-like 1 (CREBL1), aka FLJ10066, G13, CREB-RP, ACCESSION NUMBER NM_004381.3; cAMP responsive element binding protein-like 2 (CREBL2), aka MGC138362, MGC117311, ACCESSION NUMBER NM_001310.2; CREB/ATF bZIP transcription factor (CREBZF), aka ZF, ACCESSION NUMBER NM_001039618.1; cAMP responsive element modulator (CREM), transcript variant 2, aka MGC111110, ICER, MGC41893, MGC17881, hCREM-2, ACCESSION NUMBER NM_001881.2; cone-rod homeobox (CRX), aka OTX3, CRD, LCAT, CORD2, ACCESSION NUMBER NM_000554.3; cold shock domain protein A (CSDA), aka CSDA1, DBPA, ZONAB, ACCESSION NUMBER NM_003651.3; C-terminal binding protein 1 (CTBP1), transcript variant 1, aka BARS, MGC104684, ACCESSION NUMBER NM_001328.2; C-terminal binding protein 1 (CTBP1), transcript variant 2, aka BARS, MGC104684, ACCESSION NUMBER NM_001012614.1; C-terminal binding protein 1 (CTBP1), transcript variant 2, aka BARS, MGC104684, ACCESSION NUMBER NM_001012614.1; CCCTC-binding factor (zinc finger protein) (CTCF), ACCESSION NUMBER NM_006565.2; cut-like 1, CCAAT displacement protein (*Drosophila*) (CUTL1), transcript variant 1, aka p110, CASP, CUX, Nbla10317, p75, COY1, p200, p100, CDP, ACCESSION NUMBER NM_181552.1; cut-like homeobox 1 (CUX1), transcript variant 2, aka p110, CASP, GOLIM6, CUX, CDP1, Cux/CDP, Nbla10317, Clox, p75, CUTL1, COY1, p200, p100, CDP, CDP/Cut, ACCESSION NUMBER NM_001913.2; cut-like homeobox 1 (CUX1), transcript variant 3, aka p110, CASP, GOLIM6, CUX, CDP1, Cux/CDP, Nbla10317, Clox, p75, CUTL1, COY1, p200, p100, CDP, CDP/Cut, ACCESSION NUMBER NM_181500.1; cut-like homeobox 2 (CUX2), aka CUTL2, CUX2, CDP2, ACCESSION NUMBER NM_015267.2; dachshund homolog 1 (*Drosophila*) (DACH1), transcript variant 1, aka DACH, FLJ10138, ACCESSION NUMBER NM_080759.3; dachshund homolog 1 (*Drosophila*) (DACH1), transcript variant 2, aka DACH, FLJ10138, ACCESSION NUMBER NM_080760.3; dachshund homolog 1 (*Drosophila*) (DACH1), transcript variant 2, aka DACH, FLJ10138, ACCESSION NUMBER NM_080760.3; D site of albumin promoter (albumin D-box) binding protein (DBP), aka DABP, ACCESSION NUMBER NM_001352.2; developing brain homeobox 1 (DBX1), ACCESSION NUMBER NM_001029865.1; developing brain homeobox 2 (DBX2), aka FLJ16139, ACCESSION NUMBER NM_001004329.2; DNA-damage-inducible transcript 3 (DDIT3), aka MGC4154, CEBPZ, CHOP10, CHOP, GADD153, ACCESSION NUMBER NM_004083.4; distal-less homeobox 1 (DLX1), transcript variant 2, ACCESSION NUMBER NM_001038493.1; distal-less homeobox 1 (DLX1), transcript variant 1, ACCESSION NUMBER NM_178120.4; distal-less homeobox 2 (DLX2), aka TES1, TES-1, ACCESSION NUMBER NM_004405.3; distal-less homeobox 3 (DLX3), aka TDO, ACCESSION NUMBER NM_005220.2; distal-less homeobox 4 (DLX4), transcript variant 1, aka BP1, DLX9, DLX8, DLX7, ACCESSION NUMBER NM_138281.1; distal-less homeobox 4 (DLX4), transcript variant 1, aka BP1, DLX9, DLX8, DLX7, ACCESSION NUMBER NM_138281.1; distal-less homeobox 4 (DLX4), transcript variant 2, aka BP1, DLX9, DLX8, DLX7, ACCESSION NUMBER NM_001934.2; distal-less homeobox 5 (DLX5), ACCESSION NUMBER NM_005221.5; distal-less homeobox 6 (DLX6), aka MGC125283, MGC125282, MGC125285, MGC125284, ACCESSION NUMBER NM_005222.2; diencephalon/mesencephalon homeobox 1 (DMBX1), transcript variant 1, aka OTX3, PAXB, MBX, ACCESSION NUMBER NM_172225.1; doublesex and mab-3 related transcription factor 1 (DMRT1), aka DMT1, ACCESSION NUMBER NM_021951.2; doublesex and mab-3 related transcription factor 2 (DMRT2), transcript variant 1, ACCESSION NUMBER NM_006557.4; doublesex and mab-3 related transcription factor 2 (DMRT2), transcript variant 1, ACCESSION NUMBER NM_006557.4; doublesex and mab-3 related transcription factor 3 (DMRT3), aka MGC142144, DMRTA3, ACCESSION NUMBER NMO21240.2; DMRT-like family A1 (DMRTA1), aka MGC163307, DMO, MGC163309, ACCESSION NUMBER NM_022160.1; DMRT-like family B with proline-rich C-terminal, 1 (DMRTB1), ACCESSION NUMBER NM_033067.1; DMRT-like family C2 (DMRTC2), ACCESSION NUMBER NM_001040283.1; cyclin D binding myb-like transcription factor 1 (DMTF1), aka DMP1, DMTF, hDMP1, FLJ41265, ACCESSION NUMBER NM_021145.2; divergent-paired related homeobox (DPRX), ACCESSION NUMBER NM_001012728.1; DR1-associated protein 1 (negative cofactor 2 alpha) (DRAP1), aka NC2-alpha, ACCESSION NUMBER NM_006442.2; dorsal root ganglia homeobox (DRGX), aka DRG11, PRRXL1, ACCESSION NUMBER NM_001080520.1; double homeobox, 1 (DUX1), ACCESSION NUMBER NM_012146.1; double homeobox, 2 (DUX2), ACCESSION NUMBER NM_012147.2; double homeobox, 3 (DUX3), ACCESSION NUMBER NM_012148.2; double homeobox, 4 (DUX4), aka DUX10, ACCESSION NUMBER NM_033178.2; double homeobox 4c (DUX4C), ACCESSION NUMBER NM_001099853.1; double homeobox, 5 (DUX5), ACCESSION NUMBER NM_012149.2; double homeobox A (DUXA), ACCESSION NUMBER NM_001012729.1; E2F transcription factor 1 (E2F1), aka E2F-1, RBP3, RBBP3, ACCESSION NUMBER NM_005225.1; E2F transcription factor 2 (E2F2), aka E2F-2, ACCESSION NUMBER NM_004091.2; E2F transcription factor 3 (E2F3), aka KIAA0075, E2F-3, MGC104598, DKFZp686C18211, ACCESSION NUMBER NM_001949.2; E2F transcription factor 4, p107/p130-binding (E2F4), aka E2F-4, ACCESSION NUMBER NM_001950.3; E2F transcription factor 5, p130-binding (E2F5), transcript variant 1, aka E2F-5, ACCESSION NUMBER NM_001951.3; E2F transcription factor 6 (E2F6), aka E2F-6, MGC111545, ACCESSION NUMBER NM_198256.2; E2F transcription factor 6 (E2F6), transcript variant e, aka E2F-6, MGC111545, accession number NR_003095.1; E2F transcription factor 7 (E2F7), aka FLJ12981, ACCESSION NUMBER NM_203394.2; E2F transcription factor 8 (E2F8), aka FLJ23311, ACCESSION NUMBER NM_024680.2; E4F transcription factor 1 (E4F1), aka MGC99614, E4F, ACCESSION NUMBER NM_004424.3; ECSIT homolog (*Drosophila*) (ECSIT), aka SITPEC, ACCESSION NUMBER NM_016581.2; endothelial differentiation-related factor 1 (EDF1), transcript variant alpha, aka EDF-1, MBF1, MGC9058, ACCESSION NUMBER NM_003792.2; endothelial differentiation-related factor 1 (EDF1), transcript variant alpha, aka EDF-1, MBF1, MGC9058, ACCESSION NUMBER NM_003792.2; early growth response 1 (EGR1), aka G0S30, AT225, TIS8, ZNF225, NGFI-A, KROX-24, ZIF-268, ACCESSION NUMBER NM_001964.2; early growth response 2 (Krox-20 homolog, *Drosophila*) (EGR2), aka KROX20, FLJ14547, DKFZp686J1957, *CMT*4E, CMT1D, ACCESSION NUMBER NM_000399.2; early growth response 3 (EGR3), aka PILOT, MGC138484, ACCESSION NUMBER NM_004430.2; early growth response 3 (EGR3), aka PILOT, MGC138484, ACCESSION NUMBER NM_004430.2; early growth response 4 (EGR4), aka NGFI-C, NGFIC, PAT133, ACCESSION NUMBER NM_001965.1; ets homologous factor (EHF), aka ESE3, ESEJ, ACCESSION NUMBER NM_012153.3; E74-like factor 1 (ets domain transcription factor) (ELF1), ACCESSION NUMBER NM_172373.2; E74-like factor 2 (ets domain transcription factor) (ELF2), transcript variant 2, aka NERF, NERF-1A, NERF-2, EU32, NERF-1B, ACCESSION NUMBER NM_006874.2; E74-like factor 2 (ets domain transcription factor) (ELF2), transcript variant 2, aka NERF, NERF-1A, NERF-2, EU32, NERF-1B, ACCESSION NUMBER NM_006874.2; E74-like factor 2 (ets domain transcription factor) (ELF2), transcript variant 1, aka NERF, NERF-1A, NERF-2, EU32, NERF-1B, ACCESSION NUMBER NM_201999.1; E74-like factor 3 (ets domain transcription factor, epithelial-specific) (ELF3), aka ESX, ESE-1, EPR-1, ERT, ACCESSION NUMBER NM_004433.3; E74-like factor 4 (ets domain transcription factor) (ELF4), aka MEF, ELFR, ACCESSION NUMBER NM_001421.2; E74-like factor 5 (ets domain transcription factor) (ELF5), transcript variant 2, aka ESE2, ACCESSION NUMBER NM_001422.2; E74-like factor 5 (ets domain transcription factor) (ELF5), transcript variant 1, aka ESE2, ACCESSION NUMBER NM_198381.1; ELK1, member of ETS oncogene family (ELK1), ACCESSION NUMBER NM_005229.2; ELK3, ETS-domain protein (SRF accessory protein 2) (ELK3), aka SAP2, NET, ERP, ACCESSION NUMBER NM_005230.2; ELK4, ETS-domain protein (SRF accessory protein 1) (ELK4), transcript variant a, aka SAP1, ACCESSION NUMBER NM_001973.2; ELK4, ETS-domain protein (SRF accessory protein 1) (ELK4), transcript variant a, aka SAP1, ACCESSION NUMBER NM_001973.2; ELK4, ETS-domain protein (SRF accessory protein 1) (ELK4), transcript variant b, aka SAP1, ACCESSION NUMBER NMO21795.2; empty spiracles homolog 1 (*Drosophila*) (EMX1), ACCESSION NUMBER NM_004097.1, empty spiracles homeobox 1 (EMX1), transcript variant 2, ACCESSION NUMBER NM_001040404.1, empty spiracles homeobox 2 (EMX2), ACCESSION NUMBER NM_004098.2; engrailed homeobox 1 (EN1), ACCESSION NUMBER NM_001426.3; engrailed homeobox 2 (EN2), aka AUTS1, AUTS10, ACCESSION NUMBER NM_001427.3; eomesodermin homolog (*Xenopus laevis*) (EOMES), aka TBR2, ACCESSION NUMBER NM_005442.2; E1A binding protein p300 (EP300), aka p300, KAT3B, ACCESSION NUMBER NM_001429.2; endothelial PAS domain protein 1 (EPAS1), aka HIF2A, HLF, ECYT4, MOP2, PASD2, ACCESSION NUMBER NM_001430.3; Ets2 repressor factor (ERF), aka PE-2 ACCESSION NUMBER NM_006494.1; v-ets erythroblastosis virus E26 oncogene homolog (avian) (ERG), transcript variant 1, aka erg-3, p55, ACCESSION NUMBER NM_182918.2; v-ets erythroblastosis virus E26 oncogene homolog (avian) (ERG), transcript variant 1, aka erg-3, p55, ACCESSION NUMBER NM_182918.2; v-ets erythroblastosis virus E26 oncogene homolog (avian) (ERG), transcript variant 2, aka erg-3, p55, ACCESSION NUMBER NM_004449.3; estrogen receptor 1 (ESR1), aka major ORF, ESR, Era, ER, NR3A1, ESRA, DKFZp686N23123, ACCESSION NUMBER NM_000125.2; estrogen receptor 2 (ER beta) (ESR2), transcript variant b, aka ESR-BETA, ESTRB, ESRB, Erb, ER-BETA, NR3A2, ACCESSION NUMBER NM_001040275.1; estrogen receptor 2 (ER beta) (ESR2), transcript variant b, aka ESR-BETA, ESTRB, ESRB, Erb, ER-BETA, NR3A2, ACCESSION NUMBER NM_001040275.1; estrogen-related receptor alpha (ESRRA), aka NR3B1, ERRalpha, ERRa, ERR1, ESRL1, ACCESSION NUMBER NM_004451.3; estrogen-related receptor beta (ESRRB), aka ESRL2, ERRbeta, NR3B2, ERRb, ERRbeta-2, ERR2, ACCESSION NUMBER NM_004452.2; estrogen-related receptor gamma (ESRRG), transcript variant 1, aka DKFZp781L1617, ERR3, KIAA0832, FLJ16023, NR3B3; ACCESSION NUMBER NM_001438.2; estrogen-related receptor gamma (ESRRG), transcript variant 2, aka DKFZp781L1617, ERR3, KIAA0832, FLJ16023, NR3B3, ACCESSION NUMBER NM_206594.1; estrogen-related receptor gamma (ESRRG), transcript variant 2, aka DKFZp781L1617, ERR3, KIAA0832, FLJ16023, NR3B3, ACCESSION NUMBER NM_206594.1; ESX homeobox 1 (ESX1), aka ESXR1, ESX1L, ACCESSION NUMBER NM_153448.2; v-ets erythroblastosis virus E26 oncogene homolog 1 (avian) (ETS1), aka ETS-1, FLJ10768, EWSR2, ACCESSION NUMBER NM_005238.2; v-ets erythroblastosis virus E26 oncogene homolog 2 (avian) (ETS2), ACCESSION NUMBER NM_005239.4; ets variant gene 1 (ETV1), aka MGC120533, DKFZp781L0674, MGC104699, ER81, MGC120534, ACCESSION NUMBER NM_004956.3; ets variant gene 2 (ETV2), aka MGC129835, ETSRP71, ER71, MGC129834, ACCESSION NUMBER NM_014209.1; ets variant 3 (ETV3), aka bA110J1.4, PE-1, PE1, METS, ACCESSION NUMBER NM_005240.1; ets variant 3-like (ETV3L), aka FLJ16478, ACCESSION NUMBER NM_001004341.1; ets variant 4 (ETV4), transcript variant 1, aka PEA3, E1A-F, E1AF, PEAS3, ACCESSION NUMBER NM_001986.2; ets variant gene 4 (E1A enhancer binding protein, E1AF) (ETV4), aka E1A-F, PEA3, E1AF, PEAS3, ACCESSION NUMBER NM_001986.1; ets variant gene 5 (ets-related molecule) (ETV5), aka ERM, ACCESSION NUMBER NM_004454.1; ets variant gene 5 (ets-related molecule) (ETV5), aka ERM, ACCESSION NUMBER NM_004454.1; ets variant 6 (ETV6), aka TEL, TEL/ABL, ACCESSION NUMBER NM_001987.4; ecotropic viral integration site 1 (EVI1), aka EVI-1, PRDM3, MGC163392, MDS1-EVI1, AML1-EVI-1, ACCESSION NUMBER NM_005241.1; even-skipped homeobox 1 (EVX1), ACCESSION NUMBER NM_001989.3; even-skipped homeobox 2 (EVX2), ACCESSION NUMBER NM_001080458.1; FEV (ETS oncogene family) (FEV), aka PET-1, HSRNAFEV, ACCESSION NUMBER NM_017521.2; Friend leukemia virus integration 1 (FLI1), aka SIC-1, EWSR2, ACCESSION NUMBER NM_002017.2; FLJ46838 protein (FLJ46838), ACCESSION NUMBER NM_001007546.2; formin-like 2 (FMNL2), aka FLJ37546, FHOD2, ACCESSION NUMBER NM_052905.3; v-fos FBJ murine osteosarcoma viral oncogene homolog (FOS), aka c-fos, ACCESSION NUMBER NM_005252.2; FBJ murine osteosarcoma viral oncogene homolog B (FOSB), aka GOS3, G0S3, MGC42291, GOSB, DKFZp686C0818, ACCESSION NUMBER NM_006732.1; FOS-like antigen 1 (FOSL1), aka fra-1, FRA1, ACCESSION NUMBER NM_005438.2; FOS-like antigen 2 (FOSL2), aka FRA2, FLJ23306, ACCESSION NUMBER NM_005253.3; forkhead box A1 (FOXA1), aka MGC33105, TCF3A, HNF3A, ACCESSION NUMBER NM_004496.2; forkhead box A2 (FOXA2), transcript variant 1, aka MGC19807, TCF3B, HNF3B, ACCESSION NUMBER NM_021784.3; forkhead box A2 (FOXA2), transcript variant 2, aka MGC19807, TCF3B, HNF3B, ACCESSION NUMBER NM_153675.1; forkhead box A2 (FOXA2), transcript variant 2, aka MGC19807, TCF3B, HNF3B, ACCESSION NUMBER NM_153675.1; forkhead box A3 (FOXA3), aka HNF3G, TCF3G, MGC10179, FKHH3, ACCESSION NUMBER NM_004497.2; forkhead box B1 (FOXB1), aka FKH5, HFKH-5, ACCESSION NUMBER NM_012182.2; forkhead box B2 (FOXB2), aka bA159H20.4, ACCESSION NUMBER NM_001013735.1; forkhead box C1 (FOXC1), aka FREAC3, FKHL7, 1HG1, ARA, IRID1, IGDA, ACCESSION NUMBER NM_001453.1; forkhead box C2 (MFH-1, mesenchyme forkhead 1) (FOXC2), aka MFH1, MFH-1, FKHL14, LD, ACCESSION NUMBER NM_005251.1; forkhead box D1 (FOXD1), aka FREAC4, FKHL8, ACCESSION NUMBER NM_004472.2; forkhead box D2 (FOXD2), aka FREAC-9, FKHL17, FREAC9, ACCESSION NUMBER NM_004474.3; forkhead box D3 (FOXD3), aka HFH2, Genesis, ACCESSION NUMBER NM_012183.1; forkhead box D4 (FOXD4), aka FOXD4A, FKHL9, MGC105106, FREAC5, ACCESSION NUMBER NM_207305.2; forkhead box D4-like 1 (FOXD4L1), aka bA395L14.1, ACCESSION NUMBER NM_012184.3; FOXD4-like 2 (FOXD4L2), aka MGC119257, ACCESSION NUMBER NM_199135.1; forkhead box D4-like 3 (FOXD4L3), aka FOXD6, ACCESSION NUMBER NM_199358.1; forkhead box E1 (thyroid transcription factor 2) (FOXE1), aka TTF-2, TTF2, TITF2, HFKH4, FOXE2, FKHL15, HFKL5, ACCESSION NUMBER NM_004473.3; forkhead box E3 (FOXE3), aka FREAC8, FKHL12, ASMD, ACCESSION NUMBER NM_012186.2; forkhead box E3 (FOXE3), aka FREAC8, FKHL12, ASMD, ACCESSION NUMBER NM_012186.2; forkhead box F1 (FOXF1), aka MGC105125, FKHL5, FREAC1, ACCESSION NUMBER NM_001451.2; forkhead box F2 (FOXF2), aka FREAC2, FKHL6, ACCESSION NUMBER NM_001452.1; forkhead box G1 (FOXG1), aka FKHL1, KHL2, HFK3, HBF2, FOXG1C, QIN, FKHL2, HBF-2, HBF-1, FKH2, HFK1, FKHL4, HBF-G2, BF2, FHKL3, BF1, HFK2, HBF-3, FOXG1B, FKHL3, FOXG1A, ACCESSION NUMBER NM_005249.3; forkhead box H1 (FOXH1), aka FAST1, FAST-1, ACCESSION NUMBER NM_003923.1; forkhead box I1 (FOXI1), transcript variant 1, aka HFH3, FKHL10, MGC34197, FREAC6, ACCESSION NUMBER NM_012188.4; forkhead box I1 (FOXI1), transcript variant 1, aka HFH3, FKHL10, MGC34197, FREAC6, ACCESSION NUMBER NM_012188.4; forkhead box J2 (FOXI2), aka FOXI2, FLJ46831, ACCESSION NUMBER NM_207426.1; forkhead box J1 (FOXJ1), aka HFH-4, HFH4, MGC35202, FKHL13, ACCESSION NUMBER NM_001454.2; forkhead box J2 (FOXJ2), aka FHX, ACCESSION NUMBER NM_018416.2; forkhead box J3 (FOXJ3), aka MGC176686, MGC165036, ACCESSION NUMBER NM_014947.3; forkhead box K1 (FOXK1), aka FLJ14977, FOXK1, ACCESSION NUMBER NM_001037165.1; forkhead box K1 (FOXK1), aka FLJ14977, FOXK1L, ACCESSION NUMBER NM_001037165.1; forkhead box K2 (FOXK2), aka ILF-1, ILF, ILF1, ACCESSION NUMBER NM_004514.3; forkhead box K2 (FOXK2), aka ILF-1, ILF, ILF1, ACCESSION NUMBER NM_004514.3; forkhead box L1 (FOXL1), aka FREAC7, FKH6, FKHL11, ACCESSION NUMBER NM_005250.2; forkhead box L2 (FOXL2), aka BPES1, PINTO, BPES, PFRK, POF3, ACCESSION NUMBER NM_023067.2; forkhead box L2 (FOXL2), accession number XM_001131060.1; forkhead box M1 (FOXM1), transcript variant 3, aka TGT3, PIG29, HFH-11, FKHL16, MPP-2, INS-1, HFH11, MPP2, TRIDENT, MPHOSPH2, HNF-3, FOXM1B, ACCESSION NUMBER NM_202003.1; forkhead box M1 (FOXM1), transcript variant 2, aka TGT3, PIG29, HFH-11, FKHL16, MPP-2, INS-1, HFH11, MPP2, TRIDENT, MPHOSPH2, HNF-3, FOXM1B, ACCESSION NUMBER NM_021953.2; forkhead box N1 (FOXN1), aka FKHL20, WHN, RONU, ACCESSION NUMBER NM_003593.2; forkhead box N2 (FOXN2), aka HTLF, ACCESSION NUMBER NM_002158.3; forkhead box N3 (FOXN3), transcript variant 1, aka CHES1, C14orf116, PRO1635, ACCESSION NUMBER NM_001085471.1; forkhead box N4 (FOXN4), aka FLJ35967, ACCESSION NUMBER NM_213596.1; forkhead box O1 (FOXO1), aka FKHR, FKH1, FOXO1A, ACCESSION NUMBER NM_002015.3; forkhead box O3 (FOXO3), transcript variant 2, aka FOXO2, FKHRL1, AF6q21, DKFZp781A0677, MGC12739, FKHRL1P2, MGC31925, FOXO3A, ACCESSION NUMBER NM_201559.2; forkhead box O3 (FOXO3), transcript variant 1, aka FOXO2, FKHRL1, AF6q21, DKFZp781A0677, MGC12739, FKHRL1P2, MGC31925, FOXO3A ACCESSION NUMBER NM_001455.3; forkhead box O4 (FOXO4), aka AFX1, AFX, FOXO4, MGC120490, MLLT7, ACCESSION NUMBER NM_005938.2; forkhead box P1 (FOXP1), transcript variant 2, aka MGC99551, QRF1, hFKH1B, MGC88572, 12CC4, HSPC215, MGC12942, FLJ23741, ACCESSION NUMBER NM_001012505.1; forkhead box P1 (FOXP1), transcript variant 1, aka MGC99551, QRF1, hFKH1B, MGC88572, 12CC4, HSPC215, MGC12942, FLJ23741, ACCESSION NUMBER NM_032682.4; forkhead box P1 (FOXP1), transcript variant 1, aka MGC99551, QRF1, hFKH1B, MGC88572, 12CC4, HSPC215, MGC12942, FLJ23741, ACCESSION NUMBER NM_032682.4; forkhead box P2 (FOXP2), transcript variant 2, aka TNRC10, SPCH1, DKFZp686H1726, CAGH44, ACCESSION NUMBER NM_148898.2; forkhead box P2 (FOXP2), transcript variant 1, aka TNRC10, SPCH1, DKFZp686H1726, CAGH44, ACCESSION NUMBER NM_014491.1; forkhead box P3 (FOXP3), aka PIDX, AIID, MGC141961, JM2, DIETER, XPID, MGC141963, IPEX, ACCESSION NUMBER NM_014009.2; forkhead box P4 (FOXP4), transcript variant 1, aka FLJ44184, FLJ40908, hFKHLA, ACCESSION NUMBER NM_001012426.1; forkhead box P4 (FOXP4), transcript variant 1, aka FLJ44184, FLJ40908, hFKHLA, ACCESSION NUMBER NM_001012426.1; forkhead box Q1 (FOXQ1), aka HFH1, ACCESSION NUMBER NM_033260.3; forkhead box R1 (FOXR1), aka FOXN5, MGC149486, DLNB13, ACCESSION NUMBER NM_181721.2; forkhead box R1 (FOXR1), aka FOXN5, MGC149486, DLNB13, ACCESSION NUMBER NM_181721.2; forkhead box R2 (FOXR2), aka MGC21658, FOXN6, ACCESSION NUMBER NM_198451.1; forkhead box S1 (FOXS1), aka MGC4544, FREAC10, ACCESSION NUMBER NM_004118.3; far upstream element (FUSE) binding protein 1 (FUBP1), aka FBP, FUBP, ACCESSION NUMBER NM_003902.3; GA binding protein transcription factor, alpha subunit 60 kDa (GABPA), aka NRF2A, NFT2, E4TF1-60, E4TF1A, NRF2, ACCESSION NUMBER NM_002040.2; GA binding protein transcription factor, beta subunit 2 (GABPB2), transcript variant gamma-1, aka NRF2B2, GABPB, E4TF1-47, E4TF1, NRF2B1, E4TF1B, E4TF1-53, BABPB2, GABPB1, ACCESSION NUMBER NM_002041.3; GA binding protein transcription factor, beta subunit 2 (GABPB2), transcript variant gamma-2, aka NRF2B2, GABPB, E4TF1-47, E4TF1, NRF2B1, E4TF1B, E4TF1-53, BABPB2, GABPB1, ACCESSION NUMBER NM_016655.3; GA binding protein transcription factor, beta subunit 2 (GABPB2), aka RP11-68118.1, ACCESSION NUMBER NM_144618.1; growth arrest-specific 7 (GAS7), transcript variant a, aka MGC1348, MLL/GAS7, KIAA0394, ACCESSION NUMBER NM_003644.2; growth arrest-specific 7 (GAS7), transcript variant b, aka MGC1348, MLL/GAS7, KIAA0394, ACCESSION NUMBER NM_201432.1; growth arrest-specific 7 (GAS7), transcript variant c, aka MGC1348, MLL/GAS7, KIAA0394, ACCESSION NUMBER NM_201433.1; growth arrest-specific 7 (GAS7), transcript variant c, aka MGC1348, MLL/GAS7, KIAA0394, ACCESSION NUMBER NM_201433.1; GATA binding protein 1 (globin transcription factor 1) (GATA1), aka ERYF1, GF1, NFE1, ACCESSION NUMBER NM_002049.2; GATA binding protein 2 (GATA2), aka NFE1B, MGC2306, ACCESSION NUMBER NM_032638.3; GATA binding protein 3 (GATA3), transcript variant 2, aka HDR, MGC5199, MGC5445, MGC2346, ACCESSION NUMBER NM_002051.2; GATA binding protein 4 (GATA4), aka MGC126629, ACCESSION NUMBER NM_002052.2; GATA binding protein 5 (GATA5), aka bB379O24.1, ACCESSION NUMBER NM_080473.3; GATA binding protein 6 (GATA6), ACCESSION NUMBER NM_005257.3; GATA zinc finger domain containing 1 (GATAD1), aka FLJ40695, FLJ22489, ODAG, RG083M05.2, ACCESSION NUMBER NM_021167.3; GATA zinc finger domain containing 2A (GATAD2A), aka FLJ20085, p66alpha, ACCESSION NUMBER NM_017660.2; GATA zinc finger domain containing 2B (GATAD2B), aka MGC138285, P66beta, RP11-216N14.6, KIAA1150, FLJ37346, MGC138257, ACCESSION NUMBER NM_020699.1; gastrulation brain homeobox 2 (GBX2), ACCESSION NUMBER NM_001485.2; glial cells missing homolog 1 (*Drosophila*) (GCM1), aka GCMA, hGCMa, ACCESSION NUMBER NM_003643.2; glioma-associated oncogene homolog 1 (zinc finger protein) (GLI1), aka GLI, ACCESSION NUMBER NM_005269.1; GLI-Kruppel family member GLI2 (GLI2), aka HPE9, THP2, ACCESSION NUMBER NM_005270.3; GLI-Kruppel family member GLI3 (Greig cephalopolysyndactyly syndrome) (GLI3), aka PHS, PAP-A, PAPA1, GCPS, PAPB, PAPA, ACLS, PPDIV, ACCESSION NUMBER NM_000168.2; GLIS family zinc finger 3 (GLIS3), transcript variant 2, aka ZNF515, FLJ38999, MGC33662, FLJ90578, ACCESSION NUMBER NM_152629.3; GLIS family zinc finger 3 (GLIS3), transcript variant 2, aka ZNF515, FLJ38999, MGC33662, FLJ90578, ACCESSION NUMBER NM_152629.3; GLIS family zinc finger 3 (GLIS3), transcript variant 2, aka ZNF515, FLJ38999, MGC33662, FLJ90578, ACCESSION NUMBER NM_152629.3; GLIS family zinc finger 3 (GLIS3), transcript variant 2, aka ZNF515, FLJ38999, MGC33662, FLJ90578, ACCESSION NUMBER NM_152629.3; glucocorticoid modulatory element binding protein 1 (GMEB1), transcript variant 2, aka P96PIF, PIF96, ACCESSION NUMBER NM_024482.1; glucocorticoid modulatory element binding protein 1 (GMEB1), transcript variant 2, aka P96PIF, PIF96, ACCESSION NUMBER, NM_024482.1; goosecoid homeobox (GSC), ACCESSION NUMBER NM_173849.2; goosecoid homeobox 2 (GSC2), aka GSCL, ACCESSION NUMBER NM_005315.1; GS homeobox 1 (GSX1), aka Gsh-1, GSH1, ACCESSION NUMBER NM_145657.1; GS homeobox 2 (GSX2), aka GSH2, ACCESSION NUMBER NM_133267.1; general transcription factor IIA, 2, 12 kDa (GTF2A2), aka TFIIA, TF2A2, HsT18745, ACCESSION NUMBER NM_004492.1; general transcription factor IIH, polypeptide 2, 44 kDa (GTF2H2), aka T-BTF2P44, MGC102806, BTF2, TFIIH, BTF2P44, ACCESSION NUMBER NM_001515.3; general transcription factor IIH, polypeptide 3, 34 kDa (GTF2H3), aka BTF2, TFIIH, ACCESSION NUMBER NM_001516.3; general transcription factor IIH, polypeptide 4, 52 kDa (GTF2H4), aka TFIIH, ACCESSION NUMBER NM_001517.4; general transcription factor II, i (GTF2I), transcript variant 3, aka IB291, DIWS, TFII-I, SPIN, BAP135, BAP-135, BTKAP1, WBSCR6, WBS, ACCESSION NUMBER NM_033001.1; general transcription factor II, (GTF2I), transcript variant 1, aka IB291, DIWS, TFII-I, SPIN, BAP135, BAP-135, BTKAP1, WBSCR6, WBS, ACCESSION NUMBER NM_032999.1; heart and neural crest derivatives expressed 1 (HAND1), aka Thing1, eHand, Hxt, ACCESSION NUMBER NM_004821.1; heart and neural crest derivatives expressed 2 (HAND2), aka MGC125304, Thing2, Hed, dHand, MGC125303, DHAND2, FLJ16260, ACCESSION NUMBER NM_021973.2; host cell factor C1 (VP16-accessory protein) (HCFC1), aka HFC1, MGC70925, VCAF, HCF-1, CFF, HCF1, ACCESSION NUMBER NM_005334.2; hematopoietic cell-specific Lyn substrate 1 (HCLS1), aka HS1, CTTNL, ACCESSION NUMBER NM_005335.3; histone deacetylase 1 (HDAC1), aka GON-10, DKFZp686H12203, HD1, RPD3, RPD3L1, ACCESSION NUMBER NM_004964.2; histone deacetylase 2 (HDAC2), aka YAF1, RPD3, ACCESSION NUMBER NM_001527.2; highly divergent homeobox (HDX), aka D030011N01Rik, FLJ30678, MGC126771, CXorf43, MGC126769, ACCESSION NUMBER NM_144657.3; HES/HEY-like transcription factor (HELT), aka HCM1228, Mgn, HESL, ACCESSION NUMBER NM_001029887.1; hairy and enhancer of split 6 (*Drosophila*) (HES6), ACCESSION NUMBER NM_018645.3; HESX homeobox 1 (HESX1), aka RPX, ANF, MGC138294, ACCESSION NUMBER NM_003865.1; hairy/enhancer-of-split related with YRPW motif 1 (HEY1), transcript variant 2, aka MGC1274, CHF2, HERP2, HRT-1, HESR1, OAF1, ACCESSION NUMBER NM_001040708.1; hairy/enhancer-of-split related with YRPW motif 1 (HEY1), transcript variant 2, aka MGC1274, CHF2, HERP2, HRT-1, HESR1, OAF1, ACCESSION NUMBER NM_001040708.1; hairy/enhancer-of-split related with YRPW motif 2 (HEY2), aka GRL, HERP1, ACCESSION NUMBER NM_012259.1; hairy/enhancer-of-split related with YRPW motif-like (HEYL), aka MGC12623, HRT3, ACCESSION NUMBER NM_014571.3; hematopoietically expressed homeobox (HHEX), aka HEX, PRH, PRHX, HOX11L-PEN, HMPH, ACCESSION NUMBER NM_002729.4; hypermethylated in cancer 1 (HIC1), transcript variant 2, aka hic-1, ZBTB29, ACCESSION NUMBER NM_001098202.1; hypoxia-inducible factor 1, alpha subunit (basic helix-loop-helix transcription factor) (HIF1A), transcript variant 2, aka HIF-1alpha, MOP1, PASD8, HIF1-ALPHA, HIF1, ACCESSION NUMBER NM_181054.1; hypoxia-inducible factor 1, alpha subunit (basic helix-loop-helix transcription factor) (HIF1A), transcript variant 1, aka HIF-1alpha, MOP1, PASD8, HIF1-ALPHA, HIF1, ACCESSION NUMBER NM_001530.2; hypoxia inducible factor 3, alpha subunit (HIF3A), transcript variant 2, aka MOP7, HIF-3A2, HIF-3A4, PASD7, IPAS, HIF-3A, ACCESSION NUMBER NM_022462.3; hypoxia inducible factor 3, alpha subunit (HIF3A), transcript variant 2, aka MOP7, HIF-3A2, HIF-3A4, PASD7, IPAS, HIF-3A, ACCESSION NUMBER NM_022462.3; hypoxia inducible factor 3, alpha subunit (HIF3A), transcript variant 2, aka MOP7, HIF-3A2, HIF-3A4, PASD7, IPAS, HIF-3A, ACCESSION NUMBER NM_022462.3; hypoxia inducible factor 3, alpha subunit (HIF3A), transcript variant 1, aka IPAS, HIF-3A, MOP7, HIF-3A4, PASD7, ACCESSION NUMBER NM_152794.2; hypoxia inducible factor 3, alpha subunit (HIF3A), transcript variant 3, aka IPAS, HIF-3A, MOP7, HIF-3A2, HIF-3A4, PASD7, ACCESSION NUMBER NM_152795.2; huntingtin interacting protein 2 (HIP2), aka LIG, UBE2K, HYPG, ACCESSION NUMBER NM_005339.3; HIR histone cell cycle regulation defective homolog A (*S. cerevisiae*) (HIRA), aka TUP1, TUPLE1, DGCR1, ACCESSION NUMBER NM_003325.3; hepatic leukemia factor (HLF), aka MGC33822, ACCESSION NUMBER NM_002126.4; H2.0-like homeobox (HLX), aka HB24, HLX1, ACCESSION NUMBER NM_021958.2; homeobox HB9 (HLXB9), aka HB9, SCRA1, HOXHB9, ACCESSION NUMBER NM_005515.2; homeobox containing 1 (HMBOX1), aka FLJ21616, HNF1LA, PBHNF, ACCESSION NUMBER NM_024567.2; high-mobility group 20A (HMG20A), aka HMGX1, FLJ10739, ACCESSION NUMBER NM_018200.2; high-mobility group 20B (HMG20B), aka SMARCE1r, FLJ26127, HMGX2, pp 8857, PP7706, BRAF35, SOXL, BRAF25, ACCESSION NUMBER NM_006339.1; high mobility group AT-hook 1 (HMGA1), transcript variant 1, aka MGC12816, MGC4854, HMG-R, MGC4242, HMGIY, ACCESSION NUMBER NM_145899.1; high mobility group AT-hook 1 (HMGA1), transcript variant 4, aka MGC12816, MGC4854, HMG-R, MGC4242, HMGIY, ACCESSION NUMBER NM_145902.1; high mobility group AT-hook 1 (HMGA1), transcript variant 6, aka MGC12816, MGC4854, HMG-R, MGC4242, HMGIY, ACCESSION NUMBER NM_145904.1; high mobility group AT-hook 1 (HMGA1), transcript variant 7, aka MGC12816, MGC4854, HMG-R, MGC4242, HMGIY, ACCESSION NUMBER NM_145905.1; high-mobility group box 2 (HMGB2), aka HMG2, ACCESSION NUMBER NM_002129.2; homeobox (H6 family) 1 (HMX1), aka H6, ACCESSION NUMBER NM_018942.1; H6 family homeobox 2 (HMX2), aka NRx5-2, H6L, ACCESSION NUMBER NM_005519.1; hepatocyte nuclear factor 4, alpha (HNF4A), transcript variant 3, aka TCF, NR2A21, HNF4, NR2A1, HNF4a9, HNF4a7, TCF14, FLJ39654, HNF4a8, MODY1, MODY, ACCESSION NUMBER NM_178850.1; hepatocyte nuclear factor 4, alpha (HNF4A), transcript variant 6, aka TCF, NR2A21, HNF4, NR2A1, HNF4a9, HNF4a7, TCF14, FLJ39654, HNF4a8, MODY1, MODY, ACCESSION NUMBER NM_001030004.1; hepatocyte nuclear factor 4, gamma (HNF4G), aka NR2A2, ACCESSION NUMBER NM_004133.3; homeobox and leucine zipper encoding (HOMEZ), aka HOMEZ, KIAA1443, ACCESSION NUMBER NM_020834.1; HOP homeobox (HOPX), transcript variant 1, aka HOP, MGC20820, LAGY, Cameo, SMAP31, OB1, Toto, NECC1, ACCESSION NUMBER NM_032495.4; HOP homeobox (HOPX), transcript variant 3, aka HOP, MGC20820, LAGY, Cameo, SMAP31, OB1, Toto, NECC1, ACCESSION NUMBER NM_139212.2; HOP homeobox (HOPX), transcript variant 2, aka HOP, MGC20820, LAGY, Cameo, SMAP31, OB1, Toto, NECC1, ACCESSION NUMBER NM_139211.2; homeobox A1 (HOXA1), transcript variant 2, aka BSAS, HOX1, HOX1F, MGC45232, ACCESSION NUMBER NM_153620.2; homeobox A1 (HOXA1), transcript variant 1, aka BSAS, HOX1, HOX1F, MGC45232, ACCESSION NUMBER NM_005522.4; homeobox A10 (HOXA10), transcript variant 2, aka MGC12859, PL, HOX1H, HOX1, HOX1.8, ACCESSION NUMBER NM_153715.2; homeobox A10 (HOXA10), transcript variant 1, aka MGC12859, PL, HOX1H, HOX1, HOX1.8, ACCESSION NUMBER NM_018951.3; homeobox A10 (HOXA10), transcript variant 1, aka MGC12859, PL, HOX1H, HOX1, HOX1.8, ACCESSION NUMBER NM_018951.3; homeobox A11 (HOXA11), aka HOX11, HOX1, ACCESSION NUMBER NM_005523.5; homeobox A13 (HOXA13), aka HOX1, HOX1J, ACCESSION NUMBER NM_000522.3; homeobox A2 (HOXA2), aka HOX1K, ACCESSION NUMBER NM_006735.3; homeobox A3 (HOXA3), transcript variant 1, aka MGC10155, HOX1E, HOX1, ACCESSION NUMBER NM_030661.4; homeobox A3 (HOXA3), transcript variant 2, aka MGC10155, HOX1E, HOX1, ACCESSION NUMBER NM_153631.2; homeobox A3 (HOXA3), transcript variant 3, aka MGC10155, HOX1E, HOX1, ACCESSION NUMBER NM_153632.2; homeobox A3 (HOXA3), transcript variant 3, aka MGC10155, HOX1E, HOX1, ACCESSION NUMBER NM_153632.2; homeobox A4 (HOXA4), aka HOX1D, HOX1, ACCESSION NUMBER NM_002141.4; homeobox A5 (HOXA5), aka MGC9376, HOX1C, HOX1.3, HOX1, ACCESSION NUMBER NM_019102.2; homeobox A6 (HOXA6), aka HOX1B, HOX1.2, HOX1, ACCESSION NUMBER NM_024014.2; homeobox A7 (HOXA7), aka ANTP, HOX1.1, HOX1A, HOX1, ACCESSION NUMBER NM_006896.3; homeobox A9 (HOXA9), aka MGC1934, HOX1.7, HOX1G, HOX1, ABD-B, ACCESSION NUMBER NM_152739.3; homeobox A9 (HOXA9), aka MGC1934, HOX1.7, HOX1G, HOX1, ABD-B, ACCESSION NUMBER NM_152739.3; homeobox B1 (HOXB1), aka HOX2, HOX2I, MGC116843, Hox-2.9, MGC116844, MGC116845, ACCESSION NUMBER NM_002144.3; homeobox B13 (HOXB13), aka PSGD, ACCESSION NUMBER NM_006361.5; homeobox B2 (HOXB2), aka HOX2H, K8, Hox-2.8, HOX2, ACCESSION NUMBER NM_002145.3; homeobox B3 (HOXB3), aka HOX2, HOX2G, Hox-2.7, ACCESSION NUMBER NM_002146.4; homeo box B4 (HOXB4), aka HOX2, HOX-2.6, HOX2F, ACCESSION NUMBER NM_024015.3; homeobox B5 (HOXB5), aka HU-1, HOX2, HHO.C10, HOX2A, Hox2.1, ACCESSION NUMBER NM_002147.3; homeobox B6 (HOXB6), aka Hox-2.2, HOX2B, HOX2, HU-2, ACCESSION NUMBER NM_018952.4; homeobox B6 (HOXB6), aka Hox-2.2, HOX2B, HOX2, HU-2, ACCESSION NUMBER NM_018952.4; homeobox B7 (HOXB7), aka HOX2C, HOX2, HHO.C1, Hox-2.3, ACCESSION NUMBER NM_004502.3; homeobox B8 (HOXB8), aka Hox-2.4, HOX2, HOX2D, ACCESSION NUMBER NM_024016.3; homeo box B9 (HOXB9), aka HOX2, HOX-2.5, HOX2E, ACCESSION NUMBER NM_024017.3; homeobox C10 (HOXC10), aka MGC5259, HOX3I, ACCESSION NUMBER NM_017409.3; homeobox C11 (HOXC11), aka MGC4906, HOX3H, ACCESSION NUMBER NM_014212.3; homeobox C12 (HOXC12), aka HOC3F, HOX3F, HOX3, ACCESSION NUMBER NM_173860.1; homeobox C13 (HOXC13), aka HOX3, HOX3G, ACCESSION NUMBER NM_017410.2; homeobox C4 (HOXC4), transcript variant 1, aka cp19, HOX3E, HOX3, ACCESSION NUMBER NM_014620.4; homeobox C4 (HOXC4), transcript variant 1, aka cp19, HOX3E, HOX3, ACCESSION NUMBER NM_014620.4; homeobox C5 (HOXC5), transcript variant 1, aka HOX3D, CP11, HOX3, ACCESSION NUMBER NM_018953.2; homeobox C6 (HOXC6), transcript variant 1, aka HOX3C, HOX3, CP25, HHO.C8, ACCESSION NUMBER NM_004503.3; homeobox C6 (HOXC6), transcript variant 1, aka HOX3C, HOX3, CP25, HHO.C8, ACCESSION NUMBER NM_004503.3; homeobox C6 (HOXC6), transcript variant 2, aka HOX3C, HOX3, CP25, HHO.C8, ACCESSION NUMBER NM_153693.3; homeobox C8 (HOXC8), aka HOX3, HOX3A, ACCESSION NUMBER NM_022658.3; homeobox C9 (HOXC9), aka HOX3, HOX3B, ACCESSION NUMBER NM_006897.1; homeobox D1 (HOXD1), aka HOX4G, HOX4, Hox-4.7, ACCESSION NUMBER NM_024501.1; homeobox D10 (HOXD10), aka Hox-4.4, HOX4, HOX4E, HOX4D, ACCESSION NUMBER NM_002148.3; homeobox D11 (HOXD11), aka HOX4F, HOX4, ACCESSION NUMBER NM_021192.2; homeobox D12 (HOXD12), aka HOX4H, ACCESSION NUMBER NM_021193.2; homeobox D13 (HOXD13), aka SPD, BDE, HOX4I, BDSD, ACCESSION NUMBER NM_000523.3; homeobox D3 (HOXD3), aka HOX4, MGC10470, Hox-4.1, HOX1D, HOX4A, ACCESSION NUMBER NM_006898.4; homeobox D4 (HOXD4), aka HOX4B, HHO.C13, HOX4, HOX-5.1, Hox-4.2, ACCESSION NUMBER NM_014621.2; homeobox D8 (HOXD8), aka HOX4, HOX4E, HOX5.4, ACCESSION NUMBER NM_019558.2; homeobox D9 (HOXD9), aka Hox-5.2, HOX4C, HOX4, Hox-4.3, ACCESSION NUMBER NM_014213.2; hairless homolog (mouse) (HR), transcript variant 1, aka AU, HSA277165, ALUNC, ACCESSION NUMBER NM_005144.3; hairless homolog (mouse) (HR), transcript variant 2, aka AU, HSA277165, ALUNC, ACCESSION NUMBER NM_018411.3; heat shock transcription factor 1 (HSF1), aka HSTF1, ACCESSION NUMBER NM_005526.2; heat shock transcription factor 2 (HSF2), aka MGC117376, MGC75048, MGC156196 ACCESSION NUMBER NM_004506.2; heat shock transcription factor 4 (HSF4), transcript variant 1, aka CTM, ACCESSION NUMBER NM_001538.2; heat shock transcription factor 4 (HSF4), transcript variant 2, aka CTM, ACCESSION NUMBER NM_001040667.1; heat shock transcription factor family member 5 (HSF5), aka FLJ40311, MGC134827, ACCESSION NUMBER NM_001080439.1; heat shock transcription factor family, X linked 1 (HSFX1), aka LW-1, ACCESSION NUMBER NM_016153.1; heat shock transcription factor, Y-linked 1 (HSFY1), transcript variant 3, aka HSF2L, HSFY, accession number NR_003510.1; heat shock transcription factor, Y-linked 1 (HSFY1), transcript variant 2, aka HSF2L, HSFY, ACCESSION NUMBER NM_152584.1; heat shock transcription factor, Y linked 2 (HSFY2), transcript variant 1, aka HSF2L, HSFY, FLJ25453, ACCESSION NUMBER NM_153716.1; heat shock transcription factor, Y linked 2 (HSFY2), transcript variant 1, aka HSF2L, HSFY, FLJ25453, ACCESSION NUMBER NM_153716.1; IKAROS family zinc finger 1 (Ikaros) (IKZF1), aka Hs.54452, IK1, PRO0758, hIk-1, IKAROS, LYF1, ZNFN1A1, ACCESSION NUMBER NM_006060.3; IKAROS family zinc finger 3 (Aiolos) (IKZF3), transcript variant 2, aka AIOLOS, ZNFN1A3, ACCESSION NUMBER NM_183228.1; IKAROS family zinc finger 3 (Aiolos) (IKZF3), transcript variant 1, aka AIOLOS, ZNFN1A3, ACCESSION NUMBER NM_012481.3; IKAROS family zinc finger 4 (Eos) (IKZF4), aka ZNFN1A4, KIAA1782, EOS, ACCESSION NUMBER NM_022465.3; insulin promoter factor 1, homeodomain transcription factor (IPF1), aka IDX-1, IUF1, STF-1, MODY4, PDX-1, PDX1, ACCESSION NUMBER NM_000209.1; interferon regulatory factor 1 (IRF1), aka IRF-1, MAR, ACCESSION NUMBER NM_002198.1; interferon regulatory factor 2 (IRF2), aka IRF-2, DKFZp686F0244, ACCESSION NUMBER NM_002199.2; interferon regulatory factor 3 (IRF3), ACCESSION NUMBER NM_001571.2; interferon regulatory factor 4 (IRF4), aka MUM1, LSIRF, ACCESSION NUMBER NM_002460.1; interferon regulatory factor 5 (IRF5), transcript variant 1, ACCESSION NUMBER NM_002200.3; interferon regulatory factor 6 (IRF6), aka VWS, LPS, PIT, OFC6, PPS, ACCESSION NUMBER NM_006147.2; interferon regulatory factor 7 (IRF7), transcript variant b, aka IRF7A, IRF-7H, ACCESSION NUMBER NM_004029.2; interferon regulatory factor 7 (IRF7), transcript variant b, aka IRF7A, IRF-7H, ACCESSION NUMBER NM_004029.2; interferon regulatory factor 7 (IRF7), transcript variant d, aka IRF7A, IRF-7H, ACCESSION NUMBER NM_004031.2; interferon regulatory factor 8 (IRF8), aka H-ICSBP, ICSBP, IRF-8, ICSBP1, ACCESSION NUMBER NM_002163.2; interferon regulatory factor 9 (IRF9), aka IRF9, p48, ISGF3, IRF-9, ACCES- SION NUMBER NM_006084.4; iroquois homeobox 1 (IRX1), aka IRX-5, ACCESSION NUMBER NM_024337.3; iroquois homeobox 2 (IRX2), ACCESSION NUMBER NM_033267.3; iroquois homeobox 3 (IRX3), aka IRX-1, ACCESSION NUMBER NM_024336.1; iroquois homeobox 4 (IRX4), aka MGC131996, ACCESSION NUMBER NM_016358.1; iroquois homeobox protein 5 (IRX5), aka IRX-2a, ACCESSION NUMBER NM_005853.4; iroquois homeobox 6 (IRX6), aka IRX-3, IRX7, ACCESSION NUMBER NM_024335.2; ISL L1M homeobox 2 (ISL2), aka FLJ10160, ACCESSION NUMBER NM_145805.1; intestine-specific homeobox (ISX), aka MGC138417, DKFZp781N2395, Pix-1, RAXLX, ACCESSION NUMBER NM_001008494.1; jumonji, AT rich interactive domain 1A (JARID1A), transcript variant 2, aka KDM5A, RBP2, RBBP2, ACCESSION NUMBER NM_005056.2; Jun dimerization protein 2 (JDP2), aka JUNDM2, ACCESSION NUMBER NM_130469.2; jun oncogene (JUN), aka AP1, c-Jun, ACCESSION NUMBER NM_002228.3; jun B proto-oncogene (JUNB), ACCESSION NUMBER NM_002229.2; jun D proto-oncogene (JUND), ACCESSION NUMBER NM_005354.3; potassium voltage-gated channel, subfamily H (eag-related), member 8 (KCNH8), aka elk3, ELK1, Kv12.1, ELK, ACCESSION NUMBER NM_144633.2; Kruppel-like factor 1 (erythroid) (KLF1), aka EKLF, ACCESSION NUMBER NM_006563.2; Kruppel-like factor 10 (KLF10), transcript variant 1, aka TIEG, EGRA, TIEG1, ACCESSION NUMBER NM_005655.1; Kruppel-like factor 10 (KLF10), transcript variant 1, aka TIEG, EGRA, TIEG1, ACCESSION NUMBER NM_005655.1; Kruppel-like factor 10 (KLF10), transcript variant 2, aka TIEG, EGRA, TIEG1, ACCESSION NUMBER NM_001032282.1; Kruppel-like factor 11 (KLF11), accession number XM_001129527.1; Kruppel-like factor 11 (KLF11), accession number XM_001129527.1; Kruppel-like factor 12 (KLF12), aka AP-2rep, AP2REP, HSPC122, ACCESSION NUMBER NM_007249.4; Kruppel-like factor 12 (KLF12), aka AP-2rep, AP2REP, HSPC122, ACCESSION NUMBER NM_007249.4; Kruppel-like factor 15 (KLF15), aka KKLF, ACCESSION NUMBER NM_014079.2; Kruppel-like factor 16 (KLF16), aka BTEB4, DRRF, NSLP2, ACCESSION NUMBER NM_031918.1; Kruppel-like factor 17 (KLF17), aka ZNF393, Zfp393, RP4-675G8.1, FLJ40160, ACCESSION NUMBER NM_173484.3; Kruppel-like factor 2 (lung) (KLF2), aka LKLF, ACCESSION NUMBER NM_016270.2; Kruppel-like factor 3 (basic) (KLF3), aka BKLF, MGC48279, ACCESSION NUMBER NM_016531.3; Kruppel-like factor 4 (gut) (KLF4), aka GKLF, EZF, ACCESSION NUMBER NM_004235.3; Kruppel-like factor 5 (intestinal) (KLF5), aka BTEB2, CKLF, IKLF, ACCESSION NUMBER NM_001730.3; Kruppel-like factor 6 (KLF6), transcript variant 2, aka GBF, ZF9, ST12, CPBP, BCD1, PAC1, DKFZp686N0199, COPEB, ACCESSION NUMBER NM_001300.4; Kruppel-like factor 6 (KLF6), transcript variant 1, aka GBF, ST12, ZF9, CPBP, BCD1, DKFZp686N0199, PAC1, COPEB, ACCESSION NUMBER NM_001008490.1; Kruppel-like factor 7 (ubiquitous) (KLF7), aka UKLF, ACCESSION NUMBER NM_003709.2; Kruppel-like factor 9 (KLF9), aka BTEB, BTEB1, ACCESSION NUMBER NM_001206.2; kinetochore associated 1 (KNTC1), aka FLJ36151, KIAA0166, ROD, ACCESSION NUMBER NM_014708.3; keratin associated protein 5-1 (KRTAP5-1), aka KRN1L, KRTAP5.1, ACCESSION NUMBER NM_001005922.1; l(3)mbt-like (Drosophila) (L3 MBTL), transcript variant I, aka L3 MBTL1, dJ138B7.3, FLJ41181, DKFZp586P1522, KIAA0681, H-L(3)MBT, ACCESSION NUMBER NM_015478.5; l(3)mbt-like (Drosophila) (L3 MBTL), transcript variant II, aka L3 MBTL1, dJ138B7.3, DKFZp586P1522, KIAA0681, H-L(3)MBT, ACCESSION NUMBER NM_032107.2; l(3)mbt-like (Drosophila) (L3 MBTL), transcript variant II, aka L3 MBTL1, dJ138B7.3, FLJ41181, DKFZp586P1522, KIAA0681, H-L(3)MBT, ACCESSION NUMBER NM_032107.3; l(3)mbt-like (Drosophila) (L3 MBTL), transcript variant II, aka L3 MBTL1, dJ138B7.3, FLJ41181, DKFZp586P1522, KIAA0681, H-L(3)MBT, ACCESSION NUMBER NM_032107.3; l(3)mbt-like 4 (Drosophila) (L3 MBTL4), aka HsT1031, ACCESSION NUMBER NM_173464.2; LAG1 homolog, ceramide synthase 2 (LASS2), transcript variant 1, aka SP260, CerS2, MGC987, TMSG1, L3, FLJ10243, ACCESSION NUMBER NM_181746.2; LAG1 homolog, ceramide synthase 2 (LASS2), transcript variant 2, aka SP260, CerS2, MGC987, TMSG1, L3, FLJ10243, ACCESSION NUMBER NM_022075.3; LAG1 homolog, ceramide synthase 3 (LASS3), aka MGC27091, CerS3, ACCESSION NUMBER NM_178842.3; LAG1 homolog, ceramide synthase 4 (LASS4), aka FLJ12089, Trh1, CerS4, ACCESSION NUMBER NM_024552.1; LAG1 homolog, ceramide synthase 5 (S. cerevisiae) (LASS5), aka Trh4, MGC45411, FLJ25304, ACCESSION NUMBER NM_147190.1; LAG1 homolog, ceramide synthase 6 (LASS6), aka CerS6, MGC129950, MGC129949, ACCESSION NUMBER NM_203463.1; ladybird homeobox 1 (LBX1), aka LBX1H, HPX6, HPX-6, ACCESSION NUMBER NM_006562.4; ladybird homeobox 2 (LBX2), aka LP3727, ACCESSION NUMBER NM_001009812.1; ligand dependent nuclear receptor corepressor (LCOR), aka FLJ38026, MLR2, KIAA1795, RP11-175019.1, ACCESSION NUMBER NM_032440.1; lymphoid enhancer-binding factor 1 (LEF1), aka TCF1ALPHA, DKFZp586H0919, ACCESSION NUMBER NM_016269.2; LIM homeobox 1 (LHX1), aka LIM-1, LIM1, MGC138141, MGC126723, ACCESSION NUMBER NM_005568.2; LIM homeobox 2 (LHX2), aka LH2, hLhx2, MGC138390, ACCESSION NUMBER NM_004789.3; LIM homeobox 3 (LHX3), transcript variant 1, aka M2-LHX3, DKFZp762A2013, ACCESSION NUMBER NM_178138.2; LIM homeobox 3 (LHX3), transcript variant 2, aka M2-LHX3, DKFZp762A2013, ACCESSION NUMBER NM_014564.2; LIM homeobox 3 (LHX3), transcript variant 2, aka M2-LHX3, DKFZp762A2013, ACCESSION NUMBER NM_014564.2; LIM homeobox 3 (LHX3), transcript variant 2, aka M2-LHX3, DKFZp762A2013, ACCESSION NUMBER NM_014564.2; LIM homeobox 3 (LHX3), transcript variant 1, aka M2-LHX3, DKFZp762A2013, ACCESSION NUMBER NM_178138.3; LIM homeobox 4 (LHX4), aka Gsh4, Gsh-4, ACCESSION NUMBER NM_033343.2; LIM homeobox 5 (LHX5), aka MGC129689, ACCESSION NUMBER NM_022363.2; LIM homeobox 6 (LHX6), transcript variant 1, aka MGC119545, MGC119542, MGC119544, LHX6.1, ACCESSION NUMBER NM_014368.3; LIM homeobox 6 (LHX6), transcript variant 2, aka MGC119545, MGC119542, MGC119544, LHX6.1, ACCESSION NUMBER NM_199160.2; LIM homeobox 8 (LHX8), aka Lhx7, ACCESSION NUMBER NM_001001933.1; LIM homeobox 9 (LHX9), transcript variant 1, ACCESSION NUMBER NM_020204.2; LIM homeobox 9 (LHX9), transcript variant 2, ACCESSION NUMBER NM_001014434.1; LIM domain only 1 (rhombotin 1) (LMO1), aka RBTN1, MGC116692, TTG1, RHOM1, ACCESSION NUMBER NM_002315.1; LIM domain only 4 (LMO4), ACCESSION NUMBER NM_006769.2; LIM homeobox transcription factor 1, alpha (LMX1A), transcript variant 2, aka MGC87616, LMX-1, LMX1.1, LMX1, ACCESSION NUMBER NM_177399.2; LIM homeobox transcription factor 1, alpha (LMX1A), transcript variant 3, aka MGC87616, LMX-1, LMX1.1, LMX1, ACCESSION NUMBER NM_001033507.1; LIM homeobox transcription factor 1, alpha (LMX1A), transcript variant 1, aka MGC87616, LMX-1, LMX1.1, LMX1, ACCESSION NUMBER NM_177398.2; LIM homeobox transcription factor 1, alpha (LMX1A), transcript variant 1, aka MGC87616, LMX-1, LMX1.1, LMX1, ACCESSION NUMBER NM_177398.2; LIM homeobox transcription factor 1, beta (LMX1B), aka LMX1.2, MGC142051, NPS1, MGC138325, ACCESSION NUMBER NM_002316.1; leucine-zipper-like transcription regulator 1 (LZTR1), aka MGC21205, TCFL2, LZTR-1, ACCESSION NUMBER NM_006767.3; leucine zipper, putative tumor suppressor 1 (LZTS1), aka FEZ1, F37, ACCESSION NUMBER NM_021020.1; v-maf musculoaponeurotic fibrosarcoma oncogene homolog (avian) (MAF), transcript variant 2, aka MGC71685, ACCESSION NUMBER NM_001031804.1; v-maf musculoaponeurotic fibrosarcoma oncogene homolog (avian) (MAF), transcript variant 1, aka MGC71685, ACCESSION NUMBER NM_005360.3; v-maf musculoaponeurotic fibrosarcoma oncogene homolog A (avian) (MAFA), aka RIPE3b1, hMafA, ACCESSION NUMBER NM_201589.2; v-maf musculoaponeurotic fibrosarcoma oncogene homolog B (avian) (MAFB), aka KRML, MGC43127, ACCESSION NUMBER NM_005461.3; v-maf musculoaponeurotic fibrosarcoma oncogene homolog F (avian) (MAFF), transcript variant 1, aka U-MAF, ACCESSION NUMBER NM_012323.2; v-maf musculoaponeurotic fibrosarcoma oncogene homolog F (avian) (MAFF), transcript variant 1, aka U-MAF, ACCESSION NUMBER NM_012323.2; v-maf musculoaponeurotic fibrosarcoma oncogene homolog F (avian) (MAFF), transcript variant 2, aka U-MAF, ACCESSION NUMBER NM_152878.1; v-maf musculoaponeurotic fibrosarcoma oncogene homolog G (avian) (MAFG), transcript variant 1, aka MGC20149, MGC13090, ACCESSION NUMBER NM_002359.2; v-maf musculoaponeurotic fibrosarcoma oncogene homolog G (avian) (MAFG), transcript variant 2, aka MGC20149, MGC13090, ACCESSION NUMBER NM_032711.2; v-maf musculoaponeurotic fibrosarcoma oncogene homolog K (avian) (MAFK), aka FLJ32205, MGC71717, NFE2U, P18, ACCESSION NUMBER NM_002360.3; mastermind-like 3 (*Drosophila*) (MAML3), aka GDN, MAM-2, MAM2, TNRC3, ERDA3, CAGH3, ACCESSION NUMBER NM_018717.3; MYC associated factor X (MAX), transcript variant 2, aka MGC34679, MGC36767, MGC11225, MGC10775, orf1, MGC18164, ACCESSION NUMBER NM_145112.1; MYC associated factor X (MAX), transcript variant 3, aka MGC34679, MGC36767, MGC11225, MGC10775, orf1, MGC18164, ACCESSION NUMBER NM_145113.1; MYC associated factor X (MAX), transcript variant 4, aka MGC34679, MGC36767, MGC11225, MGC10775, orf1, MGC18164, ACCESSION NUMBER NM_145114.1; MYC associated factor X (MAX), transcript variant 5, aka MGC34679, MGC36767, MGC11225, MGC10775, orf1, MGC18164, ACCESSION NUMBER NM_145116.1; MYC associated factor X (MAX), transcript variant 1, aka MGC34679, MGC36767, MGC11225, MGC10775, orf1, MGC18164, ACCESSION NUMBER NM_002382.3; methyl-CpG binding domain protein 1 (MBD1), transcript variant 3, aka PCM1, RFT, CXXC3, ACCESSION NUMBER NM_015844.1; methyl-CpG binding domain protein 1 (MBD1), transcript variant 2, aka PCM1, RFL CXXC3, ACCESSION NUMBER NM_015845.2; myelodysplasia syndrome 1 (MDS1), aka PRDM3, MDS1-EVI1, ACCESSION NUMBER NM_004991.1; myocyte enhancer factor 2A (MEF2A), aka ADCAD1, RSRFC9, RSRFC4, ACCESSION NUMBER NM_005587.1; myocyte enhancer factor 2B (MEF2B), aka FLJ46391, RSRFR2, FLJ32599, ACCESSION NUMBER NM_005919.1; myocyte enhancer factor 2C (MEF2C), ACCESSION NUMBER NM_002397.2; myocyte enhancer factor 2D (MEF2D), aka DKFZp686I1536, ACCESSION NUMBER NM_005920.2; Meis homeobox 2 (MEIS2), transcript variant a, aka MGC2820, MRG1, HsT18361, ACCESSION NUMBER NM_170677.2; Meis homeobox 2 (MEIS2), transcript variant h, aka MGC2820, MRG1, HsT18361, ACCESSION NUMBER NM_172316.1; Meis homeobox 2 (MEIS2), transcript variant g, aka MGC2820, MRG1, HsT18361, ACCESSION NUMBER NM_172315.1; Meis homeobox 2 (MEIS2), transcript variant f, aka MGC2820, MRG1, HsT18361, ACCESSION NUMBER NM_002399.2; Meis homeobox 3 (MEIS3), transcript variant 2, aka DKFZp547H236, MRG2, ACCESSION NUMBER NM_001009813.1; Meis homeobox 3 pseudogene 1 (MEIS3P1), MEIS3, MRG2, MEIS4, accession number NR_002211.1; mesenchyme homeobox 1 (MEOX1), transcript variant 3, aka MOX1, ACCESSION NUMBER NM_001040002.1; mesenchyme homeobox 1 (MEOX1), transcript variant 3, aka MOX1, ACCESSION NUMBER NM_001040002.1; mesenchyme homeobox 1 (MEOX1), transcript variant 3, aka MOX1, ACCESSION NUMBER NM_001040002.1; mesenchyme homeobox 2 (MEOX2), aka MOX2, GAX, ACCESSION NUMBER NM_005924.4; mesoderm posterior 1 homolog (mouse) (MESP1), aka MGC10676, ACCESSION NUMBER NM_018670.2; MAX gene associated (MGA), aka MAD5, MXD5, FLJ12634, KIAA0518, ACCESSION NUMBER NM_001080541.1; microphthalmia-associated transcription factor (MITF), transcript variant 3, aka WS2A, ACCESSION NUMBER NM_006722.1; microphthalmia-associated transcription factor (MITF), transcript variant 1, aka WS2A, ACCESSION NUMBER NM_198159.1; microphthalmia-associated transcription factor (MITF), transcript variant 5, aka WS2A, ACCESSION NUMBER NM_198158.1; Mix1 homeobox-like 1 (*Xenopus laevis*) (MIXL1), aka MIXL, MIX, MGC138179, MILD1, ACCESSION NUMBER NM_031944.1; mohawk homeobox (MKX), aka MGC39616, IFRX, IRXL1, C10orf48, ACCESSION NUMBER NM_173576.1; myeloid/lymphoid or mixed-lineage leukemia (trithorax homolog, *Drosophila*) (MLL), aka TRX1, HRX, KMT2A, MLL/GAS7, ALL-1, CXXC7, MLL1A, HTRX1, FLJ11783, ACCESSION NUMBER NM_005933.2; myeloid/lymphoid or mixed-lineage leukemia 4 (MLL4), aka MLL2, HRX2, KIAA0304, WBP7, TRX2, ACCESSION NUMBER NM_014727.1; myeloid/lymphoid or mixed-lineage leukemia (trithorax homolog, *Drosophila*), translocated to, 10 (MLLT10), transcript variant 1, aka AF10, DKFZp686E10210, MGC75086, ACCESSION NUMBER NM_004641.2; myeloid/lymphoid or mixed-lineage leukemia (trithorax homolog, *Drosophila*), translocated to, 10 (MLLT10), transcript variant 1, aka AF10, DKFZp686E10210, MGC75086, ACCESSION NUMBER NM_004641.2; MAX-like protein X (MLX), transcript variant 1, aka MXD7, MAD7, TCFL4, ACCESSION NUMBER NM_198205.1; MAX-like protein X (MLX), transcript variant 2, aka TCFL4, MXD7, MAD7, ACCESSION NUMBER NM_198204.1; MAX binding protein (MNT), aka MXD6, ROX, MAD6, ACCESSION NUMBER NM_020310.2; mortality factor 4 (MORF4), aka CSR, SEN1, SEN, CSRB, ACCESSION NUMBER NM_006792.2; musculin (activated B-cell factor-1) (MSC), aka ABF-1, ABF1, MYOR, ACCESSION NUMBER NM_005098.3; male-specific lethal 3-like 1 (*Drosophila*) (MSL3L1), transcript variant 4, aka DKFZP586J1822, ACCESSION NUMBER NM_078628.1; male-specific lethal 3-like 1 (*Drosophila*) (MSL3L1), transcript variant 3, aka DKFZP586J1822, ACCESSION NUMBER NM_006800.2; male-specific lethal 3-like 1 (*Drosophila*) (MSL3L1), transcript variant 1, aka DKFZP586J1822, ACCESSION NUMBER NM_078629.1; male-specific lethal 3-like 1 (*Drosophila*) (MSL3L1), transcript variant 2, aka DKFZP586J1822, ACCESSION NUMBER NM_078630.1; methionine sulfoxide reductase B2 (MSRB2), aka PILB, CBS-1, MSRB, CGI-131, CBS1, MGC26104, ACCESSION NUMBER NM_012228.2; msh homeobox 1 (MSX1), aka HOX7, HYD1, ACCESSION NUMBER NM_002448.3; msh homeobox 2 (MSX2), aka FPP, PFM1, CRS2, MSH, PFM, HOX8, ACCESSION NUMBER NM_002449.4; metastasis associated 1 (MTA1), ACCESSION NUMBER NM_004689.3; metastasis associated 1 family, member 2 (MTA2), aka MTA1L1, PID, DKFZp686F2281, ACCESSION NUMBER NM_004739.2; metastasis associated 1 family, member 3 (MTA3), aka KIAA1266, ACCESSION NUMBER NM_020744.2; metal-regulatory transcription factor 1 (MTF1), aka MTF-1, MGC23036, ZRF, ACCESSION NUMBER NM_005955.2; MAX dimerization protein 1 (MXD1), aka MGC104659, MAD, MAD1, ACCESSION NUMBER NM_002357.2; v-myb myeloblastosis viral oncogene homolog (avian)-like 2 (MYBL2), aka B-MYB, MGC15600, BMYB, ACCESSION NUMBER NM_002466.2; v-myc myelocytomatosis viral oncogene homolog (avian) (MYC), aka c-Myc, ACCESSION NUMBER NM_002467.3; v-myc myelocytomatosis viral oncogene homolog 1, lung carcinoma derived (avian) (MYCL1), transcript variant 3, aka MYCL, LMYC, ACCESSION NUMBER NM_005376.3; v-myc myelocytomatosis viral oncogene homolog 1, lung carcinoma derived (avian) (MYCL1), transcript variant 1, aka MYCL, LMYC, ACCESSION NUMBER NM_001033081.1; v-myc myelocytomatosis viral oncogene homolog 1, lung carcinoma derived (avian) (MYCL1), transcript variant 2, aka MYCL, LMYC, ACCESSION NUMBER NM_001033082.1; v-myc myelocytomatosis viral related oncogene, neuroblastoma derived (avian) (MYCN), aka ODED, NMYC, MODED, N-myc, ACCESSION NUMBER NM_005378.4; myogenic factor 5 (MYF5), ACCESSION NUMBER NM_005593.1; myogenic factor 6 (herculin) (MYF6), aka HERCULIN, MRF4, ACCESSION NUMBER NM_002469.1; myoneurin (MYNN), aka ZBTB31, SBBIZ1, OSZF, ACCESSION NUMBER NM_018657.3; myogenic differentiation 1 (MYOD1), aka MYOD, PUM, MYF3, ACCESSION NUMBER NM_002478.4; myogenin (myogenic factor 4) (MYOG), aka MYF4, MYOGENIN, ACCESSION NUMBER NM_002479.4; MYST histone acetyltransferase 2 (MYST2), aka KAT7, HBOA, HBO1, ACCESSION NUMBER NM_007067.3; myelin transcription factor 1 (MYT1), aka MYTI, MTF1, C20orf36, PLPB1, ACCESSION NUMBER NM_004535.2; myelin transcription factor 1-like (MYT1L), aka NZF1, ACCESSION NUMBER NM_015025.2; myeloid zinc finger 1 (MZF1), transcript variant 2, aka MZF1B, ZSCAN6, ZNF42, MZF-1, Zfp98, ACCESSION NUMBER NM_198055.1; myeloid zinc finger 1 (MZF1), transcript variant 2, aka MZF1B, ZSCAN6, ZNF42, MZF-1, Zfp98, ACCESSION NUMBER NM_198055.1; Nanog homeobox (NANOG), ACCESSION NUMBER NM_024865.1; neurogenic differentiation 2 (NEUROD2), aka NDRF, ACCESSION NUMBER NM_006160.2; neurogenin 1 (NEUROG1), aka Math4C, ngn1, NEUROD3, AKA, ACCESSION NUMBER NM_006161.2; nuclear factor of activated T-cells 5, tonicity-responsive (NFAT5), transcript variant 2, aka NFATL1, OREBP, TONEBP, NF-AT5, KIAA0827, NFATZ, ACCESSION NUMBER NM_138713.2; nuclear factor of activated T-cells 5, tonicity-responsive (NFAT5), transcript variant 5, aka NFATL1, OREBP, TONEBP, NF-AT5, KIAA0827, NFATZ, ACCESSION NUMBER NM_173215.1; nuclear factor of activated T-cells 5, tonicity-responsive (NFAT5), transcript variant 5, aka NFATL1, OREBP, TONEBP, NF-AT5, KIAA0827, NFATZ, ACCESSION NUMBER NM_173215.1; nuclear factor of activated T-cells, cytoplasmic, calcineurin-dependent 1 (NFATC1), transcript variant 3, aka NFATc, MGC138448, NFAT2, NF-ATC, ACCESSION NUMBER NM_172387.1; nuclear factor of activated T-cells, cytoplasmic, calcineurin-dependent 1 (NFATC1), transcript variant 1, aka NFATc, MGC138448, NFAT2, NF-ATC, ACCESSION NUMBER NM_172390.1; nuclear factor of activated T-cells, cytoplasmic, calcineurin-dependent 1 (NFATC1), transcript variant 2, aka NFATc, MGC138448, NFAT2, NF-ATC, ACCESSION NUMBER NM_006162.3; nuclear factor of activated T-cells, cytoplasmic, calcineurin-dependent 1 (NFATC1), transcript variant 4, aka NFATc, MGC138448, NFAT2, NF-ATC, ACCESSION NUMBER NM_172388.1; nuclear factor of activated T-cells, cytoplasmic, calcineurin-dependent 2 (NFATC2), transcript variant 1, aka KIAA0611, NFATP, NFAT1, ACCESSION NUMBER NM_012340.3; nuclear factor of activated T-cells, cytoplasmic, calcineurin-dependent 2 (NFATC2), transcript variant 1, aka KIAA0611, NFATP, NFAT1, ACCESSION NUMBER NM_012340.3; nuclear factor of activated T-cells, cytoplasmic, calcineurin-dependent 3 (NFATC3), transcript variant 1, aka NFAT4, NFATX, ACCESSION NUMBER NM_173165.1; nuclear factor of activated T-cells, cytoplasmic, calcineurin-dependent 3 (NFATC3), transcript variant 2, aka NFAT4, NFATX, ACCESSION NUMBER NM_004555.2; nuclear factor of activated T-cells, cytoplasmic, calcineurin-dependent 3 (NFATC3), transcript variant 2, aka NFAT4, NFATX, ACCESSION NUMBER NM_004555.2; nuclear factor of activated T-cells, cytoplasmic, calcineurin-dependent 3 (NFATC3), transcript variant 4, aka NFAT4, NFATX, ACCESSION NUMBER NM_173164.1; nuclear factor of activated T-cells, cytoplasmic, calcineurin-dependent 3 (NFATC3), transcript variant 3, aka NFAT4, NFATX, ACCESSION NUMBER NM_173163.1; nuclear factor of activated T-cells, cytoplasmic, calcineurin-dependent 4 (NFATC4), aka NFAT3, NF-ATc4, ACCESSION NUMBER NM_004554.3; nuclear factor (erythroid-derived 2), 45 kDa (NFE2), aka p45, NF-E2, ACCESSION NUMBER NM_006163.1; nuclear factor (erythroid-derived 2)-like 1 (NFE2L1), aka FLJ00380, TCF11, NRF1, LCR-F1, ACCESSION NUMBER NM_003204.1; nuclear factor (erythroid-derived 2)-like 2 (NFE2L2), aka NRF2, ACCESSION NUMBER NM_006164.2; nuclear factor (erythroid-derived 2)-like 3 (NFE2L3), aka NRF3, ACCESSION NUMBER NM_004289.5; nuclear factor I/A (NFIA), aka KIAA1439, NFI-L, DKFZp434L0422, ACCESSION NUMBER NM_005595.1; nuclear factor I/B (NFIB), aka NFIB2, NFIB3, HMGIC/NFIB, NH-RED, ACCESSION NUMBER NM_005596.2; nuclear factor I/C (CCAAT-binding transcription factor) (NFIC), transcript variant 2, aka CTF5, CTF, NF-I, NFI, MGC20153, ACCESSION NUMBER NM_205843.1; nuclear factor I/C (CCAAT-binding transcription factor) (NFIC), transcript variant 1, aka CTF5, CTF, NF-I, NFI, MGC20153, ACCESSION NUMBER NM_005597.2; nuclear factor I/C (CCAAT-binding transcription factor) (NFIC), transcript variant 1, aka CTF5, CTF, NF-I, NFI, MGC20153, ACCESSION NUMBER NM_005597.2; nuclear factor, interleukin 3 regulated (NFIL3), aka IL3BP1, NF-IL3A, E4BP4, NFIL3A, ACCESSION NUMBER NM_005384.2; nuclear factor I/X (CCAAT-binding transcription factor) (NFIX), aka NF1A, ACCESSION NUMBER NM_002501.2; nuclear factor of kappa light polypeptide gene enhancer in B-cells 1 (p105) (NFKB1), aka NF-kappa-B, NFKB-p105, EBP-1, KBF1, DKFZp686C01211, MGC54151, NFKB-p50, ACCESSION NUMBER NM_003998.2; nuclear factor of kappa light polypeptide gene enhancer in B-cells 2 (p49/p100) (NFKB2), transcript variant 1, aka LYT10, LYT-10, ACCESSION NUMBER NM_001077494.1; nuclear factor of kappa light polypeptide gene enhancer in B-cells 2 (p49/p100) (NFKB2), transcript variant 3, aka LYT10, LYT-10, ACCESSION NUMBER NM_001077493.1; nuclear factor of kappa light polypeptide gene enhancer in B-cells 2 (p49/p100) (NFKB2), transcript variant 2, aka LYT10, LYT-10, ACCESSION NUMBER NM_002502.3; nuclear transcription factor, X-box binding 1 (NFX1), transcript variant 3, aka MGC20369, NFX2, DKFZp779G2416, ACCESSION NUMBER NM_147134.1; nuclear transcription factor, X-box binding 1 (NFX1), transcript variant 2, aka MGC20369, NFX2, DKFZp779G2416, ACCESSION NUMBER NM_147133.1; nuclear transcription factor, X-box binding 1 (NFX1), transcript variant 2, aka MGC20369, NFX2, DKFZp779G2416, ACCESSION NUMBER NM_147133.1; nuclear transcription factor, X-box binding 1 (NFX1), transcript variant 1, aka MGC20369, NFX2, DKFZp779G2416, ACCESSION NUMBER NM_002504.3; nuclear transcription factor, X-box binding-like 1 (NFXL1), aka HOZFP, FLJ16294, ACCESSION NUMBER NM_152995.4; nuclear transcription factor Y, alpha (NFYA), transcript variant 1, aka CBF-B, HAP2, NF-YA, CBF-A, ACCESSION NUMBER NM_002505.3; nuclear transcription factor Y, alpha (NFYA), transcript variant 1, aka CBF-B, HAP2, NF-YA, CBF-A, ACCESSION NUMBER NM_002505.3; nuclear transcription factor Y, beta (NFYB), aka HAP3, NF-YB, CBF-B, CBF-A, ACCESSION NUMBER NM_006166.3; nuclear transcription factor Y, gamma (NFYC), aka HAP5, NF-YC, hCBF-C, DKFZp667G242, H1TF2A, CBFC, CBF-C, HSM, FLJ45775, ACCESSION NUMBER NM_014223.2; NK2 homeobox 1 (NKX2-1), transcript variant 2, aka BCH, TEBP, TITF1, TTF1, NKX2.1, NK-2, TTF-1, BHC, NKX2A, ACCESSION NUMBER NM_003317.3; NK2 homeobox 1 (NKX2-1), transcript variant 2, aka BCH, TEBP, TITF1, TTF1, NKX2.1, NK-2, TTF-1, BHC, NKX2A, ACCESSION NUMBER NM_003317.3; NK2 homeobox 2 (NKX2-2), aka NKX2B, NKX2.2, ACCESSION NUMBER NM_002509.2; NK2 transcription factor related, locus 3 (*Drosophila*) (NKX2-3), aka CSX3, NKX2.3, NKX2C, NKX4-3, ACCESSION NUMBER NM_145285.2; NK2 transcription factor related, locus 5 (*Drosophila*) (NKX2-5), aka NKX2E, NKX2.5, NKX4-1, CSX, CSX1, ACCESSION NUMBER NM_004387.2; NK2 homeobox 8 (NKX2-8), aka NKX2H, NKX2.8, NRx2-9, ACCESSION NUMBER NM_014360.2; NK3 homeobox 1 (NKX3-1), aka NKX3A, BAPX2, NKX3, NKX3.1, ACCESSION NUMBER NM_006167.2; NK6 transcription factor related, locus 1 (*Drosophila*) (NKX6-1), aka NKX6A, NKX6.1, ACCESSION NUMBER NM_006168.1; NK6 homeobox 2 (NKX6-2), aka MGC126684, GTX, NKX6.2, NKX6B, ACCESSION NUMBER NM_177400.2; non-metastatic cells 2, protein (NM23B) expressed in (NME2), transcript variant 1, aka MGC111212, NM23-H2, NM23B, puf, NDPKB, NDPK-B, ACCESSION NUMBER NM_002512.2, non-metastatic cells 2, protein (NM23B) expressed in (NME2), transcript variant 3, aka MGC111212, NM23-H2, NM23B, puf, NDPKB, NDPK-B, ACCESSION NUMBER NM_001018138.1; non-metastatic cells 2, protein (NM23B) expressed in (NME2), transcript variant 4, aka MGC111212, NM23-H2, NM23B, puf, NDPKB, NDPK-B, ACCESSION NUMBER NM_001018139.1; non-metastatic cells 2, protein (NM23B) expressed in (NME2), transcript variant 2, aka MGC111212, NM23-H2, NM23B, puf, NDPKB, NDPK-B, ACCESSION NUMBER NM_001018137.1; NOBOX oogenesis homeobox (NOBOX), accession number XM_001134424.1; NOBOX oogenesis homeobox (NOBOX), aka OG2, OG-2, POF5, TCAG_12042, Og2x, ACCESSION NUMBER NM_001080413.1; neuronal PAS domain protein 1 (NPAS1), aka PASD5, MOP5, ACCESSION NUMBER NM_002517.2; neuronal PAS domain protein 2 (NPAS2), aka MGC71151, PASD4, MOP4, FLJ23138, ACCESSION NUMBER NM_002518.3; nuclear protein, ataxia-telangiectasia locus (NPAT), aka E14, ACCESSION NUMBER NM_002519.1; nuclear receptor subfamily 0, group B, member 1 (NR0B1), aka AHC, NROB1, AHX, DSS, AHCH, GTD, DAX-1, DAX1, HHG, ACCESSION NUMBER NM_000475.3; nuclear receptor subfamily 0, group B, member 2 (NR0B2), aka SHP, SHP1, ACCESSION NUMBER NM_021969.1; nuclear receptor subfamily 1, group D, member 1 (NR1D1), aka THRA1, hRev, ear-1, THRAL, EAR1, ACCESSION NUMBER NMO21724.2; nuclear receptor subfamily 1, group D, member 2 (NR1D2), accession number XM_001130839.1; nuclear receptor subfamily 1, group H, member 2 (NR1H2), aka NER, LXR-b, UNR, RIP15, NER-I, LXRB, ACCESSION NUMBER NM_007121.2; nuclear receptor subfamily 1, group H, member 3 (NR1H3), aka LXR-a, LXRA, RLD-1, ACCESSION NUMBER NM_005693.1; nuclear receptor subfamily 1, group H, member 4 (NR1H4), aka HRR1, MGC163445, FXR, HRR-1, RIP14, BAR, ACCESSION NUMBER NM_005123.1; nuclear receptor subfamily 1, group I, member 2 (NR1I2), transcript variant 3, aka PAR, PRR, SAR, PAR1, ONR1, BXR, SXR, PXR, PAR2, PARq, ACCESSION NUMBER NM_033013.1; nuclear receptor subfamily 1, group I, member 2 (NR1I2), transcript variant 2, aka PAR, PRR, SAR, PAR1, ONR1, BXR, SXR, PXR, PAR2, PARq, ACCESSION NUMBER NM_022002.1; nuclear receptor subfamily 1, group I, member 3 (NR1I3), transcript variant 6, aka MB67, CAR1, CAR, MGC97209, MGC150433, MGC97144, ACCESSION NUMBER NM_001077469.1; nuclear receptor subfamily 1, group I, member 3 (NR1I3), transcript variant 15, aka MB67, CAR1, CAR, MGC97209, MGC150433, MGC97144, ACCESSION NUMBER NM_001077475.1; nuclear receptor subfamily 2, group C, member 1 (NR2C1), transcript variant 2, aka TR2-11, TR2, ACCESSION NUMBER NM_001032287.1; nuclear receptor subfamily 2, group C, member 1 (NR2C1), transcript variant 2, aka TR2-11, TR2, ACCESSION NUMBER NM_001032287.1; nuclear receptor subfamily 2, group C, member 1 (NR2C1), transcript variant 1, aka TR2-11, TR2, ACCESSION NUMBER NM_003297.1; nuclear receptor subfamily 2, group C, member 2 (NR2C2), aka TAK1, hTAK1, TR4, TR2R1, ACCESSION NUMBER NM_003298.3; nuclear receptor subfamily 2, group E, member 1 (NR2E1), aka TLX, TLL, XTLL, ACCESSION NUMBER NM_003269.2; nuclear receptor subfamily 2, group E, member 3 (NR2E3), transcript variant 2, aka rd7, ESCS, PNR, RNR, MGC49976, ACCESSION NUMBER NM_014249.2; nuclear receptor subfamily 2, group E, member 3 (NR2E3), transcript variant 2, aka rd7, ESCS, PNR, RNR, MGC49976, ACCESSION NUMBER NM_014249.2; nuclear receptor subfamily 2, group E, member 3 (NR2E3), transcript variant 1, aka rd7, ESCS, PNR, RNR, MGC49976, ACCESSION NUMBER NM_016346.2; nuclear receptor subfamily 2, group F, member 1 (NR2F1), aka ERBAL3, COUP-TFI, TFCOUP1, EAR3, TCFCOUP1, EAR-3, NR2F2, SVP44, ACCESSION NUMBER NM_005654.4; nuclear receptor subfamily 2, group F, member 2 (NR2F2), aka COUP-TFII, TFCOUP2, MGC117452, COUPTFB, SVP40, ARP1, ACCESSION NUMBER NM_021005.2; nuclear receptor subfamily 2, group F, member 6 (NR2F6), aka EAR-2, EAR2, ERBAL2, ACCESSION NUMBER NM_005234.3; nuclear receptor subfamily 3, group C, member 1 (glucocorticoid receptor) (NR3C1), transcript variant 4, aka GCCR, GRL, GCR, GR, ACCESSION NUMBER NM_001018076.1; nuclear receptor subfamily 3, group C, member 1 (glucocorticoid receptor) (NR3C1), transcript variant 1, aka GCCR, GRL, GCR, GR, ACCESSION NUMBER NM_001018077.1; nuclear receptor subfamily 3, group C, member 1 (glucocorticoid receptor) (NR3C1), transcript variant 6, aka GCCR, GRL, GCR, GR, ACCESSION NUMBER NM_001020825.1; nuclear receptor subfamily 3, group C, member 2 (NR3C2), aka MGC133092, MR, MLR, MCR, ACCESSION NUMBER NM_000901.1; nuclear receptor subfamily 4, group A, member 1 (NR4A1), transcript variant 2, aka N10, NUR77, NP10, NAK-1, MGC9485, GFRP1, NGFIB, HMR, TR3, ACCESSION NUMBER NM_173157.1; nuclear receptor subfamily 4, group A, member 1 (NR4A1), transcript variant 3, aka N10, NUR77, NP10, NAK-1, MGC9485, GFRP1, NGFIB, HMR, TR3, ACCESSION NUMBER NM_173158.1; nuclear receptor subfamily 4, group A, member 1 (NR4A1), transcript variant 1, aka N10, NUR77, NP10, NAK-1, MGC9485, GFRP1, NGFIB, HMR, TR3, ACCESSION NUMBER NM_002135.3; nuclear receptor subfamily 4, group A, member 2 (NR4A2), transcript variant 1, aka RNR1, NOT, TINUR, NURR1, HZF-3, ACCESSION NUMBER NM_006186.2; nuclear receptor subfamily 4, group A, member 3 (NR4A3), transcript variant 4, aka CHN, CSMF, TEC, NOR1, MINOR, ACCESSION NUMBER NM_173199.1; nuclear receptor subfamily 4, group A, member 3 (NR4A3), transcript variant 3, aka CHN, CSMF, TEC, NOR1, MINOR, ACCESSION NUMBER NM_173200.1; nuclear receptor subfamily 4, group A, member 3 (NR4A3), transcript variant 1, aka CHN, CSMF, TEC, NOR1, MINOR, ACCESSION NUMBER NM_006981.2; nuclear receptor subfamily 4, group A, member 3 (NR4A3), transcript variant 2, aka CHN, CSMF, TEC, NOR1, MINOR, ACCESSION NUMBER NM_173198.1; nuclear receptor subfamily 4, group A, member 3 (NR4A3), transcript variant 2, aka CHN, CSMF, TEC, NOR1, MINOR, ACCESSION NUMBER NM_173198.1; nuclear receptor subfamily 5, group A, member 1 (NR5A1), aka SF1, PTZ1, ELP, AD4BP, SF-1, ACCESSION NUMBER NM_004959.3; nuclear receptor subfamily 5, group A, member 2 (NR5A2), transcript variant 1, aka FTF, B1F2, F1Z-F1beta, hB1F, hB1F-2, LRH-1, B1F, CPF, ACCESSION NUMBER NM_205860.1; nuclear receptor subfamily 5, group A, member 2 (NR5A2), transcript variant 2, aka FTF, B1F2, F1Z-F1beta, hB1F, hB1F-2, LRH-1, B1F, CPF, ACCESSION NUMBER NM_003822.3; nuclear receptor subfamily 5, group A, member 2 (NR5A2), transcript variant 2, aka FTF, B1F2, F1Z-F1beta, hB1F, hB1F-2, LRH-1, B1F, CPF, ACCESSION NUMBER NM_003822.3; nuclear receptor subfamily 6, group A, member 1 (NR6A1), transcript variant 2, aka NR61, GCNF1, RTR, GCNF, ACCESSION NUMBER NM_001489.3; nuclear receptor subfamily 6, group A, member 1 (NR6A1), transcript variant 2, aka NR61, GCNF1, RTR, GCNF, ACCESSION NUMBER NM_001489.3; nuclear respiratory factor 1 (NRF1), transcript variant 2, aka ALPHA-PAL, ACCESSION NUMBER NM_001040110.1; nuclear respiratory factor 1 (NRF1), transcript variant 1, aka ALPHA-PAL, ACCESSION NUMBER NM_005011.3; nuclear respiratory factor 1 (NRF1), transcript variant 1, aka ALPHA-PAL, ACCESSION NUMBER NM_005011.3; Nik related kinase (NRK), aka DKFZp686A17109, FLJ16788, NESK, MGC131849, ACCESSION NUMBER NM_198465.2; neural retina leucine zipper (NRL), aka D14S46E, RP27, ACCESSION NUMBER NM_006177.3; oligodendrocyte lineage transcription factor 2 (OLIG2), aka PRKCBP2, RACK17, OLIGO2, BHLHB1, ACCESSION NUMBER NM_005806.2; one cut homeobox 1 (ONECUT1), aka HNF-6, HNF6, HNF6A, ACCESSION NUMBER NM_004498.1; one cut homeobox 2 (ONECUT2), aka OC-2, OC2, MGC120378, MGC120377, ACCESSION NUMBER NM_004852.2; one cut homeobox 3 (ONECUT3), ACCESSION NUMBER NM_001080488.1; orthopedia homeobox (OTP), aka MGC3161, ACCESSION NUMBER NM_032109.2; orthodenticle homeobox 1 (OTX1), aka FLJ38361, MGC15736, ACCESSION NUMBER NM_014562.2; orthodenticle homeobox 2 (OTX2), transcript variant 2, aka MCOPS5, MGC45000, ACCESSION NUMBER NM_172337.1; orthodenticle homeobox 2 (OTX2), transcript variant 2, aka MCOPS5, MGC45000, ACCESSION NUMBER NM_172337.1; orthodenticle homeobox 2 (OTX2), transcript variant 1, aka MCOPS5, MGC45000, ACCESSION NUMBER NM_021728.2; ovo-like 1(*Drosophila*) (OVOL1), aka HOVO1, ACCESSION NUMBER NM_004561.2; proliferation-associated 2G4, 38 kDa (PA2G4), aka p38-2G4, HG4-1, EBP1, ACCESSION NUMBER NM_006191.2; paired box 3 (PAX3), transcript variant PAX3, aka WS1, MGC120381, HUP2, CDHS, MGC120383, MGC120384, MGC134778, MGC120382, ACCESSION NUMBER NM_181457.1; paired box 3 (PAX3), transcript variant PAX3A, aka WS1, MGC120381, HUP2, CDHS, MGC120383, MGC120384, MGC134778, MGC120382, ACCESSION NUMBER NM_000438.3; paired box 3 (PAX3), transcript variant PAX3A, aka WS1, MGC120381, HUP2, CDHS, MGC120383, MGC120384, MGC134778, MGC120382, ACCESSION NUMBER NM_000438.3; paired box 3 (PAX3), transcript variant PAX3D, aka WS1, MGC120381, HUP2, CDHS, MGC120383, MGC120384, MGC134778, MGC120382, ACCESSION NUMBER NM_181458.1; paired box 4 (PAX4), aka MGC129960, ACCESSION NUMBER NM_006193.1; paired box 5 (PAX5), aka BSAP, ACCESSION NUMBER NM_016734.1; paired box 6 (PAX6), transcript variant 1, aka WAGR, D11S812E, AN2, MGDA, MGC17209, AN, ACCESSION NUMBER NM_000280.2; paired box 6 (PAX6), transcript variant 2, aka WAGR, D11S812E, AN2, MGDA, MGC17209, AN, ACCESSION NUMBER NM_001604.3; paired box 7 (PAX7), transcript variant 1, aka PAX7B, HUP1, ACCESSION NUMBER NM_002584.1; paired box 8 (PAX8), transcript variant PAX8D, ACCESSION NUMBER NM_013953.3; paired box 8 (PAX8), transcript variant PAX8A, ACCESSION NUMBER NM_003466.3; paired box 8 (PAX8), transcript variant PAX8A, ACCESSION NUMBER NM_003466.3; pre-B-cell leukemia homeobox 1 (PBX1), aka DKFZp686B09108, MGC126627, ACCESSION NUMBER NM_002585.1; pre-B-cell leukemia homeobox 2 (PBX2), aka G17, PBX2 MHC, HOX12, ACCESSION NUMBER NM_002586.4; pre-B-cell leukemia homeobox 3 (PBX3), ACCESSION NUMBER NM_006195.4; pre-B-cell leukemia homeobox 4 (PBX4), ACCESSION NUMBER NM_025245.1; polycomb group ring finger 2 (PCGF2), aka MGC10545, RNF110, MEL-18, ZNF144, ACCESSION NUMBER NM_007144.2; polycomb group ring finger 6 (PCGF6), transcript variant 2, aka MBLR, MGC15678, MGC17541, RNF134, ACCESSION NUMBER NM_032154.3; polycomb group ring finger 6 (PCGF6), transcript variant 1, aka MBLR, MGC15678, MGC17541, RNF134, ACCESSION NUMBER NM_001011663.1; paternally expressed 3 (PEG3), aka DKFZp781A095, ZSCAN24, KIAA0287, PW1, ACCESSION NUMBER NM_006210.1; prefoldin subunit 1 (PFDN1), aka PDF, PFD1, ACCESSION NUMBER NM_002622.4; piggyBac transposable element derived 1 (PGBD1), aka dJ874C20.4, SCAND4, HUCEP-4, ACCESSION NUMBER NM_032507.2; progesterone receptor (PGR), aka PR, NR3C3, ACCESSION NUMBER NM_000926.3; PHD finger protein 1 (PHF1), transcript variant 1, aka PHF2, ACCESSION NUMBER NM_002636.3; PHD finger protein 1 (PHF1), transcript variant 2, aka PHF2, ACCESSION NUMBER NM_024165.1; PHD finger protein 1 (PHF1), transcript variant 2, aka PHF2, ACCESSION NUMBER NM_024165.1; PHD finger protein 2 (PHF2), aka MGC176680, KIAA0662, GRC5, JHDM1E, ACCESSION NUMBER NM_005392.3; PHD finger protein 2 (PHF2), aka MGC176680, KIAA0662, GRC5, JHDM1E, ACCESSION NUMBER NM_005392.3; PHD finger protein 5A (PHF5A), aka INI, bK223H9.2, SF3b14b, MGC1346, ACCESSION NUMBER NM_032758.3; paired-like homeobox 2a (PHOX2A), aka NCAM2, MGC52227, CFEOM2, PMX2A, FEOM2, ARIX, ACCESSION NUMBER NM_005169.2; paired-like homeobox 2b (PHOX2B), aka PMX2B, NBPhox, ACCESSION NUMBER NM_003924.2; putative homeodomain transcription factor 1 (PHTF1), aka PHTF, ACCESSION NUMBER NM_006608.1; paired-like homeodomain transcription factor 1 (PITX1), aka POTX, PTX1, BFT, ACCESSION NUMBER NM_002653.3; paired-like homeodomain 2 (PITX2), transcript variant 2, aka MGC111022, IGDS, RS, IDG2, RIEG, PTX2, IGDS2, Brx1, ARP1, RIEG1, 1HG2, IRID2, RGS, Otlx2, MGC20144, ACCESSION NUMBER NM_153426.1; paired-like homeodomain 2 (PITX2), transcript variant 1, aka MGC111022, IGDS, RS, IDG2, RIEG, PTX2, IGDS2, Brx1, ARP1, RIEG1, 1HG2, IRID2, RGS, Otlx2, MGC20144, ACCESSION NUMBER NM_153427.1; paired-like homeodomain 2 (PITX2), transcript variant 3, aka MGC111022, IGDS, RS, IDG2, RIEG, PTX2, IGDS2, Brx1, ARP1, RIEG1, 1HG2, IRID2, RGS, Otlx2, MGC20144, ACCESSION NUMBER NM_000325.5; paired-like homeodomain 3 (PITX3), aka PTX3, MGC12766, ACCESSION NUMBER NM_005029.3; PBX/knotted 1 homeobox 1 (PKNOX1), aka PREP1, pkonx1c, ACCESSION NUMBER NM_004571.3; PBX/knotted 1 homeobox 1 (PKNOX1), aka PREP1, pkonx1c, ACCESSION NUMBER NM_004571.3; PBX/knotted 1 homeobox 2 (PKNOX2), aka FLJ13074, PREP2, ACCESSION NUMBER NM_022062.2; pleiomorphic adenoma gene 1 (PLAG1), aka PSA, SGPA, ACCESSION NUMBER NM_002655.1; pleiomorphic adenoma gene 1 (PLAG1), Accession number XM_001126483.1; pleiomorphic adenoma gene-like 2 (PLAGL2), aka FLJ23283, ACCESSION NUMBER NM_002657.2; promyelocytic leukemia (PML), transcript variant 2, aka PP8675, RNF71, MYL, TRIM19, ACCESSION NUMBER NM_033240.2; promyelocytic leukemia (PML), transcript variant 1, aka PP8675, RNF71, MYL, TRIM19, ACCESSION NUMBER NM_033238.2; promyelocytic leukemia (PML), transcript variant 9, aka PP8675, RNF71, MYL, TRIM19 ACCESSION NUMBER NM_033239.2; promyelocytic leukemia (PML), transcript variant 9, aka PP8675, RNF71, MYL, TRIM19, ACCESSION NUMBER NM_033239.2; promyelocytic leukemia (PML), transcript variant 7, aka PP8675, RNF71, MYL, TRIM19, ACCESSION NUMBER NM_033246.2; POU class 1 homeobox 1 (POU1F1), aka GHF-1, Pit-1 beta, PIT1, Pit-1, ACCESSION NUMBER NM_000306.1; POU class 2 homeobox 1 (POU2F1), aka OCT1, OTF1, ACCESSION NUMBER NM_002697.2; POU domain, class 2, transcription factor 2 (POU2F2), aka OCT2, OTF2, Oct-2, ACCESSION NUMBER NM_002698.1; POU domain, class 2, transcription factor 3 (POU2F3), aka MGC126698, Skn-1a, FLJ40063, PLA-1, OCT11, Epoc-1, ACCESSION NUMBER NM_014352.1; POU class 3 homeobox 1 (POU3F1), aka OCT6, SCIP, OTF6, ACCESSION NUMBER NM_002699.3; POU class 3 homeobox 2 (POU3F2), aka OTF7, OCT7, BRN2, POUF3, ACCESSION NUMBER NM_005604.2; POU class 3 homeobox 3 (POU3F3), aka BRN1, OTF8, ACCESSION NUMBER NM_006236.1; POU class 3 homeobox 4 (POU3F4), aka BRN4, OTF9, BRAIN-4, DFN3, ACCESSION NUMBER NM_000307.2; POU class 4 homeobox 1 (POU4F1), aka RDC-1, Oct-T1, BRN3A, FLJ13449, ACCESSION NUMBER NM_006237.3; POU class 4 homeobox 2 (POU4F2), aka Brn-3b, BRN3.2, BRN3B, ACCESSION NUMBER NM_004575.2; POU class 4 homeobox 3 (POU4F3), aka DFNA15, MGC138412, BRN3C, ACCESSION NUMBER NM_002700.1; POU class 5 homeobox 1 (POU5F1), transcript variant 1, aka OTF4, OCT3, OCT4, MGC22487, OTF3, ACCESSION NUMBER NM_002701.4; POU domain class 5, transcription factor 2 (POU5F2), aka FLJ25680, DKFZp686P02123, SPRM-1, ACCESSION NUMBER NM_153216.1; POU class 6 homeobox 1 (POU6F1), aka BRN5, MPOU, TCFB1, ACCESSION NUMBER NM_002702.2; POU class 6 homeobox 2 (POU6F2), aka WTSL, RPF-1, WT5, ACCESSION NUMBER NM_007252.2; peroxisome proliferator-activated receptor alpha (PPARA), transcript variant 3, aka PPAR, hPPAR, MGC2452, NR1C1, MGC2237, ACCESSION NUMBER NM_001001928.2; peroxisome proliferator-activated receptor alpha (PPARA), transcript variant 3, aka PPAR, hPPAR, MGC2452, NR1C1, MGC2237, ACCESSION NUMBER NM_001001928.2; peroxisome proliferator-activated receptor alpha (PPARA), transcript variant 3, aka PPAR, hPPAR, MGC2452, NR1C1, MGC2237, ACCESSION NUMBER NM_001001928.2; peroxisome proliferative activated receptor, delta (PPARD), transcript variant 1, aka PPARB, NUC1, FAAR, PPAR-beta, NUC1, NUCII, MGC3931, NR1C2, ACCESSION NUMBER NM_006238.2; peroxisome proliferator-activated receptor delta (PPARD), aka PPARB, NUCI, FAAR, PPAR-beta, NUC1, NUCII, MGC3931, NR1C2, ACCESSION NUMBER NM_006238.3; peroxisome proliferator-activated receptor gamma (PPARG), transcript variant 3, aka NR1C3, PPARG1, PPARG2, ACCESSION NUMBER NM_138711.3; peroxisome proliferator-activated receptor gamma (PPARG), transcript variant 2, aka NR1C3, PPARG1, PPARG2, ACCESSION NUMBER NM_015869.4; peroxisome proliferator-activated receptor gamma (PPARG), transcript variant 2, aka NR1C3, PPARG1, PPARG2, ACCESSION NUMBER NM_015869.4; peroxisome proliferator-activated receptor gamma (PPARG), transcript variant 1, aka NR1C3, PPARG1, PPARG2, ACCESSION NUMBER NM_138712.3; PR domain containing 1, with ZNF domain (PRDM1), transcript variant 2, aka MGC118922, BLIMP1, PRD1-BF1, MGC118925, MGC118924, MGC118923, ACCESSION NUMBER NM_182907.1; PR domain containing 1, with ZNF domain (PRDM1), transcript variant 1, aka MGC118922, BLIMP1, PRD1-BF1, MGC118925, MGC118924, MGC118923, ACCESSION NUMBER NM_001198.2; PR domain containing 1, with ZNF domain (PRDM1), transcript variant 1, aka MGC118922, BLIMP1, PRD1-BF1, MGC118925, MGC118924, MGC118923, ACCESSION NUMBER NM_001198.2; PR domain containing 1, with ZNF domain (PRDM1), transcript variant 1, aka MGC118922, BLIMP1, PRD1-BF1, MGC118925, MGC118924, MGC118923, ACCESSION NUMBER NM_001198.2; PR domain containing 16 (PRDM16), transcript variant 1, aka PFM13, MEL1, KIAA1675, ACCESSION NUMBER NM_022114.2; PR domain containing 16 (PRDM16), transcript variant 1, aka PFM13, MEL1, KIAA1675, ACCESSION NUMBER NM_022114.2; PR domain containing 16 (PRDM16), transcript variant 1, aka PFM13, MEL1, KIAA1675, ACCESSION NUMBER NM_022114.2; PR domain containing 2, with ZNF domain (PRDM2), transcript variant 1, aka RIZ1, MTB-ZF, HUMHOXY1, RIZ2, RIZ, ACCESSION NUMBER NM_012231.3; PR domain containing 2, with ZNF domain (PRDM2), transcript variant 2, aka RIZ1, MTB-ZF, KMT8, HUMHOXY1, RIZ2, RIZ, ACCESSION NUMBER NM_015866.3; PROP paired-like homeobox 1 (PROP1), ACCESSION NUMBER NM_006261.2; prospero homeobox 1 (PROX1), ACCESSION NUMBER NM_002763.3; paired related homeobox 1 (PRRX1), transcript variant pmx-1a, aka PRX1, PMX1, PHOX1, ACCESSION NUMBER NM_006902.3; paired related homeobox 1 (PRRX1), transcript variant pmx-1a, aka PRX1, PMX1, PHOX1, ACCESSION NUMBER NM_006902.3; paired related homeobox 2 (PRRX2), aka PMX2, MGC19843, PRX2, ACCESSION NUMBER NM_016307.3; pituitary tumor-transforming 1 (PTTG1), aka PTTG, MGC126883, HPTTG, SECURIN, MGC138276, EAP1, TUTR1, ACCESSION NUMBER NM_004219.2; purine-rich element binding protein A (PURA), aka PURALPHA, PUR-ALPHA, PURL ACCESSION NUMBER NM_005859.3; purine-rich element binding protein B (PURB), aka MGC126786, MGC126784, PURBETA, ACCESSION NUMBER NM_033224.3; retinoic acid receptor, alpha (RARA), transcript variant 2, aka NR1B1, RAR, ACCESSION NUMBER NM_001024809.2; retinoic acid receptor, alpha (RARA), transcript variant 1, aka NR1B1, RAR, ACCESSION NUMBER NM_000964.2; retinoic acid receptor, alpha (RARA), transcript variant 1, aka NR1B1, RAR, ACCESSION NUMBER NM_000964.2; retinoic acid receptor, beta (RARB), transcript variant 1, aka RRB2, NR1B2, HAP, ACCESSION NUMBER NM_000965.2; retinoic acid receptor, beta (RARB), transcript variant 1, aka RRB2, NR1B2, HAP, ACCESSION NUMBER NM_000965.2; retinoic acid receptor, beta (RARB), transcript variant 2, aka RRB2, NR1B2, HAP, ACCESSION NUMBER NM_016152.2; retinoic acid receptor, gamma (RARG), aka RARC, NR1B3, ACCESSION NUMBER NM_000966.3; retina and anterior neural fold homeobox (RAX), aka RX, ACCESSION NUMBER NM_013435.2; retina and anterior neural fold homeobox like 1 (RAXL1), aka QRX, MGC15631, ARMD6, CORD11, ACCESSION NUMBER NM_032753.2; retinoblastoma 1 (RB1), aka RB, OSRC, ACCESSION NUMBER NM_000321.2; recombination signal binding protein for immunoglobulin kappa J region (RBPJ), transcript variant 3, aka SUH, KBF2, RBP-J, IGKJRB1, IGKJRB, RBPJK, CBF1, RBPSUH, csl, MGC61669, ACCESSION NUMBER NM_203283.1; recombination signal binding protein for immunoglobulin kappa J region (RBPJ), transcript variant 1, aka SUH, RBP-J, RBPJK, csl, KBF2, IGKJRB1, IGKJRB, CBF1, RBPSUH, MGC61669, ACCESSION NUMBER NM_005349.2; recombination signal binding protein for immunoglobulin kappa J region (RBPJ), transcript variant 4, aka SUH, RBP-J, RBPJK, csl, KBF2, IGKJRB1, IGKJRB, CBF1, RBPSUH, MGC61669, ACCESSION NUMBER NM_203284.1; recombination signal binding protein for immunoglobulin kappa J region-like (RBPJL), aka SUHL, RBPSUHL, SUH, RBP-L, ACCESSION NUMBER NM_014276.2; regulator of calcineurin 1 (RCAN1), transcript variant 3, aka ADAPT78, MCIP1, DSC1, CSP1, DSCR1, RCN1, ACCESSION NUMBER NM_203418.1; regulator of calcineurin 1 (RCAN1), transcript variant 2, aka ADAPT78, MCIP1, DSC1, CSP1, DSCR1, RCN1, ACCESSION NUMBER NM_203417.1; regulator of calcineurin 1 (RCAN1), transcript variant 1, aka ADAPT78, MCIP1, DSC1, CSP1, DSCR1, RCN1, ACCESSION NUMBER NM_004414.5; REST corepressor 2 (RCOR2), ACCESSION NUMBER NM_173587.2; v-rel reticuloendotheliosis viral oncogene homolog (avian) (REL), aka C-Rel, ACCESSION NUMBER NM_002908.2; v-rel reticuloendotheliosis viral oncogene homolog A (avian) (RELA), aka NFKB3, MGC131774, ACCESSION NUMBER NM_021975.2; v-rel reticuloendotheliosis viral oncogene homolog B (RELB), aka I-REL, ACCESSION NUMBER NM_006509.2; arginine-glutamic acid dipeptide (RE) repeats (RERE), transcript variant 3, aka ARP, ATN1L, ARG, KIAA0458, DNB1, FLJ38775, ACCESSION NUMBER NM_001042682.1; arginine-glutamic acid dipeptide (RE) repeats (RERE), transcript variant 1, aka ARP, ATN1L, ARG, KIAA0458, DNB1, FLJ38775, ACCESSION NUMBER NM_012102.3; arginine-glutamic acid dipeptide (RE) repeats (RERE), transcript variant 1, aka ARP, ATN1L, ARG, KIAA0458, DNB1, FLJ38775, ACCESSION NUMBER NM_012102.3; REX4, RNA exonuclease 4 homolog (S. cerevisiae) (REXO4), aka XPMC2, XPMC2H, ACCESSION NUMBER NM_020385.2; regulatory factor X, 1 (influences HLA class II expression) (RFX1), aka EF-C, ACCESSION NUMBER NM_002918.3; regulatory factor X, 3 (influences HLA class II expression) (RFX3), transcript variant 1, aka bA32F11.1, MGC87155, ACCESSION NUMBER NM_002919.2; regulatory factor X, 3 (influences HLA class II expression) (RFX3), transcript variant 2, aka bA32F11.1, MGC87155, ACCESSION NUMBER NM_134428.1; regulatory factor X, 3 (influences HLA class II expression) (RFX3), transcript variant 2, aka bA32F11.1, MGC87155, ACCESSION NUMBER NM_134428.1; regulatory factor X, 5 (influences HLA class II expression) (RFX5), transcript variant 1, ACCESSION NUMBER NM_000449.3; regulatory factor X, 5 (influences HLA class II expression) (RFX5), transcript variant 2, ACCESSION NUMBER NM_001025603.1; regulatory factor X-associated ankyrin-containing protein (RFXANK), transcript variant 1, aka BLS, RFX-B, MGC138628, F14150_1, ANKRA1, ACCESSION NUMBER NM_003721.2; regulatory factor X-associated ankyrin-containing protein (RFXANK), transcript variant 1, aka BLS, RFX-B, MGC138628, F14150_1, ANKRAL ACCESSION NUMBER NM_003721.2; regulatory factor X-associated ankyrin-containing protein (RFXANK), transcript variant 2, aka BLS, RFX-B, MGC138628, F14150_1, ANKRA1, ACCESSION NUMBER NM_134440.1; regulatory factor X-associated protein (RFXAP), ACCESSION NUMBER NM_000538.2; Rhox homeobox family, member 1 (RHOXF1), aka MGC119030, MGC119033, OTEX, PEPP1, ACCESSION NUMBER NM_139282.1; rearranged L-myc fusion (RLF), aka ZNF292L, Zn-15L, MGC142226, ACCESSION NUMBER NM_012421.2; ring finger protein 20 (RNF20), aka FLJ20382, KIAA2779, FLJ11189, BRE1A, MGC129667, MGC129668, ACCESSION NUMBER NM_019592.5; ring finger protein 4 (RNF4), aka RES4-26, SNURF, ACCESSION NUMBER NM_002938.2; RAR-related orphan receptor A (RORA), transcript variant 2, aka NR1F1, MGC119326, ROR2, RZRA, ROR1, MGC119329, ROR3, ACCESSION NUMBER NM_134260.1; RAR-related orphan receptor A (RORA), transcript variant 1, aka NR1F1, MGC119326, ROR2, RZRA, ROR1, MGC119329, ROR3, ACCESSION NUMBER NM_134261.1; RAR-related orphan receptor A (RORA), transcript variant 4, aka NR1F1, MGC119326, ROR2, RZRA, ROR1, MGC119329, ROR3, ACCESSION NUMBER NM_134262.1; RAR-related orphan receptor A (RORA), transcript variant 3, aka NR1F1, MGC119326, ROR2, RZRA, ROR1, MGC119329, ROR3, ACCESSION NUMBER NM_002943.2; RAR-related orphan receptor A (RORA), transcript variant 3, aka NR1F1, MGC119326, ROR2, RZRA, ROR1, MGC119329, ROR3, ACCESSION NUMBER NM_002943.2; RAR-related orphan receptor A (RORA), transcript variant 3, aka NR1F1, MGC119326, ROR2, RZRA, ROR1, MGC119329, ROR3, ACCESSION NUMBER NM_002943.2; RAR-related orphan receptor B (RORB), aka NR1F2, RZRB, bA133M9.1, ROR-BETA, ACCESSION NUMBER NM_006914.3; RAR-related orphan receptor C (RORC), transcript variant 2, aka MGC129539, RORG, RZRG, NR1F3, TOR, ACCESSION NUMBER NM_001001523.1; RAR-related orphan receptor C (RORC), transcript variant 2, aka MGC129539, RORG, RZRG, NR1F3, TOR, ACCESSION NUMBER NM_001001523.1; RAR-related orphan receptor C (RORC), transcript variant 2, aka MGC129539, RORG, RZRG, NR1F3, TOR, ACCESSION NUMBER NM_001001523.1; RAR-related orphan receptor C (RORC), transcript variant 1, aka MGC129539, RZRG, NR1F3, RORG, TOR, ACCESSION NUMBER NM_005060.3; runt-related transcription factor 1 (acute myeloid leukemia 1, aml1 oncogene) (RUNX1), transcript variant 2, aka AMLCR1, PEBP2aB, PEBP2A2, EVI-1, CBFA2, AML1, AML1-EVI-1, ACCESSION NUMBER NM_001001890.1; runt-related transcription factor 1 (acute myeloid leukemia 1, aml1 oncogene) (RUNX1), transcript variant 1, aka AMLCR1, PEBP2aB, EVI-1, CBFA2, AML1, AML1-EVI-1, ACCESSION NUMBER NM_001754.3; runt-related transcription factor 1 (acute myeloid leukemia 1, aml1 oncogene) (RUNX1), transcript variant 1, aka AMLCR1, PEBP2aB, EVI-1, CBFA2, AML1, AML1-EVI-1, ACCESSION NUMBER NM_001754.3; runt-related transcription factor 1, translocated to, 1 (cyclin D-related) (RUNX1T1), transcript variant 4, aka ZMYND2, MTG8b, AML1T1, MGC2796, CBFA2T1, CDR, MTG8, ETO, ACCESSION NUMBER NM_175636.1; runt-related transcription factor 1, translocated to, 1 (cyclin D-related) (RUNX1T1), transcript variant 3, aka ZMYND2, MTG8b, AML1T1, MGC2796, CBFA2T1, CDR, MTG8, ETO, ACCESSION NUMBER NM_175635.1; runt-related transcription factor 1, translocated to, 1 (cyclin D-related) (RUNX1T1), transcript variant 2, aka ZMYND2, MTG8b, AML1T1, MGC2796, CBFA2T1, CDR, MTG8, ETO, ACCESSION NUMBER NM_175634.1; runt-related transcription factor 1, translocated to, 1 (cyclin D-related) (RUNX1T1), transcript variant 1, aka ZMYND2, MTG8b, AML1T1, MGC2796, CBFA2T1, CDR, MTG8, ETO, ACCESSION NUMBER NM_004349.2; runt-related transcription factor 1, translocated to, 1 (cyclin D-related) (RUNX1T1), transcript variant 1, aka ZMYND2, MTG8b, AML1T1, MGC2796, CBFA2T1, CDR, MTG8, ETO, ACCESSION NUMBER NM_004349.2; runt-related transcription factor 2 (RUNX2), transcript variant 3, aka PEBP2A2, MGC120023, PEA2aA, CBFA1, MGC120022, AML3, OSF2, PEBP2aA1, PEBP2A1, PEBP2aA, CCD1, CCD, ACCESSION NUMBER NM_004348.3; runt-related transcription factor 2 (RUNX2), transcript variant 2, aka PEBP2A2, MGC120023, PEA2aA, CBFA1, MGC120022, AML3, OSF2, PEBP2aA1, PEBP2A1, PEBP2aA, CCD1, CCD, ACCESSION NUMBER NM_001015051.2; runt-related transcription factor 2 (RUNX2), transcript variant 1, aka PEBP2A2, MGC120023, PEA2aA, CBFA1, MGC120022, AML3, OSF2, PEBP2aA1, PEBP2A1, PEBP2aA, CCD1, CCD, ACCESSION NUMBER NM_001024630.2; runt-related transcription factor 3 (RUNX3), transcript variant 2, aka FLJ34510, MGC16070, PEBP2aC, CBFA3, AML2, ACCESSION NUMBER NM_004350.2; runt-related transcription factor 3 (RUNX3), transcript variant 1, aka FLJ34510, MGC16070, PEBP2aC, CBFA3, AML2, ACCESSION NUMBER NM_001031680.2; retinoid X receptor, alpha (RXRA), aka MGC102720, FLJ16020, FLJ16733, NR2B1, ACCESSION NUMBER NM_002957.3; retinoid X receptor, beta (RXRB), aka NR2B2, MGC1831, RCoR-1, H-2RIIBP, DAUDI6, ACCESSION NUMBER NM_021976.3; retinoid X receptor, gamma (RXRG), transcript variant 1, aka NR2B3, RXRC, ACCESSION NUMBER NM_006917.3; retinoid X receptor, gamma (RXRG), transcript variant 2, aka RXRC, NR2B3, ACCESSION NUMBER NM_001009598.1; retinoid X receptor, gamma (RXRG), transcript variant 2, aka RXRC, NR2B3, ACCESSION NUMBER NM_001009598.1; sal-like 1 (Drosophila) (SALL1), transcript variant 1, aka TBS, HSAL1, ZNF794; ACCESSION NUMBER NM_002968.2; sal-like 2 (Drosophila) (SALL2), aka FLJ10414, KIAA0360, ZNF795, HSAL2, p150 (Sa12), ACCESSION NUMBER NM_005407.1; SATB homeobox 1 (SATB1), ACCESSION NUMBER NM_002971.2; SATB homeobox 2 (SATB2), aka MGC119474, MGC119477, KIAA1034, FLJ21474, FLJ32076, ACCESSION NUMBER NM_015265.1; SCAN domain containing 1 (SCAND1), transcript variant 2, aka RAZ1, SDP1, ACCESSION NUMBER NM_033630.1; SCAN domain containing 1 (SCAND1), transcript variant 1, aka RAZ1, SDP1, ACCESSION NUMBER NM_016558.2; SCAN domain containing 1 (SCAND1), transcript variant 1, aka RAZ1, SDP1, ACCESSION NUMBER NM_016558.2; sex comb on midleg homolog 1 (Drosophila) (SCMH1), transcript variant 2, aka Scm13, ACCESSION NUMBER NM_012236.2; sex comb on midleg homolog 1 (Drosophila) (SCMH1), transcript variant 1, aka Scm13, ACCESSION NUMBER NM_001031694.1; sex comb on midleg homolog 1 (Drosophila) (SCMH1), transcript variant 1, aka Scm13, ACCESSION NUMBER NM_001031694.1; sex comb on midleg homolog 1 (Drosophila) (SCMH1), transcript variant 1, aka Scm13, ACCESSION NUMBER NM_001031694.1; sex comb on midleg-like 1 (Drosophila) (SCML1), transcript variant 1, ACCESSION NUMBER NM_001037540.1; sex comb on midleg-like 1 (Drosophila) (SCML1), transcript variant 1, ACCESSION NUMBER NM_001037540.1; sex comb on midleg-like 1 (*Drosophila*) (SCML1), transcript variant 1, ACCESSION NUMBER NM_001037540.1; sex comb on midleg-like 2 (*Drosophila*) (SCML2), ACCESSION NUMBER NM_006089.1; scratch homolog 1, zinc finger protein (*Drosophila*) (SCRT1), aka DKFZp547F072, SCRT, ACCESSION NUMBER NM_031309.4; scratch homolog 1, zinc finger protein (*Drosophila*) (SCRT1), aka DKFZp547F072, SCRT, ACCESSION NUMBER NM_031309.3; SEBOX homeobox (SEBOX), transcript variant 1, aka OG-9, OG9X, OG9, ACCESSION NUMBER NM_001080837.1; SEBOX homeobox (SEBOX), transcript variant 1, aka OG-9, OG9X, OG9, ACCESSION NUMBER NM_001080837.1; short stature homeobox (SHOX), transcript variant 2, aka GCFX, SHOXY, SS, PHOG, ACCESSION NUMBER NM_006883.2; short stature homeobox (SHOX), transcript variant 2, aka GCFX, SHOXY, SS, PHOG, ACCESSION NUMBER NM_006883.2; short stature homeobox 2 (SHOX2), transcript variant SHOX2a, aka OG12X, SHOT, OG12, OGl2X, ACCESSION NUMBER NM_006884.2; short stature homeobox 2 (SHOX2), transcript variant SHOX2a, aka OG12X, SHOT, OG12, OGl2X, ACCESSION NUMBER NM_006884.2; single-minded homolog 1 (*Drosophila*) (SIM1), ACCESSION NUMBER NM_005068.2; single-minded homolog 2 (*Drosophila*) (SIM2), transcript variant SIM2, aka MGC119447, SIM, ACCESSION NUMBER NM_005069.2; single-minded homolog 2 (*Drosophila*) (SIM2), transcript variant SIM2, aka MGC119447, SIM, ACCESSION NUMBER NM_005069.2; SIX homeobox 1 (SIX1), aka BOS3, TIP39, DFNA23, ACCESSION NUMBER NM_005982.2; SIX homeobox 2 (SIX2), ACCESSION NUMBER NM_016932.3; sine oculis homeobox homolog 3 (*Drosophila*) (SIX3), aka HPE2, ACCESSION NUMBER NM_005413.1; SIX homeobox 4 (SIX4), aka MGC119452, MGC119453, MGC119450, AREC3, ACCESSION NUMBER NM_017420.3; SIX homeobox 5 (SIX5), aka DMAHP, BOR2, ACCESSION NUMBER NM_175875.3; SIX homeobox 6 (SIX6), aka MCOPCT2, OPTX2, Six9, ACCESSION NUMBER NM_007374.1; solute carrier family 26, member 3 (SLC26A3), aka CLD, DRA, ACCESSION NUMBER NM_000111.1; SLC2A4 regulator (SLC2A4RG), aka GEF, Si-1-2, Si-1-2-19, HDBP1, ACCESSION NUMBER NM_020062.3; solute carrier family 30 (zinc transporter), member 9 (SLC30A9), aka C4orf1, HUEL, ZNT9, GAC63, ACCESSION NUMBER NM_006345.3; SMAD family member 1 (SMAD1), transcript variant 1, aka MADR1, BSP1, JV41, JV4-1, MADH1, ACCESSION NUMBER NM_005900.2; SMAD family member 1 (SMAD1), transcript variant 2, aka MADR1, JV41, JV4-1, MADH1, BSP1, ACCESSION NUMBER NM_001003688.1; SMAD family member 2 (SMAD2), transcript variant 2, aka hMAD-2, JV18, hSMAD2, MGC22139, MGC34440, MADH2, MADR2, JV18-1, ACCESSION NUMBER NM_001003652.2; SMAD family member 2 (SMAD2), transcript variant 1, aka hMAD-2, JV18, hSMAD2, MGC22139, MGC34440, MADH2, MADR2, JV18-1, ACCESSION NUMBER NM_005901.4; SMAD family member 3 (SMAD3), aka MADH3, JV15-2, HSPC193, MGC60396, Smad 3, HsT17436, DKFZp686J10186, DKFZP586N0721, ACCESSION NUMBER NM_005902.3; SMAD family member 4 (SMAD4), aka DPC4, MADH4, JIP, ACCESSION NUMBER NM_005359.3; SMAD family member 5 (SMAD5), transcript variant 1, aka Dwfc, DKFZp781O1323, MADH5, JV5-1, DKFZp781C1895, ACCESSION NUMBER NM_005903.5; SMAD family member 5 (SMAD5), transcript variant 1, aka Dwfc, DKFZp781O1323, MADH5, JV5-1, DKFZp781C1895, ACCESSION NUMBER NM_005903.5; SMAD family member 5 (SMAD5), transcript variant 2, aka Dwfc, DKFZp781O1323, MADH5, JV5-1, DKFZp781C1895, ACCESSION NUMBER NM_001001419.1; SMAD family member 6 (SMAD6), aka MADH6, HsT17432, MADH7, ACCESSION NUMBER NM_005585.3; SMAD family member 7 (SMAD7), aka MADH8, MADH7, FLJ16482, ACCESSION NUMBER NM_005904.2; SMAD family member 9 (SMAD9), aka SMAD8B, MADH9, MADH6, SMAD8A, ACCESSION NUMBER NM_005905.3; SWI/SNF related, matrix associated, actin dependent regulator of chromatin, subfamily a, member 4 (SMARCA4), aka SNF2L4, BRG1, SWI2, SNF2, hSNF2b, BAF190, FLJ39786, SNF2-BETA, SNF2LB, ACCESSION NUMBER NM_003072.2; snail homolog 3 (*Drosophila*) (SNAI3), aka SNAIL3, MGC129606, Zfp293, SMUC, ZNF293, ACCESSION NUMBER NM_178310.1; small nuclear RNA activating complex, polypeptide 2, 45 kDa (SNAPC2), aka PTFdelta, SNAP45, ACCESSION NUMBER NM_003083.2; small nuclear RNA activating complex, polypeptide 5, 19 kDa (SNAPC5), aka SNAP19, ACCESSION NUMBER NM_006049.2; small optic lobes homolog (*Drosophila*) (SOLH), aka MGC131491, CAPN15, ACCESSION NUMBER NM_005632.2; SRY (sex determining region Y)-box 1 (SOX1), ACCESSION NUMBER NM_005986.2; SRY (sex determining region Y)-box 10 (SOX10), aka WS4, DOM, WS2E, MGC15649, ACCESSION NUMBER NM_006941.3; SRY (sex determining region Y)-box 11 (SOX11), ACCESSION NUMBER NM_003108.3; SRY (sex determining region Y)-box 13 (SOX13), aka ICA12, MGC117216, Sox-13, SRY-box 13, ACCESSION NUMBER NM_005686.2; SRY (sex determining region Y)-box 14 (SOX14), aka SOX28, MGC119898, MGC119899, SRY-box 14, ACCESSION NUMBER NM_004189.2; SRY (sex determining region Y)-box 15 (SOX15), aka SOX27, SOX26, SOX20, ACCESSION NUMBER NM_006942.1; SRY (sex determining region Y)-box 18 (SOX18), aka HLTS, ACCESSION NUMBER NM_018419.2; SRY (sex determining region Y)-box 2 (SOX2), aka ANOP3, MGC2413, MCOPS3, ACCESSION NUMBER NM_003106.2; SRY (sex determining region Y)-box 21 (SOX21), aka SOX25, ACCESSION NUMBER NM_007084.2; SRY (sex determining region Y)-box 4 (SOX4), aka EVI16, ACCESSION NUMBER NM_003107.2; SRY (sex determining region Y)-box 5 (SOX5), transcript variant 2, aka MGC35153, L-SOX5, ACCESSION NUMBER NM_152989.2; SRY (sex determining region Y)-box 5 (SOX5), transcript variant 2, aka MGC35153, L-SOX5, ACCESSION NUMBER NM_152989.2; SRY (sex determining region Y)-box 5 (SOX5), transcript variant 1, aka MGC35153, L-SOX5, ACCESSION NUMBER NM_006940.4; SRY (sex determining region Y)-box 6 (SOX6), transcript variant 2, aka HSSOX6, ACCESSION NUMBER NM_033326.2; SRY (sex determining region Y)-box 6 (SOX6), transcript variant 1, aka HSSOX6, ACCESSION NUMBER NM_017508.1; SRY (sex determining region Y)-box 6 (SOX6), transcript variant 1, aka HSSOX6, ACCESSION NUMBER NM_017508.1; SRY (sex determining region Y)-box 6 (SOX6), transcript variant 1, aka HSSOX6, ACCESSION NUMBER NM_017508.1; SRY (sex determining region Y)-box 7 (SOX7), aka MGC10895, ACCESSION NUMBER NM_031439.2; SRY (sex determining region Y)-box 8 (SOX8), aka MGC24837, ACCESSION NUMBER NM_014587.2; SRY (sex determining region Y)-box 9 (campomelic dysplasia, autosomal sex-reversal) (SOX9), aka CMPD1, CMD1, SRA1, ACCESSION NUMBER NM_000346.2; Sp1 transcription factor (SP1), ACCESSION NUMBER NM_138473.2; SP140 nuclear body protein (5P140), transcript variant 1, aka MGC126440, LYSP100-B, LYSP100-A, ACCESSION NUMBER NM_007237.3; SP140 nuclear body protein (5P140), transcript variant 2, aka MGC126440, LYSP100-B, LYSP100-A, ACCESSION NUMBER NM_001005176.1; SP140 nuclear body protein (5P140), transcript variant 2, aka MGC126440, LYSP100-B, LYSP100-A, ACCESSION NUMBER NM_001005176.1; Sp4 transcription factor (SP4), aka MGC130009, SPR-1, HF1B, MGC130008, ACCESSION NUMBER NM_003112.3; SAM pointed domain containing ets transcription factor (SPDEF), aka bA375E1.3, PDEF, RP11-375E1_A.3, ACCESSION NUMBER NM_012391.1; spleen focus forming virus (SFFV) proviral integration oncogene spi1 (SPI1), transcript variant 2, aka SPI-A, SFPI1, PU.1, OF, SPI-1, ACCESSION NUMBER NM_003120.2; spleen focus forming virus (SFFV) proviral integration oncogene spi1 (SPI1), transcript variant 1, aka SPI-A, SFPI1, PU.1, OF, SPI-1, ACCESSION NUMBER NM_001080547.1; Spi-B transcription factor (Spi-1/PU.1 related) (SPIB), aka SPI-B, ACCESSION NUMBER NM_003121.2; Spi-C transcription factor (Spi-1/PU.1 related) (SPIC), aka SPI-C, MGC40611, ACCESSION NUMBER NM_152323.1; sterol regulatory element binding transcription factor 1 (SREBF1), transcript variant 2, aka SREBP1, ACCESSION NUMBER NM_004176.3; sterol regulatory element binding transcription factor 1 (SREBF1), transcript variant 1, aka SREBP1, ACCESSION NUMBER NM_001005291.1; sterol regulatory element binding transcription factor 1 (SREBF1), transcript variant 1, aka SREBP1, ACCESSION NUMBER NM_001005291.1; serum response factor (c-fos serum response element-binding transcription factor) (SRF), aka MCM1, ACCESSION NUMBER NM_003131.2; sex determining region Y (SRY), aka TDF, TDY, ACCESSION NUMBER NM_003140.1; suppression of tumorigenicity 18 (breast carcinoma) (zinc finger protein) (ST18), aka KIAA0535, ZNF387, ACCESSION NUMBER NM_014682.1; signal transducer and activator of transcription 1, 91 kDa (STAT1), transcript variant alpha, aka ISGF-3, STAT91, DKFZp686B04100, ACCESSION NUMBER NM_007315.2; signal transducer and activator of transcription 1, 91 kDa (STAT1), transcript variant alpha, aka ISGF-3, STAT91, DKFZp686B04100, ACCESSION NUMBER NM_007315.2; signal transducer and activator of transcription 1, 91 kDa (STAT1), transcript variant beta, aka ISGF-3, STAT91, DKFZp686B04100, ACCESSION NUMBER NM_139266.1; signal transducer and activator of transcription 2, 113 kDa (STAT2), aka ISGF-3, STAT113, MGC59816, P113, ACCESSION NUMBER NM_005419.2; signal transducer and activator of transcription 3 (acute-phase response factor) (STAT3), transcript variant 3, aka APRF, FLJ20882, MGC16063, ACCESSION NUMBER NM_213662.1; signal transducer and activator of transcription 4 (STAT4), ACCESSION NUMBER NM_003151.2; signal transducer and activator of transcription 5A (STAT5A), aka MGF, STAT5, ACCESSION NUMBER NM_003152.2; signal transducer and activator of transcription 5B (STAT5B), aka STAT5, ACCESSION NUMBER NM_012448.3; signal transducer and activator of transcription 6, interleukin-4 induced (STAT6), aka STAT6C, D12S1644, STAT6B, IL-4-STAT, ACCESSION NUMBER NM_003153.3; striatin, calmodulin binding protein 3 (STRN3), transcript variant 2, aka SG2NA, ACCESSION NUMBER NM_014574.3; suppressor of Ty 6 homolog (*S. cerevisiae*) (SUPT6H), aka MGC87943, SPT6H, KIAA0162, SPT6, emb-5, ACCESSION NUMBER NM_003170.3; T, brachyury homolog (mouse) (T), aka TFT, MGC104817, ACCESSION NUMBER NM_003181.2; transcriptional adaptor 2 (ADA2 homolog, yeast)-like (TADA2L), transcript variant 2, aka KLO4P, FLJ12705, ADA2, hADA2, ACCESSION NUMBER NM_133439.2; transcriptional adaptor 2 (ADA2 homolog, yeast)-like (TADA2L), transcript variant 1, aka KLO4P, FLJ12705, ADA2, hADA2, ACCESSION NUMBER NM_001488.3; transcriptional adaptor 2 (ADA2 homolog, yeast)-like (TADA2L), transcript variant 1, aka KL04P, FLJ12705, ADA2, hADA2, ACCESSION NUMBER NM_001488.3; transcriptional adaptor 3 (NGG1 homolog, yeast)-like (TADA3L), transcript variant 1, aka hADA3, FLJ20221, FLJ21329, ADA3, ACCESSION NUMBER NM_006354.2; transcriptional adaptor 3 (NGG1 homolog, yeast)-like (TADA3L), transcript variant 2, aka hADA3, FLJ20221, FLJ21329, ADA3, ACCESSION NUMBER NM_133480.1; TAF10 RNA polymerase II, TATA box binding protein (TBP)-associated factor, 30 kDa (TAF10), aka TAF2H, TAF2A, TAFII30, ACCESSION NUMBER NM_006284.2; TAF13 RNA polymerase II, TATA box binding protein (TBP)-associated factor, 18 kDa (TAF13), aka TAFII18, MGC22425, TAF2K, ACCESSION NUMBER NM_005645.3; TATA box binding protein (TBP)-associated factor, RNA polymerase I, B, 63 kDa (TAF1B), aka RAF1B, SL1, RAFI63, TAFI63, MGC:9349, ACCESSION NUMBER NM_005680.1; TAF4 RNA polymerase II, TATA box binding protein (TBP)-associated factor, 135 kDa (TAF4), aka TAFII135, TAF2C1, TAF4A, TAFII130, FLJ41943, TAF2C, ACCESSION NUMBER NM_003185.3; TAF5 RNA polymerase II, TATA box binding protein (TBP)-associated factor, 100 kDa (TAF5), aka TAFII100, TAF2D, ACCESSION NUMBER NM_006951.3; TAF5-like RNA polymerase II, p300/CBP-associated factor (PCAF)-associated factor, 65 kDa (TAF5L), transcript variant 1, mRNA aka PAF65B, ACCESSION NUMBER NM_0144093; TAF5-like RNA polymerase II, p300/CBP-associated factor (PCAF)-associated factor, 65 kDa (TAF5L), transcript variant 2, mRNA aka PAF65B, ACCESSION NUMBER NM_0010252471; TAF6 RNA polymerase II, TATA box binding protein (TBP)-associated factor, 80 kDa (TAF6), transcript variant 2, mRNA aka MGC:8964, DKFZp781E21155, TAF2E, TAFII80, TAFII85, TAFII70, ACCESSION NUMBER NM_1393151; TAF6 RNA polymerase II, TATA box binding protein (TBP)-associated factor, 80 kDa (TAF6), transcript variant 1, mRNA aka MGC:8964, DKFZp781E21155, TAF2E, TAFII80, TAFII85, TAFII70, ACCESSION NUMBER NM_0056412; TAF7 RNA polymerase II, TATA box binding protein (TBP)-associated factor, 55 kDa (TAF7) aka TAFII55, TAF2F, ACCESSION NUMBER NM_0056422; TAF7-like RNA polymerase II, TATA box binding protein (TBP)-associated factor, 50 kDa (TAF7L) aka TAF2Q, dJ738A131, FLJ23157, ACCESSION NUMBER NM_0248852; T-cell acute lymphocytic leukemia 1 (TAL1) aka tal-1, SCL, TCL5, ACCESSION NUMBER NM_0031891; TAR DNA binding protein (TARDBP) aka TDP-43, ACCESSION NUMBER NM_0073753; TATA box binding protein (TBP) aka MGC126055, SCA17, MGC117320, MGC126054, TFIID, GTF2D1, GTF2D, ACCESSION NUMBER NM_0031943; TATA box binding protein like 2 (TBPL2) aka TRF3, TBP2, ACCESSION NUMBER NM_1990472; T-box, brain, 1 (TBR1) aka TES-56, MGC141978, ACCESSION NUMBER NM_0065932; T-box 1 (TBX1), transcript variant A aka VCFS, TGA, DORY, CTHM, TBX1C, DGS, CAFS, DGCR, ACCESSION NUMBER NM_0806461;

T-box 1 (TBX1), transcript variant B aka VCFS, TGA, DORY, CTHM, TBX1C, DGS, CAFS, DGCR, ACCESSION NUMBER NM_0059921; T-box 1 (TBX1), transcript variant B aka VCFS, TGA, DORY, CTHM, TBX1C, DGS, CAFS, DGCR, ACCESSION NUMBER NM_0059921; T-box 1 (TBX1), transcript variant C aka VCFS, TGA, DORY, CTHM, TBX1C, DGS; CAFS; DGCR, ACCESSION NUMBER NM_0806471; T-box 10 (TBX10), mRNA aka TBX7; TBX13, ACCESSION NUMBER NM_0059952; T-box 15 (TBX15), mRNA aka TBX14, ACCESSION NUMBER NM_1523802; T-box 18 (TBX18), ACCESSION NUMBER NM_0010805081; T-box 18 (TBX18), ACCESSION NUMBER NM_0010805081; T-box 19 (TBX19), aka TBS19, FLJ26302, TPIT, FLJ34543, dJ747L41, TBS19, ACCESSION NUMBER NM_0051491; T-box 2 (TBX2) aka FLJ10169, ACCESSION NUMBER NM_0059943; T-box 20 (TBX20), transcript variant 2 aka ASD4, ACCESSION NUMBER NM_0204171; T-box 20 (TBX20), transcript variant 1 aka ASD4, ACCESSION NUMBER NM_0010776531; T-box 21 (TBX21) aka TBLYM, TBET, T-PET, T-bet, ACCESSION NUMBER NM_0133511; T-box 22 (TBX22), transcript variant 2 aka TBXX, dJ795G231, CLPA, ACCESSION NUMBER NM_0169542; T-box 3 (ulnar mammary syndrome) (TBX3), transcript variant 2 aka UMS, XHL, TBX3-ISO, ACCESSION NUMBER NM_0165693; T-box 3 (TBX3), transcript variant 1 aka UMS, XHL, TBX3-ISO, ACCESSION NUMBER NM_0059963; T-box 4 (TBX4) aka SPS, ACCESSION NUMBER NM_0184882; T-box 5 (TBX5), transcript variant 4 aka HOS, ACCESSION NUMBER NM_1814861; T-box 5 (TBX5), transcript variant 1 aka HOS, ACCESSION NUMBER NM_0001923; T-box 5 (TBX5), transcript variant 3 aka HOS, ACCESSION NUMBER NM_0807172; T-box 6 (TBX6), transcript variant 2 aka DFNB67, ACCESSION NUMBER NM_0807581; T-box 6 (TBX6), transcript variant 1 aka DFNB67, ACCESSION NUMBER NM_0046082; T-box 6 (TBX6), transcript variant 1 aka DFNB67, ACCESSION NUMBER NM_0046082; transcription elongation factor A (SII)-like 1 (TCEAL1), transcript variant 2 aka SIIR; p21, pp 21, ACCESSION NUMBER NM_0010066391; transcription elongation factor A (SIB-like 1 (TCEAL1), transcript variant 3 aka SIIR; p21, pp 21, ACCESSION NUMBER NM_0010066401; transcription factor 1, hepatic; LF-B1, hepatic nuclear factor (HNF1), albumin proximal factor (TCF1) aka MODY3, HNF1, HNF1A, LFB1, ACCESSION NUMBER NM_0005453; transcription factor 15 (basic helix-loop-helix) (TCF15) aka EC2, PARAXIS, ACCESSION NUMBER NM_0046093; transcription factor 19 (SC1) (TCF19), transcript variant 1 aka SC1, SC11, ACCESSION NUMBER NM_0071092; transcription factor 19 (SC1) (TCF19), transcript variant 2 aka SC1, SC11, ACCESSION NUMBER NM_0010775111; transcription factor 2, hepatic; LF-B3, variant hepatic nuclear factor (TCF2), transcript variant b, aka VHNF1, MODY5, HNF2, HNF1B, FJHN, HNF1beta, LFB3, ACCESSION NUMBER NM_0064811; transcription factor 2, hepatic, LF-B3; variant hepatic nuclear factor (TCF2), transcript variant a aka VHNF1, MODY5, HNF2, HNF1B, FJHN, HNF1beta, LFB3, ACCESSION NUMBER NM_0004581; transcription factor 2, hepatic, LF-B3, variant hepatic nuclear factor (TCF2), transcript variant a aka VHNF1, MODY5, HNF2, HNF1B, FJHN, HNF1beta, LFB3, ACCESSION NUMBER NM_0004581; transcription factor 21 (TCF21), transcript variant 1 aka POD1, ACCESSION NUMBER NM_1983921; transcription factor 21 (TCF21), transcript variant 1 aka POD1, ACCESSION NUMBER NM_1983921; transcription factor 21 (TCF21), transcript variant 2 aka POD1, ACCESSION NUMBER NM_0032062; transcription factor 25 (basic helix-loop-helix) (TCF25) aka hKIAA1049, NULP1, PRO2620, Hulp1, FKSG26, KIAA1049, ACCESSION NUMBER NM_0149721; transcription factor 3 (E2A immunoglobulin enhancer binding factors E12/E47) (TCF3) aka MGC129648, MGC129647, ITF1, E2A, ACCESSION NUMBER NM_0032001; transcription factor 7-like 1 (T-cell specific, HMG-box) (TCF7L1) aka TCF-3, TCF3, ACCESSION NUMBER NM_0312831; transcription factor 7-like 2 (T-cell specific, HMG-box) (TCF7L2) aka TCF-4, TCF4, ACCESSION NUMBER NM_0307562; transcription factor-like 5 (basic helix-loop-helix) (TCFL5) aka MGC46135, E2BP-1, CHA, Fig1b, ACCESSION NUMBER NM_0066022; TEA domain family member 1 (SV40 transcriptional enhancer factor) (TEAD1) aka AA, REF1, TCF13, TEF-1, ACCESSION NUMBER NM_0219614; TEA domain family member 1 (SV40 transcriptional enhancer factor) (TEAD1) aka AA, REF1, TCF13, TEF-1, ACCESSION NUMBER NM_0219614; TEA domain family member 2 (TEAD2) aka ETF, TEF-4, TEF4, ACCESSION NUMBER NM_0035981; TEA domain family member 3 (TEAD3) aka TEF-5, DTEF-1, TEF5, TEAD5, ETFR-1, ACCESSION NUMBER NM_0032143; TEA domain family member 4 (TEAD4), transcript variant 1 aka RTEF-1, MGC9014, TEF-3, TEFR-1, EFTR-2, TCF13L1, hRTEF-1B, RTEF1, ACCESSION NUMBER NM_0032132; TEA domain family member 4 (TEAD4), transcript variant 3 aka RTEF-1, MGC9014, TEF-3, TEFR-1, EFTR-2, TCF13L1, hRTEF-1B, RTEF1, ACCESSION NUMBER NM_2014431; TEA domain family member 4 (TEAD4), transcript variant 3 aka RTEF-1, MGC9014, TEF-3, TEFR-1, EFTR-2, TCF13L1, hRTEF-1B, RTEF1, ACCESSION NUMBER NM_2014431; thyrotrophic embryonic factor (TEF) aka ACCESSION NUMBER NM_0032162; transcription factor A, mitochondrial (TFAM), nuclear gene encoding mitochondrial protein aka MtTF1, mtTFA, TCF6, TCF6L2, ACCESSION NUMBER NM_0032011; transcription factor AP-2 alpha (activating enhancer binding protein 2 alpha) (TFAP2A), transcript variant 2 aka TFAP2, AP-2, AP2TF, AP-2alpha, ACCESSION NUMBER NM_0010322802; transcription factor AP-2 alpha (activating enhancer binding protein 2 alpha) (TFAP2A), transcript variant 2 aka TFAP2, AP-2, AP2TF, AP-2alpha, ACCESSION NUMBER NM_0010322802; transcription factor AP-2 alpha (activating enhancer binding protein 2 alpha) (TFAP2A), transcript variant 3 aka TFAP2, AP-2, AP2TF, AP-2alpha, ACCESSION NUMBER NM_0010424251; transcription factor AP-2 alpha (activating enhancer binding protein 2 alpha) (TFAP2A), transcript variant 1 aka TFAP2, AP-2, AP2TF, AP-2alpha, ACCESSION NUMBER NM_0032202; transcription factor AP-2 beta (activating enhancer binding protein 2 beta) (TFAP2B) aka MGC21381, AP-2B, AP2-B, ACCESSION NUMBER NM_0032213; transcription factor AP-2 gamma (activating enhancer binding protein 2 gamma) (TFAP2C) aka AP2-GAMMA, TFAP2G, hAP-2g, ERF1, ACCESSION NUMBER NM_0032223; transcription factor AP-2 delta (activating enhancer binding protein 2 delta) (TFAP2D) aka TFAP2BL1, ACCESSION NUMBER NM_1722383; transcription factor AP-2 epsilon (activating enhancer binding protein 2 epsilon) (TFAP2E) aka MGC49007, AP2E, ACCESSION NUMBER NM_1785482; transcription factor AP-4 (activating enhancer binding protein 4) (TFAP4) aka AP-4, ACCESSION NUMBER NM_0032231; transcription factor CP2 (TFCP2) aka LBP-1C, LSF, CP2, TFCP2C, SEF, ACCESSION NUMBER NM_0056533; transcription factor CP2-like 1 (TFCP2L1) aka LBP-9, LBP9, CRTR1, ACCESSION NUMBER NM_0145531; transcription factor Dp-1 (TFDP1) aka DP1, DRTF1, Dp-1, ACCESSION NUMBER NM_0071113; transcription factor Dp-2 (E2F dimerization partner 2) (TFDP2) aka Dp-2, DP2, ACCESSION NUMBER NM_0062861; transcription factor Dp family, member 3 (TFDP3) aka E2F-like, MGC161639, HCA661, CT30, ACCESSION NUMBER NM_0165212; transcription factor binding to IGHM enhancer 3 (TFE3) aka RCCP2, TFEA, ACCESSION NUMBER NM_0065213; transcription factor EB (TFEB) aka AlphaTFEB, TCFEB, ACCESSION NUMBER NM_0071621; transcription factor EC (TFEC), transcript variant 1 aka TCFEC, TFECL, ACCESSION NUMBER NM_0122522; transcription factor EC (TFEC), transcript variant 1 aka TCFEC, TFECL, ACCESSION NUMBER NM_0122522; TGFB-induced factor homeobox 1 (TGIF1), transcript variant 4 aka HPE4, MGC5066, MGC39747, TGIF, ACCESSION NUMBER NM_0032442; TGFB-induced factor homeobox 1 (TGIF1), transcript variant 5 aka HPE4, MGC5066, MGC39747, TGIF, ACCESSION NUMBER NM_1732091; TGFB-induced factor homeobox 1 (TGIF1), transcript variant 1 aka HPE4, MGC5066, MGC39747, TGIF, ACCESSION NUMBER NM_1706952; TGFB-induced factor homeobox 1 (TGIF1), transcript variant 1 aka HPE4, MGC5066, MGC39747, TGIF, ACCESSION NUMBER NM_1706952; TGFB-induced factor homeobox 1 (TGIF1), transcript variant 8 aka HPE4, MGC5066, MGC39747, TGIF, ACCESSION NUMBER NM_1748861; TGFB-induced factor homeobox 1 (TGIF1), transcript variant 2 aka HPE4, MGC5066, MGC39747, TGIF, ACCESSION NUMBER NM_1732071; TGFB-induced factor homeobox 2 (TGIF2), ACCESSION NUMBER NM_0218095; thyroid hormone receptor, alpha (erythroblastic leukemia viral (v-erb-a) oncogene homolog, avian) (THRA), transcript variant 1 aka NR1A1, THRA1, THRA2, ERB-T-1, ERBA, ERBA1, c-ERBA-1, AR7, MGC43240, MGC000261, EAR7, ACCESSION NUMBER NM_1993342; thyroid hormone receptor, alpha (erythroblastic leukemia viral (v-erb-a) oncogene homolog, avian) (THRA), transcript variant 2 aka NR1A1, THRA, THRA2, ERB-T-1, ERBA, ERBA1, c-ERBA-1, AR7, MGC43240, MGC000261, EAR7, ACCESSION NUMBER NM_0032504; thyroid hormone receptor, alpha (erythroblastic leukemia viral (v-erb-a) oncogene homolog, avian) (THRA), transcript variant 2 aka NR1A1, THRA1, THRA2, ERB-T-1, ERBA, ERBA1, c-ERBA-1, AR7, MGC43240, MGC000261, EAR7, ACCESSION NUMBER NM_0032504; thyroid hormone receptor, beta (erythroblastic leukemia viral (v-erb-a) oncogene homolog 2, avian) (THRB) aka MGC126110, THR1, THRB1, GRTH, ERBA-BETA, MGC126109, ERBA2, THRB2, NR1A2, ACCESSION NUMBER NM_0004613; T-cell leukemia homeobox 1 (TLX1) aka MGC163402, TCL3, HOX11, ACCESSION NUMBER NM_0055212; T-cell leukemia homeobox 2 (TLX2) aka HOX11L1, NCX, Enx, ACCESSION NUMBER NM_0161703; T-cell leukemia homeobox 2 (TLX2) aka HOX11L1, NCX, Enx, ACCESSION NUMBER NM_0161703; T-cell leukemia homeobox 3 (TLX3), aka RNX, MGC29804, HOX11L2, ACCESSION NUMBER NM_0210252; trinucleotide repeat containing 4 (TNRC4), aka MGC57297, CAGH4, BRUNOL1, CELF3, ERDA4, ACCESSION NUMBER NM_0071853; tumor protein p73 (TP73), aka P73, ACCESSION NUMBER NM_0054271; tumor protein p73-like (TP73L), aka TP63, EEC3, p63, B(p51B), p73H, p51, SHFM4, OFC8, RHS, KET, B(p51A), LMS, p73L, ACCESSION NUMBER NM_0037223; tetrapeptide repeat homeobox 1 (TPRX1), aka FLJ40321, TPRX, ACCESSION NUMBER NM_1984792; transcriptional regulating factor 1 (TRERF1), aka RP1-139D85, dJ139D85, HSA277276, RAPA, TReP-132, BCAR2, ACCESSION NUMBER NM_0335021; transcriptional regulating factor 1 (TRERF1), aka RP1-139D85, dJ139D85, HSA277276, RAPA, TReP-132, BCAR2, ACCESSION NUMBER NM_0335021; transcriptional regulating factor 1 (TRERF1), aka RP1-139D85, dJ139D85, HSA277276, RAPA, TReP-132, BCAR2, ACCESSION NUMBER NM_0335021; tripartite motif-containing 15 (TRIM15), transcript variant 2, aka ZNF178, ZNFB7, RNF93, ACCESSION NUMBER NM_0528121; tripartite motif-containing 15 (TRIM15), transcript variant 1, aka ZNF178, ZNFB7, RNF93, ACCESSION NUMBER NM_0332291; tripartite motif-containing 15 (TRIM15), aka ZNF178, ZNFB7, RNF93, ACCESSION NUMBER NM_0332292; tripartite motif-containing 16 (TRIM16), aka EBBP, ACCESSION NUMBER NM_0064703; tripartite motif-containing 22 (TRIM22), aka STAF50, RNF94, GPSTAF50, ACCESSION NUMBER NM_0060743; tripartite motif-containing 25 (TRIM25), aka Z147, ZNF147, EFP, RNF147, ACCESSION NUMBER NM_0050824; tripartite motif-containing 28 (TRIM28), aka FLJ29029, TIF1B, RNF96, TF1B, KAP1, ACCESSION NUMBER NM_0057622; tripartite motif-containing 29 (TRIM29), aka FLJ36085, ATDC, ACCESSION NUMBER NM_0121013; tripartite motif-containing 29 (TRIM29), aka FLJ36085, ATDC, ACCESSION NUMBER NM_0121013; trichorhinophalangeal syndrome I (TRPS1), aka MGC134928, GC79, ACCESSION NUMBER NM_0141122; TSC22 domain family, member 1 (TSC22D1), transcript variant 2, aka TSC22, TGFB114, RP11-269C232, DKFZp686O19206, MGC17597, ACCESSION NUMBER NM_0060222; TSC22 domain family, member 1 (TSC22D1), transcript variant 1, aka TSC22, RP11-269C232, DKFZp686O19206, TGFB114, MGC17597, ACCESSION NUMBER NM_1834221; TSC22 domain family, member 1 (TSC22D1), transcript variant 1, aka TSC22, RP11-269C232, DKFZp686O19206, TGFB114, MGC17597, ACCESSION NUMBER NM_1834221; TSC22 domain family, member 2 (TSC22D2), aka KIAA0669, TILZ4a, TILZ4c, TILZ4b, ACCESSION NUMBER NM_0147792; TSC22 domain family, member 3 (TSC22D3), transcript variant 2, aka hDIP, DIP, DKFZp313A1123, DSIPI, TSC-22R, GILZ, ACCESSION NUMBER NM_0040893; TSC22 domain family, member 3 (TSC22D3), transcript variant 2, aka hDIP, DIP, DKFZp313A1123, DSIPI, TSC-22R, GILZ, ACCESSION NUMBER NM_0040893; TSC22 domain family, member 3 (TSC22D3), transcript variant 3, aka hDIP, DIP, DKFZp313A1123, DSIPI, TSC-22R, GILZ, ACCESSION NUMBER NM_0010158811; TSC22 domain family, member 3 (TSC22D3), transcript variant 1, aka hDIP, DIP, DKFZp313A1123, DSIPI, TSC-22R, GILZ, ACCESSION NUMBER NM_1980572; TSC22 domain family, member 3 (TSC22D3), transcript variant 1, aka hDIP, DIP, DKFZp313A1123, DSIPI, TSC-22R, GILZ, ACCESSION NUMBER NM_1980572; TSC22 domain family, member 4 (TSC22D4), aka THG-1, ACCESSION NUMBER NM_0309353; teashirt zinc finger homeobox 1 (TSHZ1), aka TSH1, SDCCAG33, NY-CO-33, ACCESSION NUMBER NM_0057864; teashirt zinc finger homeobox 2 (TSHZ2), aka C20orf17, OVC10-2, TSH2, ZNF218, FLJ33887, DKFZp686K2480, ZABC2, ACCESSION NUMBER NM_1734854; teashirt zinc finger homeobox 3 (TSHZ3), aka ZNF537, TSH3, KIAA1474, ACCESSION NUMBER NM_0208562; tubby like protein 4 (TULP4), transcript variant 2, aka TUSP, RP3-442A171, KIAA1397, ACCESSION NUMBER NM_0010074661; tubby like protein 4 (TULP4), transcript variant 1, aka TUSP, RP3-442A171, KIAA1397, ACCESSION NUMBER NM_0202453; tubby like protein 4 (TULP4), transcript variant 1, aka TUSP, RP3-442A171, KIAA1397, ACCESSION NUMBER NM_0202453; ubinuclein 1 (UBN1), transcript variant 2, aka VT4, VT, ACCESSION NUMBER NM_0010795141; ubinuclein 1 (UBN1), transcript variant 2, aka VT4, VT, ACCESSION NUMBER NM_0010795141; upstream binding protein 1 (LBP-1a) (UBP1), aka LBP-1B, LBP1A, LBP1B, LBP-1a, DKFZp686L1745, ACCESSION NUMBER NM_0145173; ubiquitin-like with PHD and ring finger domains 1 (UHRF1), transcript variant 2, aka Np95, hNP95, MGC138707, ICBP90, RNF106, FLJ21925, ACCESSION NUMBER NM_0132823; UNC homeobox (UNCX), aka UNCX41, ACCESSION NUMBER NM_0010804611; upstream transcription factor 1 (USF1), transcript variant 2, aka HYPLIP1, FCHL1, MLTF, FCHL, UEF, MLTFI, ACCESSION NUMBER NM_2070051; upstream transcription factor 1 (USF1), transcript variant 1, aka HYPLIP1, FCHL1, MLTF, FCHL, UEF, MLTFI, ACCESSION NUMBER NM_0071223; upstream transcription factor 2, c-fos interacting (USF2), transcript variant 2, aka HP, ACCESSION NUMBER NM_2072911; upstream transcription factor 2, c-fos interacting (USF2), transcript variant 2, aka FIP, ACCESSION NUMBER NM_2072911; upstream transcription factor 2, c-fos interacting (USF2), transcript variant 1, aka HP, ACCESSION NUMBER NM_0033672; vav 1 guanine nucleotide exchange factor (VAV1), aka VAV, ACCESSION NUMBER NM_0054282; ventral anterior homeobox 1 (VAX1) aka MGC126745, MGC126743, ACCESSION NUMBER NM_1991311; ventral anterior homeobox 2 (VAX2) aka DRES93, ACCESSION NUMBER NM_0124761; vitamin D (1,25-dihydroxyvitamin D3) receptor (VDR), transcript variant 2 aka NR1I1, ACCESSION NUMBER NM_0010175351; vitamin D (1,25-dihydroxyvitamin D3) receptor (VDR), transcript variant 1 aka NR1I1, ACCESSION NUMBER NM_0003762; VENT homeobox homolog (*Xenopus laevis*) (VENTX) aka HPX42B, MGC119910, MGC119911, VENTX2, NA88A, ACCESSION NUMBER NM_0144682; vacuolar protein sorting 72 homolog (*S aka cerevisiae*) (VPS72) aka TCFL1, Swc2, YL1, CFL1, YL-1, ACCESSION NUMBER NM_0059971; visual system homeobox 1 (VSX1), transcript variant 1 aka RINX, PPD, KTCN, PPCD, ACCESSION NUMBER NM_0145884; visual system homeobox 1 (VSX1), transcript variant 1 aka RINX, PPD, KTCN, PPCD, ACCESSION NUMBER NM_0145884; visual system homeobox 1 (VSX1), transcript variant 2 aka RINX, PPD, KTCN, PPCD, ACCESSION NUMBER NM_1994251; Wilms tumor 1 (WT1), transcript variant A aka GUD, WT33, WAGR, WIT-2, ACCESSION NUMBER NM_0003783; Wilms tumor 1 (WT1), transcript variant D aka GUD, WT33, WAGR, WIT-2, ACCESSION NUMBER NM_0244263; X-box binding protein 1 (XBP1), transcript variant 1 aka TREB5, XBP2, ACCESSION NUMBER NM_0050802; X-box binding protein 1 (XBP1), transcript variant 2 aka TREB5, XBP2, ACCESSION NUMBER NM_0010795391; YEATS domain containing 4 (YEATS4) aka B230215M10Rik, GAS41, NUBI-1, YAF9, 4930573H17Rik, ACCESSION NUMBER NM_0065302; YY1 transcription factor (YY1) aka UCRBP, YIN-YANG-1, DELTA, NF-E1, ACCESSION NUMBER NM_0034033; zinc finger and BTB domain containing 17 (ZBTB17) aka ZNF60, pHZ-67, ZNF151, MIZ-1, ACCESSION NUMBER NM_0034431; zinc finger and BTB domain containing 25 (ZBTB25) aka KUP, ZNF46, ACCESSION NUMBER NM_0069772; zinc finger and BTB domain containing 38 (ZBTB38) aka FLJ31131, FLJ22332, FLJ35036, ACCESSION NUMBER NM_0010804121; zinc finger and BTB domain containing 48 (ZBTB48) aka pp 9964, HKR3, ACCESSION NUMBER NM_0053411; zinc finger CCCH-type containing 8 (ZC3H8) aka Fliz1, ZC3HDC8, ACCESSION NUMBER NM_0324941; zinc finger E-box binding homeobox 1 (ZEB1) aka NIL-2A, ZFHEP, ZEB, BZP, NIL-2-A, AREB6, MGC133261, TCF8, ZFHX1A, ACCESSION NUMBER NM_0307513; zinc finger E-box binding homeobox 2 (ZEB2) aka KIAA0569, SMADIP1, ZFHX1B, SIP1, SIP-1, ACCESSION NUMBER NM_0147952; zinc finger homeobox 3 (ZFHX3) aka ATBF1, ZFHX3, ATBT, ACCESSION NUMBER NM_0068853; zinc finger homeobox 4 (ZFHX4) aka ZHF4, ZFH4, ZFH-4, FLJ20980, FLJ16514, ACCESSION NUMBER NM_0247213; zinc finger protein 36, C3H type-like 1 (ZFP36L1) aka TIS11B, Berg36, cMG1, ERF1, BRF1, RNF162B, ERF-1, ACCESSION NUMBER NM_0049262; zinc finger protein 36, C3H type-like 2 (ZFP36L2) aka ERF2, ERF-2, TIS11D, RNF162C, BRF2, ACCESSION NUMBER NM_0068873; zinc finger protein 37 homolog (mouse) (ZFP37) aka FLJ38524, ACCESSION NUMBER NM_0034081; zinc finger protein 42 homolog (mouse) (ZFP42) aka REX1, ZNF754, ACCESSION NUMBER NM_1749003; zinc finger protein 95 homolog (mouse) (ZFP95), transcript variant 1 aka MGC33710, KIAA1015, ACCESSION NUMBER NM_0145692; zinc finger, CCCH-type with G patch domain (ZGPAT), transcript variant 3, aka RP4-583P153, GPATC6, ZC3H9, ZC3HDC9, MGC44880, KIAA1847, GPATCH6, ACCESSION NUMBER NM_1814851; zinc finger, CCCH-type with G patch domain (ZGPAT), transcript variant 2 aka RP4-583P153, GPATC6, ZC3H9, ZC3HDC9, MGC44880, KIAA1847, GPATCH6, ACCESSION NUMBER NM_1814841; zinc finger, CCCH-type with G patch domain (ZGPAT), transcript variant 1 aka RP4-583P153, GPATC6, ZC3H9, ZC3HDC9, MGC44880, KIAA1847, GPATCH6, ACCESSION NUMBER NM_0325272; zinc finger, CCCH-type with G patch domain (ZGPAT), transcript variant 1 aka RP4-583P153, GPATC6, ZC3H9, ZC3HDC9, MGC44880, KIAA1847, GPATCH6, ACCESSION NUMBER NM_0325273; zinc fingers and homeoboxes 1 (ZHX1), transcript variant 2, ACCESSION NUMBER NM_0072223; zinc fingers and homeoboxes 1 (ZHX1), transcript variant 2, ACCESSION NUMBER NM_0072223; zinc fingers and homeoboxes 1 (ZHX1), transcript variant 1, ACCESSION NUMBER NM_0010179261; zinc fingers and homeoboxes 2 (ZHX2) aka KIAA0854, ACCESSION NUMBER NM_0149433; zinc fingers and homeoboxes 3 (ZHX3) aka KIAA0395, TIX1, ACCESSION NUMBER NM_0150353; Zic family member 1 (odd-paired homolog, *Drosophila*) (ZIC1) aka ZNF201, ZIC, ACCESSION NUMBER NM_0034123; Zic family member 3 heterotaxy 1 (odd-paired homolog, *Drosophila*) (ZIC3) aka HTX1, ZNF203, HTX, ACCESSION NUMBER NM_0034132; zinc finger with KRAB and SCAN domains 1 (ZKSCAN1) aka MGC138429, 9130423L19Rik, KOX18, ZNF139, PHZ-37, ZNF36, ACCESSION NUMBER NM_0034391; zinc finger with KRAB and SCAN domains 2 (ZKSCAN2) aka ZNF694, ZSCAN31, FLJ23199, ACCESSION NUMBER NM_0010129813; zinc finger with KRAB and SCAN domains 3 (ZKSCAN3) aka ZSCAN13, ZF47, dJ874C201, ZFP306, KIAA0426, Zfp47, ZNF309, FLJ33906, ZNF306, ACCESSION NUMBER NM_024491; zinc finger with KRAB and SCAN domains 4 (ZKSCAN4) aka FLJ32136, ZNF307, p373c61, P1P373C6, ACCESSION NUMBER NM_0191103; zinc finger with KRAB and SCAN domains 5 (ZKSCAN5), transcript variant 2 aka ZFP95, FLJ39233, MGC33710, KIAA1015, ACCESSION NUMBER NM_1451022; zinc finger with KRAB and SCAN domains 5 (ZKSCAN5), transcript variant 2 aka ZFP95, FLJ39233, MGC33710, KIAA1015, ACCESSION NUMBER NM_1451022; zinc finger protein 117 (ZNF117) aka HPF9, ACCESSION NUMBER NM_0244981; zinc finger protein 117 (ZNF117) aka H-plk, MGC22613, HPF9, ACCESSION NUMBER NM_0158523; zinc finger protein 131 (ZNF131) aka pHZ-10, ACCESSION NUMBER NM_0034321; zinc finger protein 132 (ZNF132) aka MGC126390, pHZ-12, MGC126391, ACCESSION NUMBER NM_0034332; zinc finger protein 133 (ZNF133) aka ZNF150, pHZ-13, pHZ-66, ACCESSION NUMBER NM_0034343; zinc finger protein 134 (ZNF134) aka MGC141970, pHZ-15, MGC138499, ACCESSION NUMBER NM_0034352; zinc finger protein 135 (ZNF135) aka ZNF61, pT3, pHZ-17, ZNF78L1, ACCESSION NUMBER NM_0034362; zinc finger protein 137 (ZNF137) aka pHZ-30, MGC119991, MGC119990, ACCESSION NUMBER NM_0034382; zinc finger protein 140 (ZNF140) aka pHZ-39, ACCESSION NUMBER NM_0034402; zinc finger protein 142 (ZNF142), transcript variant 2 aka pHZ-49, ACCESSION NUMBER NM_0050812; zinc finger protein 155 (ZNF155), transcript variant 1 aka MGC161655, pHZ-96, ACCESSION NUMBER NM_0034452; zinc finger protein 155 (ZNF155), transcript variant 1 aka MGC161655, pHZ-96, ACCESSION NUMBER NM_0034452; zinc finger protein 155 (ZNF155), transcript variant 2 aka MGC161655, pHZ-96, ACCESSION NUMBER NM_1980891; zinc finger protein 157 (ZNF157) aka HZF22, ACCESSION NUMBER NM_0034463; zinc finger protein 165 (ZNF165) aka ZSCAN7, LD65, ACCESSION NUMBER NM_0034472; zinc finger protein 167 (ZNF167), transcript variant 2 aka FLJ12738, ZNF64, ZFP, ZNF448, ZKSCAN7, ACCESSION NUMBER NM_0251691; zinc finger protein 167 (ZNF167), transcript variant 1 aka FLJ12738, ZNF64, ZFP, ZNF448, ZKSCAN7, ACCESSION NUMBER NM_0186512; zinc finger protein 167 (ZNF167), transcript variant 1 aka FLJ12738, ZNF64, ZFP, ZNF448, ZKSCAN7, ACCESSION NUMBER NM_0186512; zinc finger protein 169 (ZNF169) aka MGC51961, ACCESSION NUMBER NM_1943202; zinc finger protein 174 (ZNF174), transcript variant 2 aka ZSCAN8, ACCESSION NUMBER NM_0010322921; zinc finger protein 174 (ZNF174), transcript variant 2, aka ZSCAN8, ACCESSION NUMBER NM_0010322921; zinc finger protein 174 (ZNF174), transcript variant 1, aka ZSCAN8, ACCESSION NUMBER NM_0034501; zinc finger protein 175 (ZNF175), aka OTK18, ACCESSION NUMBER NM_0071472; zinc finger protein 18 (ZNF18), aka KOX11, ZKSCAN6, HDSG1, ZNF535, Zfp535, ACCESSION NUMBER NM_1446802; zinc finger protein 187 (ZNF187), transcript variant 1, aka ZSCAN26, MGC2815, SRE-ZBP, ACCESSION NUMBER NM_0071511; zinc finger protein 187 (ZNF187), transcript variant 1, aka ZSCAN26, MGC2815, SRE-ZBP, ACCESSION NUMBER NM_0071511; zinc finger protein 189 (ZNF189), transcript variant 2, ACCESSION NUMBER NM_1979771; zinc finger protein 189 (ZNF189), transcript variant 1, ACCESSION NUMBER NM_0034522; zinc finger protein 19 (ZNF19), aka KOX12, MGC51021, ACCESSION NUMBER NM_0069613; zinc finger protein 192 (ZNF192), aka LD5-1, ZKSCAN8, ACCESSION NUMBER NM_0062982; zinc finger protein 193 (ZNF193), aka ZSCAN9, PRD51, ACCESSION NUMBER NM_0062993; zinc finger protein 197 (ZNF197), transcript variant 2, aka ZNF20, D3S1363E, VHLaK, P18, ZKSCAN9, ZNF166, ACCESSION NUMBER NM_0010248551; zinc finger protein 197 (ZNF197), transcript variant 1, aka ZNF20, D3S1363E, VHLaK, P18, ZKSCAN9, ZNF166, ACCESSION NUMBER NM_0069913; zinc finger protein 197 (ZNF197), transcript variant 1, aka ZNF20, D3S1363E, VHLaK, P18, ZKSCAN9, ZNF166, ACCESSION NUMBER NM_0069913; zinc finger protein 202 (ZNF202), aka ZKSCAN10, ACCESSION NUMBER NM_0034552; zinc finger protein 207 (ZNF207), transcript variant 2, aka DKFZp761N202, ACCESSION NUMBER NM_0010322932; zinc finger protein 207 (ZNF207), transcript variant 2, aka DKFZp761N202, ACCESSION NUMBER NM_0010322932; zinc finger protein 211 (ZNF211), transcript variant 1, aka C2H2-25, ZNF-25, ZNFC25, MGC131841, CH2H2-25, ACCESSION NUMBER NM_0063852; zinc finger protein 213 (ZNF213), aka ZKSCAN21, CR53, ACCESSION NUMBER NM_0042201; zinc finger protein 215 (ZNF215), aka BAZ2, ACCESSION NUMBER NM_0132501; zinc finger protein 217 (ZNF217), aka ZABC1, ACCESSION NUMBER NM_0065262; zinc finger protein 219 (ZNF219), aka ZFP219, ACCESSION NUMBER NM_0164231; zinc finger protein 232 (ZNF232), aka ZSCAN11, ACCESSION NUMBER NM_0145192; zinc finger protein 236 (ZNF236), aka ZNF236B, ZNF236A, ACCESSION NUMBER NM_0073451; zinc finger protein 238 (ZNF238), transcript variant 1, aka RP58, ZBTB18, TAZ-1, C2H2-171, ACCESSION NUMBER NM_2057681; zinc finger protein 238 (ZNF238), transcript variant 1, aka RP58, ZBTB18, TAZ-1, C2H2-171, ACCESSION NUMBER NM_2057681; zinc finger protein 238 (ZNF238), transcript variant 2, aka RP58, ZBTB18, TAZ-1, C2H2-171, ACCESSION NUMBER NM_0063523; zinc finger protein 24 (ZNF24), aka KOX17, ZSCAN3, RSG-A, ZNF191, Zfp191, ACCESSION NUMBER NM_0069651; zinc finger protein 256 (ZNF256), aka BMZF-3, BMZF3, ACCESSION NUMBER NM_0057732; zinc finger protein 263 (ZNF263), aka ZKSCAN12, FPM315, ACCESSION NUMBER NM_0057413; zinc finger protein 268 (ZNF268), aka HZF3, MGC126498, ACCESSION NUMBER NM_0034151; zinc finger protein 268 (ZNF268), aka HZF3, MGC126498, ACCESSION NUMBER NM_0034151; zinc finger protein 274 (ZNF274), transcript variant ZNF274c, aka ZKSCAN19, DKFZp686K08243, FLJ37843, HFB101, ZF2, ACCESSION NUMBER NM_1335021; zinc finger protein 274 (ZNF274), transcript variant ZNF274b, aka ZKSCAN19, DKFZp686K08243, FLJ37843, HFB101, ZF2, ACCESSION NUMBER NM_0163242; zinc finger protein 274 (ZNF274), transcript variant ZNF274b, aka ZKSCAN19, DKFZp686K08243, FLJ37843, HFB101, ZF2, ACCESSION NUMBER NM_0163242; zinc finger protein 277 (ZNF277), aka ZNF277P, ZNF277, NRIF4, ACCESSION NUMBER NMO219942; zinc finger protein 287 (ZNF287), aka MGC126536, ZKSCAN13, MGC141923 ACCESSION NUMBER NM_0206531; zinc finger protein 3 (ZNF3), transcript variant 2, aka HF12, KOX25, PP838, Zfp113, FLJ20216, A8-51, ACCESSION NUMBER NM_0329243; zinc finger protein 3 (ZNF3), transcript variant 2, aka HF12, KOX25, PP838, Zfp113, FLJ20216, A8-51, ACCESSION NUMBER NM_0329243; zinc finger protein 3 (ZNF3), transcript variant 1, aka HF12, KOX25, PP838, Zfp113, FLJ20216, A8-51, ACCESSION NUMBER NM_0177152; zinc finger protein 3 (ZNF3), transcript variant 1, aka HFaka12, KOX25, PP838, Zfp113, FLJ20216, A8-51, ACCESSION NUMBER NM_0177152; zinc finger protein 323

(ZNF323), transcript variant 1, aka ZNF20-Lp, dJ874C202, ZNF310P, FLJ23407, ACCESSION NUMBER NM_0308992; zinc finger protein 323 (ZNF323), transcript variant 2, aka ZNF20-Lp, dJ874C202, ZNF310P, FLJ23407, ACCESSION NUMBER NM_1459092; zinc finger protein 33A (ZNF33A), transcript variant 2, aka ZNF11A, KOX5, FLJ23404, KIAA0065, KOX2, NF11A, ZNF11, ZZAPK, ZNF33, KOX31, ACCESSION NUMBER NM_0069742; zinc finger protein 33A (ZNF33A), transcript variant 2, aka ZNF11A, KOX5, FLJ23404, KIAA0065, KOX2, NF11A, ZNF11, ZZAPK, ZNF33, KOX31, ACCESSION NUMBER NM_0069742; zinc finger protein 33B (ZNF33B), aka FLJ23327, MGC129696, KOX2, ZNF11B, KOX31, ACCESSION NUMBER NM_0069551; zinc finger protein 35 (ZNF35), aka Zfp105, HF aka10, HF10, ACCESSION NUMBER NM_0034203; zinc finger protein 367 (ZNF367), aka ZFF29, CDC14B, FLJ33970, ACCESSION NUMBER NM_1536952; zinc finger protein 37A (ZNF37A), transcript variant 1, aka KOX21, FLJ3472, ZNF37, ACCESSION NUMBER NM_0010070941; zinc finger protein 37A (ZNF37A), transcript variant 2, aka KOX21, FLJ3472, ZNF37, ACCESSION NUMBER NM_0034211; zinc finger protein 37A (ZNF37A), transcript variant 2, aka KOX21, FLJ3472, ZNF37, ACCESSION NUMBER NM_0034211; zinc finger protein 394 (ZNF394), aka FLJ12298, ZKSCAN14, ACCESSION NUMBER NM_0321642; zinc finger protein 396 (ZNF396), aka FLJ31213, ZSCAN14, ACCESSION NUMBER NM_1457561; zinc finger protein 397 (ZNF397), transcript variant 2, aka ZNF47, ZSCAN15, MGC13250, ACCESSION NUMBER NM_0323471; zinc finger protein 41 (ZNF41), transcript variant 2, aka MRX89, MGC8941, ACCESSION NUMBER NM_1533801; zinc finger protein 41 (ZNF41), transcript variant 1, aka MRX89; MGC8941, ACCESSION NUMBER NM_0071301; zinc finger protein 41 (ZNF41), transcript variant 1, aka MRX89, MGC8941, ACCESSION NUMBER NM_0071301; zinc finger protein 434 (ZNF434), aka FLJ20417, FLJ31901, MGC4179, ACCESSION NUMBER NM_0178102; zinc finger protein 444 (ZNF444), aka FLJ11137, EZF-2, EZF2, ZSCAN17, ACCESSION NUMBER NM_0183372; zinc finger protein 445 (ZNF445), aka ZNF168, MGC126535, ZKSCAN15, ACCESSION NUMBER NM_1814895; zinc finger protein 446 (ZNF446), aka ZKSCAN20, FLJ20626, ZSCAN30, ACCESSION NUMBER NM_0179082; zinc finger protein 449 (ZNF449), aka FLJ23614, ZSCAN19, ACCESSION NUMBER NM_1526954; zinc finger protein 45 (ZNF45), aka KOX5, ZNF13, ACCESSION NUMBER NM_0034252; zinc finger protein 483 (ZNF483), transcript variant 1, aka ZKSCAN16, ACCESSION NUMBER NM_1334641; zinc finger protein 483 (ZNF483), transcript variant 2, aka ZKSCAN16, ACCESSION NUMBER NM_0010071691; zinc finger protein 483 (ZNF483), transcript variant 2, aka ZKSCAN16, ACCESSION NUMBER NM_0010071691; zinc finger protein 496 (ZNF496), aka ZKSCAN17, MGC15548, NIZP1, ACCESSION NUMBER NM_0327521; zinc finger protein 498 (ZNF498), aka ZSCAN25, ACCESSION NUMBER NM_1451152; zinc finger protein 500 (ZNF500), aka ZKSCAN18, ACCESSION NUMBER NM_0216461; zinc finger protein 69 (ZNF69), aka MGC59928, Cos5, ACCESSION NUMBER NM_0219151; zinc finger protein 70 (ZNF70), aka Cos17, MGC48959, ACCESSION NUMBER NM_0219162; zinc finger protein 71 (ZNF71), aka EZFIT, ACCESSION NUMBER NM_0212163; zinc finger protein 80 (ZNF80), aka pT17, ACCESSION NUMBER NM_0071362; zinc finger protein 81 (ZNF81), aka FLJ44367, HFZ0, MRX45, ACCESSION NUMBER NM_0071372; zinc finger protein 83 (ZNF83), aka MGC33853, FLJ90585, HPF1, FLJ11015, ZNF816B, FLJ14876, ACCESSION NUMBER NM_0183002; zinc finger protein 85 (ZNF85), aka HTF1, MGC78566, HPF4, ACCESSION NUMBER NM_0034292; zinc finger protein 91 (ZNF91), aka HTF10, HPF7, ACCESSION NUMBER NM_0034302; zinc finger protein 92 (ZNF92), transcript variant 1, aka HPF12, HTF12, TF12, ACCESSION NUMBER NM_0071392; zinc finger protein 92 (ZNF92), transcript variant 2, aka HPF12, TF12, ACCESSION NUMBER NM_1526262; zinc finger protein 93 (ZNF93), aka ZNF505, HTF34, HPF34, TF34, ACCESSION NUMBER NM_0312182; zinc finger protein 93 (ZNF93), aka ZNF505, HTF34, HPF34, TF34, ACCESSION NUMBER NM_0312182; zinc finger, NFX1-type containing 1 (ZNFX1), aka MGC131926, FLJ39275, ACCESSION NUMBER NM_0210352; zinc finger, RAN-binding domain containing 2 (ZRANB2), transcript variant 2, aka DKFZp686J1831, ZIS1, FLJ41119, ZIS, DKFZp686N09117, ZNF265, ZIS2, ACCESSION NUMBER NM_0054553; zinc finger, RAN-binding domain containing 2 (ZRANB2), transcript variant 2, aka DKFZp686J1831, ZIS1, FLJ41119, ZIS, DKFZp686N09117, ZNF265, ZIS2, ACCESSION NUMBER NM_0054553; zinc finger and SCAN domain containing 1 (ZSCAN1), aka MGC104472, MZF-1, FLJ33779, ACCESSION NUMBER NM_1825723; zinc finger and SCAN domain containing 10 (ZSCAN10), aka ZNF206, FLJ14549, ACCESSION NUMBER NM_0328051; zinc finger and SCAN domain containing 12 (ZSCAN12), aka ZNF305, ZNF29K1, KIAA0426, dJ29K12, ZNF96, ZFP96, ACCESSION NUMBER NM_0010396431; zinc finger and SCAN domain containing 16 (ZSCAN16), aka ZNF392, ZNF435, FLJ22191, dJ265C243, ACCESSION NUMBER NMO252311; zinc finger and SCAN domain containing 18 (ZSCAN18), aka ZNF447, DKFZp586B1122, FLJ44152, MGC2427, MGC8682, MGC4074, FLJ12895, ACCESSION NUMBER NM_0239263; zinc finger and SCAN domain containing 2 (ZSCAN2), transcript variant 2, aka FLJ20595, ZFP29, ACCESSION NUMBER NM_0178944; zinc finger and SCAN domain containing 2 (ZSCAN2), transcript variant 3, aka FLJ20595, ZFP29, ACCESSION NUMBER NM_0010070721; zinc finger and SCAN domain containing 2 (ZSCAN2), transcript variant 3, aka FLJ20595, ZFP29, ACCESSION NUMBER NM_0010070721; zinc finger and SCAN domain containing 2 (ZSCAN2), transcript variant 1, aka FLJ20595, ZFP2, ACCESSION NUMBER NM_1818773; zinc finger and SCAN domain containing 20 (ZSCAN20), aka ZFP-31, ZNF31, KOX29, ZNF360, ACCESSION NUMBER NM_1452383; zinc finger and SCAN domain containing 22 (ZSCAN22), aka ZNF50, MGC126679, MGC138482, HKR2, ACCESSION NUMBER NM_1818461; zinc finger and SCAN domain containing 29 (ZSCAN29), aka MGC129895, MGC129894, FLJ35867, Zfp690, ZNF690, ACCESSION NUMBER NM_1524553; zinc finger and SCAN domain containing 4 (ZSCAN4), aka FLJ35105, ZNF494, MGC126789, MGC126787, ACCESSION NUMBER NM_1526771; zinc finger, X-linked, duplicated A (ZXDA), ACCESSION NUMBER NM_0071563; zinc finger, X-linked, duplicated A (ZXDA), ACCESSION NUMBER NM_0071563; ZXD family zinc finger C (ZXDC), aka FLJ13861, DKFZp547N024, ZXDL, MGC11349, ACCESSION NUMBER NM_0251123; ZXD family zinc finger C (ZXDC), transcript variant 2, aka DKFZp547N024, FLJ13861, ZXDL, MGC11349, ACCESSION NUMBER NM_0010406531. Additional genes with DNA binding domains that are useful in modifying the gene expression profiles of the cells of the present invention include: ADAMTS17, ADAMTS19, ADAR, AEBP2, AFF3, AHCTF1, AHDC1, AKAP8, AKAP8L, AKNA, ALX1, ANAPC2, ANKZF1, APTX, ARID2, ARID5B, ASCL1, ASCL3, ASCL4, ASH1L, ATMIN, ATOH7, ATOH8, ATXN7, BAZ2A, BAZ2B, BBX, BCL11A, BCL11B, BCL6B, BCLAF1, BDP1, BHLHB4, BHLHB5, BHLHB8, BMP2, BNC2, BOLA1, BOLA3, BPNT1, BRD9, BRPF1, BSX, C10orf140, C12orf28, C14orf106, C14orf43, C17orf49, C1orf25, C20orf194, CAMTA1, CAMTA2, CARHSP1, CASP8AP2, CASZ1, CBLL1, CBX2, CCDC71, CCDC79, CD36, CDC5L, CEBPZ, CENPB, CENPT, CHD1, CHD2, CHD6, CHD7, CHD9, CHRAC1, CIC, CIZ1, COPS2, COPS3, COPS4, CPSF4, CPSF4L, CPXCR1, CRAMP1L, CSDC2, CSDE1, CTCFL, CUL1, CUL2, CUL3, CUL4A, CUL4B, CUL5, CXXC1, DACH2, DEAF1, DEK, DEPDC1, DEPDC1B, DEPDC2, DEPDC4, DEPDC5, DEPDC6, DEPDC7, DHX34, DHX57, DMAP1, DMC1, DMRTA2, DNAJC1, DNAJC2, DNAJC21, DOT1L, DPF1, DPF2, DPF3, DR1, DSP, DUS3L, DUSP12, DVL1, DVL2, DVL3, DZIP1, DZIP1L, EBF1, EBF3, EBF4, EEA1, EIF3K, EMX2, EP400, ETV7, EWSR1, EXOC2, EZH1, EZH2, FAM170A, FAM171B, FAM44A, FARSA, FARSB, FBN1, FBXO41, FERD3L, FEZF1, FEZF2, FGD1, FIGLA, FIZZ, FOXD4L5, FOXD4L6, FOXO6, GABPB1, GBX1, GCM2, GFI1, GFI1B, GLIS1, GLIS2, GMEB2, GON4L, GPATCH8, GPR123, GPR155, GRHL1, GRHL2, GRHL3, GRLF1, GRM6, GTF2E2, GTF2F1, GTF2F2, GTF21RD2, GTF21RD2B, GTF3A, GZF1, H1F0, H1FOO, H1FX, HBP1, HELZ, HES1, HES2, HES5, HES4, HES5, HES7, HIC2, HILS1, HIST1H1A, HIST1H1B, HIST1H1C, HIST1H1D, HIST1H1E, HIST1H1T, HIVEP1, HIVEP2, HIVEP3, HKR1, HLA-DQB1, HLA-DQB2, HLA-DRB3, HMG1L1, HMG2L1, HMGA2, HMGB1, HMGB3, HMGB4, HMX3, HNF1A, HNF1B, HP1BP3, ID1, ID2, ID3, ID4, IFI16, IGHM, IKZF2, IKZF5, INF2, INSM1, INSM2, ISL1, JAZF1, JRKL, KAT5, KCMF1, KIAA0415, KIAA1549, KIAA1618, KIAA1683, KIAA2018, KIN, KLF13, KLF14, KLF8, KRTAP5-9, LARP1, LARP2, LARP4, LARP5, LARP6, LARP7, LBXCOR1, LCORL, LENG9, LEUTX, LGR4, LIN28, LIN28B, LYL1, MACF1, MAEL, MATR3, MAZ, MBD2, MBD3, MBD4, MBNL1, MBNL2, MBNL3, MECP2, MEIS1, MESP2, MET, MGMT, MIER1, MIER2, MIER3, MINK1, MIZF, MKR1VL MKRN2, MKRN3, MLL2, MLL3, MLLT1, MLLT3, MLXIP, MLXIPL, MNX1, MRPL28, MRRF, MSGN1, MST1R, MXD3, MXD4, MXI1, MYB, MYBL1, MYCL2, MYSM1, MYST1, MYST3, MYST4, NCOA1, NCOA2, NCOA3, NCOR1, NCOR2, NEUROD1, NEUROD4, NEUROD6, NEUROG2, NEUROG3, NFRKB, NHLH1, NHLH2, NKRF, NKX2-4, NKX2-6, NKX3-2, NKX6-3, NOC3L, NOC4L, NOTO, NPAS3, NPAS4, NUFIP1, NUPL2, OLIG1, OLIG3, OSR1, OSR2, OTOP3, OVOL2, PARP12, PATZL PAWR, PAX1, PAX2, PAX9, PBRM1, PCSK6, PDS5B, PDX1, PHB2, PHF20, PHF21A, PIP5K3, PKHD1, PKHD1L1, PLAGL1, PLEK, PLEK2, PLEKHA4, PLXNA1, PLXNA2, PLXNA3, PLXNA4, PLXNB1, PLXNB2, PLXNB3, PLXNC1, PLXND1, PMS1, POGK, POGZ, POLE3, POLE4, POLR2L, PPP1R10, PPP1R13L, PPP2R3B, PRB3, PRB4, PRDM10, PRDM12, PRDM13, PRDM14, PRDM15, PRDM4, PRDM5, PRDM6, PRDM7, PRDM8, PRDM9, PREB, PRKRIR, PRMT3, PROX2, PRR12, PRR3, PSMD11, PSMD12, PTCHD2, PTF1A, RAD51, RAG1, RAPGEF3, RAPGEF4, RAPGEF5, RAX2, RBAK, RBM10, RBM20, RBM22, RBM26, RBM27, RBM5, RBM6, RC3H1, RC3H2, RCOR1, RCOR3, RELL2, REPIN1, REST, RFX2, RFX4, RFX6, RFX7, RGS11, RGS6, RGS7, RGS9, RHOXF2, RHOXF2B, R10K2, RNASE2, RNF113A, RNF113B, RNF114, RNF125, RNF138, RNF166, RPA2, RPA4, RREB1, SALL3, SALL4, SCAPER, SCML4, SCRT2, SEMA4A, SETBP1, SETDB1, SETDB2, SF3A2, SF3A3, SHPRH, SKI, SKIL, SLC22A4, SLC26A10, SLC39A10, SLC4A10, SMARCA1, SMARCA5, SMARCC1, SMARCC2, SMARCE1, SNAIL SNAI2, SNAPC4, SOHLH1, SOHLH2, SORBS2, SOX12, SOX17, SOX3, SOX30, SP100, SP110, SP2, SP3, SP5, SP6, SP7, SP8, SRCAP, SREBF2, SSB, SSH1, SSH2, SSH3, SSRP1, SUZ12, TAL2, TAX1BP1, TCEAL8, TCF12, TCF20, TCF23, TCF24, TCF4, TCF7, TERF1, TERF2, TERF21P, TGIF2LX, TGIF2LY, THAP1, THAP10, THAP11, THAP2, THAP3, THAP4, THAP5, THAP6, THAP7, THAP8, THAP9, TIGD2, TIGD3, TIGD4, TIGD5, TIGD6, TIGD7, TIPARP, TOE1, TOX, TOX2, TOX3, TOX4, TP53, TP63, TRAFD1, TRIM23, TRIMS, TRIM32, TRIP, TRMT1, ITF1, TUB, TUT1, TWIST1, U2AF1, U2AF1L4, UBE2K, UBR4, UBTF, UNK, UNKL, USP39, VEZF1, VSX2, WDHD1, WHSC1, WIZ, WNT8B, XPA, YBX1, YBX2, YEATS2, YOD1, YY2, ZBED1, ZBED2, ZBED3, ZBED4, ZBP1, ZBTB1, ZBTB10, ZBTB11, ZBTB12, ZBTB16, ZBTB20, ZBTB22, ZBTB24, ZBTB26, ZBTB3, ZBTB32, ZBTB33, ZBTB34, ZBTB37, ZBTB39, ZBTB4, ZBTB40, ZBTB41, ZBTB43, ZBTB44, ZBTB45, ZBTB46, ZBTB47, ZBTB5, ZBTB6, ZBTB7A, ZBTB7B, ZBTB7C, ZBTB9, ZC3H10, ZC3H11A, ZC3H13, ZC3H14, ZC3H15, ZC3H18, ZC3H3, ZC3H4, ZC3H6, ZC3H7A, ZC3H7B, ZC3HAV1, ZCCHC11, ZCCHC6, ZDHHC11, ZDHHC19, ZFAT, ZFHX2, ZFP1, ZFP106, ZFP112, ZFP14, ZFP161, ZFP2, ZFP28, ZFP3, ZFP30, ZFP36, ZFP41, ZFP57, ZFP62, ZFP64, ZFP82, ZFP90, ZFP91, ZFP92, ZFPM1, ZFPM2, ZFR, ZFR2, ZFX, ZFY, ZFYVE20, ZFYVE26, ZIC2, ZIC4, ZIC5, ZIK1, ZIM2, ZIM3, ZMAT1, ZMAT2, ZMAT3, ZMAT4, ZMAT5, ZNF10, ZNF100, ZNF101, ZNF107, ZNF114, ZNF12, ZNF121, ZNF124, ZNF136, ZNF138, ZNF14, ZNF141, ZNF143, ZNF146, ZNF148, ZNF154, ZNF16, ZNF160, ZNF17, ZNF177, ZNF180, ZNF181, ZNF182, ZNF184, ZNF195, ZNF2, ZNF20, ZNF200, ZNF205, ZNF208, ZNF212, ZNF214, ZNF22, ZNF221, ZNF222, ZNF223, ZNF224, ZNF225, ZNF226, ZNF227, ZNF229, ZNF23, ZNF230, ZNF233, ZNF234, ZNF235, ZNF239, ZNF248, ZNF5, ZNF250, ZNF251, ZNF252, ZNF253, ZNF254, ZNF257, ZNF26, ZNF260, ZNF264, ZNF266, ZNF267, ZNF271, ZNF273, ZNF275, ZNF276, ZNF28, ZNF280A, ZNF280B, ZNF280C, ZNF280D, ZNF281, ZNF282, ZNF283, ZNF284, ZNF285A, ZNF286A, ZNF292, ZNF295, ZNF296, ZNF30, ZNF300, ZNF302, ZNF304, ZNF311, ZNF316, ZNF317, ZNF318, ZNF319, ZNF32, ZNF320, ZNF321, ZNF322A, ZNF322B, ZNF324, ZNF326, ZNF329, ZNF331, ZNF333, ZNF334, ZNF335, ZNF337, ZNF34, ZNF341, ZNF343, ZNF345, ZNF346, ZNF347, ZNF350, ZNF354A, ZNF354B, ZNF354C, ZNF358, ZNF362, ZNF365, ZNF366, ZNF382, ZNF383, ZNF384, ZNF385A, ZNF385B, ZNF385C, ZNF385D, ZNF391, ZNF395, ZNF398, ZNF404, ZNF407, ZNF408, ZNF409, ZNF410, ZNF414, ZNF415, ZNF416, ZNF417, ZNF418, ZNF419, ZNF420, ZNF423, ZNF425, ZNF426, ZNF428, ZNF429, ZNF43, ZNF430, ZNF431, ZNF432, ZNF433, ZNF436, ZNF438, ZNF439, ZNF44, ZNF440, ZNF441, ZNF442, ZNF443, ZNF451, ZNF454, ZNF460, ZNF461, ZNF462, ZNF467, ZNF468, ZNF470, ZNF471, ZNF473, ZNF474, ZNF479, ZNF48, ZNF480, ZNF484, ZNF485, ZNF486, ZNF487, ZNF488, ZNF490, ZNF491, ZNF493, ZNF497, ZNF501, ZNF502, ZNF503, ZNF506, ZNF507, ZNF509, ZNF510, ZNF511, ZNF512, ZNF512B, ZNF513, ZNF514, ZNF516, ZNF517, ZNF518A, ZNF518B, ZNF519, ZNF521, ZNF524, ZNF526, ZNF527, ZNF528, ZNF529, ZNF530, ZNF532, ZNF536, ZNF540, ZNF541, ZNF542, ZNF543, ZNF544, ZNF546, ZNF547, ZNF548, ZNF549, ZNF550, ZNF551, ZNF552, ZNF554, ZNF555, ZNF556, ZNF557, ZNF558, ZNF559, ZNF56, ZNF560, ZNF561, ZNF562, ZNF563, ZNF564, ZNF565, ZNF566, ZNF567, ZNF568, ZNF569, ZNF57, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF589, ZNF592, ZNF593, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF615, ZNF616, ZNF618, ZNF619, ZNF620, ZNF621, ZNF622, ZNF623, ZNF624, ZNF625, ZNF626, ZNF627, ZNF628, ZNF629, ZNF638, ZNF639, ZNF641, ZNF642, ZNF643, ZNF644, ZNF645, ZNF646, ZNF648, ZNF649, ZNF652, ZNF653, ZNF654, ZNF655, ZNF658, ZNF660, ZNF662, ZNF663, ZNF664, ZNF665, ZNF667, ZNF668, ZNF669, ZNF670, ZNF671, ZNF672, ZNF674, ZNF675, ZNF676, ZNF677, ZNF678, ZNF679, ZNF680, ZNF681, ZNF682, ZNF683, ZNF684, ZNF687, ZNF688, ZNF689, ZNF691, ZNF692, ZNF695, ZNF696, ZNF697, ZNF699, ZNF7, ZNF700, ZNF701, ZNF703, ZNF704, ZNF705A, ZNF705D, ZNF705F, ZNF706, ZNF707, ZNF708, ZNF709, ZNF710, ZNF711, ZNF713, ZNF714, ZNF716, ZNF717, ZNF718, ZNF720, ZNF721, ZNF725, ZNF733, ZNF734, ZNF738, ZNF74, ZNF740, ZNF746, ZNF747, ZNF749, ZNF750, ZNF75A, ZNF75D, ZNF76, ZNF761, ZNF763, ZNF764, ZNF765, ZNF766, ZNF768, ZNF77, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF786, ZNF787, ZNF788, ZNF789, ZNF79, ZNF790, ZNF791, ZNF792, ZNF793, ZNF799, ZNF8, ZNF800, ZNF804A, ZNF804B, ZNF805, ZNF808, ZNF821, ZNF823, ZNF826, ZNF827, ZNF828, ZNF829, ZNF830, ZNF831, ZNF833, ZNF834, ZNF835, ZNF836, ZNF837, ZNF839, ZNF84, ZNF841, ZNF843, ZNF845, ZNF846, ZNF90, ZNF98, ZNF99, ZRSR1, ZRSR2, ZSCAN21, ZSCAN23, ZSCAN5A, ZSCAN5B, ZSCAN5C, ZUFSP, ZXDB, and ZZZ3. All of these genes capable of modulating differentiated gene expression in a trans manner can include their splice variants and their analogs in other animal species many of which are readily found in the scientific literature or in online databases such as http://www.ihop-net.org/UniPub/iHOP/. Chromatin-modifying molecules include but are not limited to: K-demethylases including: KDM1, KDM2, KDM2A, KDM2B, KDM3A, KDM3B, KDM4, KDM4A, KDM4B, KDM4C, KDM4D, KDM5, KDM5A, KDM5B, KDM5C, KDM5D, KDM6A, and KDM6B; K-acetylytransferases including: KAT1, KAT2, KAT2A, KAT2B, KAT3, KAT3A, KAT3B, Kat4, KAT5, KAT6, KAT6A, KAT6B, KAT7, KAT8, KAT9, KAT10, KAT11, KAT12, KAT13A, KAT13B, KAT13C, and KAT13D; K-methyltransferases including: KMT1, KMT1A, KMT1B, KMT1C, KMT1D, KMT1E, KMT1F, KMT2, KMT2A, KMT2B, KMT2C, KMT2D, KMT2E, KMT2F, KMT2G, KMT2H, KMT3, KMT3A, KMT3B, KMT3C, KMT4, KMT5, KMT5A, KMT5B, KMT5C, KMT6, KMT7, and KMT8; members of the histone deacetylase (HDAC) family including: HDAC1, HDAC2, HDAC3, HDAC4, HDAC5, HDAC6, HDAC7, HDAC8, HDAC9, HDAC10, and HDAC11; members of the protein arginine methyltransferase (PRMT) family including: PRMT1, PRMT2, PRMT3, PRMT5, PRMT6, PRMT7, and PRMT8.

III. Driving Cell Proliferation

In addition to the expression of transcription factors (as described above), clonal or oligoclonal cells isolated according to the present invention may further be modified to artificially inhibit cell cycle inhibitory factors or to otherwise stimulate the cells to replicate. Any convenient modification for inducing cell replication may be employed, including those described in U.S. patent application Ser. No. 12/504,630, filed on Jul. 16, 2009 (US Patent Pub. No. 2010/0184033) entitled "Methods to accelerate the isolation of novel cell strains from pluripotent stem cells and cells obtained thereby" (incorporated herein by reference in its entirety). The artificial stimulation of the cell cycle may be made reversible through any convenient means, many of which are known in the art, including but not limited to, the use of inducible promoters, temperature sensitive promoters, RNAi, transient delivery of transcript as described in Transient Expression Vector Methods below, or the delivery of proteins into the cells (e.g., cell permeable proteins/peptides, e.g., as described in U.S. Pat. No. 7,928,186 entitled "Cell permeable bioactive peptide conjugates", incorporated herein by reference in its entirety), or by other means known in the art whereby factors are modulated that lead to an increase in cell proliferation, more preferably, in a bypass of cell cycle checkpoints. In certain embodiments, the means of overcoming cell cycle inhibition is specific to cell cycle control with relatively little effect on the differentiated state of the cell. By way of nonlimiting example, the retinoblastoma and p53 pathways may be inhibited, such as by the use of SV40 T-antigen, the adenovirus proteins E1A and E1B, or the papillomavirus proteins E6 and E7 or the cell cycle can be induced by other means such as by the up-regulation of CDK4 as is known in the art to override p16 cell cycle checkpoint. In certain embodiments, protein agents may be modified with protein transduction domains as described herein. By way of nonlimiting example, pluripotent stem cells such as ES, EG, EC, iPS or ED cells, including pluripotent stem cells not derived from a human embryo, are modified to transiently express CDK4 to facilitate expansion, that is to say proliferation of the cells before, during, or after the cells have been similarly modified to alter transcriptional regulators as described herein. Vectors used to introduce such agents to increase the proliferation rate of the cells can be in various forms known in the art and as described herein under the heading "Means of altering the expression of transcriptional regulators or cell cycle drivers" below.

IV. Means of Altering the Expression of Transcriptional Regulators or Cell Cycle Drivers:

Coding sequences for transcriptional regulators or cell cycle drivers may be transfected via a construct that leads to an inducible transcriptional regulator as described herein or cell cycle driver including but not limited to SV40 T-antigen or CDK4. Said vector may be designed to allow regulated expression such as a temperature or tetracycline in a tet-on or tet-off system as is known in the art. As a result, cells can be allowed to differentiate into an initial heterogeneity of cell types and then clonally or oligoclonally expanded under conditions wherein the transcriptional regulator and/or SV40 T-antigen or CDK4 genes are induced to stimulate the proliferation of the cells. When sufficient numbers of cells are obtained, the expression of the transcriptional regulator or SV40 T-antigen or CDK4 may be downregulated by reversing the steps that led to the activation of the gene, or by the physical removal of the gene or genes using recombinase technology as is well known in the art, such as through the use of the CRE recombinase system or the use of FLP recombinase.

In certain embodiments, the transcriptional regulator or SV40 T-antigen or CDK4 may be added during the first differentiation step or at the beginning of the clonal or oligoclonal expansion/propagation step. In certain embodiments, the import of the transcriptional regulator or SV40 T-antigen or CDK4 may be improved by delivery with liposomes, electroporation, or by permeabilization (see U.S. Patent Application No. 2005/0014258, incorporated by reference herein). For example, cells may be permeabilized using any standard procedure, such as permeabilization with digitonin or Streptolysin O. Briefly, cells are harvested using standard procedures and washed with PBS. For digitonin permeabilization, cells are resuspended in culture medium containing digitonin at a concentration of approximately 0.001-0.1% and incubated on ice for 10 minutes. For permeabilization with Streptolysin O, cells are incubated in Streptolysin O solution (see, for example, Maghazachi et al., FASEB J. 1997 Aug.; 11(10):765-74) for 15-30 minutes at room temperature. After either incubation, the cells are washed by centrifugation at 400×g for 10 minutes. This washing step is repeated twice by resuspension and sedimentation in PBS. Cells are kept in PBS at room temperature until use. Alternatively, the cells can be permeabilized while placed on coverslips to minimize the handling of the cells and to eliminate the centrifugation of the cells, thereby maximizing the viability of the cells.

Delivery of the transcriptional regulator, T-antigen, CDK4, or other proteins may be accomplished indirectly by transfecting transcriptionally active DNA into living cells (such as the cells of this invention) where the gene is expressed and the protein is made by cellular machinery. Similarly, only the RNA for these proteins may be expressed to reduce the likelihood of integration of the DNA. Several methods are known to one of skill in the art to effectively transfect plasmid DNA including calcium phosphate coprecipitation, DEAE dextran facilitated transfection, electroporation, microinjection, cationic liposomes and retroviruses, including, by way of nonlimiting example, Transfection Protocol 1 and Expression Vector Protocol 1 shown in Table I. Any method known in the art may be used with this invention to deliver the transcriptional regulator or T-antigen or CDK4 or other proteins into cells.

In certain embodiments, protein is delivered directly into cells of this invention, thereby bypassing the DNA transfection step. Several methods are known to one of skill in the art to effectively deliver proteins into cells including microinjection, electroporation, the construction of viral fusion proteins, and the use of cationic lipids.

Electroporation may be used to introduce foreign DNA into mammalian (Neumann, E. et al. (1982) EMBO J. 1, 841-845), plant and bacterial cells, and may also be used to introduce proteins (Marrero, M. B. et al. (1995) J. Biol. Chem. 270, 15734-15738; Nolkrantz, K. et al. (2002) Anal. Chem. 74, 4300-4305; Rui, M. et al. (2002) Life Sci. 71, 1771-1778). Cells (such as the cells of this invention) suspended in a buffered solution of the purified protein of interest are placed in a pulsed electrical field. Briefly, high-voltage electric pulses result in the formation of small (nanometer-sized) pores in the cell membrane. Proteins enter the cell via these small pores or during the process of membrane reorganization as the pores close and the cell returns to its normal state. The efficiency of delivery is dependent upon the strength of the applied electrical field, the length of the pulses, temperature and the composition of the buffered medium. Electroporation is successful with a variety of cell types, even some cell lines that are resistant to other delivery methods, although the overall efficiency is often quite low. Some cell lines remain refractory even to electroporation unless partially activated.

Microinjection was first used to introduce femtoliter volumes of DNA directly into the nucleus of a cell (Capecchi, M. R. (1980) Cell 22, 470-488) where it can be integrated directly into the host cell genome, thus creating an established cell line bearing the sequence of interest. Proteins such as antibodies (Abarzua, P. et al. (1995) Cancer Res. 55, 3490-3494; Theiss, C. and Meller, K. (2002) Exp. Cell Res. 281, 197-204) and mutant proteins (Naryanan, A. et al. (2003) J. Cell Sci. 116, 177-186) can also be directly delivered into cells via microinjection to determine their effects on cellular processes first hand. Microinjection has the advantage of introducing macromolecules directly into the cell, thereby bypassing exposure to potentially undesirable cellular compartments such as low-pH endosomes. All of these techniques can be used on the cells of this invention or the parent pluripotent cells.

Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the *Drosophila* Antennapedia (Antp) homeotic transcription factor. The small protein transduction domains (PTDs) from these proteins can be fused to other macromolecules, peptides or proteins to successfully transport them into a cell (Schwarze, S. R. et al. (2000) Trends Cell Biol. 10, 290-295). Sequence alignments of the transduction domains from these proteins show a high basic amino acid content (Lys and Arg) which may facilitate interaction of these regions with negatively charged lipids in the membrane. Secondary structure analyses show no consistent structure between all three domains. The advantages of using fusions of these transduction domains is that protein entry is rapid, concentration-dependent and appears to work with difficult cell types (Fenton, M. et al. (1998) J. Immunol. Methods 212, 41-48.). All of these techniques can be used on the cells of this invention or the parent pluripotent cells.

Liposomes have been rigorously investigated as vehicles to deliver oligonucleotides, DNA (gene) constructs and small drug molecules into cells (Zabner, J. et al. (1995) J. Biol. Chem. 270, 18997-19007; Feigner, P. L. et al. (1987) Proc. Natl. Acad. Sci. USA 84, 7413-7417). Certain lipids, when placed in an aqueous solution and sonicated, form closed vesicles consisting of a circularized lipid bilayer surrounding an aqueous compartment. These vesicles or liposomes can be formed in a solution containing the molecule to be delivered. In addition to encapsulating DNA in an aqueous solution, cationic liposomes can spontaneously and efficiently form complexes with DNA, with the positively charged head groups on the lipids interacting with the negatively charged backbone of the DNA. The exact composition and/or mixture of cationic lipids used can be altered, depending upon the macromolecule of interest and the cell type used (Feigner, J. H. et al. (1994) J. Biol. Chem. 269, 2550-2561). The cationic liposome strategy has also been applied successfully to protein delivery (Zelphati, O. et al. (2001) J. Biol. Chem. 276, 35103-35110). Because proteins are more heterogeneous than DNA, the physical characteristics of the protein such as its charge and hydrophobicity will influence the extent of its interaction with the cationic lipids. All of these techniques can be used on the cells of this invention or the parent pluripotent cells.

In certain embodiments Pro-Ject Protein Transfection Reagent may be used. Pro-Ject Protein Transfection Reagent utilizes a unique cationic lipid formulation that is noncytotoxic and is capable of delivering a variety of proteins into numerous cell types. The protein being studied is mixed with the liposome reagent and is overlayed onto cultured cells. The liposome:protein complex fuses with the cell membrane or is internalized via an endosome. The protein or macromolecule of interest is released from the complex into the cytoplasm free of lipids (Zelphati, O. and Szoka, Jr., F. C. (1996) Proc. Natl. Acad. Sci. USA 93, 11493-11498) and escaping lysosomal degradation. The noncovalent nature of these complexes is a major advantage of the liposome strategy as the delivered protein is not modified and therefore is less likely to lose its activity. All of these techniques can be used on the cells of this invention or the parent pluripotent cells.

In certain embodiments, the nuclear localization sequence of SV40 T-antigen may be modified. Protein transduction domains (PTD), covalently or non-covalently linked to the transcriptional regulator or T-antigen, allow the translocation of T-antigen across the cell membranes so the protein may ultimately reach the nuclear compartments of the cells. PTDs that may be fused with a Tag protein include the PTD of the HIV transactivating protein (TAT) (Tat 47-57) (Schwarze and Dowdy (2000) Trends Pharmacol. Sci. 21: 45-48; Krosl et al. (2003) Nature Medicine 9: 1428-1432). For the HIV TAT protein, the amino acid sequence conferring membrane translocation activity 5 corresponds to residues 47-57 (YGRKKRRQRRR) (SEQ ID NO: 1) (Ho et al. (2001) Cancer Research 61: 473-477; Vives et al. (1997) J. Biol. Chem. 272: 16010-16017). This sequence alone can confer protein translocation activity. The TAT PTD may also be the nine amino acids peptide sequence RKKRRQRRR (SEQ ID NO: 2) (Pauk et al. Mol Cells (2002) 30:202-8). The TAT PTD sequences may be any of the peptide sequences disclosed in Ho et al. (2001) Cancer Research 61: 473-477, including YARKARRQARR (SEQ ID NO: 3), YARZLAARQARA (SEQ ID NO: 4), YARAARRAARR (SEQ ID NO: 5), and RARAARRAARA (SEQ ID NO: 6). Other proteins that contain PTDs that may be fused with Tag include the herpes simplex virus 1 (HSV-1) DNA-binding protein VP22 and the Drosophila Antennapedia (Antp) transcription factor (Schwarze et al. (2000) Trends Cell Biol 10: 290-295). For Antp, amino acids 43-58 (RQIKIWFQNRRMKWM) (SEQ ID NO: 7) represent the protein transduction domain, and for HSV VP22 the PTD is represented by the residues DAATATRGRSAASRPTERPRAPARSASRPRRPVE (SEQ ID NO: 8). Alternatively, HeptaARG (RRRRRRR) (SEQ ID NO: 9) or artificial peptides that confer transduction activity may be used as a PTD. The PTD may be a PTD peptide that is duplicated or multimerized; including one or more of the TAT PTD peptide YARAAARQARA (SEQ ID NO: 10), or a multimer consisting of three of the TAT PTD peptide YARARARQARA (SEQ ID NO: 11). Techniques for making fusion genes encoding fusion proteins are well known in the art. The joining of various DNA fragments coding for different polypeptide sequences may be performed in accordance with conventional techniques. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & 20 Sons: 1992). A fusion gene coding for a purification leader sequence, such as a poly-(His) sequence, may be linked to the N-terminus or C-terminus of the desired portion of the Tag polypeptide or Tag-fusion protein allowing the fusion protein be purified by affinity chromatography using a metal resin. The purification leader sequence can then be subsequently removed by treatment with enterokinase to provide the purified Tag polypeptide (e.g., see Hochuli, E., et al (1987) J. Chromatog. 411:177-184). T antigen that is provided in the media may be excreted by another cell type. The other cell type may be a feeder layer, such as a mouse stromal cell layer transduced to express secretable T antigen. For example, T antigen may be fused to or engineered to comprise a signal peptide, or a hydrophobic sequence that facilitates export and secretion of the protein. Alternatively, T antigen, as a fusion protein covalently or linked to a PTD or as a protein or a fusion protein non-covalently linked to a PTD, may be added directly to the media. In certain embodiments, cell lines are created that secrete the TAT-T antigen fusion protein (see Derer, W. et al. (2001) The FASEB Journal, Published online). Conditioned medium from TAT-T antigen secreting cell lines is subsequently added to recipient cell lines to promote cell growth.

Transient Expression Vector Methods

The transcriptional regulator genes and/or cell cycle drivers of the present invention may be introduced into cells using vectors for transient expression known in the art. These include, without limitation, those described in Yu, J et al, 2009 Science 324: 797-801. In brief, Epstein-Barr virus, oriP/EBNA1 vectors are utilized for introducing reprogramming factors into human somatic cells, hES cells, iPS cells, or other pluripotent stem cells not derived from a human embryo. Efficiency can be improved through the use of linkers to coexpress combinations of transcriptional regulators or cell cycle drivers with the use of internal ribosome entry site 2 (IRES2).

V. Use of Oligonucleotide Transcription Factor Binding Site Decoys

The moduclation of transcription factor activity in cells can be achieved in a number of ways. One method for repressing or blocking the activity of a transcription factor is through the use of a transcription factor ODN decoys, which floods the cell with competing synthetic, transcription factor-specific consensus sequences. These synthetic decoys "compete" for binding of the transcription factor with consensus sequences in target genes. If delivered into the cell in sufficient concentrations these "decoys" thus have the potential to attenuate the binding of the transcription factor to promoter regions of target genes and thus attenuate the function of the transcription factor to regulate the expression of its target gene(s). Transfected at high concentrations these decoys have been reported in the literature to completely block transcription factor function and thus represent powerful research tools for studying gene regulation in the cells of the present invention.

ODN decoys are generally double-stranded synthetic phosphorothioate deoxynucleotides which range in length from 20-28 base pairs. The transcription factor consensus sequence occurs within the middle of the decoy sequence and is flanked by carefully selected base-pairs that allow for "optimized" transcription factor binding. ODN decoys may be labeled to allow imaging of the passage of the decoy into the cell (for example by fluorescence microscopy). ODN decoys may be produced using any convenient method and may be highly purified (e.g., by HPLC). In certain embodiments, matching mutant decoys are employed for each transcription factor, where the mutant decoys have the same flanking sequences but contain a disrupted consensus sequence in comparison with the (wild type) ODN decoy. Such controls may be employed to determine the specificity of the activity of the wild type ODN in affecting the growth, proliferation and/or differentiation of progenitor cells according to the present invention.

In certain embodiments, naked ODN decoys are added directly into the cell culture media along with the cells of interest, whereby the cells uptake the ODN decoys where they can have their transcription factor repressing effect. In other embodiments, ODN decoys are introduced into cells via transfection protocols as known in the art, e.g., using a cationic lipid to form a liposome complex before adding the ODN decoy/liposome mixture directly to the media (e.g., OligofectAMINE reagent, InVitrogen). Other transfection reagents and processes may also be employed (e.g., FuGene 6 from Roche Diagnostics and Superfect Transfection Reagent from Qiagen).

Cells are contacted to the ODN decoys for a time sufficient for repression of the specific transcription factor being targeted. This time may vary, where in certain embodiments the time ranges from hours to days or even weeks. Such parameters may be determined empirically. It may be necessary to re-apply the ODN decoys one or more additional time during the incubation period to achieve the desired effect. ODN decoy concentrations used may very, ranging from 0.1 µM to 5 mM or more.

References describing the use of ODN decoys include the following, which are incorporated herein byb reference: Morishita, R., Higaki, J., Tomita N. and Ogihara T. (1998) Application of transcription factor "decoy" strategy as means of gene therapy and study of gene expression in cardiovascular disease. Circ Res 82, 1023-1028; and Mann, M. J. and Dzau, V. J. (2000) Therapeutic applications of transcription factor decoy oligonucleotides. J. Clin. Invest. 106, 1071-1075.

VI. Cells and Methods

Human embryo-derived (hED) cells are cells that are derived from human embryos such as human preimplantation embryos, postimplantation embryos (such as aborted embryonic tissue) or pluripotent cell lines such as ES cell lines derived from human preimplantation embryos wherein the embryo may be destroyed in the process of producing the cells. Human zygotes, 2 or more cell premorula stage such as blastomeres, morula stage, compacting morula, blastocyst embryo inner cell masses, or cells from developing embryos all contain pluripotent cells. Such cells may be differentiated using techniques described herein to yield the initial heterogeneous population of cells of the first step. Because such culture conditions may induce the direct differentiation of the ED cells without allowing the propagation of a hES cell line, the probability of a hES cell contaminating the resulting clonal or oligoclonal cultures is reduced.

Human somatic cells reprogrammed to pluripotency such as hiPS cells are cells that have the properties of hES cells including the presence of pluripotency markers such as OCT4, SOX2, CDH2, NANOG, are capable of differentiating into the three primary germ layers, but which do not require the use of cells from a human embryo that was destroyed.

The clonal, oligoclonal, or polyclonal cells of this invention (made by the methods of this invention) may be used as the starting point for deriving various differentiated cell types. The single cells of this invention may be the precursors of any cell or tissue lineage.

There have been numerous attempts in the prior art to differentiate embryonic stem cells, embryonal carcinoma cells, iPS cells, and embryonic germ cells into various cell types. These methods have been only marginally successful due to problems with culturing and characterizing the complex mixture of cell types originating out of differentiating ES, EC, iPS and EG cell cultures in vitro. It has not been possible to preserve a pure culture of the differentiated cell type without having the culture overgrown with fibroblastic or other contaminating cell types. See, Ian Freshney, Culture of Animal Cells: A Manual of Basic Technique (5th Ed.), New York: Wiley Publishing, 2005, p. 217. The methods of the present application can overcome those difficulties due in part to the unexpected clonogenicity of ES, EC, EG, iPS and ED cell-derived cells.

In one embodiment of the application, any methods of differentiating, propagating, identifying, isolating, or using stem cells known in the art (for example, U.S. Pat. Nos. 6,953,799, 7,029,915, 7,101,546, 7,129,034, 6,887,706, 7,033,831, 6,989,271, 7,132,286, 7,132,287, 6,844,312, 6,841,386, 6,565,843, 6,908,732, 6,902,881, 6,602,680, 6,719,970, 7,112,437, 6,897,061, 6,506,574, 6,458,589, 6,774,120, 6,673,606, 6,602,711, 6,770,478, 6,610,535, 7,045,353, 6,903,073, 6,613,568, 6,878,543, 6,670,397, 6,555,374, 6,261,841, 6,815,203, 6,967,019, 7,022,666, 6,423,681, 6,638,765, 7,041,507, 6,949,380, 6,087,168, 6,919,209, 6,676,655, 6,761,887, 6,548,299, 6,280,718, 6,656,708, 6,255,112, 6,413,773, 6,225,119, 6,056,777, 6,962,698, 6,936,254, 6,942,995, 6,924,142, 6,165,783, 6,093,531, 6,379,953, 6,022,540, 6,586,243, 6,093,557, 5,968,546, 6,562,619, 5,914,121, 6,251,665, 6,228,640, 5,948,623, 5,766,944, 6,783,775, 6,372,262, 6,147,052, 5,928,945, 6,096,540, 6,709,864, 6,322,784, 5,827,740, 6,040,180, 6,613,565, 5,908,784, 5,854,292, 6,790,826, 5,677,139, 5,942,225, 5,736,396, 5,648,248, 5,610,056, 5,695,995, 6,248,791, 6,051,415, 5,939,529, 5,922,572, 6,610,656, 6,607,913, 5,844,079, 6,686,198, 6,033,906, 6,340,668, 6,020,197, 5,766,948, 5,369,030, 6,001,654, 5,955,357, 5,700,691, 5,498,698, 5,733,878, 5,384,331, 5,981,165, 6,464,983, 6,531,445, 5,849,686, 5,197,985, 5,246,699, 6,177,402, 5,488,040, 6,667,034, 5,635,386, 5,126,325, 5,994,518, 5,032,507, 5,847,078, 6,004,548, 5,529,982, 4,342,828, 7,105,344, 7,078,230, 7,074,911, 7,053,187, 7,041,438, 7,030,292, 7,015,037, 7,011,828, 6,995,011, 6,969,608, 6,967,102, 6,960,444, 6,929,948, 6,878,542, 6,867,035, 6,866,843, 6,833,269, 6,828,144, 6,818,210, 6,800,480, 6,787,355, 6,777,231, 6,777,230, 6,749,847, 6,737,054, 6,706,867, 6,677,306, 6,667,391, 6,642,048, 6,638,501, 6,607,720, 6,576,464, 6,555,318, 6,545,199, 6,534,052, RE37,978, 6,461,865, 6,432,711, 6,399,300, 6,372,958, 6,369,294, 6,342,356, 6,337,184, 6,331,406, 6,271,436, 6,245,566, 6,235,970, 6,235,969, 6,215,041, 6,204,364, 6,194,635, 6,171,824, 6,090,622, 6,015,671, 5,955,290, 5,945,577, 5,914,268, 5,874,301, 5,866,759, 5,865,744, 5,843,422, 5,830,510, 5,795,569, 5,766,581, 5,733,727, 5,725,851, 5,712,156, 5,688,692, 5,656,479, 5,602,301, 5,370,870, 5,366,888, and 5,332,672, and U.S. patent publication nos. 20060251642, 20060217301, 20060216820, 20060193769, 20060161996, 20060134784, 20060134782, 20060110828, 20060104961, 20060088890, 20060079488, 20060078989, 20060068496, 20060062769, 20060024280, 20060015961, 20060009433, 20050244969, 20050244386, 20050233447, 20050221483, 20050164377, 20050153425, 20050149998, 20050142102, 20050130147, 20050118228, 20050106211, 20050054102, 20050032207, 20040260079, 20040228899, 20040193274, 20040152189, 20040151701, 20040141946, 20040121464, 20040110287, 20040052768, 20040028660, 20040028655, 20040018178, 20040009595, 20030203003, 20030175680, 20030161819, 20030148510, 20030082155, 20030040111, 20030040023, 20030036799, 20030032187, 20030032183, 20030031657, 20020197240, 20020164307, 20020098584, 20020098582, 20020090714, 20020022259, 20020019018, 20010046489, 20010024824, and 20010016203) are used in combination with the methods of the present application in differentiating, propagating, identifying, isolating, or using directly differentiated derivatives of pluripotent stem cells such as ES, iPS, or embryo-derived cells (i.e., substituting ED cells for ES cells and directly differentiating the ED cells). In certain embodiments, only the initial differentiation procedure from the prior art is used in combination with the present methods. In certain embodiments, pluripotent stem cells such as ES, iPS, ED cells are directly differentiated in the manner disclosed in the art for ES cells, and following differentiation, cells are plated resulting in isolating a number of individual clonal cultures of cells or a number of individual clonal cultures of cells that are subsequently combined (oligoclonal), or a large number of individual clonal cultures of cells that are subsequently combined (polyclonal), wherein one or more of said cultures comprise cells with reduced differentiation potential than the starting pluripotent stem cells and wherein each of said individual cultures having only one cell may be propagated into a pure clonal culture of cells and wherein each of said individual cultures of cells having cells that are oligoclonal may be propagated into a larger number of cells, and one or more (or all) of said individual cultures of cells is propagated. To summarize, pluripotent stem cells such as ES, iPS, or ED cells are differentiated in step 1 of this invention according to the methods in the art and then the heterogenous population of cells so generated are cultured and propagated according to step 2 of this invention.

In another aspect of the invention, the methods of this invention result in the derivation of endodermal cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of mesodermal cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of ectodermal cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of neuroglial precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of hepatic cells or hepatic precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of chondrocyte or chondrocyte precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of myocardial or myocardial precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of gingival fibroblast or gingival fibroblast precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of pancreatic beta cells or pancreatic beta precursor cells from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of retinal precursor cells with from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of hemangioblasts from a single cell differentiated or in the process of differentiating from pluripotent stem cells such as, but not limited to, hES, hEG, hiPS, hEC or hED cells, including pluripotent stem cells not derived from a human embryo.

In another aspect of the invention, the methods of this invention result in the derivation of dermal fibroblasts with prenatal patterns of gene expression from a single cell differentiated or in the process of differentiating from pluripotent stem cells such as, but not limited to, hES, hEG, hiPS, hEC or hED cells, including pluripotent stem cells not derived from a human embryo.

Dermal fibroblasts derived according to the invention can be grown on a biocompatible substratum and engrafted on the neodermis of artificial skin covering a wound. Autologous keratinocytes may also be cultivated on a commercially available membrane such as Laserskin™ using the methods provided in this invention.

In another embodiment of the present invention, it is possible to simplify burn treatment further and to save lives of patients having extensive burns where sufficient autologous skin grafts cannot be repeatedly harvested in a short period of time. The dead skin tissue of a patient with extensive burns can be excised within about three to seven days after injury. The wound can be covered with any artificial skin, for example Integra™, or any dermal equivalent thereof, and dermal keratinocytes or dermal fibroblasts produced according to the methods of this invention or derived from said cells may thereafter be engrafted on the neodermis of the artificial skin, with resultant lower rejection and infection incidences.

VII. Isolation of Cells

In certain embodiments of the invention, specific cell binding moieties are employed to isolate one or more cell of interest from a heterogenous population of cells and/or for re-deriving clonal or oligo clonal cell lines from a population after one or more culturing steps. Any convenient method for using specific cell binding moieties to isolate one or more cell may be employed, where in many embodiments the specific cell binding moiety is an antibody that recognizes a specific cell surface molecule (e.g., a receptor, CD antigen, etc.). The isolation of cells can be achieved using any convenient method, including but not milited to, fluorescence activated cell sorting (FACS), solid phase isolation processes using substrate-bound antibodies (e.g., on plates, columns, beads, and the like). Exemplary bead based sorting reagents include para-magnetic beads coated with antigen specific antibodies, e.g., as provided by Miltenyi Biotech. In certain embodiments, the cells are isolated based on the presence or absence of multiple cell surface molecules (e.g., multiple CD antigens). For example, in FACS applications, the cells may be sorted according to the cell surface expression level of multiple different cell surface antigens to make clonal cell lines, e.g., by use of an automated cell deposition device (ACDU). The ability to isolate cells by virtue of their cell surface antigen profile can be very useful in many steps of the subject invention, for example in re-deriving clonal cell lines after prolonged culture periods.

VIII. Methods of Network Analysis.

A Bayesian network is a graphical model that encodes probabilistic relationships among variables of interest. When used in conjunction with statistical techniques, the graphical model has several advantages for data analysis. One, because the model encodes dependencies among all variables, it readily handles situations where some data entries are missing. Two, a Bayesian network can be used to learn causal relationships, and hence can be used to gain understanding about a problem domain and to predict the consequences of intervention. Three, because the model has both a causal and probabilistic semantics, it is an ideal representation for combining prior knowledge (which often comes in causal form) and data. Four, Bayesian statistical methods in conjunction with bayesian networks offer an efficient and principled approach for avoiding the overfitting of data.

IX. Exemplary Uses of the Cell Lines of the Present Invention

Uses in making novel cells for therapy and research and embedded in gels are provided.

Secreted Protein Isolation Protocol 1—Conditioned Medium

Cells are grown in either their normal propagation medium (West et al., 2008, *Regen Med* vol. 3(3) pp. 287-308) or the differentiation conditions described herein. To obtain conditioned medium on a smaller scale (typically 1-2 L or less), the cells are grown in monolayer cultures in T150, T175 or T225 flasks (Corning or BD Falcon) in a 37° C. incubator with 10% $CO_2$ atmosphere. For larger volume medium collections, the cells are typically grown either in 2 L roller bottles, on microcarrier suspensions (porous such as Cytodex varieties from Sigma-Aldrich, St. Louis, Mo., or non-porous such as from SoloHill Engineering, Ann Arbor, Mich.) in spinner flasks or other bioreactors, or in hollow fiber cartridge bioreactors (GE Healthcare, Piscataway, N.J.). Prior to conditioned medium collection, the cultures are rinsed twice with PBS and then incubated for 2 hours at 37° C. in the presence of serum-free medium (e.g., the same basal medium as described herein for the propagation or differentiation of the cells) in order to remove fetal serum proteins. The serum-free medium is then removed and replaced with fresh medium, followed by continued culture at 37° C. for 24-48 hours.

The culture-conditioned medium is then collected by separation from the cell-bound vessel surface or matrix (e.g., by pouring off directly or after sedimentation) and processed further for secreted protein concentration, enrichment or purification. As deemed appropriate for the collection volume, the culture medium is first centrifuged at 500 to 10,000×g to remove residual cells and cellular debris in 15 or 50 ml centrifuge tubes or 250 ml bottles. It is then passaged through successive 1 μm or 0.45 μm and 0.2 μm filter units (Corning) to remove additional debris, and then concentrated using 10,000 MW cutoff ultrafiltration in a stirred cell or Centricon centrifuge filter (Amicon-Millipore) for smaller volumes, or using a tangential flow ultrafiltration unit (Amicon-Millipore) for larger volumes. The retained protein concentrate is then dialyzed into an appropriate buffer for subsequent purification of specific proteins, and further purified using a combination of isoelectric focusing, size exclusion chromatography, ion exchange chromatography, hydrophobic or reverse phase chromatography, antibody affinity chromatography or other well-known methods appropriate for the specific proteins. During the various steps in the purification process, collection fractions are tested for the presence and quantity of the specific secreted protein by ELISA. The purified proteins are then kept in solution or lyophilized and then stored at 4 or minus 20-80° C.

Secreted Protein Isolation Protocol 2—Urea-Mediated Protein Extraction

In the case of some secreted proteins, interactions with the cell or ECM components may reduce the simple diffusion of factors into the medium as described above in Secreted Protein Isolation Protocol 1. A simple comparison of the yield in the two protocols will suffice to determine which protocol provides the highest yield of the desired factors. In the case of Secreted Protein Isolation Protocol 2, a low concentration of urea is added to facilitate the removal of factors. Urea extractions can be performed two days subsequent to feeding. On the second day, cell monolayers in T-150 cell culture flasks are rinsed twice with CMF-PBS and then incubated for two hours at 37° C. in the presence of serum-free medium. The rinse with CMF-PBS and the incubation in serum-free medium together aid in the removal of fetal serum proteins from the surface of the cells. The serum-free medium is then removed and 10 ml/T150 of freshly made 200 mM urea in CMF-PBS is added. The flasks are then placed on a rocker at 37° C. for 6.0 hours. The urea solution is then removed and immediately frozen at −70° C.

Extracellular Matrix Isolation Protocol 1—Doc-Mediated Preparation

Extracellular matrix proteins can be extracted using the method of Hedman et al, 1979 (Isolation of the pericellular matrix of human fibroblast cultures. J. Cell Biol. 81: 83-91). Cell layers are rinsed three times with CMF-PBS buffer at ambient temperature and then washed with 30 mL of 0.5% sodium deoxycholate (DOC), 1 mM phenylmethylsulfonylfluride (PMSF, from 0.4M solution in EtOH), CMF-PBS buffer 3×10 mM on ice while on a rocking platform. The flasks are then washed in the same manner with 2 mM Tris-HCl, pH 8.0 and 1 mM PMSF 3×5 mM The protein remaining attached to the flask is then removed in 2 mL of gel loading buffer with a rubber policeman.

Cellular and Acellular Formulations

In certain aspects, the represent invention includes the production and use of cellular and acellular formulations that find use in therapeutic applications, where the formulations include one or more cell according to the subject invention and/or one or more cellular product produced from one or more cell according to the subject invention. Any convenient method for generating cellular or acellular formulations, e.g., for therapeutic use (e.g., either topically or internally) may be employed.

Exemplary formulations include cellular and acellular formulations that provide for the slow release of components in a subject or patient, e.g., at a specific site where the components can provide a therapeutic benefit. Such formulations are described, for example, in US Patent Publications 20090105193 (entitled "Crosslinked compounds and methods of making and using thereof"), 20090117078 (entitled "Crosslinked compounds and methods of making and using thereof"), and 20080025950 (entitled "Modified macromolecules and associated methods of synthesis and use"), each of which is incorporated herein by reference. These patent publications describe macromolecular compounds that have been modified in order to facilitate crosslinking by introduction of at least one hydrazide-reactive group and/or aminooxy-reactive group, and methods of making and using in therapeutic applications (e.g., for scar-free wound healing, for delivering bioactive agents or living cells to a subject, for preventing adhesion after a surgical procedure or for bone and cartilage repair). The macromolecule can be an oligonucleotide, a nucleic acid, a polypeptide, a lipid, a glycoprotein, a glycolipid, a polysaccharide, a protein or a synthetic polymer (e.g., a glycosaminoglycan like hyaluronan). Natural extracellular matrix proteins and chemically modified versions thereof are used in many embodiments.

Any of the macromolecular compounds and compositions described in the above patent applications can include one or more pharmaceutically-active agent. The resulting pharmaceutical composition can provide a system for sustained, continuous delivery of biologically-active agents, including those produced by the cells of the present invention, to tissues adjacent to or distant from the application site. The biologically-active agent is capable of providing a local or systemic biological, physiological or therapeutic effect in the biological system to which it is applied. For example, the agent can act to enhance cell growth and tissue regeneration, control tumor growth, and enhance bone or cartilage growth, among other functions. Exemplary substances or metabolic precursors derived from the cells of the present invention that are capable of promoting growth and survival of cells and tissues, or augmenting the functioning of cells, include but are not limited to: a nerve growth promoting substance such as a nerve growth factor, and the like; a hard or soft tissue growth promoting agent such as fibronectin (FN), human growth hormone (HGH), a colony stimulating factor, bone morphogenic protein (BMP), platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF). Additional non-cell derived components may also be present in the formulations, for example: dried bone material, and the like; antineoplastic agents such as methotrexate, 5-fluorouracil, adriamycin, vinblastine, cisplatin, tumor-specific antibodies conjugated to toxins, tumor necrosis factor, and the like.

The formulations can contain one or a combination of cells according to the present invention and/or products from one or a combination of cells according to the present invention, e.g., secreted factors present in culture supernatants. In certain embodiments, therapeutic formulations, e.g., slow release formulations, are prepared by combining the macromolecular compositions described in this section with the cellular factors and components isolated according to the Secreted Protein Isolation Protocol 1 (Conditioned medium), Secreted Protein Isolation Protocol 2 (Urea-mediated protein extraction) and Extracellular Matrix Isolation Protocol 1 (DOC-Mediated Preparation) detailed above.

Systems and Kits

Also provided by the subject invention are systems and kits that include the cells of the invention for use in various applications, as described herein. The systems and kits may further include reagents and materials for the propagation and use of the cells for research and/or therapeutic applications as described herein.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the cells and method for producing the same are specifically embraced by the present invention and are disclosed herein just as if each and every combination was individually and explicitly disclosed. In addition, all sub-combinations of the factors (e.g., transcription factors) listed in the embodiments describing such variables are also specifically embraced by the present invention and are disclosed herein just as if each and every such sub-combination of factors was individually and explicitly disclosed herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Novel Clonal Human Progenitors Derived from hES Cells that Constitutively Express the Transcription Factor OCT4

Clonal progenitor lines from iPS cells constitutively expressing POU class 5 homeobox 1 (POU5F1), transcript variant 1, aka OTF4, OCT3, OCT4, MGC22487, OTF3, ACCESSION NUMBER NM_002701.4 were created using Reprogramming Protocol 1 described herein (See Table I). An iPS clone that did not silence OCT4 following differentiation was identified and used to generate clonal progenitors as described herein. In incubators using 5% oxygen, the iPS colonies were grown to confluence, then differentiated in DMEM supplemented with 10% FBS or endothelial MV2 media (Promocell) for seven days. The cells were then replated and expanded in four different media on gelatin coated plates. The latter four media used were: DMEM supplemented with 10% FBS, Promocell MV2 endothelial media, Promocell smooth muscle cell media, and Promocell skeletal muscle media. As the cells approached confluence, they were designated candidate cultures, and were plated at clonal densities or 500-2,500 cells/15 cm tissue culture plates coated with gelatin and incubated in 5% oxygen. After 14 days, visibly distinct colonies were identified and isolated using cloning cylinders with trypsin and scaled up in 24, 12, 6 well and subsequently larger flasks. After 6 passages, the cells were synchronized for five days in confluence in media with 10% of the normal mitogens and RNA was isolated for use in gene expression microarray analysis using Illumina bead arrays. The cell lines subjected to microarray analysis where the initial iPS cells were differentiated in DMEM supplemented with 10% FBS and later isolated from candidate cultures cultured in Promocell skeletal muscle medium were: 14SKEL7X, and 14SKEL18X. The cell lines subjected to microarray analysis where the initial iPS cells were differentiated in Promocell MV2 endothelial media and later isolated from candidate cultures cultured in Promocell skeletal muscle medium were: 14SKEL12Z, 14SKEL14Z, 14SKEL15Z, 14SKEL20Z, and 14SKEL24Z. The cell lines subjected to microarray analysis where the initial iPS cells were differentiated in DMEM supplemented with 10% FBS and later isolated from candidate cultures cultured in Promocell MV2 endothelial media were: 14PEND2X, 14PEND11X, 14PEND12X, 14PEND14X, 14PEND20X, 14PEND23X and 14PEND24X. The cell lines subjected to microarray analysis where the initial iPS cells were differentiated in DMEM supplemented with 10% FBS and later isolated from candidate cultures cultured in Promocell smooth muscle media were: 14SMOO2X and 14SMOO8X. The cell line subjected to microarray analysis where the initial iPS cells were differentiated in DMEM supplemented with 10% FBS and later isolated from candidate cultures cultured in Promocell MV2 endothelial media was: 14PEND17Z.

As can be seen in FIG. 1, all of these clonal progenitor cell lines continued to constitutively express OCT4 at levels comparable to hES and hiPS cell lines. As can be seen in Table II, where relative fluorescence units (RFUs) of greater than 100 are considered positive, and where genes are ranked with highest differential expression listed first, the clonal progenitors expressed a diverse array of differentiated patterns of gene expression and showed that many unique phenotypes were captured using the present invention.

It is noted here that the progenitor cell lines described herein have the unique gene expression patterns markers shown in Table II. These clonal progenitor cell lines can thus be identified and distinguished from other clonal progenitors in their unique pattern of most infrequently-expressed genes, that is with high filter scores as shown in Table II. For example, such progenitor cell lines can be identified from other cell types by using the top 5, top 6, top 7, top 8, top 9, top 10, up to the top 20 or more genes listed for each cell line. Thus, one aspect of the subject invention includes progenitor cell lines having the unique pattern of gene expression for the top 5 to top 20 or more genes as shown in Table II.

Figure 2:
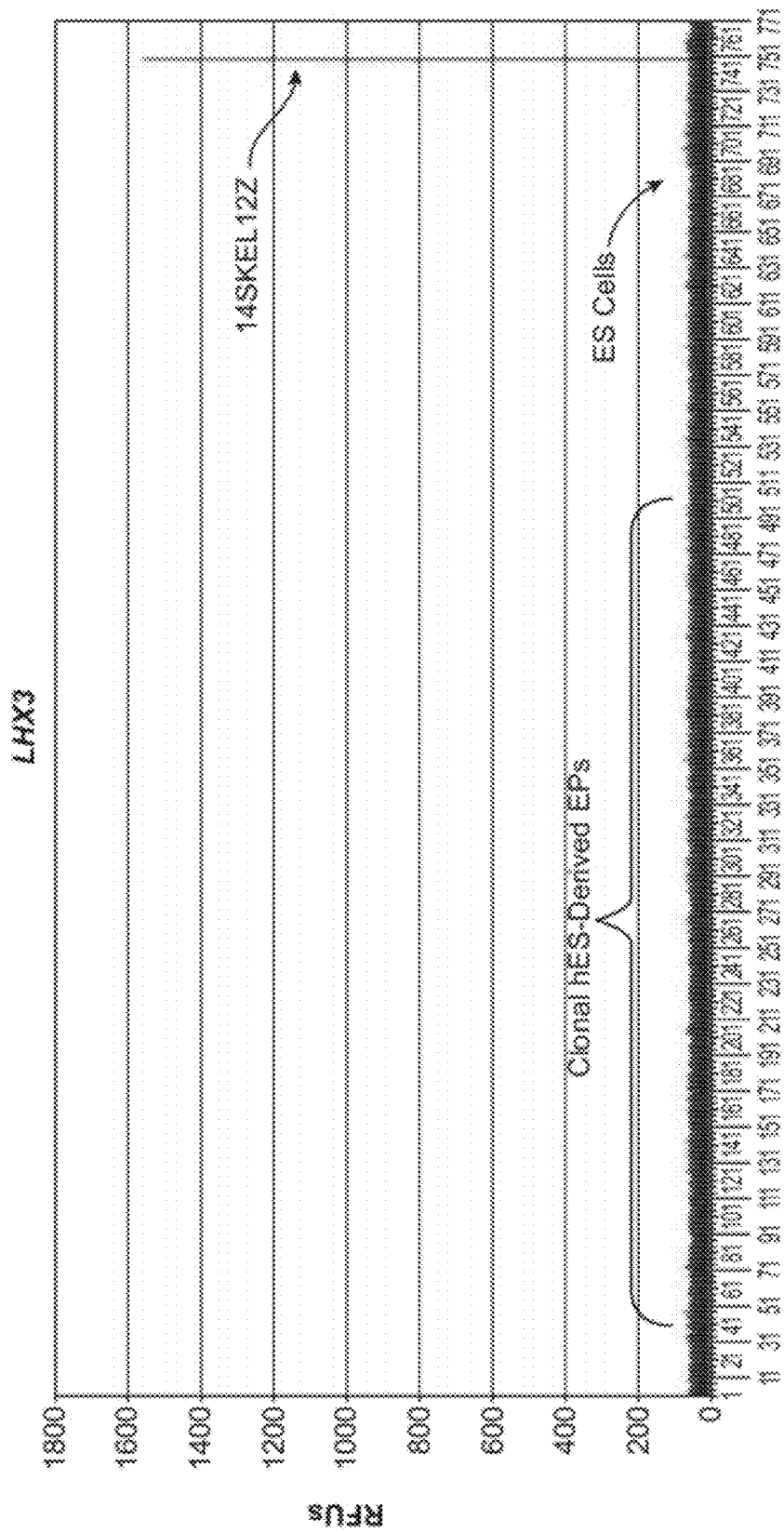
FIG. 2: Graph of microarray data for LHX3 isoform 1 and RESP18 transcript levels in diverse clonal progenitorprogenitors, cultured somatic cell types, hES cells, and hiPS cells as well as clonal progenitors made from hiPS cells constitutively expressing the transcriptional regulator OCT4.
Figure 2:
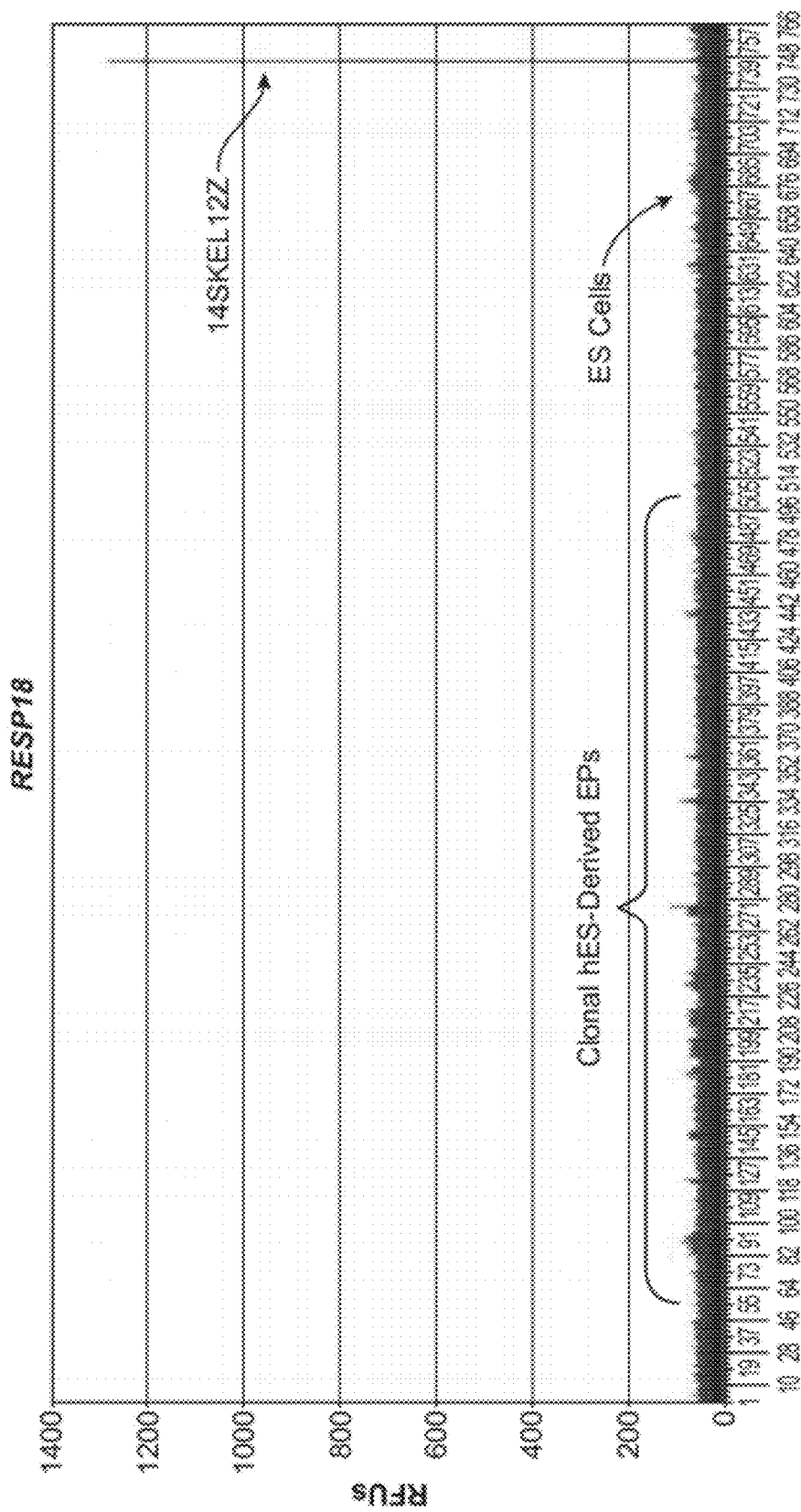

By way of example, the cell line 14SKEL12Z can be seen in Table II to have the gene LHX3 (Accession number NM_178138.2) expressed at 1716 RFUs which is 29-fold higher than the average of 253 other lines, and a filter score of 252 indicating that it was the only line in 253 lines expressing the gene. This can be seen in FIG. 2. The line 14SKEL12Z also expressed the relatively rare transcript RESP18 (Accession number NM_001007089.2). The expression of both LHX3 and RESP18 as well as PITX1 and PITX2 is consistent with progenitors of the anterior and intermediate lobes of the pituitary. Such purified pituitary cells have not been previously produced from pluripotent stem cells and are useful in research and therapy wherein said cells are transplanted to restore pituitary function impaired by disease.

Figure 3:
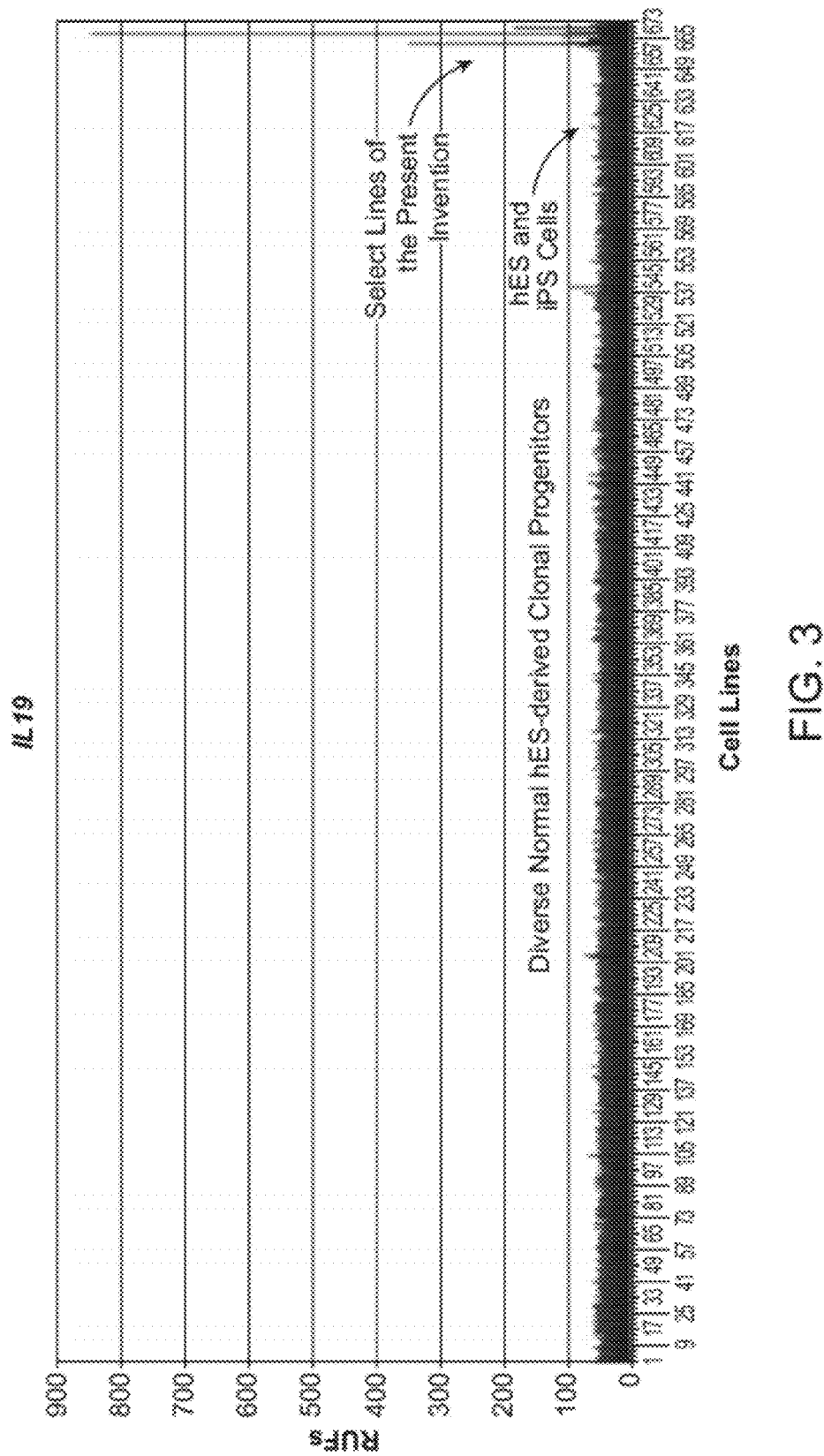
FIG. 3: Microarray gene expression analysis of the expression of IL19 (Accession number NM_013371.2) in diverse normal cultured cell types, diverse normal clonal progenitor cell lines derived from hES cells, hES and iPS cells, and select cell lines of the present invention including 14SMOO8X, 14PEND11X, and 14PEND20X.

In addition, other useful cell types include those expressing IL19 as shown in FIG. 3 and Table II. Microarray gene expression analysis of the expression of IL19 (Accession number NM_013371.2) in diverse normal cultured cell types, diverse normal clonal progenitor cell lines derived from hES cells, hES and iPS cells, and select cell lines of the present invention showed that pluripotent rarely if ever express IL19, but that the clonal cell lines of the present invention 14SMOO8X, 14PEND11X, and 14PEND20X express the rare gene. Cells expressing the gene can be used to manufacture the protein in vivo for therapeutic effect such as to provide a function normally provided by monocytes. It can bind the IL20 receptor complex and lead to the activation of the signal transducer and activator of transcription 3 (STAT3). It can be used to up-regulate the expression of IL6 and TNF-alpha and induce apoptosis, or used to manufacture the secreted protein as described in the sections above titled Secreted Protein Isolation Protocol 1 or Secreted Protein Isolation Protocol.

Figure 4:
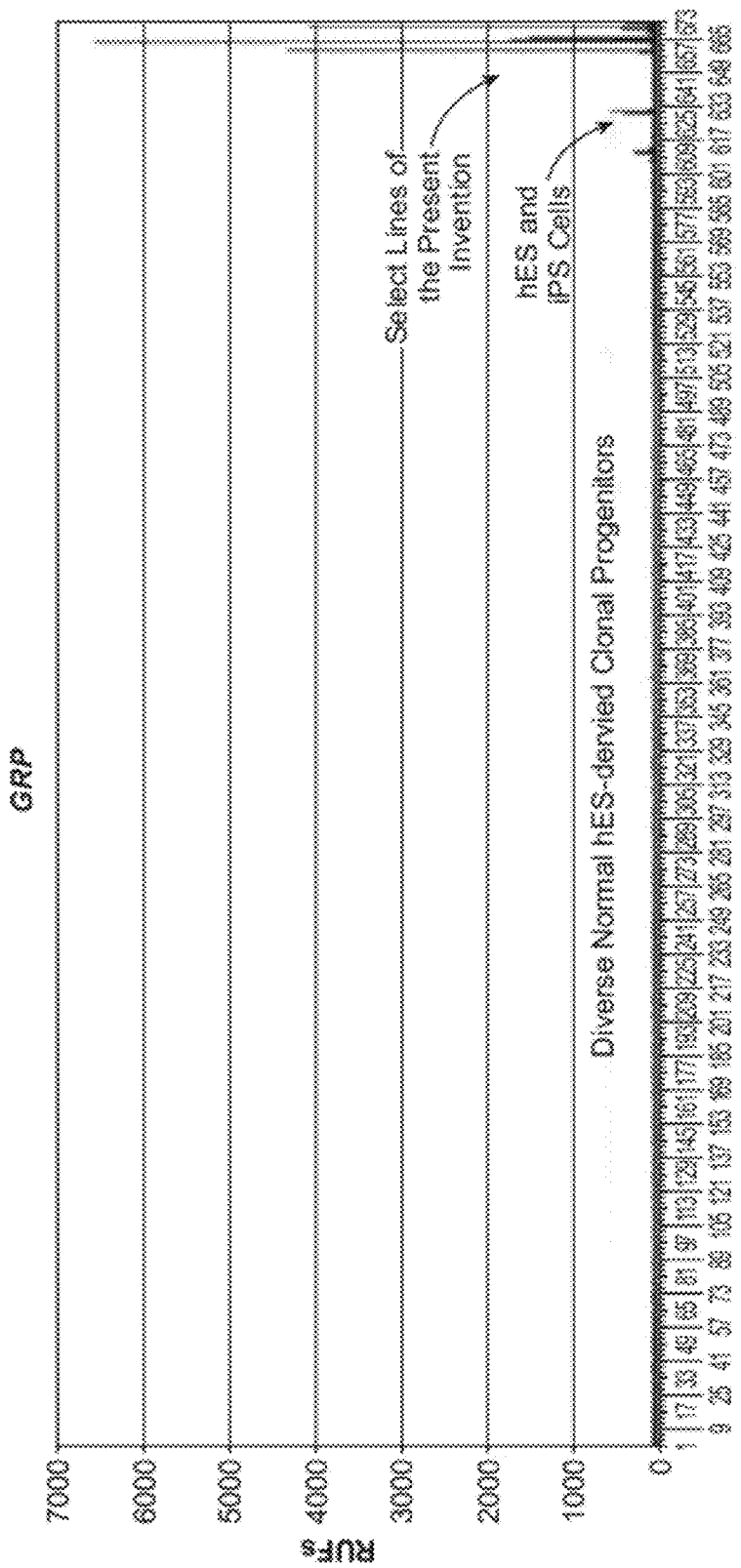
FIG. 4: Microarray gene expression analysis of the expression of Gastrin-releasing peptide (GRP) (Accession number NM_001012513.1) in diverse normal cultured cell types, diverse normal clonal progenitor cell lines derived from hES cells, hES and iPS cells, and select cell lines of the present invention including 14SKEL14Z, 14SKEL15Z, 14SKEL20Z, 14SKEL24Z, and 14PEND20X.

In addition, other useful cell types include those expressing gastrin-releasing peptide RNA as shown in FIG. 4 and Table II. Microarray gene expression analysis of the expression of Gastrin-releasing peptide (GRP) (Accession number NM_001012513.1) in diverse normal cultured cell types, diverse normal clonal progenitor cell lines derived from hES cells, hES and iPS cells rarely showed expression of the gene, while select cell lines of the present invention including 14SKEL14Z, 14SKEL15Z, 14SKEL20Z, 14SKEL24Z, and 14PEND20X expressed abundant levels of the transcript (>1,000 RFUs). Cells expressing the gene can be used to manufacture the protein in vivo for therapeutic effect such as to regulate numerous functions of the gastrointestinal and central nervous systems, including release of gastrointestinal hormones, smooth muscle cell contraction, and epithelial cell proliferation as is known in the art for the normal protein, or used to manufacture the secreted protein as described in the sections above titled Secreted Protein Isolation Protocol 1 or Secreted Protein Isolation Protocol.

Figure 5:
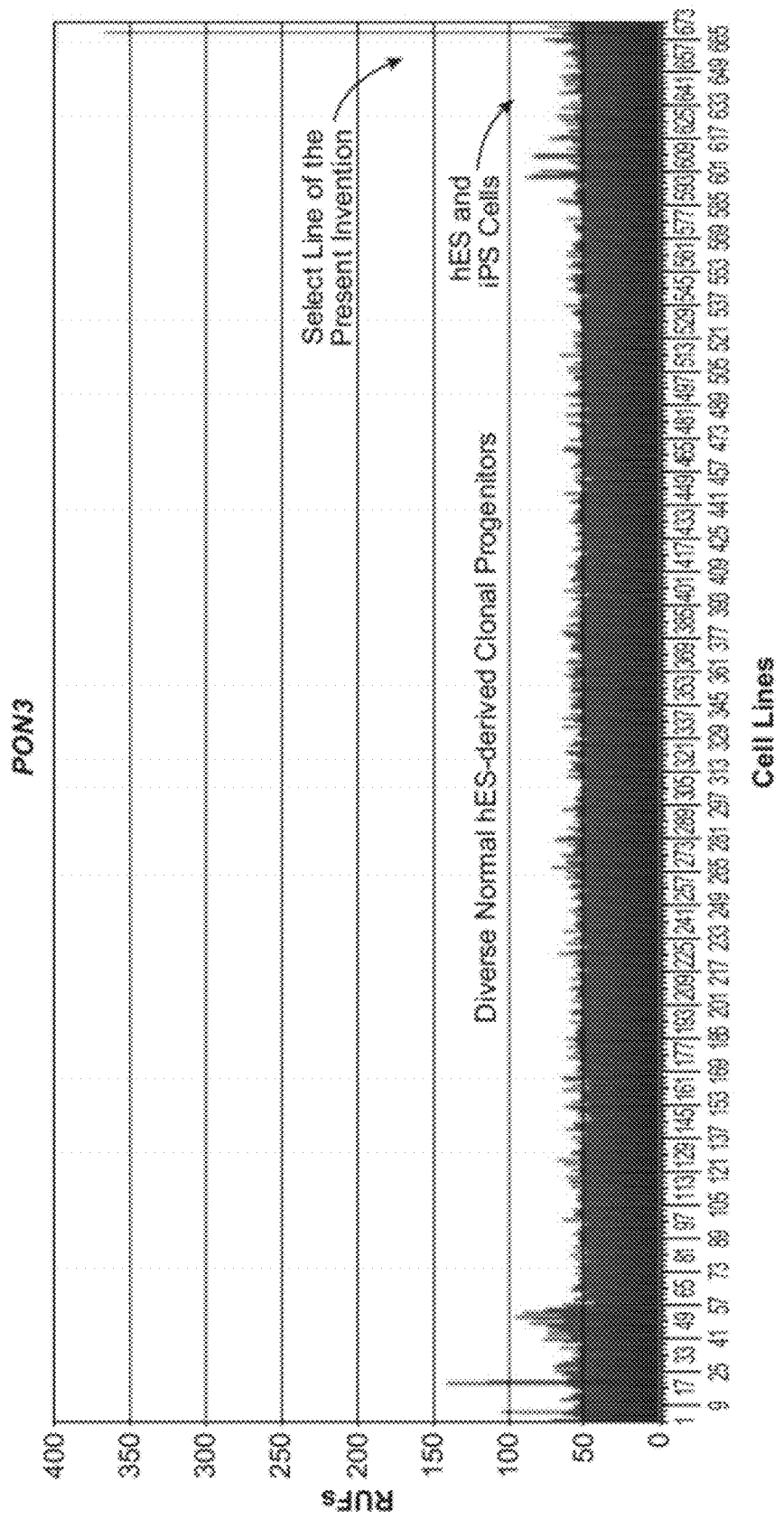
FIG. 5: Microarray gene expression analysis of the expression of paraoxonase 3 (PON3) (Accession number NM_000940.1) in diverse normal cultured cell types, diverse normal clonal progenitor cell lines derived from hES cells, hES and iPS cells, and the select cell lines of the present invention 14PEND2X.

In addition, another useful cell type includes one expressing paraoxonase 3 RNA (PON3) as shown in FIG. 5 and Table II. Microarray gene expression analysis of paraoxonase 3 (PON3) (Accession number NM_000940.1) in diverse normal cultured cell types, diverse normal clonal progenitor cell lines derived from hES cells, hES and iPS cells, and the select cell lines of the present invention shows rare and low expression of the gene, while the line 14PEND2X expressed abundant levels of the gene. Cells expressing the gene can be used to manufacture the protein in vivo for therapeutic effect such as when it is secreted into the blood as a protein and associates with high-density lipoprotein (HDL). The protein also rapidly hydrolyzes lactones and can inhibit the oxidation of low-density lipoprotein (LDL), a function that is believed to slow the initiation and progression of atherosclerosis, or used to manufacture the secreted protein as described in the sections above titled Secreted Protein Isolation Protocol 1 or Secreted Protein Isolation Protocol.

Example 2

Novel clonal human progenitors derived from hES cells with inducible expression of the transcription factors SIX1 and SIX2 are generated in hES and hiPS cells as described herein. Clonal progenitor lines are assayed for their capacity to undergo chondrogenesis in micromass conditions in the presence of TGFB3, e.g., as described in PCT Patent Application Serial No. PCT/US2010/042369 filed on Jul. 16, 2010, entitled "Methods and Compositions for In Vitro and In Vivo Chondrogenesis", incorporated herein by reference.

Example 3

Novel clonal human progenitors are isolated, expanded, and microarray analysis is performed from hES and somatic cells reprogrammed to a pluripotent stem cell state (hiPS cells) overexpressing each of the CNS transcription factors SOX2, SOX21, and PAX6 introduced by an expression plasmid as described herein. hES cells are also isolated where there is separately-inducible expression of the genes for the pair of factors SOX2/SOX21, and PAX6/SOX21. In the case where separately-inducible pairs of factors are introduced, SOX21 is induced only after expansion of the clonal progenitors to induce terminal neuronal differentiation which is assayed by microarray analysis.

Example 4

Novel clonal human progenitors are isolated, expanded, and microarray analysis is performed from hES cells and somatic cells reprogrammed to a pluripotent stem cell state (hiPS cells) overexpressing each of the endoderm transcription factors FOXA1, and SOX17 introduced by an expression plasmid as described herein. hES and hiPS cells are also isolated where there is separately-inducible expression of the genes for the pair of factors FOXA1, and SOX17. The resulting clonal, oligoclonal, or pooled polyclonal progenitor cell lines are useful in the treatment of diseases associated with dysfunctional endoderm-derived cells including pancreatic beta cells for the treatment of diabetes, lung epithelial cells for the treatment of lung disease, intestinal epithelium for the treatment of digestive disorders, and so on.

Example 5

Novel clonal human progenitors are isolated, expanded, and microarray analysis is performed from hES cells and somatic cells reprogrammed to a pluripotent stem cell state (hiPS cells) overexpressing cardiac field transcription factor NKX2.5 introduced by an expression plasmid as described herein. hES and hiPS cells are also isolated where there is inducible expression of the gene. The resulting clonal, oligoclonal, or pooled polyclonal progenitor cell lines are useful in the treatment of diseases associated with dysfunctional myocardium such as heart failure or acute myocardial infarction wherein the resulting cells are injected into the heart tissue by means of a catheter or other means known in the art, together with matrix such as HyStem hydrogel (www.biotimeinc.com) to promote engraftment.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

TABLES

TABLE I

Protocols

Transfection Protocol 1

By way on nonlimiting example, for stable transfections, plasmids are linearized by restriction digest such that 0.2 microgram of DNA is contained within 1 microliter of the restriction digest mixture, and such that approximately 1 microgram of DNA per 5 square centimeters of the tissue culture dish/plate/flask into which cells are seeded during the transfection process can be used. Linearized plasmids are diluted in mTeSR1 Basal Medium (STEMCELL Technologies Inc.), and supplemented with FuGENE HD (Roche) such that the ratio of DNA (in microgram):FuGENE HD (in microliter):mTeSR1 Basal Medium (in milliliter) is 1:3:0.25. The DNA/FuGENE HD mixture is incubated at room temperature (RT) for 30 minutes-2 hours. In the meantime, pluripotent stem cells such as hES cells or hiPS cells are grown on Matrigel (BD Biosciences)-coated tissue culture ware are detached with Accutase, and an aliquot of the single cell suspension used for cell counting. Cells are spun at 200 x g for 5 minutes at RT and suspended to 1.5 × 10e6 cells per milliliter in mTeSR1 complete medium supplemented with 10 micromolar Y27632 (ROCK inhibitor). Approximately 0.75 × 10e6 cells per 1 microgram of DNA are combined with the DNA/FuGENE HD mixture, then plated on Matrigel-coated tissue culture ware, and incubated at 37 centigrades/5% oxygen/10% carbon dioxide. 3 hours later, 1 volume of mTeSR1 complete medium supplemented with 2X Penicillin/Streptomycin and 10 micromolar Y27632 is added. The next day, medium is replaced by mTeSR1 complete medium containing Penicillin/Streptomycin and 10 micromolar Y27632. Selection for hES cells or iPS cells with stably integrated transgenes is carried out 2 days or later after transfection. For transient transfections, a similar procedure is carried out also relying on a ratio of DNA:FuGENE HD:mTeSR1 Basal Medium = 1:3:0.25.

TABLE I-continued

Protocols

Reprogramming Protocol 1:

Somatic cells are reprogrammed using retroviral-mediated expression of OCT4, SOX2, and KLF4 (pMx-OCT4/pMx-SOX2/pMx-KLF4 viruses) as described in PCT Application Serial No. PCT/US2011/025316, published as WO 2011/103343 and entitled "METHODS FOR TELOMERE LENGTH AND GENOMIC DNA QUALITY CONTROL ANALYSIS IN PLURIPOTENT STEM CELLS", incorporated herein by reference in its entirety. The somatic cells (including those genetically modified to display altered transcriptional regulators as described herein) are infected with the SOK (SOX2, OCT4 and KLF4) viruses for 20 hours in presence of 8 µg/ml of polybrene. After infection, media is changed and cells are plated onto irradiated feeders (12 Gy). Co-cultures are then switched to knock-out DMEM hES media (Invitrogen, cat# 10829-018) containing 16% KOSR media (Invitrogen); 1X Glutamax (Invitrogen); pen/strep (Invitrogen); non-essential amino acids (Invitrogen); 0.6 ml β-Mercaptoethanol (Invitrogen) per 500 ml of media and 50 ng/ml of bFGF (Millipore, cat#GF003). Media is changed daily until iPS colonies appear. The colonies are manually picked with a pipette tip (p200) or by using plastic cloning rings, washed in PBS and manually removed to 24 well dishes containing radiated feeders. The hES media is changed completely everyday. The cells are subsequently transferred to six well dishes and eventually moved to feeder free 10 cm$^2$ dishes (Corning). Matrigel (BD Bioscience) is thawed at 4° C. and diluted 1:12 with cold DMEM (Invitrogen). A final concentration of 100 ng/ml of bFGF (Millipore) is added to mTESR1 media (Stem Cell Technologies, Vancouver). Media is changed every day and the differentiated or near differentiated colonies are removed. Cell lines are subcultured on average once per week.

TABLE II

| ProbeID | RefSeq_ID | Symbol | Definition | Synonyms | RFUs | Fold over Ave. | Filter Score |
|---|---|---|---|---|---|---|---|
| | | | 14PEND11X P6 | | | | |
| 3180068 | NM_013371.2 | IL19 | *Homo sapiens* interleukin 19 (IL19), transcript variant 2, mRNA. | NG.1; IL-10C; ZMDA1; MDA1 | 888.5502538 | 15.96168331 | 247 |
| 5860504 | NM_001080848.1 | CSAG3B | *Homo sapiens* CSAG family, member 3B (CSAG3B), mRNA. | CSAG2 | 274.1073604 | 3.806242927 | 247 |
| 6350682 | NM_016102.2 | TRIM17 | *Homo sapiens* tripartite motif-containing 17 (TRIM17), transcript variant 1, mRNA. | RBCC; terf; RNF16 | 241.0488156 | 3.04374161 | 247 |
| 4010095 | NM_203311.1 | CSAG3A | *Homo sapiens* CSAG family, member 3A (CSAG3A), mRNA. | MGC17065 | 708.1494078 | 8.825421693 | 246 |
| 6900377 | NM_001080848.1 | CSAG3B | *Homo sapiens* CSAG family, member 3B (CSAG3B), mRNA. | CSAG2 | 444.11489 | 5.81561537 | 246 |
| 630619 | NM_006665.3 | HPSE | *Homo sapiens* heparanase (HPSE), mRNA. | HPA; HSE1; HPSE1; HPR1 | 326.830203 | 3.839238782 | 246 |
| 1770603 | NM_001062.3 | TCN1 | *Homo sapiens* transcobalamin I (vitamin B12 binding protein, R binder family) (TCN1), mRNA. | TCI; TC1 | 30460.03096 | 145.1865227 | 244 |
| 7160192 | NM_139319.1 | SLC17A8 | *Homo sapiens* solute carrier family 17 (sodium-dependent inorganic phosphate cotransporter), member 8 (SLC17A8), mRNA. | VGLUT3 | 483.2905245 | 7.840373688 | 244 |
| 6900196 | NM_004975.2 | KCNB1 | *Homo sapiens* potassium voltage-gated channel, Shab-related subfamily, member 1 (KCNB1), mRNA. | KV2.1; h-DRK1; DRK1 | 1279.524365 | 17.97978203 | 243 |
| 3450544 | NM_138569.2 | C6orf142 | *Homo sapiens* chromosome 6 open reading frame 142 (C6orf142), mRNA. | MGC18257 | 188.5175973 | 2.228827544 | 243 |
| 6510274 | NM_022124.3 | CDH23 | *Homo sapiens* cadherin-like 23 (CDH23), transcript variant 1, mRNA. | DKFZp434P2350; USH1H; KIAA1774; FLJ00233; MGC102761; FLJ36499; DFNB12; USH1D; KIAA1812 | 213.8431472 | 2.220053223 | 242 |
| 5360064 | NM_012483.1 | GNLY | *Homo sapiens* granulysin (GNLY), transcript variant 519, mRNA. | D2S69E; 519; LAG2; NKG5; LAG-2; TLA519 | 215.1233503 | 2.422329434 | 241 |
| 5860075 | NM_004345.3 | CAMP | *Homo sapiens* cathelicidin antimicrobial peptide (CAMP), mRNA. | HSD26; LL37; FALL39; FALL-39; CAP18 | 187.4673435 | 2.075440453 | 241 |
| 360379 | NM_194435.1 | VIP | *Homo sapiens* vasoactive intestinal peptide (VIP), transcript variant 2, mRNA. | MGC13587; PHM27 | 259.2274112 | 3.052114612 | 240 |

TABLE II-continued

| ProbeID | RefSeq_ID | Symbol | Definition | Synonyms | RFUs | Fold over Ave. | Filter Score |
|---|---|---|---|---|---|---|---|
| 6270022 | NM_002110.2 | HCK | Homo sapiens hemopoietic cell kinase (HCK), mRNA. | JTK9 | 610.5037225 | 7.680844729 | 239 |
| 840017 | NM_206819.1 | MYBPC1 | Homo sapiens myosin binding protein C, slow type (MYBPC1), transcript variant 2, mRNA. | slow-type; MYBPCS; MYBPCC | 305.5191201 | 3.198362009 | 239 |
| 5910056 | NM_206821.1 | MYBPC1 | Homo sapiens myosin binding protein C, slow type (MYBPC1), transcript variant 4, mRNA. | slow-type; MYBPCS; MYBPCC | 236.6600677 | 2.283355152 | 239 |
| 3390523 | NM_001010971.1 | SAMD13 | Homo sapiens sterile alpha motif domain containing 13 (SAMD13), mRNA. | RP11-376N17.1 | 227.2099831 | 2.282533933 | 239 |
| 7610441 | NM_002509.2 | NKX2-2 | Homo sapiens NK2 homeobox 2 (NKX2-2), mRNA. | NKX2B; NKX2.2 | 5979.623181 | 34.51368017 | 238 |
| 4670138 | NM_003645.2 | SLC27A2 | Homo sapiens solute carrier family 27 (fatty acid transporter), member 2 (SLC27A2), mRNA. | HsT17226; FATP2; FACVL1; hFACVL1; VLACS; VLCS; ACSVL1 | 258.8497462 | 2.27246929 | 238 |
| 5270520 | NM_005449.3 | FAIM3 | Homo sapiens Fas apoptotic inhibitory molecule 3 (FAIM3), mRNA. | TOSO | 796.8850254 | 10.50369487 | 237 |
| 730093 | NM_020209.2 | SHD | Homo sapiens Src homology 2 domain containing transforming protein D (SHD), mRNA. | | 270.9575296 | 2.750523803 | 237 |
| 1190592 | NM_000827.2 | GRIA1 | Homo sapiens glutamate receptor, ionotropic, AMPA 1 (GRIA1), mRNA. | HBGR1; GLURA; GLUH1; GLUR1; MGC133252 | 233.2972927 | 2.357055576 | 237 |
| 1110564 | NM_006419.1 | CXCL13 | Homo sapiens chemokine (C—X—C motif) ligand 13 (B-cell chemoattractant) (CXCL13), mRNA. | SCYB13; ANGIE; BCA1; ANGIE2; BCA-1; BLR1L; BLC | 5015.168866 | 41.6397734 | 236 |
| 4860403 | NM_002747.3 | MAPK4 | Homo sapiens mitogen-activated protein kinase 4 (MAPK4), mRNA. | Erk4; p63MAPK; ERK3; PRKM4 | 681.5299492 | 9.892172042 | 236 |
| 6330070 | NM_013371.2 | IL19 | Homo sapiens interleukin 19 (IL19), transcript variant 2, mRNA. | NG.1; IL-10C; ZMDA1; MDA1 | 698.1584602 | 8.432367471 | 235 |
| 7000176 | NM_152679.2 | SLC10A4 | Homo sapiens solute carrier family 10 (sodium/bile acid cotransporter family), member 4 (SLC10A4), mRNA. | MGC29802; P4 | 627.2695431 | 7.965185955 | 235 |
| 270487 | NM_170600.1 | SH2D3C | Homo sapiens SH2 domain containing 3C (SH2D3C), transcript variant 2, mRNA. | NSP3; PRO34088; CHAT; FLJ39664 | 296.3759729 | 3.171074362 | 235 |
| 60278 | NM_001048164.1 | SLC7A3 | Homo sapiens solute carrier family 7 (cationic amino acid transporter, y+ system), member 3 (SLC7A3), transcript variant 2, mRNA. | CAT-3; ATRC3; FLJ14541; MGC20687 | 707.6612521 | 5.26365107 | 234 |
| 6020224 | NM_000507.2 | FBP1 | Homo sapiens fructose-1,6-bisphosphatase 1 (FBP1), mRNA. | FBP | 277.680203 | 3.741121248 | 234 |
| 7550358 | NM_006159.1 | NELL2 | Homo sapiens NEL-like 2 (chicken) (NELL2), mRNA. | NRP2 | 741.8240271 | 4.338251013 | 233 |
| 1260180 | NM_004100.3 | EYA4 | Homo sapiens eyes absent homolog 4 (Drosophila) (EYA4), transcript variant 1, mRNA. | CMD1J; DFNA10 | 389.3572758 | 2.833686856 | 233 |
| 1070162 | NM_020116.2 | FSTL5 | Homo sapiens follistatin-like 5 (FSTL5), mRNA. | KIAA1263; DKFZp566D234 | 378.9091371 | 4.110594619 | 232 |
| 580187 | NM_001029851.1 | PDE8B | Homo sapiens phosphodiesterase 8B (PDE8B), transcript variant 3, mRNA. | FLJ11212 | 351.5852792 | 3.117135307 | 232 |
| 150066 | NM_006011.3 | ST8SIA2 | Homo sapiens ST8 alpha-N-acetyl-neuraminide alpha-2,8-sialyltransferase 2 (ST8SIA2), mRNA. | MGC116857; HsT19690; ST8SIA-II; SIAT8B; MGC116854; STX | 268.872758 | 2.751244758 | 232 |
| 1010360 | NM_001024070.1 | GCH1 | Homo sapiens GTP cyclohydrolase 1 (GCH1), transcript variant 3, mRNA. | DYT5; GTP-CH-1; GTPCH1; GCH | 287.9126058 | 3.574011669 | 230 |
| 510452 | NM_002012.1 | FHIT | Homo sapiens fragile histidine triad gene (FHIT), mRNA. | FRA3B; AP3Aase | 228.7604061 | 2.317346033 | 230 |

TABLE II-continued

| ProbeID | RefSeq_ID | Symbol | Definition | Synonyms | RFUs | Fold over Ave. | Filter Score |
|---|---|---|---|---|---|---|---|
| 3310037 | NM_005634.2 | SOX3 | *Homo sapiens* SRY (sex determining region Y)-box 3 (SOX3), mRNA. | SOXB; MRGH | 1479.767174 | 10.8216027 | 229 |
| 1090561 | NM_145740.2 | GSTA1 | *Homo sapiens* glutathione S-transferase A1 (GSTA1), mRNA. | GTH1; GST2; MGC131939; GSTA1-1 | 556.5102369 | 5.787657576 | 229 |
| 3870246 | NM_001007097.1 | NTRK2 | *Homo sapiens* neurotrophic tyrosine kinase, receptor, type 2 (NTRK2), transcript variant b, mRNA. | GP145-TrkB; TRKB | 847.2759729 | 6.532092112 | 228 |
| 430102 | NM_001018065.1 | NTRK2 | *Homo sapiens* neurotrophic tyrosine kinase, receptor, type 2 (NTRK2), transcript variant d, mRNA. | GP145-TrkB; TRKB | 961.9575296 | 6.967734817 | 227 |
| 2350201 | NM_181670.2 | ANKS1B | *Homo sapiens* ankyrin repeat and sterile alpha motif domain containing 1B (ANKS1B), transcript variant 2, mRNA. | MGC26087; EB-1; ANKS2; AIDA-1; AIDA; cajalin-2 | 285.6676819 | 3.125722047 | 227 |
| 1450634 | NM_022164.1 | TINAGL1 | *Homo sapiens* tubulointerstitial nephritis antigen-like 1 (TINAGL1), mRNA. | LIECG3; LCN7; TINAGRP; ARG1 | 270.9575296 | 2.631481406 | 227 |
| 2320369 | NM_015063.1 | SLC8A2 | *Homo sapiens* solute carrier family 8 (sodium/calcium exchanger), member 2 (SLC8A2), mRNA. | NCX2 | 1108.214552 | 8.081731657 | 226 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 9900.403892 | 14.71166303 | 225 |
| 940630 | NM_024761.3 | MOBKL2B | *Homo sapiens* MOB1, Mps One Binder kinase activator-like 2B (yeast) (MOBKL2B), mRNA. | FLJ13204; FLJ23916; MOB3B; MGC32960 | 343.5135364 | 3.171424587 | 224 |
| 2850458 | NM_201572.1 | CACNB2 | *Homo sapiens* calcium channel, voltage-dependent, beta 2 subunit (CACNB2), transcript variant 8, mRNA. | CACNLB2; MYSB; FLJ23743 | 277.0624365 | 3.125835177 | 224 |
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 11585.36311 | 19.28453406 | 223 |
| | | | 14PEND12X P6 | | | | |
| 7610746 | NM_024019.2 | NEUROG2 | *Homo sapiens* neurogenin 2 (NEUROG2), mRNA. | ngn-2; NGN2; MGC46562; Math4A; Atoh4 | 297.4715736 | 3.41521657 | 250 |
| 2360743 | NM_173355.2 | UPP2 | *Homo sapiens* uridine phosphorylase 2 (UPP2), mRNA. | UPASE2; UDRPASE2; UP2 | 209.841286 | 2.786979154 | 250 |
| 2640068 | NM_002934.2 | RNASE2 | *Homo sapiens* ribonuclease, RNase A family, 2 (liver, eosinophil-derived neurotoxin) (RNASE2), mRNA. | EDN; RNS2 | 1769.958037 | 26.4030724 | 245 |
| 2600424 | NM_000331.3 | SAA1 | *Homo sapiens* serum amyloid A1 (SAA1), transcript variant 1, mRNA. | MGC111216; SAA; PIG4; TP53I4 | 902.0096447 | 10.77448424 | 245 |
| 6220750 | NM_000826.2 | GRIA2 | *Homo sapiens* glutamate receptor, ionotropic, AMPA 2 (GRIA2), mRNA. | HBGR2; GLURB; GLUR2 | 431.6473773 | 3.605401705 | 245 |
| 1770603 | NM_001062.3 | TCN1 | *Homo sapiens* transcobalamin I (vitamin B12 binding protein, R binder family) (TCN1), mRNA. | TCI; TC1 | 11220.49662 | 52.85041744 | 244 |
| 1010097 | NM_021815.2 | SLC5A7 | *Homo sapiens* solute carrier family 5 (choline transporter), member 7 (SLC5A7), mRNA. | MGC126299; MGC126300; CHT1; hCHT; CHT | 247.5932318 | 3.254269838 | 244 |
| 7320471 | NM_003221.3 | TFAP2B | *Homo sapiens* transcription factor AP-2 beta (activating enhancer binding protein 2 beta) (TFAP2B), mRNA. | MGC21381; AP-2B; AP2-B | 438.5033841 | 5.285112768 | 243 |
| 2230088 | NM_213609.2 | FAM19A1 | *Homo sapiens* family with sequence similarity 19 (chemokine (C-C motif)-like), member A1 (FAM19A1), mRNA. | TAFA-1; TAFA1 | 230.4490694 | 2.471180495 | 243 |

TABLE II-continued

| ProbeID | RefSeq_ID | Symbol | Definition | Synonyms | RFUs | Fold over Ave. | Filter Score |
|---|---|---|---|---|---|---|---|
| 4810487 | NM_018712.2 | ELMOD1 | *Homo sapiens* ELMO/CED-12 domain containing 1 (ELMOD1), mRNA. | DKFZp547C176 | 423.9783418 | 4.891351541 | 242 |
| 160500 | NM_001012513.1 | GRP | *Homo sapiens* gastrin-releasing peptide (GRP), transcript variant 3, mRNA. | proGRP; GRP-10; BN; preproGRP | 390.171912 | 3.35811555 | 242 |
| 6560487 | NM_001842.3 | CNTFR | *Homo sapiens* ciliary neurotrophic factor receptor (CNTFR), transcript variant 2, mRNA. | MGC1774 | 235.391709 | 2.429155916 | 242 |
| 3390372 | NM_001843.2 | CNTN1 | *Homo sapiens* contactin 1 (CNTN1), transcript variant 1, mRNA. | GP135; F3 | 682.6843486 | 8.726416526 | 241 |
| 4880138 | NM_000905.2 | NPY | *Homo sapiens* neuropeptide Y (NPY), mRNA. | PYY4 | 1095.820812 | 8.509567707 | 241 |
| 6270022 | NM_002110.2 | HCK | *Homo sapiens* hemopoietic cell kinase (HCK), mRNA. | JTK9 | 263.4060914 | 2.745411036 | 239 |
| 7610441 | NM_002509.2 | NKX2-2 | *Homo sapiens* NK2 homeobox 2 (NKX2-2), mRNA. | NKX2B; NKX2.2 | 1223.904569 | 6.268912118 | 238 |
| 3840192 | NM_000817.2 | GAD1 | *Homo sapiens* glutamate decarboxylase 1 (brain, 67 kDa) (GAD1), transcript variant GAD67, mRNA. | SCP; FLJ45882; GAD | 284.7027073 | 3.402376455 | 238 |
| 1190592 | NM_000827.2 | GRIA1 | *Homo sapiens* glutamate receptor, ionotropic, AMPA 1 (GRIA1), mRNA. | HBGR1; GLURA; GLUH1; GLUR1; MGC133252 | 289.4909475 | 3.165659996 | 237 |
| 1340551 | NM_024674.4 | LIN28 | *Homo sapiens* lin-28 homolog (*C. elegans*) (LIN28), mRNA. | CSDD1; LIN28A; FLJ12457; LIN-28; ZCCHC1 | 2479.402538 | 2.210091192 | 237 |
| 840291 | NM_013251.2 | TAC3 | *Homo sapiens* tachykinin 3 (TAC3), transcript variant 2, mRNA. | PRO1155; NKB; ZNEUROK1; NKNB | 298.9903553 | 2.009165335 | 237 |
| 5870435 | NM_006043.1 | HS3ST2 | *Homo sapiens* heparan sulfate (glucosamine) 3-O-sulfotransferase 2 (HS3ST2), mRNA. | 3OST2; 30ST2 | 273.9906937 | 2.977575504 | 236 |
| 2570538 | NM_007084.2 | SOX21 | *Homo sapiens* SRY (sex determining region Y)-box 21 (SOX21), mRNA. | SOX25 | 1192.648308 | 7.92266175 | 235 |
| 2350139 | NM_004100.3 | EYA4 | *Homo sapiens* eyes absent homolog 4 (*Drosophila*) (EYA4), transcript variant 1, mRNA. | CMD1J; DFNA10 | 373.3384095 | 4.344035695 | 235 |
| 5550414 | NM_019845.2 | RPRM | *Homo sapiens* reprimo, TP53 dependent G2 arrest mediator candidate (RPRM), mRNA. | FLJ90327; REPRIMO | 594.4890017 | 3.325358686 | 234 |
| 7160437 | NM_001025068.1 | ARPP-21 | *Homo sapiens* cyclic AMP-regulated phosphoprotein, 21 kD (ARPP-21), transcript variant 3, mRNA. | FLJ32997 | 228.1532149 | 2.224344891 | 234 |
| 5130156 | NM_003106.2 | SOX2 | *Homo sapiens* SRY (sex determining region Y)-box 2 (SOX2), mRNA. | ANOP3; MGC2413; MCOPS3 | 815.6978003 | 1.950260059 | 234 |
| 1260180 | NM_004100.3 | EYA4 | *Homo sapiens* eyes absent homolog 4 (*Drosophila*) (EYA4), transcript variant 1, mRNA. | CMD1J; DFNA10 | 787.1558376 | 6.750488243 | 233 |
| 6200333 | NM_021977.2 | SLC22A3 | *Homo sapiens* solute carrier family 22 (extraneuronal monoamine transporter), member 3 (SLC22A3), mRNA. | EMT; OCT3; EMTH | 402.0670051 | 4.584713555 | 233 |
| 5860689 | NM_016335.2 | PRODH | *Homo sapiens* proline dehydrogenase (oxidase) 1 (PRODH), nuclear gene encoding mitochondrial protein, mRNA. | HSPOX2; MGC148078; PIG6; SCZD4; FLJ33744; PRODH1; TP53I6; MGC148079; PRODH2 | 378.1150592 | 2.479178716 | 233 |
| 3190246 | NM_004067.2 | CHN2 | *Homo sapiens* chimerin (chimaerin) 2 (CHN2), transcript variant 2, mRNA. | BCH; ARHGAP3; RHOGAP3; MGC138360 | 226.9649746 | 2.379830339 | 233 |
| 2810673 | NM_152739.3 | HOXA9 | *Homo sapiens* homeobox A9 (HOXA9), mRNA. | MGC1934; HOX1.7; HOX1G; HOX1; ABD-B | 446.3071066 | 1.957145588 | 233 |
| 7320348 | NM_016511.2 | CLEC1A | *Homo sapiens* C-type lectin domain family 1, member A (CLEC1A), mRNA. | CLEC1; MGC34328 | 613.7247885 | 7.363051918 | 232 |

TABLE II-continued

| ProbeID | RefSeq_ID | Symbol | Definition | Synonyms | RFUs | Fold over Ave. | Filter Score |
|---|---|---|---|---|---|---|---|
| 670414 | NM_003413.2 | ZIC3 | *Homo sapiens* Zic family member 3 heterotaxy 1 (odd-paired homolog, *Drosophila*) (ZIC3), mRNA. | HTX1; ZNF203; HTX | 1096.337563 | 4.255659158 | 232 |
| 150066 | NM_006011.3 | ST8SIA2 | *Homo sapiens* ST8 alpha-N-acetyl-neuraminide alpha-2,8-sialyltransferase 2 (ST8SIA2), mRNA. | MGC116857; HsT19690; ST8SIA-II; SIAT8B; MGC116854; STX | 367.6824027 | 4.129811944 | 232 |
| 7040497 | NM_001179.3 | ART3 | *Homo sapiens* ADP-ribosyltransferase 3 (ART3), mRNA. | | 401.8192893 | 3.053793795 | 232 |
| 7400392 | NM_021186.2 | ZP4 | *Homo sapiens* zona pellucida glycoprotein 4 (ZP4), mRNA. | ZBP; ZPB; ZP1 | 162.1536379 | 1.916272182 | 232 |
| 240592 | NM_001094.4 | ACCN1 | *Homo sapiens* amiloride-sensitive cation channel 1, neuronal (ACCN1), transcript variant 2, mRNA. | BNC1; hBNaC1; MDEG; BNaC1; ASIC2a; ACCN; ASIC2 | 270.8832487 | 2.445203911 | 231 |
| 1090561 | NM_145740.2 | GSTA1 | *Homo sapiens* glutathione S-transferase A1 (GSTA1), mRNA. | GTH1; GST2; MGC131939; GSTA1-1 | 1261.548562 | 14.38688614 | 229 |
| 3310037 | NM_005634.2 | SOX3 | *Homo sapiens* SRY (sex determining region Y)-box 3 (SOX3), mRNA. | SOXB; MRGH | 428.3458545 | 2.421980564 | 229 |
| 3870246 | NM_001007097.1 | NTRK2 | *Homo sapiens* neurotrophic tyrosine kinase, receptor, type 2 (NTRK2), transcript variant b, mRNA. | GP145-TrkB; TRKB | 805.6666667 | 6.162194773 | 228 |
| 2750154 | NM_014800.9 | ELMO1 | *Homo sapiens* engulfment and cell motility 1 (ELMO1), transcript variant 1, mRNA. | MGC126406; CED12; CED-12; KIAA0281; ELMO-1 | 217.5994924 | 2.081154468 | 228 |
| 430102 | NM_001018065.1 | NTRK2 | *Homo sapiens* neurotrophic tyrosine kinase, receptor, type 2 (NTRK2), transcript variant d, mRNA. | GP145-TrkB; TRKB | 786.8602369 | 5.517432956 | 227 |
| 2320369 | NM_015063.1 | SLC8A2 | *Homo sapiens* solute carrier family 8 (sodium/calcium exchanger), member 2 (SLC8A2), mRNA. | NCX2 | 934.3940778 | 6.657286456 | 226 |
| 2030445 | NM_002025.2 | AFF2 | *Homo sapiens* AF4/FMR2 family, member 2 (AFF2), mRNA. | FMR2; MRX2; OX19; FRAXE | 327.9978003 | 3.313605756 | 226 |
| 430204 | NM_005378.4 | MYCN | *Homo sapiens* v-myc myelocytomatosis viral related oncogene, neuroblastoma derived (avian) (MYCN), mRNA. | ODED; NMYC; MODED; N-myc | 941.0628596 | 2.503281932 | 226 |
| 7210554 | NM_016300.4 | ARPP-21 | *Homo sapiens* cyclic AMP-regulated phosphoprotein, 21 kD (ARPP-21), transcript variant 1, mRNA. | FLJ32997 | 258.5707276 | 2.320790506 | 226 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 9406.515059 | 13.92787532 | 225 |
| 4920047 | NM_001008223.1 | C1QL4 | *Homo sapiens* complement component 1, q subcomponent-like 4 (C1QL4), mRNA. | MGC131708 | 432.9840948 | 4.255154143 | 225 |
| 1770603 | NM_001062.3 | TCN1 | *Homo sapiens* transcobalamin (vitamin B12 binding protein, R binder family) (TCN1), mRNA. | ITCI; TC1 | 11101.23858 | 52.27806354 | 244 |
| 2640068 | NM_002934.2 | RNASE2 | *Homo sapiens* ribonuclease, RNase A family, 2 (liver, eosinophil-derived neurotoxin) (RNASE2), mRNA. | EDN; RNS2 | 1819.413367 | 27.16875608 | 245 |
| 1690563 | NM_199161.1 | SAA1 | *Homo sapiens* serum amyloid A1 (SAA1), transcript variant 2, mRNA. | MGC111216; SAA; PIG4; TP53I4 | 3500.000677 | 21.66993608 | 212 |
| 2510132 | NM_004378.1 | CRABP1 | *Homo sapiens* cellular retinoic acid binding protein 1 (CRABP1), mRNA. | RBP5; CRABPI; CRABP; CRABP-I | 6268.61709 | 18.92144854 | 212 |
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 10441.29577 | 17.28141402 | 223 |

TABLE II-continued

| ProbeID | RefSeq_ID | Symbol | Definition | Synonyms | RFUs | Fold over Ave. | Filter Score |
|---|---|---|---|---|---|---|---|
| 1780273 | XM_001127464.1 | ALOX5 | PREDICTED: *Homo sapiens* arachidonate 5-lipoxygenase (ALOX5), mRNA. | | 3381.302876 | 16.67848822 | 134 |
| 1430750 | NM_031461.3 | CRISPLD1 | *Homo sapiens* cysteine-rich secretory protein LCCL domain containing 1 (CRISPLD1), mRNA. | CRISP10; DKFZp762F133; LCRISP1 | 2605.396785 | 16.48430171 | 146 |
| 1090561 | NM_145740.2 | GSTA1 | *Homo sapiens* glutathione S-transferase A1 (GSTA1), mRNA. | GTH1; GST2; MGC131939; GSTA1-1 | 1349.498139 | 15.45959168 | 229 |
| 1570382 | NM_182920.1 | ADAMTS9 | *Homo sapiens* ADAM metallopeptidase with thrombospondin type 1 motif, 9 (ADAMTS9), mRNA. | KIAA1312; FLJ42955 | 3201.370558 | 14.36094098 | 123 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 9064.077834 | 13.38443706 | 225 |
| 6110044 | NM_001875.2 | CPS1 | *Homo sapiens* carbamoyl-phosphate synthetase 1, mitochondrial (CPS1), mRNA. | | 10310.73926 | 12.85053084 | 17 |
| 2600424 | NM_000331.3 | SAA1 | *Homo sapiens* serum amyloid A1 (SAA1), transcript variant 1, mRNA. | MGC111216; SAA; PIG4; TP53I4 | 976.8588832 | 11.75153719 | 245 |
| 6510554 | NM_080760.3 | DACH1 | *Homo sapiens* dachshund homolog 1 (*Drosophila*) (DACH1), transcript variant 2, mRNA. | DACH; FLJ10138 | 1421.217259 | 10.37859753 | 197 |
| 6580626 | NM_018015.4 | CXorf57 | *Homo sapiens* chromosome X open reading frame 57 (CXorf57), mRNA. | RP11-647M7.1; FLJ10178; FLJ14191 | 2530.088663 | 10.13675566 | 146 |
| 7380239 | NM_004114.2 | FGF13 | *Homo sapiens* fibroblast growth factor 13 (FGF13), transcript variant 1A, mRNA. | FGF2; FHF2 | 1914.284941 | 9.747040198 | 197 |
| 3930424 | NM_053277.1 | CLIC6 | *Homo sapiens* chloride intracellular channel 6 (CLIC6), mRNA. | CLIC1L | 1425.501692 | 9.24057445 | 195 |
| 2750092 | NM_005010.3 | NRCAM | *Homo sapiens* neuronal cell adhesion molecule (NRCAM), transcript variant 2, mRNA. | MGC138845; MGC138846; KIAA0343 | 1556.537902 | 9.101003472 | 194 |
| 6520064 | NM_152390.1 | TMEM178 | *Homo sapiens* transmembrane protein 178 (TMEM178), mRNA. | MGC33926 | 3950.689509 | 8.83406618 | 41 |
| 4280739 | NM_153000.3 | APCDD1 | *Homo sapiens* adenomatosis polyposis coli down-regulated 1 (APCDD1), mRNA. | DRAPC1; B7323; FP7019 | 3228.213536 | 8.42766302 | 195 |
| 3390372 | NM_001843.2 | CNTN1 | *Homo sapiens* contactin 1 (CNTN1), transcript variant 1, mRNA. | GP135; F3 | 652.6756345 | 8.298873032 | 241 |
| 2320598 | NM_000266.1 | NDP | *Homo sapiens* Norrie disease (pseudoglioma) (NDP), mRNA. | ND; EVR2; FEVR | 2015.200508 | 8.108560783 | 112 |
| 4880138 | NM_000905.2 | NPY | *Homo sapiens* neuropeptide Y (NPY), mRNA. | PYY4 | 1008.01489 | 7.747585134 | 241 |
| 5810678 | NM_002910.4 | RENBP | *Homo sapiens* renin binding protein (RENBP), mRNA. | RNBP; RBP | 1564.592386 | 7.643734819 | 192 |
| 3140139 | NM_006158.2 | NEFL | *Homo sapiens* neurofilament, light polypeptide 68 kDa (NEFL), mRNA. | NF68; CMT2E; NFL; CMT1F; NF-L | 733.3238579 | 7.460258344 | 220 |
| 2570538 | NM_007084.2 | SOX21 | *Homo sapiens* SRY (sex determining region Y)-box 21 (SOX21), mRNA. | SOX25 | 1089.118274 | 7.148113657 | 235 |
| 1940747 | NM_181505.1 | PPP1R1B | *Homo sapiens* protein phosphatase 1, regulatory (inhibitor) subunit 1B (dopamine and cAMP regulated phosphoprotein, DARPP-32) (PPP1R1B), transcript variant 2, mRNA. | DARPP-32; FLJ20940; DARPP32 | 974.3307107 | 7.112562778 | 215 |
| 6020523 | NM_181676.1 | PPP2R2B | *Homo sapiens* protein phosphatase 2 (formerly 2A), regulatory subunit B, beta isoform (PPP2R2B), transcript variant 4, mRNA. | PR2AB-BETA; PR52B; PR2APR55-BETA; PR2AB55-BETA; MGC24888; PR55-BETA; PP2A-PR55B; SCA12 | 4083.244332 | 7.054715728 | 1 |

TABLE II-continued

| ProbeID | RefSeq_ID | Symbol | Definition | Synonyms | RFUs | Fold over Ave. | Filter Score |
|---|---|---|---|---|---|---|---|
| 2320369 | NM_015063.1 | SLC8A2 | Homo sapiens solute carrier family 8 (sodium/calcium exchanger), member 2 (SLC8A2), mRNA. | NCX2 | 974.3307107 | 6.984564041 | 226 |
| 7320348 | NM_016511.2 | CLEC1A | Homo sapiens C-type lectin domain family 1, member A (CLEC1A), mRNA. | CLEC1; MGC34328 | 583.3066836 | 6.948553114 | 232 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 882.4951777 | 6.845182891 | 228 |
| 3520246 | NM_004887.3 | CXCL14 | Homo sapiens chemokine (C—X—C motif) ligand 14 (CXCL14), mRNA. | SCYB14; KS1; Kec; bolekine; MGC10687; NJAC; MIP-2g; BRAK; BMAC | 1439.55753 | 6.784666288 | 204 |
| 1260180 | NM_004100.3 | EYA4 | Homo sapiens eyes absent homolog 4 (Drosophila) (EYA4), transcript variant 1, mRNA. | CMD1J; DFNA10 | 781.6235195 | 6.696015971 | 233 |
| 1400520 | NM_014141.4 | CNTNAP2 | Homo sapiens contactin associated protein-like 2 (CNTNAP2), mRNA. | NRXN4; CDFE; DKFZp781D1846; CASPR2 | 2559.152792 | 6.560386834 | 224 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 512.0135364 | 6.338741117 | 243 |
| 1770754 | NM_014988.1 | LIMCH1 | Homo sapiens LIM and calponin homology domains 1 (LIMCH1), mRNA. | DKFZp686B2470; DKFZp781I1455; DKFZp781C1754; LMO7B; DKFZp686G18243; DKFZp686G2094; MGC72127; DKFZp434I0312; DKFZp686A01247; LIMCH1A | 2178.018105 | 6.025738134 | 143 |
| 3840753 | NM_001040708.1 | HEY1 | Homo sapiens hairy/enhancer-of-split related with YRPW motif 1 (HEY1), transcript variant 2, mRNA. | MGC1274; CHF2; HERP2; HRT-1; HESR1; OAF1 | 3693.71912 | 5.946625326 | 22 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 835.6263959 | 5.921354971 | 227 |
| 2350139 | NM_004100.3 | EYA4 | Homo sapiens eyes absent homolog 4 (Drosophila) (EYA4), transcript variant 1, mRNA. | CMD1J; DFNA10 | 475.4637902 | 5.805877462 | 235 |
| 6980301 | NM_005010.3 | NRCAM | Homo sapiens neuronal cell adhesion molecule (NRCAM), transcript variant 2, mRNA. | MGC138845; MGC138846; KIAA0343 | 1029.687986 | 5.590344651 | 164 |
| 2320626 | NM_198391.1 | FLRT3 | Homo sapiens fibronectin leucine rich transmembrane protein 3 (FLRT3), transcript variant 2, mRNA. | | 1876.306599 | 5.521362941 | 108 |
| 7610441 | NM_002509.2 | NKX2-2 | Homo sapiens NK2 homeobox 2 (NKX2-2), mRNA. | NKX2B; NKX2.2 | 1080.23198 | 5.41562384 | 238 |
| 10543 | NM_001039582.1 | PNCK | Homo sapiens pregnancy upregulated non-ubiquitously expressed CaM kinase (PNCK), mRNA. | MGC45419; CaMK1b; BSTK3 | 1640.675635 | 5.316271349 | 69 |
| 6200333 | NM_021977.2 | SLC22A3 | Homo sapiens solute carrier family 22 (extraneuronal monoamine transporter), member 3 (SLC22A3), mRNA. | EMT; OCT3; EMTH | 452.1553299 | 5.280440743 | 233 |
| 830491 | NM_001077188.1 | HS6ST2 | Homo sapiens heparan sulfate 6-O-sulfotransferase 2 (HS6ST2), transcript variant L, mRNA. | MGC130022; MGC130023 | 536.6374788 | 5.175125686 | 213 |
| 4250463 | NM_000275.1 | OCA2 | Homo sapiens oculocutaneous albinism II (pink-eye dilution homolog, mouse) (OCA2), mRNA. | D15S12; EYCL3; PED; P; BOCA | 633.0969543 | 5.162611074 | 214 |
| 5720523 | NM_000681.2 | ADRA2A | Homo sapiens adrenergic, alpha-2A-, | ZNF32; ALPHA2AAR; | 567.8824027 | 4.983295682 | 164 |

TABLE II-continued

| ProbeID | RefSeq_ID | Symbol | Definition | Synonyms | RFUs | Fold over Ave. | Filter Score |
|---|---|---|---|---|---|---|---|
| 840324 | NM_006984.3 | CLDN10 | receptor (ADRA2A), mRNA. *Homo sapiens* claudin 10 (CLDN10), transcript variant 2, mRNA. | ADRA2R; ADRA2; ADRAR CPETRL3; OSP-L | 985.0699662 | 4.972328566 | 214 |
| 1010097 | NM_021815.2 | SLC5A7 | *Homo sapiens* solute carrier family 5 (choline transporter), member 7 (SLC5A7), mRNA. | MGC126299; MGC126300; CHT1; hCHT; CHT 14PEND14X P6 | 346.5666667 | 4.954880535 | 244 |
| 4010040 | NM_000184.2 | HBG2 | *Homo sapiens* hemoglobin, gamma G (HBG2), mRNA. | | 313.7634518 | 4.211275238 | 251 |
| 430088 | NM_006487.2 | FBLN1 | *Homo sapiens* fibulin 1 (FBLN1), transcript variant A, mRNA. | FBLN | 316.600423 | 4.041834655 | 251 |
| 3370452 | NM_004877.1 | GMFG | *Homo sapiens* glia maturation factor, gamma (GMFG), mRNA. | MGC126867; GMF-GAMMA | 628.971066 | 7.266782539 | 241 |
| 7210136 | NM_001770.4 | CD19 | *Homo sapiens* CD19 molecule (CD19), mRNA. | B4; MGC12802 | 164.8480541 | 1.723527702 | 241 |
| 7610441 | NM_002509.2 | NKX2-2 | *Homo sapiens* NK2 homeobox 2 (NKX2-2), mRNA. | NKX2B; NKX2.2 | 8958.460406 | 52.20534222 | 238 |
| 6760725 | NM_172105.2 | EYA4 | *Homo sapiens* eyes absent homolog 4 (*Drosophila*) (EYA4), transcript variant 4, mRNA. | CMD1J; DFNA10 | 296.6160745 | 3.231332733 | 237 |
| 1110564 | NM_006419.1 | CXCL13 | *Homo sapiens* chemokine (C—X—C motif) ligand 13 (B-cell chemoattractant) (CXCL13), mRNA. | SCYB13; ANGIE; BCA1; ANGIE2; BCA-1; BLR1L; BLC | 1235.339255 | 9.503053304 | 236 |
| 5700753 | NM_001024912.1 | CEACAM1 | *Homo sapiens* carcinoembryonic antigen-related cell adhesion molecule 1 (biliary glycoprotein) (CEACAM1), transcript variant 2, mRNA. | BGPI; BGP; BGP1 | 189.4456853 | 1.8757467 | 236 |
| 2350139 | NM_004100.3 | EYA4 | *Homo sapiens* eyes absent homolog 4 (*Drosophila*) (EYA4), transcript variant 1, mRNA. | CMD1J; DFNA10 | 696.336379 | 8.967488935 | 235 |
| 3440068 | NM_022469.3 | GREM2 | *Homo sapiens* gremlin 2, cysteine knot superfamily, homolog (*Xenopus laevis*) (GREM2), mRNA. | DAND3; PRDC; CKTSF1B2 | 415.1347716 | 4.635949325 | 235 |
| 1980639 | NM_030923.3 | TMEM163 | *Homo sapiens* transmembrane protein 163 (TMEM163), mRNA. | SV31; DC29; DKFZP566N034; DKFZp666J217 | 277.7566836 | 3.054668594 | 235 |
| 4220674 | NM_152709.3 | STOX1 | *Homo sapiens* storkhead box 1 (STOX1), transcript variant 1, mRNA. | PEE4; C10orf24 | 247.1394247 | 2.622790499 | 234 |
| 1260180 | NM_004100.3 | EYA4 | *Homo sapiens* eyes absent homolog 4 (*Drosophila*) (EYA4), transcript variant 1, mRNA. | CMD1J; DFNA10 | 1038.350761 | 9.223801926 | 233 |
| 5390463 | NM_001076778.1 | FAM107A | *Homo sapiens* family with sequence similarity 107, member A (FAM107A), transcript variant 2, mRNA. | FLJ30158; DRR1; TU3A; FLJ45473 | 237.4274958 | 1.720487646 | 233 |
| 4120408 | NM_003822.3 | NR5A2 | *Homo sapiens* nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 525.6414552 | 6.760066797 | 231 |
| 3170152 | NM_000878.2 | IL2RB | *Homo sapiens* interleukin 2 receptor, beta (IL2RB), mRNA. | CD122; P7075 | 335.7822335 | 3.395880134 | 230 |
| 4220209 | NM_012309.1 | SHANK2 | *Homo sapiens* SH3 and multiple ankyrin repeat domains 2 (SHANK2), transcript variant 1, mRNA. | ProSAP1; CTTNBP1; CORTBP1; SPANK-3; SHANK | 291.9580372 | 2.668218497 | 229 |
| 3850112 | NM_052960.1 | RBP7 | *Homo sapiens* retinol binding protein 7, cellular (RBP7), mRNA. | MGC70641; CRBPIV; CRBP4 | 306.2944162 | 3.090247686 | 227 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 4508.640609 | 6.155086072 | 225 |
| 510687 | NM_170697.1 | ALDH1A2 | *Homo sapiens* aldehyde dehydrogenase 1 family, | MGC26444; RALDH(II); | 299.6906091 | 2.700072881 | 225 |

TABLE II-continued

| ProbeID | RefSeq_ID | Symbol | Definition | Synonyms | RFUs | Fold over Ave. | Filter Score |
|---|---|---|---|---|---|---|---|
| 3930546 | NM_001001290.1 | SLC2A9 | member A2 (ALDH1A2), transcript variant 3, mRNA. *Homo sapiens* solute carrier family 2 (facilitated glucose transporter), member 9 (SLC2A9), transcript variant 2, mRNA. | RALDH2; RALDH2-T GLUTX; GLUT9 | 498.1417936 | 4.834247907 | 224 |
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 4465.328088 | 6.818235718 | 223 |
| 5290711 | NM_004143.2 | CITED1 | *Homo sapiens* Cbp/p300-interacting transactivator, with Glu/Asp-rich carboxy-terminal domain, 1 (CITED1), mRNA. | MSG1 | 528.443824 | 5.473851143 | 222 |
| 2760228 | NM_001001994.1 | GPM6B | *Homo sapiens* glycoprotein M6B (GPM6B), transcript variant 4, mRNA. | MGC54284; M6B; MGC17150 | 660.5593909 | 6.510212216 | 221 |
| 1450358 | NM_000519.3 | HBD | *Homo sapiens* hemoglobin, delta (HBD), mRNA. | | 270.141286 | 2.855395504 | 221 |
| 4810273 | NM_015464.2 | SOSTDC1 | *Homo sapiens* sclerostin domain containing 1 (SOSTDC1), mRNA. | CDA019; USAG1; ECTODIN; DKFZp564D206 | 1933.582403 | 17.29690634 | 219 |
| 6400358 | NM_001766.3 | CD1D | *Homo sapiens* CD1d molecule (CD1D), mRNA. | MGC34622; R3; CD1A | 1065.026058 | 9.934318891 | 217 |
| 2690279 | NM_173798.2 | ZCCHC12 | *Homo sapiens* zinc finger, CCHC domain containing 12 (ZCCHC12), mRNA. | SIZN; FLJ16123; SIZN1 | 707.9072758 | 8.633550582 | 217 |
| 7330639 | NM_003822.3 | NR5A2 | *Homo sapiens* nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 668.3686971 | 7.66113023 | 217 |
| 5720075 | NM_003638.1 | ITGA8 | *Homo sapiens* integrin, alpha 8 (ITGA8), mRNA. | | 329.7620981 | 3.642052083 | 217 |
| 4590129 | NM_006438.2 | COLEC10 | *Homo sapiens* collectin sub-family member 10 (C-type lectin) (COLEC10), mRNA. | MGC118794; CLL1; MGC118795 | 317.2076142 | 2.295375699 | 216 |
| 5690301 | NM_001704.1 | BAI3 | *Homo sapiens* brain-specific angiogenesis inhibitor 3 (BAI3), mRNA. | KIAA0550; MGC133100 | 302.9328257 | 2.80249768 | 213 |
| 1070594 | NM_018850.2 | ABCB4 | *Homo sapiens* ATP-binding cassette, sub-family B (MDR/TAP), member 4 (ABCB4), transcript variant C, mRNA. | PGY3; PFIC-3; MDR2/3; MDR3; MDR2; ABC21; GBD1 | 214.2930626 | 2.022388164 | 210 |
| 2630279 | NM_001001995.1 | GPM6B | *Homo sapiens* glycoprotein M6B (GPM6B), transcript variant 1, mRNA. | MGC54284; M6B; MGC17150 | 2439.674788 | 9.540605397 | 205 |
| 6940037 | NM_000867.3 | HTR2B | *Homo sapiens* 5-hydroxytryptamine (serotonin) receptor 2B (HTR2B), mRNA. | 5-HT2B; 5-HT(2B) | 304.8783418 | 2.079311279 | 205 |
| 7160102 | NM_017954.9 | CADPS2 | *Homo sapiens* Ca++-dependent secretion activator 2 (CADPS2), transcript variant 1, mRNA. | KIAA1591; FLJ40851 | 819.379357 | 6.295499352 | 199 |
| 3870202 | NM_01001995.1 | GPM6B | *Homo sapiens* glycoprotein M6B (GPM6B), transcript variant 1, mRNA. | MGC54284; M6B; MGC17150 | 2486.648393 | 5.998064449 | 199 |
| 620112 | NM_001079691.1 | N4BP2L1 | *Homo sapiens* NEDD4 binding protein 2-like (N4BP2L1), transcript variant 2, mRNA. | CG018 | 353.541709 | 3.406839005 | 198 |
| 7380239 | NM_004114.2 | FGF13 | *Homo sapiens* fibroblast growth factor 13 (FGF13), transcript variant 1A, mRNA. | FGF2; FHF2 | 1352.223689 | 6.591556528 | 197 |
| 460575 | NM_080647.1 | TBX1 | *Homo sapiens* T-box 1 (TBX1), transcript variant C, mRNA. | VCFS; TGA; DORV; CTHM; TBX1C; DGS; CAFS; DGCR | 268.2879865 | 1.904340449 | 197 |
| 3710253 | NM_144691.3 | CAPN12 | *Homo sapiens* calpain 12 (CAPN12), mRNA. | MGC20576 | 404.0658206 | 3.489635797 | 196 |
| 6550133 | NM_001079691.1 | N4BP2L1 | *Homo sapiens* NEDD4 binding protein 2-like 1 | CG018 | 337.4719966 | 3.235131775 | 196 |

TABLE II-continued

| ProbeID | RefSeq_ID | Symbol | Definition | Synonyms | RFUs | Fold over Ave. | Filter Score |
|---|---|---|---|---|---|---|---|
| 630181 | NM_006647.1 | NOXA1 | (N4BP2L1), transcript variant 2, mRNA. *Homo sapiens* NADPH oxidase activator 1 (NOXA1), mRNA. | MGC131800; FLJ25475; SDCCAG31; p51NOX; NY-CO-31 | 252.3011844 | 2.035903839 | 195 |
| 5810678 | NM_002910.4 | RENBP | *Homo sapiens* renin binding protein (RENBP), mRNA. | RNBP; RBP | 1070.759898 | 4.915511734 | 192 |
| 4230750 | NM_023067.2 | FOXL2 | *Homo sapiens* forkhead box L2 (FOXL2), mRNA. | BPES1; PINTO; BPES; PFRK; POF3 | 254.4526227 | 1.947051692 | 191 |
| 5310646 | NM_020299.3 | AKR1B10 | *Homo sapiens* aldo-keto reductase family 1, member B10 (aldose reductase) (AKR1B10), mRNA. | ARL-1; AKR1B11; HSI; AKR1B12; ALDRLn; MGC14103; HIS; ARL1 | 361.3534687 | 2.790458805 | 186 |
| 3840554 | NM_014767.1 | SPOCK2 | *Homo sapiens* sparc/osteonectin, cwcv and kazal-like domains proteoglycan (testican) 2 (SPOCK2), mRNA. | testican-2 | 565.0042301 | 3.698112666 | 179 |
| 2510369 | NM_006867.2 | RBPMS | *Homo sapiens* RNA binding protein with multiple splicing (RBPMS), transcript variant 4, mRNA. | HERMES | 366.4856176 | 3.304611272 | 179 |
| | | | 14PEND17Z P6 | | | | |
| 7400280 | NM_033069.2 | C6orf114 | *Homo sapiens* chromosome 6 open reading frame 114 (C6orf114), mRNA. | RP11-501I19.1; ADG-90; FLJ20330 | 284.8199662 | 3.970829122 | 247 |
| 4210274 | NM_002976.2 | SCN7A | *Homo sapiens* sodium channel, voltage-gated, type VII, alpha (SCN7A), mRNA. | SCN6A | 324.3121827 | 3.784997675 | 247 |
| 6860762 | NM_020204.2 | LHX9 | *Homo sapiens* LIM homeobox 9 (LHX9), transcript variant 1, mRNA. | | 221.878511 | 3.038891353 | 247 |
| 670736 | NM_002150.2 | HPD | *Homo sapiens* 4-hydroxyphenylpyruvate dioxygenase (HPD), mRNA. | 4HPPD; GLOD3; PPD; 4-HPPD | 314.7539763 | 3.523995488 | 246 |
| 6940400 | NM_003924.2 | PHOX2B | *Homo sapiens* paired-like homeobox 2b (PHOX2B), mRNA. | PMX2B; NBPhox | 2477.42132 | 35.40956947 | 245 |
| 6420113 | NM_080723.3 | NRSN1 | *Homo sapiens* neurensin 1 (NRSN1), mRNA. | p24; VMP | 338.6403553 | 4.466916441 | 245 |
| 2640068 | NM_002934.2 | RNASE2 | *Homo sapiens* ribonuclease, RNase A family, 2 (liver, eosinophil-derived neurotoxin) (RNASE2), mRNA. | EDN; RNS2 | 269.6680203 | 3.175088973 | 245 |
| 6220750 | NM_000826.2 | GRIA2 | *Homo sapiens* glutamate receptor, ionotropic, AMPA 2 (GRIA2), mRNA. | HBGR2; GLURB; GLUR2 | 380.2961929 | 3.057517379 | 245 |
| 1010097 | NM_021815.2 | SLC5A7 | *Homo sapiens* solute carrier family 5 (choline transporter), member 7 (SLC5A7), mRNA. | MGC126299; MGC126300; CHT1; hCHT; CHT | 440.9554992 | 6.576716319 | 244 |
| 1170739 | NM_015236.3 | LPHN3 | *Homo sapiens* latrophilin 3 (LPHN3), mRNA. | LEC3; CIRL3 | 311.1620981 | 4.228710899 | 244 |
| 2230088 | NM_213609.2 | FAM19A1 | *Homo sapiens* family with sequence similarity 19 (chemokine (C-C motif)-like), member A1 (FAM19A1), mRNA. | TAFA-1; TAFA1 | 2621.940609 | 38.49345131 | 243 |
| 7320471 | NM_003221.3 | TFAP2B | *Homo sapiens* transcription factor AP-2 beta (activating enhancer binding protein 2 beta) (TFAP2B), mRNA. | MGC21381; AP-2B; AP2-B | 719.314044 | 9.309999981 | 243 |
| 4760626 | NM_002426.2 | MMP12 | *Homo sapiens* matrix metallopeptidase 12 (macrophage elastase) (MMP12), mRNA. | MGC138506; MME; HME | 477.83511 | 7.099577237 | 243 |
| 6900196 | NM_004975.2 | KCNB1 | *Homo sapiens* potassium voltage-gated channel, Shab-related subfamily, member 1 (KCNB1), mRNA. | KV2.1; h-DRK1; DRK1 | 373.3384095 | 4.537902853 | 243 |

TABLE II-continued

| ProbeID | RefSeq_ID | Symbol | Definition | Synonyms | RFUs | Fold over Ave. | Filter Score |
|---|---|---|---|---|---|---|---|
| 1660152 | NM_001080534.1 | UNC13C | *Homo sapiens* unc-13 homolog C (*C. elegans*) (UNC13C), mRNA. | DKFZp547H074 | 877.1373942 | 13.19629982 | 242 |
| 6370315 | NM_002125.3 | HLA-DRB5 | *Homo sapiens* major histocompatibility complex, class II, DR beta 5 (HLA-DRB5), mRNA. | HLA-DRB1 | 641.5165821 | 4.660709429 | 242 |
| 160500 | NM_001012513.1 | GRP | *Homo sapiens* gastrin-releasing peptide (GRP), transcript variant 3, mRNA. | proGRP; GRP-10; BN; preproGRP | 428.8714044 | 3.790378495 | 242 |
| 6220332 | NM_003044.2 | SLC6A12 | *Homo sapiens* solute carrier family 6 (neurotransmitter transporter, betaine/GABA), member 12 (SLC6A12), mRNA. | BGT-1; BGT1; FLJ38727 | 269.6680203 | 2.80365914 | 240 |
| 840017 | NM_206819.1 | MYBPC1 | *Homo sapiens* myosin binding protein C, slow type (MYBPC1), transcript variant 2, mRNA. | slow-type; MYBPCS; MYBPCC | 1449.060914 | 18.91260739 | 239 |
| 5910056 | NM_206821.1 | MYBPC1 | *Homo sapiens* myosin binding protein C, slow type (MYBPC1), transcript variant 4, mRNA. | slow-type; MYBPCS; MYBPCC | 948.8686971 | 12.16433717 | 239 |
| 1010592 | NM_001001548.1 | CD36 | *Homo sapiens* CD36 molecule (thrombospondin receptor) (CD36), transcript variant 1, mRNA. | GPIV; FAT; GP3B; CHDS7; SCARB3; PASIV; GP4 | 1243.074027 | 12.92549177 | 238 |
| 6620369 | NM_015236.3 | LPHN3 | *Homo sapiens* latrophilin 3 (LPHN3), mRNA. | LEC3; CIRL3 | 700.2458545 | 9.729724226 | 238 |
| 7610441 | NM_002509.2 | NKX2-2 | *Homo sapiens* NK2 homeobox 2 (NKX2-2), mRNA. | NKX2B; NKX2.2 | 1796.867005 | 9.67180292 | 238 |
| 5130471 | NM_000922.2 | PDE3B | *Homo sapiens* phosphodiesterase 3B, cGMP-inhibited (PDE3B), mRNA. | HcGIP1; cGIPDE1 | 806.7043147 | 11.36131335 | 237 |
| 6760725 | NM_172105.2 | EYA4 | *Homo sapiens* eyes absent homolog 4 (*Drosophila*) (EYA4), transcript variant 4, mRNA. | CMD1J; DFNA10 | 333.1470389 | 3.752459802 | 237 |
| 1110564 | NM_006419.1 | CXCL13 | *Homo sapiens* chemokine (C—X—C motif) ligand 13 (B-cell chemoattractant) (CXCL13), mRNA. | SCYB13; ANGIE; BCA1; ANGIE2; BCA-1; BLR1L; BLC | 493.3796954 | 3.19479363 | 236 |
| 3940292 | NM_001482.2 | GATM | *Homo sapiens* glycine amidinotransferase (L-arginine:glycine amidinotransferase) (GATM), nuclear gene encoding mitochondrial protein, mRNA. | AT; AGAT | 281.8204738 | 3.07380463 | 236 |
| 7000176 | NM_152679.2 | SLC10A4 | *Homo sapiens* solute carrier family 10 (sodium/bile acid cotransporter family), member 4 (SLC10A4), mRNA. | MGC29802; P4 | 523.5020305 | 6.482099366 | 235 |
| 2350139 | NM_004100.3 | EYA4 | *Homo sapiens* eyes absent homolog 4 (*Drosophila*) (EYA4), transcript variant 1, mRNA. | CMD1J; DFNA10 | 493.8817259 | 6.069515232 | 235 |
| 2640348 | NM_021146.2 | ANGPTL7 | *Homo sapiens* angiopoietin-like 7 (ANGPTL7), mRNA. | RP4-647M16.2; dJ647M16.1; AngX; CDT6 | 1412.57445 | 6.571285458 | 234 |
| 4220674 | NM_152709.3 | STOX1 | *Homo sapiens* storkhead box 1 (STOX1), transcript variant 1, mRNA. | PEE4; C10orf24 | 349.6734349 | 4.125825631 | 234 |
| 3520255 | NM_004731.3 | SLC16A7 | *Homo sapiens* solute carrier family 16, member 7 (monocarboxylic acid transporter 2) (SLC16A7), mRNA. | MCT2 | 326.5969543 | 3.555242703 | 234 |
| 7160437 | NM_001025068.1 | ARPP-21 | *Homo sapiens* cyclic AMP-regulated phosphoprotein, 21 kD (ARPP-21), transcript variant 3, mRNA. | FLJ32997 | 322.0407783 | 3.551198363 | 234 |
| 1260180 | NM_004100.3 | EYA4 | *Homo sapiens* eyes absent homolog 4 (*Drosophila*) | CMD1J; DFNA10 | 1359.628257 | 12.38716213 | 233 |

TABLE II-continued

| ProbeID | RefSeq_ID | Symbol | Definition | Synonyms | RFUs | Fold over Ave. | Filter Score |
|---|---|---|---|---|---|---|---|
| | | | (EYA4), transcript variant 1, mRNA. | | | | |
| 1990731 | NM_006157.2 | NELL1 | Homo sapiens NEL-like 1 (chicken) (NELL1), mRNA. | FLJ45906; IDH3GL; NRP1 | 587.851269 | 6.119205435 | 233 |
| 6200333 | NM_021977.2 | SLC22A3 | Homo sapiens solute carrier family 22 (extra-neuronal monoamine transporter), member 3 (SLC22A3), mRNA. | EMT; OCT3; EMTH | 398.2453469 | 4.531630695 | 233 |
| 7320348 | NM_016511.2 | CLEC1A | Homo sapiens C-type lectin domain family 1, member A (CLEC1A), mRNA. | CLEC1; MGC34328 | 673.8399323 | 8.182223765 | 232 |
| 620349 | NM_006180.3 | NTRK2 | Homo sapiens neurotrophic tyrosine kinase, receptor, type 2 (NTRK2), transcript variant a, mRNA. | GP145-TrkB; TRKB | 470.8583756 | 5.477254002 | 232 |
| 3310538 | NM_000072.2 | CD36 | Homo sapiens CD36 molecule (thrombospondin receptor) (CD36), transcript variant 3, mRNA. | GPIV; FAT; GP3B; CHDS7; SCARB3; PASIV; GP4 | 2198.552961 | 18.19294729 | 229 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 1484.388494 | 12.19587859 | 228 |
| 3840465 | NM_003991.1 | EDNRB | Homo sapiens endothelin receptor type B (EDNRB), transcript variant 2, mRNA. | ABCDS; HSCR2; ETRB; HSCR; ETB | 326.9213198 | 2.735607746 | 228 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 1612.340102 | 12.35474589 | 227 |
| 7210554 | NM_016300.4 | ARPP-21 | Homo sapiens cyclic AMP-regulated phosphoprotein, 21 kD (ARPP-21), transcript variant 1, mRNA. | FLJ32997 | 364.6739425 | 3.68346041 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 9463.014721 | 14.0175387 | 225 |
| 5260484 | NM_002124.1 | HLA-DRB1 | Homo sapiens major histocompatibility complex, class II, DR beta 1 (HLA-DRB1), mRNA. | HLA-DRB1*; HLA-DR1B; HLA DRB1; DRB1 | 835.7881557 | 5.665449167 | 225 |
| 7000181 | NM_001037317.1 | PAP2D | Homo sapiens phosphatidic acid phosphatase type 2 (PAP2D), transcript variant 1, mRNA. | PAP2 | 488.528511 | 5.88468091 | 224 |
| 3930546 | NM_001001290.1 | SLC2A9 | Homo sapiens solute carrier family 2 (facilitated glucose transporter), member 9 (SLC2A9), transcript variant 2, mRNA. | GLUTX; GLUT9 | 570.7226734 | 5.684316806 | 224 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 12076.53553 | 20.14451606 | 223 |
| | | | 14PEND20X P6 | | | | |
| 1780537 | NM_152701.2 | ABCA13 | Homo sapiens ATP-binding cassette, sub-family A (ABC1), member 13 (ABCA13), mRNA. | DKFZp313D2411; FLJ33951; FLJ33876; FLJ16398 | 323.0055838 | 5.357087727 | 250 |
| 2490551 | NM_005604.2 | POU3F2 | Homo sapiens POU class 3 homeobox 2 (POU3F2), mRNA. | OTF7; OCT7; BRN2; POUF3 | 370.4913706 | 4.261487952 | 250 |
| 1050040 | NM_004925.3 | AQP3 | Homo sapiens aquaporin 3 (Gill blood group) (AQP3), mRNA. | GIL | 311.0724196 | 3.69052413 | 248 |
| 1260370 | NM_175611.2 | GRIK1 | Homo sapiens glutamate receptor, | GLUR5; EEA3; | 289.4507614 | 3.52290451 | 248 |

TABLE II-continued

| ProbeID | RefSeq_ID | Symbol | Definition | Synonyms | RFUs | Fold over Ave. | Filter Score |
|---|---|---|---|---|---|---|---|
| | | | ionotropic, kainate 1 (GRIK1), transcript variant 2, mRNA. | GLR5; EAA3 | | | |
| 1010189 | NM_033225.3 | CSMD1 | Homo sapiens CUB and Sushi multiple domains 1 (CSMD1), mRNA. | KIAA1890 | 191.4615905 | 2.820872145 | 248 |
| 6860762 | NM_020204.2 | LHX9 | Homo sapiens LIM homeobox 9 (LHX9), transcript variant 1, mRNA. | | 269.1796954 | 3.899922662 | 247 |
| 6350682 | NM_016102.2 | TRIM17 | Homo sapiens tripartite motif-containing 17 (TRIM17), transcript variant 1, mRNA. | RBCC; terf; RNF16 | 256.5441624 | 3.303685551 | 247 |
| 3180068 | NM_013371.2 | IL19 | Homo sapiens interleukin 19 (IL19), transcript variant 2, mRNA. | NG.1; IL-10C; ZMDA1; MDA1 | 190.142132 | 2.629654724 | 247 |
| 1400053 | NM_001012513.1 | GRP | Homo sapiens gastrin-releasing peptide (GRP), transcript variant 3, mRNA. | proGRP; GRP-10; BN; preproGRP | 1112.613029 | 15.26540634 | 245 |
| 6220750 | NM_000826.2 | GRIA2 | Homo sapiens glutamate receptor, ionotropic, AMPA 2 (GRIA2), mRNA. | HBGR2; GLURB; GLUR2 | 1194.494755 | 11.74449578 | 245 |
| 7650168 | NM_002942.2 | ROBO2 | Homo sapiens roundabout, axon guidance receptor, homolog 2 (Drosophila) (ROBO2), mRNA. | KIAA1568; SAX3 | 253.7025381 | 3.197433272 | 245 |
| 6400131 | NM_000782.3 | CYP24A1 | Homo sapiens cytochrome P450, family 24, subfamily A, polypeptide 1 (CYP24A1), nuclear gene encoding mitochondrial protein, mRNA. | CYP24; P450-CC24; MGC126274; CP24; MGC126273 | 206.1935702 | 2.725350393 | 245 |
| 1010097 | NM_021815.2 | SLC5A7 | Homo sapiens solute carrier family 5 (choline transporter), member 7 (SLC5A7), mRNA. | MGC126299; MGC126300; CHT1; hCHT; CHT | 918.8030457 | 14.78733011 | 244 |
| 7160192 | NM_139319.1 | SLC17A8 | Homo sapiens solute carrier family 17 (sodium-dependent inorganic phosphate cotransporter), member 8 (SLC17A8), mRNA. | VGLUT3 | 705.6516074 | 11.90781339 | 244 |
| 6900196 | NM_004975.2 | KCNB1 | Homo sapiens potassium voltage-gated channel, Shab-related subfamily, member 1 (KCNB1), mRNA. | KV2.1; h-DRK1; DRK1 | 1022.349915 | 14.16499339 | 243 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 760.6098139 | 9.901896372 | 243 |
| 4570639 | NM_003063.2 | SLN | Homo sapiens sarcolipin (SLN), mRNA. | MGC12301; MGC125854; MGC125855 | 868.8908629 | 5.60439611 | 243 |
| 160500 | NM_001012513.1 | GRP | Homo sapiens gastrin-releasing peptide (GRP), transcript variant 3, mRNA. | proGRP; GRP-10; BN; preproGRP | 4223.607614 | 46.1765636 | 242 |
| 4810487 | NM_018712.2 | ELMOD1 | Homo sapiens ELMO/CED-12 domain containing 1 (ELMOD1), mRNA. | DKEZp547C176 | 1332.051269 | 17.50939429 | 242 |
| 1660152 | NM_001080534.1 | UNC13C | Homo sapiens unc-13 homolog C (C. elegans) (UNC13C), mRNA. | DKEZp547H074 | 479.4463621 | 6.759747045 | 242 |
| 6370315 | NM_002125.3 | HLA-DRB5 | Homo sapiens major histocompatibility complex, class II, DR beta 5 (HLA-DRB5), mRNA. | HLA-DRB1 | 597.7241963 | 4.274287662 | 242 |
| 6660463 | NM_020140.2 | ANKS1B | Homo sapiens ankyrin repeat and sterile alpha motif domain containing 1B (ANKS1B), transcript variant 3, mRNA. | MGC26087; ANKS2; AIDA; cajalin-2; EB-1; AIDA-1 | 326.001269 | 3.806471071 | 242 |
| 6510274 | NM_022124.3 | CDH23 | Homo sapiens cadherin-like 23 (CDH23), transcript | DKFZp434P2350; USH1H; KIAA1774; | 257.7777496 | 2.881621105 | 242 |

TABLE II-continued

| ProbeID | RefSeq_ID | Symbol | Definition | Synonyms | RFUs | Fold over Ave. | Filter Score |
|---|---|---|---|---|---|---|---|
| | | | variant 1, mRNA. | FLJ00233; MGC102761; FLJ36499; DFNB12; USH1D; KIAA1812 | | | |
| 4920075 | NM_003245.2 | TGM3 | Homo sapiens transglutaminase 3 (E polypeptide, protein-glutamine-gamma-glutamyltransferase) (TGM3), mRNA. | MGC126249; TGE; MGC126250 | 622.6956007 | 5.779798736 | 240 |
| 6270022 | NM_002110.2 | HCK | Homo sapiens hemopoietic cell kinase (HCK), mRNA. | JTK9 | 1388.537733 | 18.74382795 | 239 |
| 840017 | NM_206819.1 | MYBPC1 | Homo sapiens myosin binding protein C, slow type (MYBPC1), transcript variant 2, mRNA. | slow-type; MYBPCS; MYBPCC | 297.1455161 | 3.083294182 | 239 |
| 3390523 | NM_001010971.1 | SAMD13 | Homo sapiens sterile alpha motif domain containing 13 (SAMD13), mRNA. | RP11-376N17.1 | 242.1697124 | 2.498659203 | 239 |
| 7610441 | NM_002509.2 | NKX2-2 | Homo sapiens NK2 homeobox 2 (NKX2-2), mRNA. | NKX2B; NKX2.2 | 5085.8978 | 29.20574079 | 238 |
| 1710131 | NM_172078.1 | CAMK2B | Homo sapiens calcium/calmodulin-dependent protein kinase (CaM kinase) II beta (CAMK2B), transcript variant 2, mRNA. | CAMKB; CAM2; MGC29528; CAMK2 | 234.6614213 | 2.900738101 | 238 |
| 5270520 | NM_005449.3 | FAIM3 | Homo sapiens Fas apoptotic inhibitory molecule 3 (FAIM3), mRNA. | TOSO | 418.2686971 | 5.038054817 | 237 |
| 6760725 | NM_172105.2 | EYA4 | Homo sapiens eyes absent homolog 4 (Drosophila) (EYA4), transcript variant 4, mRNA. | CMD1J; DFNA10 | 291.1939086 | 3.153983628 | 237 |
| 730093 | NM_020209.2 | SHD | Homo sapiens Src homology 2 domain containing transforming protein D (SHD), mRNA. | | 247.6580372 | 2.428018276 | 237 |
| 1110564 | NM_006419.1 | CXCL13 | Homo sapiens chemokine (C—X—C motif) ligand 13 (B-cell chemoattractant) (CXCL13), mRNA. | SCYB13; ANGIE; ANGIE2; BCA-1; BLR1L; BLC | 920.6203046 | 6.827262097 | 236 |
| 4860403 | NM_002747.3 | MAPK4 | Homo sapiens mitogen-activated protein kinase 4 (MAPK4), mRNA. | Erk4; p63MAPK; ERK3; PRKM4 | 206.8522843 | 2.305901186 | 236 |
| 7000176 | NM_152679.2 | SLC10A4 | Homo sapiens solute carrier family 10 (sodium/bile acid cotransporter family), member 4 (SLC10A4), mRNA. | MGC29802; P4 | 2764.305584 | 38.50855556 | 235 |
| 2350139 | NM_004100.3 | EYA4 | Homo sapiens eyes absent homolog 4 (Drosophila) (EYA4), transcript variant 1, mRNA. | CMD1J; DFNA10 | 348.5341794 | 3.988983315 | 235 |
| 6020224 | NM_000507.2 | FBP1 | Homo sapiens fructose-1,6-bisphosphatase 1 (FBP1), mRNA. | FBP | 250.6651438 | 3.279865206 | 234 |
| 1260180 | NM_004100.3 | EYA4 | Homo sapiens eyes absent homolog 4 (Drosophila) (EYA4), transcript variant 1, mRNA. | CMD1J; DFNA10 | 1071.213113 | 9.547370984 | 233 |
| 1230477 | NM_005853.4 | IRX5 | Homo sapiens iroquois homeobox protein 5 (IRX5), mRNA. | IRX-2a | 924.7071066 | 8.927866096 | 233 |
| 7550358 | NM_006159.1 | NELL2 | Homo sapiens NEL-like 2 (chicken) (NELL2), mRNA. | NRP2 | 517.2309645 | 2.722053505 | 233 |
| 1070162 | NM_020116.2 | FSTL5 | Homo sapiens follistatin-like 5 (FSTL5), mRNA. | KIAA1263; DKFZp566D234 | 1344.380541 | 17.13253704 | 232 |
| 580187 | NM_001029851.1 | PDE8B | Homo sapiens phosphodiesterase 8B (PDE8B), transcript variant 3, mRNA. | FLJ11212 | 554.7313029 | 5.496016666 | 232 |

TABLE II-continued

| ProbeID | RefSeq_ID | Symbol | Definition | Synonyms | RFUs | Fold over Ave. | Filter Score |
|---|---|---|---|---|---|---|---|
| 5860093 | XM_940314.2 | NLF2 | PREDICTED: *Homo sapiens* nuclear localized factor 2 (NLF2), mRNA. | | 322.1834179 | 3.42630665 | 230 |
| 510452 | NM_002012.1 | FHIT | *Homo sapiens* fragile histidine triad gene (FHIT), mRNA. | FRA3B; AP3Aase | 251.7199662 | 2.650291786 | 230 |
| 2940189 | NM_020929.1 | LRRC4C | *Homo sapiens* leucine rich repeat containing 4C (LRRC4C), mRNA. | KIAA1580; NGL1; NGL-1 | 273.0175973 | 2.546513329 | 230 |
| 1090561 | NM_145740.2 | GSTA1 | *Homo sapiens* glutathione S-transferase A1 (GSTA1), mRNA. | GTH1; GST2; MGC131939; GSTA1-1 | 495.3754653 | 5.042007509 | 229 |
| 3310037 | NM_005634.2 | SOX3 | *Homo sapiens* SRY (sex determining region Y)-box 3 (SOX3), mRNA. | SOXB; MRGH | 561.513621 | 3.485834699 | 229 |
| 360014 | NM_052836.1 | CDH23 | *Homo sapiens* cadherin-like 23 (CDH23), transcript variant 2, mRNA. | DKFZp434P2350; USH1H; KIAA1774; FLJ00233; MGC102761; FLJ36499; DFNB12; USH1D; KIAA1812 | 257.0951777 | 2.527703313 | 229 |
| 14PEND23X P6 | | | | | | | |
| 4010040 | NM_000184.2 | HBG2 | *Homo sapiens* hemoglobin, gamma G (HBG2), mRNA. | | 269.1013536 | 3.469485572 | 251 |
| 6380328 | NM_198529.2 | EFCAB5 | *Homo sapiens* EF-hand calcium binding domain 5 (EFCAB5), mRNA. | DKFZp686I0638; FLJ46247; DKFZp434G2420 | 155.8787648 | 1.861978037 | 248 |
| 6940400 | NM_003924.2 | PHOX2B | *Homo sapiens* paired-like homeobox 2b (PHOX2B), mRNA. | PMX2B; NBPhox | 296.7730964 | 3.361543426 | 245 |
| 1010097 | NM_021815.2 | SLC5A7 | *Homo sapiens* solute carrier family 5 (choline transporter), member 7 (SLC5A7), mRNA. | MGC126299; MGC126300; CHT1; hCHT; CHT | 155.6969543 | 1.675262372 | 244 |
| 4010224 | NM_199353.1 | PRB1 | *Homo sapiens* proline-rich protein BstNI subfamily 1 (PRB1), transcript variant 2, mRNA. | Ps 1; PMF; PRB1L; Ps 2; PM; PMS; PRB1M | 190.9407783 | 1.731192933 | 243 |
| 6370189 | NM_006248.2 | PRB2 | *Homo sapiens* proline-rich protein BstNI subfamily 2 (PRB2), mRNA. | cP7; Ps; PRPPRB1 | 240.0468697 | 2.376676938 | 242 |
| 3370452 | NM_004877.1 | GMFG | *Homo sapiens* glia maturation factor, gamma (GMFG), mRNA. | MGC126867; GMF-GAMMA | 554.7313029 | 6.291023858 | 241 |
| 5860075 | NM_004345.3 | CAMP | *Homo sapiens* cathelicidin antimicrobial peptide (CAMP), mRNA. | HSD26; LL37; FALL39; FALL-39; CAP18 | 205.6200508 | 2.373239362 | 241 |
| 7610441 | NM_002509.2 | NKX2-2 | *Homo sapiens* NK2 homeobox 2 (NKX2-2), mRNA. | NKX2B; NKX2.2 | 6656.180372 | 38.53183231 | 238 |
| 6760725 | NM_172105.2 | EYA4 | *Homo sapiens* eyes absent homolog 4 (*Drosophila*) (EYA4), transcript variant 4, mRNA. | CMD1J; DFNA10 | 324.8649746 | 3.634313239 | 237 |
| 730093 | NM_020209.2 | SHD | *Homo sapiens* Src homology 2 domain containing transforming protein D (SHD), mRNA. | | 199.1903553 | 1.757141202 | 237 |
| 1110564 | NM_006419.1 | CXCL13 | *Homo sapiens* chemokine (C—X—C motif) ligand 13 (B-cell chemoattractant) (CXCL13), mRNA. | SCYB13; ANGIE; BCA1; ANGIE2; BCA-1; BLR1L; BLC | 989.5116751 | 7.412987625 | 236 |
| 5870435 | NM_006043.1 | HS3ST2 | *Homo sapiens* heparan sulfate (glucosamine) 3-O-sulfotransferase 2 (HS3ST2), mRNA. | 3OST2; 30ST2 | 244.043824 | 2.542831047 | 236 |
| 2350139 | NM_004100.3 | EYA4 | *Homo sapiens* eyes absent homolog 4 (*Drosophila*) (EYA4), transcript variant 1, mRNA. | CMD1J; DFNA10 | 584.2120135 | 7.362519834 | 235 |

TABLE II-continued

| ProbeID | RefSeq_ID | Symbol | Definition | Synonyms | RFUs | Fold over Ave. | Filter Score |
|---|---|---|---|---|---|---|---|
| 4220674 | NM_152709.3 | STOX1 | Homo sapiens storkhead box 1 (STOX1), transcript variant 1, mRNA. | PEE4; C10orf24 | 481.828511 | 6.063072814 | 234 |
| 5390463 | NM_001076778.1 | FAM107A | Homo sapiens family with sequence similarity 107, member A (FAM107A), transcript variant 2, mRNA. | FLJ30158; DRR1; TU3A; FLJ45473 | 951.3730118 | 9.901005872 | 233 |
| 1260180 | NM_004100.3 | EYA4 | Homo sapiens eyes absent homolog 4 (Drosophila) (EYA4), transcript variant 1, mRNA. | CMD1J; DFNA10 | 1059.589002 | 9.432917738 | 233 |
| 1070162 | NM_020116.2 | FSTL5 | Homo sapiens follistatin-like 5 (FSTL5), mRNA. | KIAA1263; DKFZp566D234 | 403.7604061 | 4.44577989 | 232 |
| 7320348 | NM_016511.2 | CLEC1A | Homo sapiens C-type lectin domain family 1, member A (CLEC1A), mRNA. | CLEC1; MGC34328 | 357.271912 | 3.86844202 | 232 |
| 4120408 | NM_003822.3 | NR5A2 | Homo sapiens nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 808.8181895 | 10.94061677 | 231 |
| 3170152 | NM_000878.2 | IL2RB | Homo sapiens interleukin 2 receptor, beta (IL2RB), mRNA. | CD122; P70-75 | 235.0103215 | 2.076628542 | 230 |
| 4220209 | NM_012309.1 | SHANK2 | Homo sapiens SH3 and multiple ankyrin repeat domains 2 (SHANK2), transcript variant 1, mRNA. | ProSAP1; CTTNBP1; CORTBP1; SPANK-3; SHANK | 204.2963621 | 1.566819881 | 229 |
| 2320369 | NM_015063.1 | SLC8A2 | Homo sapiens solute carrier family 8 (sodium/calcium exchanger), member 2 (SLC8A2), mRNA. | NCX2 | 458.9714044 | 2.761234796 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 5102.421658 | 7.097399927 | 225 |
| 3930546 | NM_001001290.1 | SLC2A9 | Homo sapiens solute carrier family 2 (facilitated glucose transporter), member 9 (SLC2A9), transcript variant 2, mRNA. | GLUTX; GLUT9 | 511.514044 | 4.990864005 | 224 |
| 940630 | NM_024761.3 | MOBKL2B | Homo sapiens MOB1, Mps One Binder kinase activator-like 2B (yeast) (MOBKL2B), mRNA. | FLJ13204; FLJ23916; MOB3B; MGC32960 | 217.462775 | 1.640738923 | 224 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 5565.606091 | 8.744686051 | 223 |
| 4490333 | NM_024581.4 | FAM184A | Homo sapiens family with sequence similarity 184, member A (FAM184A), transcript variant 1, mRNA. | FLJ13942 | 262.1167513 | 1.847581012 | 223 |
| 5290711 | NM_004143.2 | CITED1 | Homo sapiens Cbp/p300-interacting transactivator, with Glu/Asp-rich carboxy-terminal domain, 1 (CITED1), mRNA. | MSG1 | 405.5830795 | 3.968710701 | 222 |
| 2760228 | NM_001001994.1 | GPM6B | Homo sapiens glycoprotein M6B (GPM6B), transcript variant 4, mRNA. | MGC54284; M6B; MGC17150 | 405.100846 | 3.605783166 | 221 |
| 1450358 | NM_000519.3 | HBD | Homo sapiens hemoglobin, delta (HBD), mRNA. | | 233.172335 | 2.327782975 | 221 |
| 4810273 | NM_015464.2 | SOSTDC1 | Homo sapiens sclerostin domain containing 1 (SOSTDC1), mRNA. | CDA019; USAG1; ECTODIN; DKFZp564D206 | 2865.606768 | 26.11637144 | 219 |
| 7330639 | NM_003822.3 | NR5A2 | Homo sapiens nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 1121.432487 | 13.53220783 | 217 |
| 2690279 | NM_173798.2 | ZCCHC12 | Homo sapiens zinc finger, CCHC domain containing 12 (ZCCHC12), mRNA. | SIZN; FLJ16123; SIZN1 | 834.3165821 | 10.35379063 | 217 |

TABLE II-continued

| ProbeID | RefSeq_ID | Symbol | Definition | Synonyms | RFUs | Fold over Ave. | Filter Score |
|---|---|---|---|---|---|---|---|
| 6400358 | NM_001766.3 | CD1D | Homo sapiens CD1d molecule (CD1D), mRNA. | MGC34622; R3; CD1A | 752.6918782 | 6.727672919 | 217 |
| 5720075 | NM_003638.1 | ITGA8 | Homo sapiens integrin, alpha 8 (ITGA8), mRNA. | | 276.5741117 | 2.893326245 | 217 |
| 4040398 | NM_022440.1 | MAL | Homo sapiens mal, T-cell differentiation protein (MAL), transcript variant d, mRNA. | | 1193.45313 | 2.345562437 | 216 |
| 380561 | NM_006393.1 | NEBL | Homo sapiens nebulette (NEBL), transcript variant 1, mRNA. | bA56H7.1; MGC119746; LNEBL; MGC119747 | 283.8456007 | 1.924644406 | 215 |
| 630452 | NM_005568.2 | LHX1 | Homo sapiens LIM homeobox 1 (LHX1), mRNA. | LIM-1; LIM1; MGC138141; MGC126723 | 259.5757191 | 1.757318091 | 215 |
| 5690301 | NM_001704.1 | BAI3 | Homo sapiens brain-specific angiogenesis inhibitor 3 (BAI3), mRNA. | KIAA0550; MGC133100 | 573.1351946 | 6.194153497 | 213 |
| 4640386 | NM_024494.1 | WNT2B | Homo sapiens wingless-type MMTV integration site family, member 2B (WNT2B), transcript variant WNT-2B2, mRNA. | WNT13; XWNT2 | 342.0128596 | 2.97194221 | 213 |
| 830348 | NM_001104.1 | ACTN3 | Homo sapiens actinin, alpha 3 (ACTN3), mRNA. | MGC117002; MGC117005 | 394.3165821 | 2.318724864 | 208 |
| 2630279 | NM_001001995.1 | GPM6B | Homo sapiens glycoprotein M6B (GPM6B), transcript variant 1, mRNA. | MGC54284; M6B; MGC17150 | 1635.314044 | 6.065367942 | 205 |
| 2000471 | NM_021073.2 | BMP5 | Homo sapiens bone morphogenetic protein 5 (BMP5), mRNA. | MGC34244 | 670.784264 | 6.188059646 | 204 |
| 5810209 | NM_080284.2 | ABCA6 | Homo sapiens ATP-binding cassette, sub-family A (ABC1), member 6 (ABCA6), mRNA. | FLJ43498; EST155051 | 264.3340102 | 1.65136103 | 200 |
| 7160102 | NM_017954.9 | CADPS2 | Homo sapiens Ca++-dependent secretion activator 2 (CADPS2), transcript variant 1, mRNA. | KIAA1591; FLJ40851 | 1047.691201 | 8.328317116 | 199 |
| 3870202 | NM_001001995.1 | GPM6B | Homo sapiens glycoprotein M6B (GPM6B), transcript variant 1, mRNA. | MGC54284; M6B; MGC17150 | 1569.374619 | 3.416621491 | 199 |
| 620112 | NM_001079691.1 | N4BP2L1 | Homo sapiens NEDD4 binding protein 2-like 1 (N4BP2L1), transcript variant 2, mRNA. | CG018 | 302.4654822 | 2.770182275 | 198 |
| 14PEND24X P6 | | | | | | | |
| 6380328 | NM_198529.2 | EFCAB5 | Homo sapiens EF-hand calcium binding domain 5 (EFCAB5), mRNA. | DKFZp686I0638; FLJ46247; DKFZp434G2420 | 874.0688663 | 15.04815063 | 248 |
| 650669 | NM_001025232.1 | CLLU1OS | Homo sapiens chronic lymphocytic leukemia up-regulated 1 opposite strand (CLLU1OS), mRNA. | | 298.8708122 | 3.682272662 | 248 |
| 2470184 | NM_014479.2 | ADAMDEC1 | Homo sapiens ADAM-like, decysin 1 (ADAMDEC1), mRNA. | M12.219 | 356.441709 | 4.958405482 | 246 |
| 4010095 | NM_203311.1 | CSAG3A | Homo sapiens CSAG family, member 3A (CSAG3A), mRNA. | MGC17065 | 285.7824873 | 2.965170936 | 246 |
| 6400131 | NM_000782.3 | CYP24A1 | Homo sapiens cytochrome P450, family 24, subfamily A, polypeptide 1 (CYP24A1), nuclear gene encoding mitochondrial protein, mRNA. | CYP24; P450-CC24; MGC126274; CP24; MGC126273 | 254.3592217 | 3.595571168 | 245 |
| 1770603 | NM_001062.3 | TCN1 | Homo sapiens transcobalamin I (vitamin B12 binding protein, R binder family) (TCN1), mRNA. | TCI; TC1 | 30460.03096 | 145.1865227 | 244 |

TABLE II-continued

| ProbeID | RefSeq_ID | Symbol | Definition | Synonyms | RFUs | Fold over Ave. | Filter Score |
|---|---|---|---|---|---|---|---|
| 1010097 | NM_021815.2 | SLC5A7 | Homo sapiens solute carrier family 5 (choline transporter), member 7 (SLC5A7), mRNA. | MGC126299; MGC126300; CHT1; hCHT; CHT | 829.8722504 | 13.25927703 | 244 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 885.4104907 | 11.69067693 | 243 |
| 6900196 | NM_004975.2 | KCNB1 | Homo sapiens potassium voltage-gated channel, Shab-related subfamily, member 1 (KCNB1), mRNA. | KV2.1; h-DRK1; DRK1 | 500.2368866 | 6.420247184 | 243 |
| 4010224 | NM_199353.1 | PRB1 | Homo sapiens proline-rich protein BstNI subfamily 1 (PRB1), transcript variant 2, mRNA. | Ps 1; PMF; PRB1L; Ps 2; PM; PMS; PRB1M | 273.3172589 | 2.909495773 | 243 |
| 4810487 | NM_018712.2 | ELMOD1 | Homo sapiens ELMO/CED-12 domain containing 1 (ELMOD1), mRNA. | DKEZp547C176 | 400.5093063 | 4.565239745 | 242 |
| 6370189 | NM_006248.2 | PRB2 | Homo sapiens proline-rich protein BstNI subfamily 2 (PRB2), mRNA. | cP7; Ps; PRPPRB1 | 377.4169205 | 4.309025745 | 242 |
| 4040286 | NM_001184.2 | ATR | Homo sapiens ataxia telangiectasia and Rad3 related (ATR), mRNA. | SCKL1; MEC1; FRP1; SCKL | 284.2343486 | 3.022407115 | 242 |
| 6660463 | NM_020140.2 | ANKS1B | Homo sapiens ankyrin repeat and sterile alpha motif domain containing 1B (ANKS1B), transcript variant 3, mRNA. | MGC26087; ANKS2; AIDA; cajalin-2; EB-1; AIDA-1 | 225.6940778 | 2.327570041 | 242 |
| 4880138 | NM_000905.2 | NPY | Homo sapiens neuropeptide Y (NPY), mRNA. | PYY4 | 5085.8978 | 43.13558215 | 241 |
| 1400392 | NM_006790.1 | MYOT | Homo sapiens myotilin (MYOT), mRNA. | LGMD1A; LGMD1; TTID | 363.1686971 | 4.418465629 | 241 |
| 6270022 | NM_002110.2 | HCK | Homo sapiens hemopoietic cell kinase (HCK), mRNA. | JTK9 | 599.1159052 | 7.518919634 | 239 |
| 7610441 | NM_002509.2 | NKX2-2 | Homo sapiens NK2 homeobox 2 (NKX2-2), mRNA. | NKX2B; NKX2.2 | 6605.236887 | 38.229273 | 238 |
| 1010592 | NM_001001548.1 | CD36 | Homo sapiens CD36 molecule (thrombospondin receptor) (CD36), transcript variant 1, mRNA. | GPIV; FAT; GP3B; CHDS7; SCARB3; PASIV; GP4 | 1040.994416 | 10.66170225 | 238 |
| 730093 | NM_020209.2 | SHD | Homo sapiens Src homology 2 domain containing transforming protein D (SHD), mRNA. | | 799.1094755 | 10.06106597 | 237 |
| 2000292 | NM_052863.2 | SCGB3A1 | Homo sapiens secretoglobin, family 3A, member 1 (SCGB3A1), mRNA. | MGC87867; PnSP-2; HIN1; HIN-1; UGRP2; LU105 | 591.5932318 | 8.643090782 | 237 |
| 6760725 | NM_172105.2 | EYA4 | Homo sapiens eyes absent homolog 4 (Drosophila) (EYA4), transcript variant 4, mRNA. | CMD1J; DFNA10 | 366.4281726 | 4.227226892 | 237 |
| 5270520 | NM_005449.3 | FAIM3 | Homo sapiens Fas apoptotic inhibitory molecule 3 (FAIM3), mRNA. | TOSO | 283.4650592 | 3.092052735 | 237 |
| 1190592 | NM_000827.2 | GRIA1 | Homo sapiens glutamate receptor, ionotropic, AMPA 1 (GRIA1), mRNA. | HBGR1; GLURA; GLUH1; GLUR1; MGC133252 | 274.6204738 | 2.951679773 | 237 |
| 6380689 | NM_004842.2 | AKAP7 | Homo sapiens A kinase (PRKA) anchor protein 7 (AKAP7), transcript variant alpha, mRNA. | AKAP18 | 241.7647208 | 2.655316984 | 237 |
| 5870435 | NM_006043.1 | HS3ST2 | Homo sapiens heparan sulfate (glucosamine) 3-O-sulfotransferase 2 (HS3ST2), mRNA. | 3OST2; 30ST2 | 1421.217259 | 19.6320838 | 236 |
| 1110564 | NM_006419.1 | CXCL13 | Homo sapiens chemokine (C—X—C motif) ligand 13 (B- | SCYB13; ANGIE; BCA1; ANGIE2; BCA-1; | 681.3115059 | 4.79262015 | 236 |

TABLE II-continued

| ProbeID | RefSeq_ID | Symbol | Definition | Synonyms | RFUs | Fold over Ave. | Filter Score |
|---|---|---|---|---|---|---|---|
| 4860403 | NM_002747.3 | MAPK4 | cell chemoattractant) (CXCL13), mRNA. Homo sapiens mitogen-activated protein kinase 4 (MAPK4), mRNA. | BLR1L; BLC Erk4; p63MAPK; ERK3; PRKM4 | 289.0861252 | 3.620157653 | 236 |
| 2350139 | NM_004100.3 | EYA4 | Homo sapiens eyes absent homolog 4 (Drosophila) (EYA4), transcript variant 1, mRNA. | CMD1J; DFNA10 | 654.2714044 | 8.365363035 | 235 |
| 7000176 | NM_152679.2 | SLC10A4 | Homo sapiens solute carrier family 10 (sodium/bile acid cotransporter family), member 4 (SLC10A4), mRNA. | MGC29802; P4 | 302.4654822 | 3.322957049 | 235 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 601.7113367 | 7.503605242 | 234 |
| 5910521 | NM_014996.1 | PLCH1 | Homo sapiens phospholipase C, eta 1 (PLCH1), mRNA. | DKFZp434C1372; PLCeta1; PLCL3; MGC117152 | 310.5576988 | 3.860094424 | 234 |
| 1260180 | NM_004100.3 | EYA4 | Homo sapiens eyes absent homolog 4 (Drosophila) (EYA4), transcript variant 1, mRNA. | CMD1J; DFNA10 | 1302.621827 | 11.82586583 | 233 |
| 6200333 | NM_021977.2 | SLC22A3 | Homo sapiens solute carrier family 22 (extraneuronal monoamine transporter), member 3 (SLC22A3), mRNA. | EMT; OCT3; EMTH | 284.351269 | 2.949641146 | 233 |
| 580187 | NM_001029851.1 | PDE8B | Homo sapiens phosphodiesterase 8B (PDE8B), transcript variant 3, mRNA. | FLJ11212 | 679.4294416 | 6.956257297 | 232 |
| 150066 | NM_006011.3 | ST8SIA2 | Homo sapiens ST8 alpha-N-acetyl-neuraminide alpha-2,8-sialyltransferase 2 (ST8SIA2), mRNA. | MGC116857; HsT19690; ST8SIA-II; SIAT8B; MGC116854; STX | 372.3873096 | 4.195453617 | 232 |
| 1010360 | NM_001024070.1 | GCH1 | Homo sapiens GTP cyclohydrolase 1 (GCH1), transcript variant 3, mRNA. | DYT5; GTP-CH-1; GTPCH1; GCH | 316.4216582 | 4.026929451 | 230 |
| 3310538 | NM_000072.2 | CD36 | Homo sapiens CD36 molecule (thrombospondin receptor) (CD36), transcript variant 3, mRNA. | GPIV; FAT; GP3B; CHDS7; SCARB3; PASIV; GP4 | 1115.056007 | 8.734225894 | 229 |
| 1090561 | NM_145740.2 | GSTA1 | Homo sapiens glutathione S-transferase A1 (GSTA1), mRNA. | GTH1; GST2; MGC131939; GSTA1-1 | 311.9514382 | 2.80481688 | 229 |
| 2750154 | NM_014800.9 | ELMO1 | Homo sapiens engulfment and cell motility 1 (ELMO1), transcript variant 1, mRNA. | MGC126406; CED12; CED-12; KIAA0281; ELMO-1 | 294.8979695 | 3.1756816 | 228 |
| 2350201 | NM_181670.2 | ANKS1B | Homo sapiens ankyrin repeat and sterile alpha motif domain containing 1B (ANKS1B), transcript variant 2, mRNA. | MGC26087; EB-1; ANKS2; AIDA-1; AIDA; cajalin-2 | 879.8979695 | 11.7078234 | 227 |
| 7210554 | NM_016300.4 | ARPP-21 | Homo sapiens cyclic AMP-regulated phosphoprotein, 21 kD (ARPP-21), transcript variant 1, mRNA. | FLJ32997 | 698.5147208 | 7.970934471 | 226 |
| 2320369 | NM_015063.1 | SLC8A2 | Homo sapiens solute carrier family 8 (sodium/calcium exchanger), member 2 (SLC8A2), mRNA. | NCX2 | 1094.461421 | 7.969025829 | 226 |
| 2030445 | NM_002025.2 | AFF2 | Homo sapiens AF4/FMR2 family, member 2 (AFF2), mRNA. | FMR2; MRX2; OX19; FRAXE | 262.3605753 | 2.45038926 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 12941.20931 | 19.53733586 | 225 |

TABLE II-continued

| ProbeID | RefSeq_ID | Symbol | Definition | Synonyms | RFUs | Fold over Ave. | Filter Score |
|---|---|---|---|---|---|---|---|
| 3930546 | NM_001001290.1 | SLC2A9 | Homo sapiens solute carrier family 2 (facilitated glucose transporter), member 9 (SLC2A9), transcript variant 2, mRNA. | GLUTX; GLUT9 | 1780.868697 | 19.85757429 | 224 |
| 6330196 | NM_002371.2 | MAL | Homo sapiens mal, T-cell differentiation protein (MAL), transcript variant a, mRNA. | | 1343.049746 | 8.160066235 | 224 |
| 2850458 | NM_201572.1 | CACNB2 | Homo sapiens calcium channel, voltage-dependent, beta 2 subunit (CACNB2), transcript variant 8, mRNA. | CACNLB2; MYSB; FLJ23743 | 352.0490694 | 4.242487768 | 224 |
| | | | 14PEND2X P6 | | | | |
| 5550035 | NM_178452.3 | LRRC50 | Homo sapiens leucine rich repeat containing 50 (LRRC50), mRNA. | DKFZp434A119; FLJ25330 | 281.2668359 | 3.469960436 | 252 |
| 4210228 | NM_000940.1 | PON3 | Homo sapiens paraoxonase 3 (PON3), mRNA. | | 387.3813875 | 5.771377998 | 252 |
| 1780537 | NM_152701.2 | ABCA13 | Homo sapiens ATP-binding cassette, sub-family A (ABC1), member 13 (ABCA13), mRNA. | DKFZp313D2411; FLJ33951; FLJ33876; FLJ16398 | 162.742555 | 2.202943698 | 250 |
| 1050168 | NM_002638.2 | PI3 | Homo sapiens peptidase inhibitor 3, skin-derived (SKALP) (PI3), mRNA. | SKALP; ESI; WAP3; WFDC14; MGC13613 | 457.8076142 | 2.647403708 | 248 |
| 6400131 | NM_000782.3 | CYP24A1 | Homo sapiens cytochrome P450, family 24, subfamily A, polypeptide 1 (CYP24A1), nuclear gene encoding mitochondrial protein, mRNA. | CYP24; P450-CC24; MGC126274; CP24; MGC126273 | 415.3350254 | 6.503960954 | 245 |
| 1770603 | NM_001062.3 | TCN1 | Homo sapiens transcobalamin I (vitamin B12 binding protein, R binder family) (TCN1), mRNA. | TCI; TC1 | 1603.025719 | 6.693385338 | 244 |
| 6900196 | NM_004975.2 | KCNB1 | Homo sapiens potassium voltage-gated channel, Shab-related subfamily, member 1 (KCNB1), mRNA. | KV2.1; h-DRK1; DRK1 | 317.1188663 | 3.703972133 | 243 |
| 6860736 | NM_000260.2 | MYO7A | Homo sapiens myosin VIIA (MYO7A), mRNA. | USH1B; DFNA11; NSRD2; MYU7A; DFNB2 | 185.2216582 | 2.03369506 | 243 |
| 6510274 | NM_022124.3 | CDH23 | Homo sapiens cadherin-like 23 (CDH23), transcript variant 1, mRNA. | DKFZp434P2350; USH1H; KIAA1774; FLJ00233; MGC102761; FLJ36499; DFNB12; USH1D; KIAA1812 | 352.7102369 | 4.311115881 | 242 |
| 2970170 | NM_007289.1 | MME | Homo sapiens membrane metallo-endopeptidase (neutral endopeptidase, enkephalinase, CALLA, CD10) (MME), transcript variant 2b, mRNA. | NEP; MGC126681; CD10; MGC126707; CALLA | 222.9884941 | 2.111541705 | 241 |
| 6270022 | NM_002110.2 | HCK | Homo sapiens hemopoietic cell kinase (HCK), mRNA. | JTK9 | 993.442978 | 13.1259159 | 239 |
| 5910056 | NM_206821.1 | MYBPC1 | Homo sapiens myosin binding protein C, slow type (MYBPC1), transcript variant 4, mRNA. | slow-type; MYBPCS; MYBPCC | 1139.82335 | 14.81358827 | 239 |
| 4860554 | NM_033641.1 | COL4A6 | Homo sapiens collagen, type IV, alpha 6 (COL4A6), transcript variant B, mRNA. | MGC88184 | 194.3451777 | 2.095551883 | 239 |

TABLE II-continued

| ProbeID | RefSeq_ID | Symbol | Definition | Synonyms | RFUs | Fold over Ave. | Filter Score |
|---|---|---|---|---|---|---|---|
| 3390523 | NM_001010971.1 | SAMD13 | *Homo sapiens* sterile alpha motif domain containing 13 (SAMD13), mRNA. | RP11-376N17.1 | 269.2588832 | 2.890020188 | 239 |
| 840017 | NM_206819.1 | MYBPC1 | *Homo sapiens* myosin binding protein C, slow type (MYBPC1), transcript variant 2, mRNA. | slow-type; MYBPCS; MYBPCC | 1484.388494 | 19.39806955 | 239 |
| 7610441 | NM_002509.2 | NKX2-2 | *Homo sapiens* NK2 homeobox 2 (NKX2-2), mRNA. | NKX2B; NKX2.2 | 682.2215736 | 3.051793572 | 238 |
| 6760725 | NM_172105.2 | EYA4 | *Homo sapiens* eyes absent homolog 4 (*Drosophila*) (EYA4), transcript variant 4, mRNA. | CMD1J; DFNA10 | 615.8304569 | 7.785038284 | 237 |
| 5270520 | NM_005449.3 | FAIM3 | *Homo sapiens* Fas apoptotic inhibitory molecule 3 (FAIM3), mRNA. | TOSO | 360.872758 | 4.209496933 | 237 |
| 1190592 | NM_000827.2 | GRIA1 | *Homo sapiens* glutamate receptor, ionotropic, AMPA 1 (GRIA1), mRNA. | HBGR1; GLURA; GLUH1; GLUR1; MGC133252 | 358.9098139 | 4.164569969 | 237 |
| 730093 | NM_020209.2 | SHD | *Homo sapiens* Src homology 2 domain containing transforming protein D (SHD), mRNA. | | 367.9559222 | 4.093150379 | 237 |
| 4860403 | NM_002747.3 | MAPK4 | *Homo sapiens* mitogen-activated protein kinase 4 (MAPK4), mRNA. | Erk4; p63MAPK; ERK3; PRKM4 | 671.6402707 | 9.734115774 | 236 |
| 7000176 | NM_152679.2 | SLC10A4 | *Homo sapiens* solute carrier family 10 (sodium/bile acid cotransporter family), member 4 (SLC10A4), mRNA. | MGC29802; P4 | 598.3299492 | 7.551569762 | 235 |
| 2350139 | NM_004100.3 | EYA4 | *Homo sapiens* eyes absent homolog 4 (*Drosophila*) (EYA4), transcript variant 1, mRNA. | CMD1J; DFNA10 | 1123.959052 | 15.08855972 | 235 |
| 4220674 | NM_152709.3 | STOX1 | *Homo sapiens* storkhead box 1 (STOX1), transcript variant 1, mRNA. | PEE4; C10orf24 | 257.8137056 | 2.779263646 | 234 |
| 1260180 | NM_004100.3 | EYA4 | *Homo sapiens* eyes absent homolog 4 (*Drosophila*) (EYA4), transcript variant 1, mRNA. | CMD1J; DFNA10 | 1881.794247 | 17.52850921 | 233 |
| 580187 | NM_001029851.1 | PDE8B | *Homo sapiens* phosphodiesterase 8B (PDE8B), transcript variant 3, mRNA. | FLJ11212 | 603.5299492 | 6.067458765 | 232 |
| 150066 | NM_006011.3 | ST8SIA2 | *Homo sapiens* ST8 alpha-N-acetyl-neuraminide alpha-2,8-sialyltransferase 2 (ST8SIA2), mRNA. | MGC116857; HsT19690; ST8SIA-II; SIAT8B; MGC116854; STX | 434.1379019 | 5.056982271 | 232 |
| 1010360 | NM_001024070.1 | GCH1 | *Homo sapiens* GTP cyclohydrolase 1 (GCH1), transcript variant 3, mRNA. | DYT5; GTP-CH-1; GTPCH1; GCH | 234.7860406 | 2.730000243 | 230 |
| 510452 | NM_002012.1 | FHIT | *Homo sapiens* fragile histidine triad gene (FHIT), mRNA. | FRA3B; AP3Aase | 325.31489 | 3.717521176 | 230 |
| 3310037 | NM_005634.2 | SOX3 | *Homo sapiens* SRY (sex determining region Y)-box 3 (SOX3), mRNA. | SOXB; MRGH | 636.1100677 | 4.081772744 | 229 |
| 2750154 | NM_014800.9 | ELMO1 | *Homo sapiens* engulfment and cell motility 1 (ELMO1), transcript variant 1, mRNA. | MGC126406; CED12; CED-12; KIAA0281; ELMO-1 | 405.992132 | 4.748747195 | 228 |
| 1850138 | NM_001029858.2 | SLC35F1 | *Homo sapiens* solute carrier family 35, member F1 (SLC35F1), mRNA. | dJ230I3.1; C6orf169; FLJ13018 | 286.021489 | 2.510643626 | 228 |
| 2030445 | NM_002025.2 | AFF2 | *Homo sapiens* AF4/FMR2 family, member 2 (AFF2), mRNA. | FMR2; MRX2; OX19; FRAXE | 363.8155668 | 3.784656853 | 226 |
| 5290753 | NM_007191.2 | WIF1 | *Homo sapiens* WNT inhibitory factor 1 (WIF1), mRNA. | WIF-1 | 344.5483926 | 3.384810371 | 225 |
| 770615 | NM_002701.4 | POU5F1 | *Homo sapiens* POU class 5 homeobox 1 | OTF4; OCT3; OCT4; | 6175.480203 | 8.800313713 | 225 |

TABLE II-continued

| ProbeID | RefSeq_ID | Symbol | Definition | Synonyms | RFUs | Fold over Ave. | Filter Score |
|---|---|---|---|---|---|---|---|
| 3930546 | NM_001001290.1 | SLC2A9 | (POU5F1), transcript variant 1, mRNA. Homo sapiens solute carrier family 2 (facilitated glucose transporter), member 9 (SLC2A9), transcript variant 2, mRNA. | MGC22487; OTF3 GLUTX; GLUT9 | 1241.419628 | 13.53953464 | 224 |
| 940630 | NM_024761.3 | MOBKL2B | Homo sapiens MOB1, Mps One Binder kinase activator-like 2B (yeast) (MOBKL2B), mRNA. | FLJ13204; FLJ23916; MOB3B; MGC32960 | 307.0633672 | 2.728795357 | 224 |
| 6650477 | NM_006984.3 | CLDN10 | Homo sapiens claudin 10 (CLDN10), transcript variant 2, mRNA. | CPETRL3; OSP-L | 839.9659052 | 7.360713685 | 223 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 6747.353469 | 10.81377916 | 223 |
| 5290711 | NM_004143.2 | CITED1 | Homo sapiens Cbp/p300-interacting transactivator, with Glu/Asp-rich carboxy-terminal domain, 1 (CITED1), mRNA. | MSG1 | 386.8 | 3.73860325 | 222 |
| 4150068 | NM_005097.1 | LGI1 | Homo sapiens leucine-rich, glioma inactivated 1 (LGI1), mRNA. | EPT; IB1099; ETL1 | 285.4045685 | 2.902197226 | 222 |
| 1990019 | NM_181676.1 | PPP2R2B | Homo sapiens protein phosphatase 2 (formerly 2A), regulatory subunit B, beta isoform (PPP2R2B), transcript variant 4, mRNA. | PR2AB-BETA; PR52B; PR2APR55-BETA; PR2AB55-BETA; MGC24888; PR55-BETA; PP2A-PR55B; SCA12 | 425.4836717 | 3.638701943 | 218 |
| 2370646 | NM_173698.1 | FAM133A | Homo sapiens family with sequence similarity 133, member A (FAM133A), mRNA. | RP1-32F7.2; FLJ37659 | 788.9001692 | 7.657158909 | 217 |
| 1070343 | NM_012464.3 | TLL1 | Homo sapiens tolloid-like 1 (TLL1), mRNA. | TLL | 698.1584602 | 8.078011573 | 217 |
| 4250463 | NM_000275.1 | OCA2 | Homo sapiens oculocutaneous albinism II (pink-eye dilution homolog, mouse) (OCA2), mRNA. | D15S12; EYCL3; PED; P; BOCA | 554.7313029 | 4.399794213 | 214 |
| 840324 | NM_006984.3 | CLDN10 | Homo sapiens claudin 10 (CLDN10), transcript variant 2, mRNA. | CPETRL3; OSP-L | 1460.319628 | 7.853694588 | 214 |
| 7000669 | NM_003087.1 | SNCG | Homo sapiens synuclein, gamma (breast cancer-specific protein 1) (SNCG), mRNA. | BCSG1; SR | 362.6211506 | 2.944794824 | 213 |
| 2360164 | NM_002260.3 | KLRC2 | Homo sapiens killer cell lectin-like receptor subfamily C, member 2 (KLRC2), mRNA. | CD159c; NKG2C; MGC138244; NKG2-C | 859.998308 | 7.658976864 | 209 |
| | | | 14SKEL12Z P6 | | | | |
| 7550056 | NM_178138.2 | LHX3 | Homo sapiens LIM homeobox 3 (LHX3), transcript variant 1, mRNA. | M2-LHX3; DKFZp762A2013 | 1715.749408 | 28.92056157 | 252 |
| 6560440 | NM_001007089.2 | RESP18 | Homo sapiens regulated endocrine-specific protein 18 (RESP18), mRNA. | | 1416.78714 | 23.3987498 | 252 |
| 2360743 | NM_173355.2 | UPP2 | Homo sapiens uridine phosphorylase 2 (UPP2), mRNA. | UPASE2; UDRPASE2; UP2 | 427.8104907 | 6.720641831 | 250 |
| 1050040 | NM_004925.3 | AQP3 | Homo sapiens aquaporin 3 (Gill blood group) (AQP3), mRNA. | GIL | 482.9805415 | 6.282651052 | 248 |
| 4010544 | NM_001040275.1 | ESR2 | Homo sapiens estrogen receptor 2 (ER beta) (ESR2), transcript variant b, mRNA. | ESR-BETA; ESTRB; ESRB; Erb; ER-BETA; NR3A2 | 283.658714 | 3.698811776 | 248 |

TABLE II-continued

| ProbeID | RefSeq_ID | Symbol | Definition | Synonyms | RFUs | Fold over Ave. | Filter Score |
|---|---|---|---|---|---|---|---|
| 1770504 | NM_022555.3 | HLA-DRB3 | *Homo sapiens* major histocompatibility complex, class II, DR beta 3 (HLA-DRB3), mRNA. | MGC117330; HLA-DR3B | 472.3668359 | 6.504149016 | 247 |
| 4210274 | NM_002976.2 | SCN7A | *Homo sapiens* sodium channel, voltage-gated, type VII, alpha (SCN7A), mRNA. | SCN6A | 432.6501692 | 5.383448306 | 247 |
| 6220750 | NM_000826.2 | GRIA2 | *Homo sapiens* glutamate receptor, ionotropic, AMPA 2 (GRIA2), mRNA. | HBGR2; GLURB; GLUR2 | 2105.021997 | 21.45923965 | 245 |
| 6420113 | NM_080723.3 | NRSN1 | *Homo sapiens* neurensin 1 (NRSN1), mRNA. | p24; VMP | 650.2043993 | 9.496720384 | 245 |
| 6940400 | NM_003924.2 | PHOX2B | *Homo sapiens* paired-like homeobox 2b (PHOX2B), mRNA. | PMX2B; NBPhox | 338.2059222 | 3.970463408 | 245 |
| 1010097 | NM_021815.2 | SLC5A7 | *Homo sapiens* solute carrier family 5 (choline transporter), member 7 (SLC5A7), mRNA. | MGC126299; MGC126300; CHT1; hCHT; CHT | 698.7585448 | 11.00641625 | 244 |
| 2230088 | NM_213609.2 | FAM19A1 | *Homo sapiens* family with sequence similarity 19 (chemokine (C-C motif)-like), member A1 (FAM19A1), mRNA. | TAFA-1; TAFA1 | 3235.903976 | 47.74138479 | 243 |
| 7320471 | NM_003221.3 | TFAP2B | *Homo sapiens* transcription factor AP-2 beta (activating enhancer binding protein 2 beta) | MGC21381; AP-2B; AP2-B | 474.3918782 | 5.799506135 | 243 |
| 4760626 | NM_002426.2 | MMP12 | *Homo sapiens* matrix metallopeptidase 12 (macrophage elastase) (MMP12), mRNA. | MGC138506; MME; HME | 377.5335025 | 5.39940787 | 243 |
| 6370315 | NM_002125.3 | HLA-DRB5 | *Homo sapiens* major histocompatibility complex, class II, DR beta 5 (HLA-DRB5), mRNA. | HLA-DRB1 | 1682.866328 | 13.8495262 | 242 |
| 1660152 | NM_001080534.1 | UNC13C | *Homo sapiens* unc-13 homolog C (*C. elegans*) (UNC13C), mRNA. | DKFZp547H074 | 693.9843486 | 10.23200304 | 242 |
| 4880138 | NM_000905.2 | NPY | *Homo sapiens* neuropeptide Y (NPY), mRNA. | PYY4 | 1080.668528 | 8.378075704 | 241 |
| 840017 | NM_206819.1 | MYBPC1 | *Homo sapiens* myosin binding protein C, slow type (MYBPC1), transcript variant 2, mRNA. | slow-type; MYBPCS; MYBPCC | 2533.879695 | 33.81989685 | 239 |
| 5910056 | NM_206821.1 | MYBPC1 | *Homo sapiens* myosin binding protein C, slow type (MYBPC1), transcript variant 4, mRNA. | slow-type; MYBPCS; MYBPCC | 1800.997462 | 23.98653175 | 239 |
| 830687 | NM_004067.2 | CHN2 | *Homo sapiens* chimerin (chimaerin) 2 (CHN2), transcript variant 2, mRNA. | BCH; ARHGAP3; RHOGAP3; MGC138360 | 311.2939086 | 4.156162991 | 239 |
| 7610441 | NM_002509.2 | NKX2-2 | *Homo sapiens* NK2 homeobox 2 (NKX2-2), mRNA. | NKX2B; NKX2.2 | 2063.805584 | 11.2571823 | 238 |
| 1010592 | NM_001001548.1 | CD36 | *Homo sapiens* CD36 molecule (thrombospondin receptor) (CD36), transcript variant 1, mRNA. | GPIV; FAT; GP3B; CHDS7; SCARB3; PASIV; GP4 | 968.6395939 | 9.851149972 | 238 |
| 6620369 | NM_015236.3 | LPHN3 | *Homo sapiens* latrophilin 3 (LPHN3), mRNA. | LEC3; CIRL3 | 290.9576988 | 3.4582854 | 238 |
| 6040673 | NM_004726.2 | REPS2 | *Homo sapiens* RALBP1 associated Eps domain containing 2 (REPS2), transcript variant 1, mRNA. | POB1 | 309.1473773 | 3.31580158 | 238 |
| 5130471 | NM_000922.2 | PDE3B | *Homo sapiens* phosphodiesterase 3B, cGMP-inhibited (PDE3B), mRNA. | HcGIP1; cGIPDE1 | 881.636379 | 12.50951438 | 237 |
| 6760725 | NM_172105.2 | EYA4 | *Homo sapiens* eyes absent homolog 4 (*Drosophila*) (EYA4), transcript variant 4, mRNA. | CMD1J; DFNA10 | 294.8572758 | 3.206242851 | 237 |
| 2600465 | NM_003026.1 | SH3GL2 | *Homo sapiens* SH3-domain GRB2-like 2 (SH3GL2), mRNA. | CNSA2; SH3P4; SH3D2A; EEN-B1; FLJ25015; FLJ20276 | 835.2967851 | 9.345269638 | 235 |

TABLE II-continued

| ProbeID | RefSeq_ID | Symbol | Definition | Synonyms | RFUs | Fold over Ave. | Filter Score |
|---|---|---|---|---|---|---|---|
| 2350139 | NM_004100.3 | EYA4 | Homo sapiens eyes absent homolog 4 (Drosophila) (EYA4), transcript variant 1, mRNA. | CMD1J; DFNA10 | 553.6543147 | 6.925111228 | 235 |
| 5550414 | NM_019845.2 | RPRM | Homo sapiens reprimo, TP53 dependent G2 arrest mediator candidate (RPRM), mRNA. | FLJ90327; REPRIMO | 964.7199662 | 6.019069947 | 234 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 372.5032149 | 4.26435202 | 234 |
| 460010 | NM_004615.2 | TSPAN7 | Homo sapiens tetraspanin 7 (TSPAN7), mRNA. | TM4SF2; MRX58; MXS1; DXS1692E; CD231; CCG-B7; TALLA-1; A15; TM4SF2b | 1098.523942 | 11.51349763 | 233 |
| 3190246 | NM_004067.2 | CHN2 | Homo sapiens chimerin (chimaerin) 2 (CHN2), transcript variant 2, mRNA. | BCH; ARHGAP3; RHOGAP3; MGC138360 | 718.3005076 | 9.696513205 | 233 |
| 6200333 | NM_021977.2 | SLC22A3 | Homo sapiens solute carrier family 22 (extraneuronal monoamine transporter), member 3 (SLC22A3), mRNA. | EMT; OCT3; EMTH | 718.3005076 | 8.97719915 | 233 |
| 1260180 | NM_004100.3 | EYA4 | Homo sapiens eyes absent homolog 4 (Drosophila) (EYA4), transcript variant 1, mRNA. | CMD1J; DFNA10 | 993.442978 | 8.781631227 | 233 |
| 4200725 | NR_001298.1 | HLA-DRB6 | Homo sapiens major histocompatibility complex, class II, DR beta 6 (pseudogene) (HLA-DRB6), non-coding RNA. | | 910.5795262 | 9.069933352 | 232 |
| 620349 | NM_006180.3 | NTRK2 | Homo sapiens neurotrophic tyrosine kinase, receptor, type 2 (NTRK2), transcript variant a, mRNA. | GP145-TrkB; TRKB | 391.6777496 | 4.38802409 | 232 |
| 7320348 | NM_016511.2 | CLEC1A | Homo sapiens C-type lectin domain family 1, member A (CLEC1A), mRNA. | CLEC1; MGC34328 | 313.5815567 | 3.273086061 | 232 |
| 5860093 | XM_940314.2 | NLF2 | PREDICTED: Homo sapiens nuclear localized factor 2 (NLF2), mRNA. | | 360.5552453 | 3.953476782 | 230 |
| 3310538 | NM_000072.2 | CD36 | Homo sapiens CD36 molecule (thrombospondin receptor) (CD36), transcript variant 3, mRNA. | GPIV; FAT; GP3B; CHDS7; SCARB3; PASIV; GP4 | 1493.647208 | 12.03925475 | 229 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 2332.756684 | 19.73768026 | 228 |
| 3840465 | NM_003991.1 | EDNRB | Homo sapiens endothelin receptor type B (EDNRB), transcript variant 2, mRNA. | ABCDS; HSCR2; ETRB; HSCR; ETB | 418.4676819 | 3.781673814 | 228 |
| 2750154 | NM_014800.9 | ELMO1 | Homo sapiens engulfment and cell motility 1 (ELMO1), transcript variant 1, mRNA. | MGC126406; CED12; CED-12; KIAA0281; ELMO-1 | 335.9739425 | 3.757307118 | 228 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 3018.60846 | 24.00263368 | 227 |
| 2320369 | NM_015063.1 | SLC8A2 | Homo sapiens solute carrier family 8 (sodium/calcium exchanger), member 2 (SLC8A2), mRNA. | NCX2 | 1053.866328 | 7.636352213 | 226 |
| 7210554 | NM_016300.4 | ARPP-21 | Homo sapiens cyclic AMP-regulated phosphoprotein, 21 kD (ARPP-21), transcript variant 1, mRNA. | FLJ32997 | 469.9600677 | 5.035636538 | 226 |

TABLE II-continued

| ProbeID | RefSeq_ID | Symbol | Definition | Synonyms | RFUs | Fold over Ave. | Filter Score |
|---|---|---|---|---|---|---|---|
| 5260484 | NM_002124.1 | HLA-DRB1 | Homo sapiens major histocompatibility complex, class II, DR beta 1 (HLA-DRB1), mRNA. | HLA-DRB1*; HLA-DR1B; HLA DRB1; DRB1 | 2762.059052 | 21.02754859 | 225 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 13222.53147 | 19.98378624 | 225 |
| 5360301 | NM_018640.3 | LMO3 | Homo sapiens LIM domain only 3 (rhombotin-like 2) (LMO3), transcript variant 1, mRNA. | RHOM3; Rhom-3; RBTNL2; RBTN3; DAT1; MGC26081 | 431.6473773 | 3.570645215 | 225 |
| | | | 14SKEL14Z P6 | | | | |
| 4390403 | NM_004042.3 | ARSF | Homo sapiens arylsulfatase F (ARSF), mRNA. | ASF | 272.7984772 | 4.107960639 | 251 |
| 7200753 | NM_016562.3 | TLR7 | Homo sapiens toll-like receptor 7 (TLR7), mRNA. | | 293.7142132 | 4.289026084 | 250 |
| 6380328 | NM_198529.2 | EFCAB5 | Homo sapiens EF-hand calcium binding domain 5 (EFCAB5), mRNA. | DKFZp686I0638; FLJ46247; DKFZp434G2420 | 345.2602369 | 5.339075217 | 248 |
| 5270619 | NM_033086.2 | FGD3 | Homo sapiens FYVE, RhoGEF and PH domain containing 3 (FGD3), transcript variant 2, mRNA. | MGC117260; FLJ00004; ZFYVE5 | 2567.253299 | 36.84135495 | 247 |
| 1400053 | NM_001012513.1 | GRP | Homo sapiens gastrin-releasing peptide (GRP), transcript variant 3, mRNA. | proGRP; GRP-10; BN; preproGRP | 2049.811168 | 28.96640405 | 245 |
| 6420113 | NM_080723.3 | NRSN1 | Homo sapiens neurensin 1 (NRSN1), mRNA. | p24; VMP | 1207.042301 | 18.4861578 | 245 |
| 2640068 | NM_002934.2 | RNASE2 | Homo sapiens ribonuclease, RNase A family, 2 (liver, eosinophil-derived neurotoxin) (RNASE2), mRNA. | EDN; RNS2 | 779.2021151 | 11.06386339 | 245 |
| 670707 | NM_182532.1 | TMEM61 | Homo sapiens transmembrane protein 61 (TMEM61), mRNA. | | 422.2224196 | 5.791838821 | 245 |
| 1170739 | NM_015236.3 | LPHN3 | Homo sapiens latrophilin 3 (LPHN3), mRNA. | LEC3; CIRL3 | 196.6147208 | 2.303877753 | 244 |
| 4760626 | NM_002426.2 | MMP12 | Homo sapiens matrix metallopeptidase 12 (macrophage elastase) (MMP12), mRNA. | MGC138506; MME; HME | 706.0241963 | 10.9675122 | 243 |
| 2230088 | NM_213609.2 | FAM19A1 | Homo sapiens family with sequence similarity 19 (chemokine (C-C motif)-like), member A1 (FAM19A1), mRNA. | TAFA-1; TAFA1 | 409.9824873 | 5.175434846 | 243 |
| 160500 | NM_001012513.1 | GRP | Homo sapiens gastrin-releasing peptide (GRP), transcript variant 3, mRNA. | proGRP; GRP-10; BN; preproGRP | 6826.28308 | 75.24775009 | 242 |
| 2370056 | NM_199296.1 | THSD3 | Homo sapiens thrombospondin, type I, domain containing 3 (THSD3), transcript variant 1, mRNA. | TAIL1; MGC119416; DKFZp686E0215; FLJ32147 | 338.0033841 | 4.087053364 | 242 |
| 6370315 | NM_002125.3 | HLA-DRB5 | Homo sapiens major histocompatibility complex, class II, DR beta 5 (HLA-DRB5), mRNA. | HLA-DRB1 | 453.5716582 | 3.002293057 | 242 |
| 4880138 | NM_000905.2 | NPY | Homo sapiens neuropeptide Y (NPY), mRNA. | PYY4 | 1426.187479 | 11.3765001 | 241 |
| 1400392 | NM_006790.1 | MYOT | Homo sapiens myotilin (MYOT), mRNA. | LGMD1A; LGMD1; TTID | 269.7420474 | 3.02454293 | 241 |
| 2850075 | NM_052846.1 | EMILIN3 | Homo sapiens elastin microfibril interfacer 3 (EMILIN3), mRNA. | DKFZp434A2410; dJ620E11.4; C20orf130; EMILIN5 | 568.5527919 | 7.086278387 | 239 |
| 1170048 | NM_001364.2 | DLG2 | Homo sapiens discs, large homolog 2, chapsyn-110 (Drosophila) (DLG2), mRNA. | PSD-93; DKFZp781E0954; FLJ37266; MGC131811; DKFZp781D1854 | 264.0153976 | 3.025665964 | 239 |
| 840017 | NM_206819.1 | MYBPC1 | Homo sapiens myosin binding protein C, | slow-type; MYBPCS; | 270.3671743 | 2.715313374 | 239 |

TABLE II-continued

| ProbeID | RefSeq_ID | Symbol | Definition | Synonyms | RFUs | Fold over Ave. | Filter Score |
|---|---|---|---|---|---|---|---|
| | | | slow type (MYBPC1), transcript variant 2, mRNA. | MYBPCC | | | |
| 7610441 | NM_002509.2 | NKX2-2 | Homo sapiens NK2 homeobox 2 (NKX2-2), mRNA. | NKX2B; NKX2.2 | 4647.176311 | 26.60012265 | 238 |
| 6620369 | NM_015236.3 | LPHN3 | Homo sapiens latrophilin 3 (LPHN3), mRNA. | LEC3; CIRL3 | 308.6822335 | 3.729874826 | 238 |
| 1190592 | NM_000827.2 | GRIA1 | Homo sapiens glutamate receptor, ionotropic, AMPA 1 (GRIA1), mRNA. | HBGR1; GLURA; GLUH1; GLUR1; MGC133252 | 288.6207276 | 3.153137876 | 237 |
| 6760725 | NM_172105.2 | EYA4 | Homo sapiens eyes absent homolog 4 (Drosophila) (EYA4), transcript variant 4, mRNA. | CMD1J; DFNA10 | 237.8099831 | 2.392443135 | 237 |
| 5270520 | NM_005449.3 | FAIM3 | Homo sapiens Fas apoptotic inhibitory molecule 3 (FAIM3), mRNA. | TOSO | 231.4650592 | 2.341389698 | 237 |
| 1110564 | NM_006419.1 | CXCL13 | Homo sapiens chemokine (C—X—C motif) ligand 13 (B-cell chemoattractant) (CXCL13), mRNA. | SCYB13; ANGIE; BCA1; ANGIE2; BCA-1; BLR1L; BLC | 1892.78731 | 15.09278254 | 236 |
| 5700753 | NM_001024912.1 | CEACAM1 | Homo sapiens carcinoembryonic antigen-related cell adhesion molecule 1 (biliary glycoprotein) (CEACAM1), transcript variant 2, mRNA. | BGPI; BGP; BGP1 | 244.5307107 | 2.711926103 | 236 |
| 2350139 | NM_004100.3 | EYA4 | Homo sapiens eyes absent homolog 4 (Drosophila) (EYA4), transcript variant 1, mRNA. | CMD1J; DFNA10 | 313.7634518 | 3.491268628 | 235 |
| 6200333 | NM_021977.2 | SLC22A3 | Homo sapiens solute carrier family 22 (extraneuronal monoamine transporter), member 3 (SLC22A3), mRNA. | EMT; OCT3; EMTH | 575.5480541 | 6.994366558 | 233 |
| 1260180 | NM_004100.3 | EYA4 | Homo sapiens eyes absent homolog 4 (Drosophila) (EYA4), transcript variant 1, mRNA. | CMD1J; DFNA10 | 588.1519459 | 4.791057531 | 233 |
| 1070162 | NM_020116.2 | FSTL5 | Homo sapiens follistatin-like 5 (FSTL5), mRNA. | KIAA1263; DKFZp566D234 | 253.8345178 | 2.423631667 | 232 |
| 240592 | NM_001094.4 | ACCN1 | Homo sapiens amiloride-sensitive cation channel 1, neuronal (ACCN1), transcript variant 2, mRNA. | BNC1; hBNaC1; MDEG; BNaC1; ASIC2a; ACCN; ASIC2 | 289.3739425 | 2.680376114 | 231 |
| 1010360 | NM_001024070.1 | GCH1 | Homo sapiens GTP cyclohydrolase 1 (GCH1), transcript variant 3, mRNA. | DYT5; GTP-CH-1; GTPCH1; GCH | 206.8774112 | 2.286621266 | 230 |
| 1090561 | NM_145740.2 | GSTA1 | Homo sapiens glutathione S-transferase A1 (GSTA1), mRNA. | GTH1; GST2; MGC131939; GSTA1-1 | 976.4761421 | 10.90990793 | 229 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 526.958291 | 3.684540237 | 228 |
| 3840465 | NM_003991.1 | EDNRB | Homo sapiens endothelin receptor type B (EDNRB), transcript variant 2, mRNA. | ABCDS; HSCR2; ETRB; HSCR; ETB | 288.1918782 | 2.293060891 | 228 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 582.5891709 | 3.825489565 | 227 |
| 2320369 | NM_015063.1 | SLC8A2 | Homo sapiens solute carrier family 8 (sodium/calcium exchanger), member 2 (SLC8A2), mRNA. | NCX2 | 596.0085448 | 3.884243454 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 14012.64179 | 21.23766914 | 225 |

TABLE II-continued

| ProbeID | RefSeq_ID | Symbol | Definition | Synonyms | RFUs | Fold over Ave. | Filter Score |
|---|---|---|---|---|---|---|---|
| 870524 | NM_024016.3 | HOXB8 | Homo sapiens homeobox B8 (HOXB8), mRNA. | Hox-2.4; HOX2; HOX2D | 2523.421997 | 13.98125023 | 225 |
| 5260484 | NM_002124.1 | HLA-DRB1 | Homo sapiens major histocompatibility complex, class II, DR beta 1 (HLA-DRB1), mRNA. | HLA-DRB1*; HLA-DR1B; HLA DRB1; DRB1 | 610.6073604 | 3.869621918 | 225 |
| 2850458 | NM_201572.1 | CACNB2 | Homo sapiens calcium channel, voltage-dependent, beta 2 subunit (CACNB2), transcript variant 8, mRNA. | CACNLB2; MYSB; FLJ23743 | 498.4685279 | 6.422871945 | 224 |
| 940630 | NM_024761.3 | MOBKL2B | Homo sapiens MOB1, Mps One Binder kinase activator-like 2B (yeast) (MOBKL2B), mRNA. | FLJ13204; FLJ23916; MOB3B; MGC32960 | 393.0116751 | 3.772500617 | 224 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 13697.71506 | 22.98300036 | 223 |
| 6650477 | NM_006984.3 | CLDN10 | Homo sapiens claudin 10 (CLDN10), transcript variant 2, mRNA. | CPETRL3; OSP-L | 871.7714044 | 7.677294001 | 223 |
| 5290711 | NM_004143.2 | CITED1 | Homo sapiens Cbp/p300-interacting transactivator, with Glu/Asp-rich carboxy-terminal domain, 1 (CITED1), mRNA. | MSG1 | 280.2225888 | 2.432946407 | 222 |
| 2760228 | NM_001001994.1 | GPM6B | Homo sapiens glycoprotein M6B (GPM6B), transcript variant 4, mRNA. | MGC54284; M6B; MGC17150 | 501.0681895 | 4.696881295 | 221 |
| 2450307 | NM_000325.5 | PITX2 | Homo sapiens paired-like homeodomain 2 (PITX2), transcript variant 3, mRNA. | MGC111022; IGDS; RS; IDG2; RIEG; PTX2; IGDS2; Brx1; ARP1; RIEG1; IHG2; IRID2; RGS; Otlx2; MGC20144 | 445.4820643 | 4.071059972 | 221 |
| 6250349 | NM_182826.1 | SCARA3 | Homo sapiens scavenger receptor class A, member 3 (SCARA3), transcript variant 2, mRNA. | APC7; MSLR1; MSRL1; CSR; CSR1 | 433.1906937 | 2.811591852 | 221 |

14SKEL15Z P6

| 2230241 | NM_000129.3 | F13A1 | Homo sapiens coagulation factor XIII, A1 polypeptide (F13A1), mRNA. | F13A | 440.5475465 | 6.112055101 | 250 |
|---|---|---|---|---|---|---|---|
| 6860762 | NM_020204.2 | LHX9 | Homo sapiens LIM homeobox 9 (LHX9), transcript variant 1, mRNA. | | 459.7507614 | 7.368919399 | 247 |
| 5270619 | NM_033086.2 | FGD3 | Homo sapiens FYVE, RhoGEF and PH domain containing 3 (FGD3), transcript variant 2, mRNA. | MGC117260; FLJ00004; ZFYVE5 | 344.2062606 | 4.07360582 | 247 |
| 6940400 | NM_003924.2 | PHOX2B | Homo sapiens paired-like homeobox 2b (PHOX2B), mRNA. | PMX2B; NBPhox | 2197.065821 | 31.28930823 | 245 |
| 2640068 | NM_002934.2 | RNASE2 | Homo sapiens ribonuclease, RNase A family, 2 (liver, eosinophil-derived neurotoxin) (RNASE2), mRNA. | EDN; RNS2 | 988.8883249 | 14.31029425 | 245 |
| 1400053 | NM_001012513.1 | GRP | Homo sapiens gastrin-releasing peptide (GRP), transcript variant 3, mRNA. | proGRP; GRP-10; BN; preproGRP | 518.7756345 | 6.58403531 | 245 |
| 6420113 | NM_080723.3 | NRSN1 | Homo sapiens neurensin 1 (NRSN1), mRNA. | p24; VMP | 266.6759729 | 3.305143312 | 245 |
| 1170739 | NM_015236.3 | LPHN3 | Homo sapiens latrophilin 3 (LPHN3), mRNA. | LEC3; CIRL3 | 250.6325719 | 3.211583828 | 244 |
| 2230088 | NM_213609.2 | FAM19A1 | Homo sapiens family with sequence similarity 19 (chemokine (C-C | TAFA-1; TAFA1 | 861.2979695 | 11.97345535 | 243 |

TABLE II-continued

| ProbeID | RefSeq_ID | Symbol | Definition | Synonyms | RFUs | Fold over Ave. | Filter Score |
|---|---|---|---|---|---|---|---|
| 4760626 | NM_002426.2 | MMP12 | motif)-like), member A1 (FAM19A1), mRNA. Homo sapiens matrix metallopeptidase 12 (macrophage elastase) (MMP12), mRNA. | MGC138506; MME; HME | 252.8263113 | 3.28554996 | 243 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 220.2191201 | 2.156422627 | 243 |
| 160500 | NM_001012513.1 | GRP | Homo sapiens gastrin-releasing peptide (GRP), transcript variant 3, mRNA. | proGRP; GRP-10; BN; preproGRP | 1784.910998 | 18.93697685 | 242 |
| 1400392 | NM_006790.1 | MYOT | Homo sapiens myotilin (MYOT), mRNA. | LGMD1A; LGMD1; TTID | 456.4598985 | 5.810367443 | 241 |
| 4880138 | NM_000905.2 | NPY | Homo sapiens neuropeptide Y (NPY), mRNA. | PYY4 | 421.7678511 | 2.660114767 | 241 |
| 2850075 | NM_052846.1 | EMILIN3 | Homo sapiens elastin microfibril interfacer 3 (EMILIN3), mRNA. | DKFZp434A2410; dJ620E11.4; C20orf130; EMILIN5 | 810.0241963 | 10.52062085 | 239 |
| 840017 | NM_206819.1 | MYBPC1 | Homo sapiens myosin binding protein C, slow type (MYBPC1), transcript variant 2, mRNA. | slow-type; MYBPCS; MYBPCC | 285.7054992 | 2.92608853 | 239 |
| 5910056 | NM_206821.1 | MYBPC1 | Homo sapiens myosin binding protein C, slow type (MYBPC1), transcript variant 4, mRNA. | slow-type; MYBPCS; MYBPCC | 254.1605753 | 2.526152268 | 239 |
| 7610441 | NM_002509.2 | NKX2-2 | Homo sapiens NK2 homeo-box 2 (NKX2-2), mRNA. | NKX2B; NKX2.2 | 3219.130795 | 18.11879361 | 238 |
| 1010592 | NM_001001548.1 | CD36 | Homo sapiens CD36 molecule (thrombospondin receptor) (CD36), transcript variant 1, mRNA. | GPIV; FAT; GP3B; CHDS7; SCARB3; PASIV; GP4 | 635.4603215 | 6.118721239 | 238 |
| 6620369 | NM_015236.3 | LPHN3 | Homo sapiens latrophilin 3 (LPHN3), mRNA. | LEC3; CIRL3 | 305.8598985 | 3.686628763 | 238 |
| 6760725 | NM_172105.2 | EYA4 | Homo sapiens eyes absent homolog 4 (Drosophila) (EYA4), transcript variant 4, mRNA. | CMD1J; DFNA10 | 339.2258037 | 3.839175522 | 237 |
| 1190592 | NM_000827.2 | GRIA1 | Homo sapiens glutamate receptor, ionotropic, AMPA 1 (GRIA1), mRNA. | HBGR1; GLURA; GLUH1; GLUR1; MGC133252 | 262.4681049 | 2.776812001 | 237 |
| 1110564 | NM_006419.1 | CXCL13 | Homo sapiens chemokine (C—X—C motif) ligand 13 (B-cell chemoattractant) (CXCL13), mRNA. | SCYB13; ANGIE; BCA1; ANGIE2; BCA-1; BLR1L; BLC | 4686.629611 | 38.84647974 | 236 |
| 2350139 | NM_004100.3 | EYA4 | Homo sapiens eyes absent homolog 4 (Drosophila) (EYA4), transcript variant 1, mRNA. | CMD1J; DFNA10 | 548.1777496 | 6.846718652 | 235 |
| 7000176 | NM_152679.2 | SLC10A4 | Homo sapiens solute carrier family 10 (sodium/bile acid cotransporter family), member 4 (SLC10A4), mRNA. | MGC29802; P4 | 342.5005076 | 3.895153565 | 235 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 252.2692047 | 2.565160902 | 234 |
| 1260180 | NM_004100.3 | EYA4 | Homo sapiens eyes absent homolog 4 (Drosophila) (EYA4), transcript variant 1, mRNA. | CMD1J; DFNA10 | 1118.943824 | 10.01733677 | 233 |
| 6200333 | NM_021977.2 | SLC22A3 | Homo sapiens solute carrier family 22 (extraneuronal monoamine transporter), member 3 (SLC22A3), mRNA. | EMT; OCT3; EMTH | 258.298308 | 2.587765331 | 233 |
| 7320348 | NM_016511.2 | CLEC1A | Homo sapiens C-type lectin domain family 1, member A (CLEC1A), mRNA. | CLEC1; MGC34328 | 958.858714 | 12.06609307 | 232 |

TABLE II-continued

| ProbeID | RefSeq_ID | Symbol | Definition | Synonyms | RFUs | Fold over Ave. | Filter Score |
|---|---|---|---|---|---|---|---|
| 7040497 | NM_001179.3 | ART3 | *Homo sapiens* ADP-ribosyltransferase 3 (ART3), mRNA. | | 1167.680711 | 10.78026278 | 232 |
| 1070162 | NM_020116.2 | FSTL5 | *Homo sapiens* follistatin-like 5 (FSTL5), mRNA. | KIAA1263; DKFZp566D234 | 271.7681895 | 2.665514793 | 232 |
| 3310538 | NM_000072.2 | CD36 | *Homo sapiens* CD36 molecule (thrombospondin receptor) (CD36), transcript variant 3, mRNA. | GPIV; FAT; GP3B; CHDS7; SCARB3; PASIV; GP4 | 993.442978 | 7.672567389 | 229 |
| 1090561 | NM_145740.2 | GSTA1 | *Homo sapiens* glutathione S-transferase A1 (GSTA1), mRNA. | GTH1; GST2; MGC131939; GSTA1-1 | 404.4903553 | 3.933497792 | 229 |
| 3870246 | NM_001007097.1 | NTRK2 | *Homo sapiens* neurotrophic tyrosine kinase, receptor, type 2 (NTRK2), transcript variant b, mRNA. | GP145-TrkB; TRKB | 597.5196277 | 4.31181459 | 228 |
| 3840465 | NM_003991.1 | EDNRB | *Homo sapiens* endothelin receptor type B (EDNRB), transcript variant 2, mRNA. | ABCDS; HSCR2; ETRB; HSCR; ETB | 289.7688663 | 2.311080545 | 228 |
| 430102 | NM_001018065.1 | NTRK2 | *Homo sapiens* neurotrophic tyrosine kinase, receptor, type 2 (NTRK2), transcript variant d, mRNA. | GP145-TrkB; TRKB | 599.1159052 | 3.962377767 | 227 |
| 7210180 | NM_012281.2 | KCND2 | *Homo sapiens* potassium voltage-gated channel, Shal-related subfamily, member 2 (KCND2), mRNA. | KV4.2; MGC119703; RK5; KIAA1044; MGC119702 | 310.3406091 | 3.197940639 | 226 |
| 7210554 | NM_016300.4 | ARPP-21 | *Homo sapiens* cyclic AMP-regulated phosphoprotein, 21 kD (ARPP-21), transcript variant 1, mRNA. | FLJ32997 | 325.6401015 | 3.182153825 | 226 |
| 2030445 | NM_002025.2 | AFF2 | *Homo sapiens* AF4/FMR2 family, member 2 (AFF2), mRNA. | FMR2; MRX2; OX19; FRAXE | 271.2492386 | 2.567286962 | 226 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 7959.854484 | 11.6320656 | 225 |
| 870524 | NM_024016.3 | HOXB8 | *Homo sapiens* homeobox B8 (HOXB8), mRNA. | Hox-2.4; HOX2; HOX2D | 1165.569543 | 5.91984496 | 225 |
| 5360301 | NM_018640.3 | LMO3 | *Homo sapiens* LIM domain only 3 (rhombotin-like 2) (LMO3), transcript variant 1, mRNA. | RHOM3; Rhom-3; RBTNL2; RBTN3; DAT1; MGC26081 | 363.6567682 | 2.850703502 | 225 |
| 5260484 | NM_002124.1 | HLA-DRB1 | *Homo sapiens* major histocompatibility complex, class II, DR beta 1 (HLA-DRB1), mRNA. | HLA-DRB1*; HLA-DR1B; HLA DRB1; DRB1 | 451.157022 | 2.5979981 | 225 |
| 2850458 | NM_201572.1 | CACNB2 | *Homo sapiens* calcium channel, voltage-dependent, beta 2 subunit (CACNB2), transcript variant 8, mRNA. | CACNLB2; MYSB; FLJ23743 | 366.9722504 | 4.464714159 | 224 |
| 3930546 | NM_001001290.1 | SLC2A9 | *Homo sapiens* solute carrier family 2 (facilitated glucose transporter), member 9 (SLC2A9), transcript variant 2, mRNA. | GLUTX; GLUT9 | 463.7666667 | 4.431645646 | 224 |
| 7000181 | NM_001037317.1 | PAP2D | *Homo sapiens* phosphatidic acid phosphatase type 2 (PAP2D), transcript variant 1, mRNA. | PAP2 | 277.1762267 | 2.906158666 | 224 |
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 9294.629103 | 15.27374289 | 223 |
| 6650477 | NM_006984.3 | CLDN10 | *Homo sapiens* claudin 10 (CLDN10), transcript variant 2, mRNA. | CPETRL3; OSP-L | 1256.821151 | 11.50993847 | 223 |

TABLE II-continued

| ProbeID | RefSeq_ID | Symbol | Definition | Synonyms | RFUs | Fold over Ave. | Filter Score |
|---|---|---|---|---|---|---|---|
| | | | 14SKEL18X P6 | | | | |
| 2480040 | NM_001010925.2 | ANKRD19 | *Homo sapiens* ankyrin repeat domain 19 (ANKRD19), mRNA. | FLJ36178; bA526D8.2 | 359.6522843 | 5.188399301 | 251 |
| 5820402 | NM_182801.1 | EGFLAM | *Homo sapiens* EGF-like, fibronectin type III and laminin G domains (EGFLAM), transcript variant 4, mRNA. | AGRINL; AGRNL; FLJ39155 | 533.0456853 | 6.541888158 | 250 |
| 1260370 | NM_175611.2 | GRIK1 | *Homo sapiens* glutamate receptor, ionotropic, kainate 1 (GRIK1), transcript variant 2, mRNA. | GLUR5; EEA3; GLR5; EAA3 | 199.6889171 | 2.120302394 | 248 |
| 1170739 | NM_015236.3 | LPHN3 | *Homo sapiens* latrophilin 3 (LPHN3), mRNA. | LEC3; CIRL3 | 202.4005922 | 2.401102476 | 244 |
| 2120064 | NM_130808.1 | CPNE4 | *Homo sapiens* copine IV (CPNE4), mRNA. | MGC15604; COPN4; CPN4 | 980.1950085 | 15.17169906 | 243 |
| 3450544 | NM_138569.2 | C6orf142 | *Homo sapiens* chromosome 6 open reading frame 142 (C6orf142), mRNA. | MGC18257 | 546.9849408 | 8.36846251 | 243 |
| 4760626 | NM_002426.2 | MMP12 | *Homo sapiens* matrix metallopeptidase 12 (macrophage elastase) (MMP12), mRNA. | MGC138506; MME; HME | 332.3773266 | 4.633984971 | 243 |
| 4900731 | NM_002118.3 | HLA-DMB | *Homo sapiens* major histocompatibility complex, class II, DM beta (HLA-DMB), mRNA. | D6S221E; RING7 | 669.7582064 | 7.661512105 | 241 |
| 7610441 | NM_002509.2 | NKX2-2 | *Homo sapiens* NK2 homeo-box 2 (NKX2-2), mRNA. | NKX2B; NKX2.2 | 3485.537394 | 19.70101351 | 238 |
| 6620369 | NM_015236.3 | LPHN3 | *Homo sapiens* latrophilin 3 (LPHN3), mRNA. | LEC3; CIRL3 | 321.4711506 | 3.925836791 | 238 |
| 1110564 | NM_006419.1 | CXCL13 | *Homo sapiens* chemokine (C—X—C motif) ligand 13 (B-cell chemoattractant) (CXCL13), mRNA. | SCYB13; ANGIE; BCA1; ANGIE2; BCA-1; BLR1L; BLC | 5484.610152 | 45.63103882 | 236 |
| 2350139 | NM_004100.3 | EYA4 | *Homo sapiens* eyes absent homolog 4 (*Drosophila*) (EYA4), transcript variant 1, mRNA. | CMD1J; DFNA10 | 346.9730964 | 3.966637682 | 235 |
| 4220674 | NM_152709.3 | STOX1 | *Homo sapiens* storkhead box 1 (STOX1), transcript variant 1, mRNA. | PEE4; C10orf24 | 620.9840102 | 8.102938452 | 234 |
| 5390463 | NM_001076778.1 | FAM107A | *Homo sapiens* family with sequence similarity 107, member A (FAM107A), transcript variant 2, mRNA. | FLJ30158; DRR1; TU3A; FLJ45473 | 1172.72775 | 12.43732892 | 233 |
| 4060100 | NM_006063.2 | KBTBD10 | *Homo sapiens* kelch repeat and BTB (POZ) domain containing 10 (KBTBD10), mRNA. | SARCOSIN | 746.1352792 | 7.630117274 | 233 |
| 1260180 | NM_004100.3 | EYA4 | *Homo sapiens* eyes absent homolog 4 (*Drosophila*) (EYA4), transcript variant 1, mRNA. | CMD1J; DFNA10 | 703.8910321 | 5.930646904 | 233 |
| 6200333 | NM_021977.2 | SLC22A3 | *Homo sapiens* solute carrier family 22 (extraneuronal monoamine transporter), member 3 (SLC22A3), mRNA. | EMT; OCT3; EMTH | 496.9555838 | 5.902716586 | 233 |
| 4890292 | NM_173485.4 | TSHZ2 | *Homo sapiens* teashirt zinc finger homeobox 2 (TSHZ2), mRNA. | C20orf17; OVC10-2; TSH2; ZNF218; FLJ33887; DKFZp686K2480; ZABC2 | 449.3137056 | 3.151526978 | 233 |
| 1070162 | NM_020116.2 | FSTL5 | *Homo sapiens* follistatin-like 5 (FSTL5), mRNA. | KIAA1263; DKFZp566D234 | 1038.350761 | 13.00491383 | 232 |
| 7320348 | NM_016511.2 | CLEC1A | *Homo sapiens* C-type lectin domain family 1, member A (CLEC1A), mRNA. | CLEC1; MGC34328 | 407.8927242 | 4.558237329 | 232 |
| 4120408 | NM_003822.3 | NR5A2 | *Homo sapiens* nuclear receptor subfamily 5, | FTF; B1F2; FTZ-F1beta; | 276.1617597 | 3.076987614 | 231 |

TABLE II-continued

| ProbeID | RefSeq_ID | Symbol | Definition | Synonyms | RFUs | Fold over Ave. | Filter Score |
|---|---|---|---|---|---|---|---|
| | | | group A, member 2 (NR5A2), transcript variant 2, mRNA. | hB1F; hB1F-2; LRH-1; B1F; FTZ-F1; CPF | | | |
| 3310037 | NM_005634.2 | SOX3 | *Homo sapiens* SRY (sex determining region Y)-box 3 (SOX3), mRNA. | SOXB; MRGH | 523.942132 | 3.185682606 | 229 |
| 3460474 | NM_001672.2 | ASIP | *Homo sapiens* agouti signaling protein, nonagouti homolog (mouse) (ASIP), mRNA. | ASP; MGC126092; SHEP9; AGTIL; MGC126093; AGSW; AGTI | 298.8708122 | 3.121804793 | 229 |
| 3180615 | NM_001001552.3 | LEMD1 | *Homo sapiens* LEM domain containing 1 (LEMD1), mRNA. | LEMP-1 | 246.1758037 | 2.288059176 | 228 |
| 4810482 | NM_002547.1 | OPHN1 | *Homo sapiens* oligophrenin 1 (OPHN1), mRNA. | OPN1; MRX60 | 265.1473773 | 2.256012172 | 227 |
| 5860088 | NM_018647.2 | TNFRSF19 | *Homo sapiens* tumor necrosis factor receptor superfamily, member 19 (TNFRSF19), transcript variant 1, mRNA. | TAJ; TAJ-alpha; TRADE; TROY | 491.405753 | 6.185357859 | 226 |
| 770615 | NM_002701.4 | POU5F1 | *Homo sapiens* POU class 5 homeobox 1 (POU5F1), transcript variant 1, mRNA. | OTF4; OCT3; OCT4; MGC22487; OTF3 | 9603.588832 | 14.24062587 | 225 |
| 2850458 | NM_201572.1 | CACNB2 | *Homo sapiens* calcium channel, voltage-dependent, beta 2 subunit (CACNB2), transcript variant 8, mRNA. | CACNLB2; MYSB; FLJ23743 | 291.1939086 | 3.336271949 | 224 |
| 940630 | NM_024761.3 | MOBKL2B | *Homo sapiens* MOB1, Mps One Binder kinase activator-like 2B (yeast) (MOBKL2B), mRNA. | FLJ13204; FLJ23916; MOB3B; MGC32960 | 268.001692 | 2.254453549 | 224 |
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 8934.08731 | 14.64247892 | 223 |
| 2760228 | NM_001001994.1 | GPM6B | *Homo sapiens* glycoprotein M6B (GPM6B), transcript variant 4, mRNA. | MGC54284; M6B; MGC17150 | 1369.750931 | 14.57334634 | 221 |
| 3130110 | NM_153355.2 | TCBA1 | *Homo sapiens* T-cell lymphoma breakpoint associated target 1 (TCBA1), mRNA. | FAM77B; MGC41924 | 351.7424704 | 4.463403314 | 220 |
| 4180289 | NM_001538.2 | HSF4 | *Homo sapiens* heat shock transcription factor 4 (HSF4), transcript variant 1, mRNA. | CTM | 318.9629442 | 3.015795147 | 219 |
| 4890274 | NM_001040667.1 | HSF4 | *Homo sapiens* heat shock transcription factor 4 (HSF4), transcript variant 2, mRNA. | CTM | 301.9978003 | 2.750469569 | 219 |
| 2320373 | NM_006928.3 | SILV | *Homo sapiens* silver homolog (mouse) (SILV), mRNA. | PMEL17; D12S53E; SIL; SI; ME20; gp100 | 8583.009475 | 35.8241112 | 217 |
| 7330639 | NM_003822.3 | NR5A2 | *Homo sapiens* nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 378.2843486 | 3.902039879 | 217 |
| 5690301 | NM_001704.1 | BAI3 | *Homo sapiens* brain-specific angiogenesis inhibitor 3 (BAI3), mRNA. | KIAA0550; MGC133100 | 2264.844839 | 27.4289668 | 213 |
| 2260424 | NM_006727.2 | CDH10 | *Homo sapiens* cadherin 10, type 2 (T2-cadherin) (CDH10), mRNA. | | 737.2966159 | 6.321713796 | 213 |
| 2370438 | NM_000014.4 | A2M | *Homo sapiens* alpha-2-macroglobulin (A2M), mRNA. | alpha 2M; CPAMD5; S863-7; FWP007; DKFZp779B086 | 430.47022 | 2.947254375 | 212 |
| 6420050 | NM_002523.1 | NPTX2 | *Homo sapiens* neuronal pentraxin II (NPTX2), mRNA. | NARP; NP-II; NP2 | 605.2751269 | 1.942645888 | 210 |
| 830348 | NM_001104.1 | ACTN3 | *Homo sapiens* actinin, alpha 3 (ACTN3), mRNA. | MGC117002; MGC117005 | 433.5448393 | 2.648885447 | 208 |

TABLE II-continued

| ProbeID | RefSeq_ID | Symbol | Definition | Synonyms | RFUs | Fold over Ave. | Filter Score |
|---|---|---|---|---|---|---|---|
| 2630279 | NM_001001995.1 | GPM6B | *Homo sapiens* glycoprotein M6B (GPM6B), transcript variant 1, mRNA. | MGC54284; M6B; MGC17150 | 4741.316582 | 19.48483978 | 205 |
| 3850059 | NM_005574.2 | LMO2 | *Homo sapiens* LIM domain only 2 (rhombotin-like 1) (LMO2), mRNA. | TTG2; RBTN2; RBTNL1; RHOM2 | 4977.640102 | 34.52136268 | 204 |
| 2030026 | NM_007029.2 | STMN2 | *Homo sapiens* stathmin-like 2 (STMN2), mRNA. | SCG10; SCGN10; SGC10 | 1060.256007 | 3.899915903 | 204 |
| 270114 | NM_001034850.1 | FAM134B | *Homo sapiens* family with sequence similarity 134, member B (FAM134B), transcript variant 1, mRNA. | FLJ22155; FLJ20152; FLJ22179 | 324.0881557 | 3.396395642 | 202 |
| 3870202 | NM_001001995.1 | GPM6B | *Homo sapiens* glycoprotein M6B (GPM6B), transcript variant 1, mRNA. | MGC54284; M6B; MGC17150 | 3927.222843 | 10.05220933 | 199 |
| 7160102 | NM_017954.9 | CADPS2 | *Homo sapiens* Ca++-dependent secretion activator 2 (CADPS2), transcript variant 1, mRNA. | KIAA1591; FLJ40851 | 893.6523689 | 6.956803185 | 199 |
| 1430521 | NM_053276.2 | VIT | *Homo sapiens* vitrin (VIT), mRNA. | MGC70561; DKFZp313L1517; MGC149746 | 310.6416244 | 2.046705424 | 198 |
| 14SKEL20Z P6 | | | | | | | |
| 2640315 | NM_004245.2 | TGM5 | *Homo sapiens* transglutaminase 5 (TGM5), transcript variant 2, mRNA. | MGC141907; TGM6; TGMX; TGX | 322.4014382 | 4.527626051 | 251 |
| 4390403 | NM_004042.3 | ARSF | *Homo sapiens* arylsulfatase F (ARSF), mRNA. | ASF | 252.3662437 | 3.725381361 | 251 |
| 2230241 | NM_000129.3 | F13A1 | *Homo sapiens* coagulation factor XIII, A1 polypeptide (F13A1), mRNA. | F13A | 264.7620135 | 3.27423111 | 250 |
| 2350730 | NM_000735.2 | CGA | *Homo sapiens* glycoprotein hormones, alpha polypeptide (CGA), mRNA. | GPHa; TSHA; FSHA; LHA; HCG; GPHA1; CG-ALPHA | 289.5708968 | 3.124125522 | 248 |
| 5270619 | NM_033086.2 | FGD3 | *Homo sapiens* FYVE, RhoGEF and PH domain containing 3 (FGD3), transcript variant 2, mRNA. | MGC117260; FLJ00004; ZFYVE5 | 2125.546531 | 30.33059008 | 247 |
| 6420113 | NM_080723.3 | NRSN1 | *Homo sapiens* neurensin 1 (NRSN1), mRNA. | p24; VMP | 2742.191709 | 43.26918618 | 245 |
| 670707 | NM_182532.1 | TMEM61 | *Homo sapiens* transmembrane protein 61 (TMEM61), mRNA. | | 426.8898477 | 5.866918726 | 245 |
| 1400053 | NM_001012513.1 | GRP | *Homo sapiens* gastrin-releasing peptide (GRP), transcript variant 3, mRNA. | proGRP; GRP-10; BN; preproGRP | 417.9384095 | 5.109885361 | 245 |
| 1170739 | NM_015236.3 | LPHN3 | *Homo sapiens* latrophilin 3 (LPHN3), mRNA. | LEC3; CIRL3 | 214.8902707 | 2.610976746 | 244 |
| 4760626 | NM_002426.2 | MMP12 | *Homo sapiens* matrix metallopeptidase 12 (macrophage elastase) (MMP12), mRNA. | MGC138506; MME; HME | 343.4598139 | 4.821839443 | 243 |
| 2230088 | NM_213609.2 | FAM19A1 | *Homo sapiens* family with sequence similarity 19 (chemokine (C-C motif)-like), member A1 (FAM19A1), mRNA. | TAFA-1; TAFA1 | 377.1337563 | 4.680644936 | 243 |
| 160500 | NM_001012513.1 | GRP | *Homo sapiens* gastrin-releasing peptide (GRP), transcript variant 3, mRNA. | proGRP; GRP-10; BN; preproGRP | 1558.146531 | 16.40407861 | 242 |
| 1660152 | NM_001080534.1 | UNC13C | *Homo sapiens* unc-13 homolog C (*C. elegans*) (UNC13C), mRNA. | DKFZp547H074 | 288.2288494 | 3.664928424 | 242 |
| 2370056 | NM_199296.1 | THSD3 | *Homo sapiens* thrombospondin, type I, domain containing 3 (THSD3), transcript variant 1, mRNA. | TAIL1; MGC119416; DKFZp686E0215; FLJ32147 | 241.4720812 | 2.634228001 | 242 |
| 2120670 | NM_203339.1 | CLU | *Homo sapiens* clusterin (CLU), transcript variant 2, | SP-40; MGC24903; CLI; APOJ; SGP-2; | 194.7063452 | 2.075885335 | 242 |

TABLE II-continued

| ProbeID | RefSeq_ID | Symbol | Definition | Synonyms | RFUs | Fold over Ave. | Filter Score |
|---|---|---|---|---|---|---|---|
| | | | mRNA. | TRPM-2; AAG4; TRPM2; KUB1; SGP2 | | | |
| 4880138 | NM_000905.2 | NPY | *Homo sapiens* neuropeptide Y (NPY), mRNA. | PYY4 | 1119.913029 | 8.718640725 | 241 |
| 5860075 | NM_004345.3 | CAMP | *Homo sapiens* cathelicidin antimicrobial peptide (CAMP), mRNA. | HSD26; LL37; FALL39; FALL-39; CAP18 | 188.0182741 | 2.084478584 | 241 |
| 2850075 | NM_052846.1 | EMILIN3 | *Homo sapiens* elastin microfibril interfacer 3 (EMILIN3), mRNA. | DKFZp434A2410; dJ620E11.4; C20orf130; EMILIN5 | 330.1922166 | 3.696179884 | 239 |
| 1170048 | NM_001364.2 | DLG2 | *Homo sapiens* discs, large homolog 2, chapsyn-110 (*Drosophila*) (DLG2), mRNA. | PSD-93; DKFZp781E0954; FLJ37266; MGC131811; DKFZp781D1854 | 262.294247 | 2.999422126 | 239 |
| 7610441 | NM_002509.2 | NKX2-2 | *Homo sapiens* NK2 homeo-box 2 (NKX2-2), mRNA. | NKX2B; NKX2.2 | 5007.687986 | 28.74124358 | 238 |
| 6620369 | NM_015236.3 | LPHN3 | *Homo sapiens* latrophilin 3 (LPHN3), mRNA. | LEC3; CIRL3 | 281.5400169 | 3.313980184 | 238 |
| 1010592 | NM_001001548.1 | CD36 | *Homo sapiens* CD36 molecule (thrombospondin receptor) (CD36), transcript variant 1, mRNA. | GPIV; FAT; GP3B; CHDS7; SCARB3; PASIV; GP4 | 307.7571912 | 2.447638789 | 238 |
| 6040673 | NM_004726.2 | REPS2 | *Homo sapiens* RALBP1 associated Eps domain containing 2 (REPS2), transcript variant 1, mRNA. | POB1 | 213.0592217 | 1.974378542 | 238 |
| 1820315 | NM_178497.2 | C4orf26 | *Homo sapiens* chromosome 4 open reading frame 26 (C4orf26), mRNA. | FLJ23657 | 590.8124365 | 7.871936118 | 237 |
| 6760725 | NM_172105.2 | EYA4 | *Homo sapiens* eyes absent homolog 4 (*Drosophila*) (EYA4), transcript variant 4, mRNA. | CMD1J; DFNA10 | 275.4266497 | 2.929058129 | 237 |
| 5270520 | NM_005449.3 | FAIM3 | *Homo sapiens* Fas apoptotic inhibitory molecule 3 (FAIM3), mRNA. | TOSO | 261.0450931 | 2.768401968 | 237 |
| 1190592 | NM_000827.2 | GRIA1 | *Homo sapiens* glutamate receptor, ionotropic, AMPA 1 (GRIA1), mRNA. | HBGR1; GLURA; GLUH1; GLUR1; MGC133252 | 223.508714 | 2.216201808 | 237 |
| 1110564 | NM_006419.1 | CXCL13 | *Homo sapiens* chemokine (C—X—C motif) ligand 13 (B-cell chemoattractant) (CXCL13), mRNA. | SCYB13; ANGIE; BCA1; ANGIE2; BCA-1; BLR1L; BLC | 1855.520812 | 14.77593678 | 236 |
| 5700753 | NM_001024912.1 | CEACAM1 | *Homo sapiens* carcinoembryonic antigen-related cell adhesion molecule 1 (biliary glycoprotein) (CEACAM1), transcript variant 2, mRNA. | BGPI; BGP; BGP1 | 321.3001692 | 3.87727076 | 236 |
| 5570170 | NM_002686.2 | PNMT | *Homo sapiens* phenylethanolamine N-methyltransferase (PNMT), mRNA. | PENT | 291.4395939 | 2.965819489 | 236 |
| 2350139 | NM_004100.3 | EYA4 | *Homo sapiens* eyes absent homolog 4 (*Drosophila*) (EYA4), transcript variant 1, mRNA. | CMD1J; DFNA10 | 392.9013536 | 4.624063331 | 235 |
| 5290707 | NM_004917.3 | KLK4 | *Homo sapiens* kallikrein-related peptidase 4 (KLK4), mRNA. | PSTS; MGC116827; KLK-L1; ARM1; PRSS17; MGC116828; EMSP; EMSP1 | 1017.200508 | 4.866990617 | 234 |
| 1260180 | NM_004100.3 | EYA4 | *Homo sapiens* eyes absent homolog 4 (*Drosophila*) (EYA4), transcript variant 1, mRNA. | CMD1J; DFNA10 | 850.9565144 | 7.378682016 | 233 |
| 1070162 | NM_020116.2 | FSTL5 | *Homo sapiens* follistatin-like 5 (FSTL5), mRNA. | KIAA1263; DKFZp566D234 | 227.3607445 | 2.066562624 | 232 |

TABLE II-continued

| ProbeID | RefSeq_ID | Symbol | Definition | Synonyms | RFUs | Fold over Ave. | Filter Score |
|---|---|---|---|---|---|---|---|
| 1010360 | NM_001024070.1 | GCH1 | Homo sapiens GTP cyclohydrolase 1 (GCH1), transcript variant 3, mRNA. | DYT5; GTP-CH-1; GTPCH1; GCH | 275.8187817 | 3.381879435 | 230 |
| 1090561 | NM_145740.2 | GSTA1 | Homo sapiens glutathione S-transferase A1 (GSTA1), mRNA. | GTH1; GST2; MGC131939; GSTA1-1 | 731.4600677 | 7.921489922 | 229 |
| 290445 | NM_022144.1 | TNMD | Homo sapiens tenomodulin (TNMD), mRNA. | tendin; CHM1L; BRICD4; myodulin; TEM; CHM1-LIKE | 434.3483926 | 3.253058383 | 229 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 425.414044 | 2.781834807 | 228 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 462.4351946 | 2.830274089 | 227 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 7939.72758 | 11.60012477 | 225 |
| 870524 | NM_024016.3 | HOXB8 | Homo sapiens homeobox B8 (HOXB8), mRNA. | Hox-2.4; HOX2; HOX2D | 1959.584433 | 10.63381502 | 225 |
| 940630 | NM_024761.3 | MOBKL2B | Homo sapiens MOB1, Mps One Binder kinase activator-like 2B (yeast) (MOBKL2B), mRNA. | FLJ13204; FLJ23916; MOB3B; MGC32960 | 427.8771574 | 4.195886349 | 224 |
| 2850458 | NM_201572.1 | CACNB2 | Homo sapiens calcium channel, voltage-dependent, beta 2 subunit (CACNB2), transcript variant 8, mRNA. | CACNLB2; MYSB; FLJ23743 | 293.2337563 | 3.366648046 | 224 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 8719.425381 | 14.26663251 | 223 |
| 6650477 | NM_006984.3 | CLDN10 | Homo sapiens claudin 10 (CLDN10), transcript variant 2, mRNA. | CPETRL3; OSP-L | 827.6888325 | 7.238512189 | 223 |
| 2450307 | NM_000325.5 | PITX2 | Homo sapiens paired-like homeodomain 2 (PITX2), transcript variant 3, mRNA. | MGC111022; IGDS; RS; IDG2; RIEG; PTX2; IGDS2; Brx1; ARP1; RIEG1; IHG2; IRID2; RGS; Otlx2; MGC20144 | 463.842555 | 4.280063111 | 221 |
| 6250349 | NM_182826.1 | SCARA3 | Homo sapiens scavenger receptor class A, member 3 (SCARA3), transcript variant 2, mRNA. | APC7; MSLR1; MSRL1; CSR; CSR1 | 462.7282572 | 3.071489254 | 221 |
| 6480593 | NM_020809.2 | ARHGAP20 | Homo sapiens Rho GTPase activating protein 20 (ARHGAP20), mRNA. | KIAA1391; RARHOGAP | 302.63511 | 2.853079344 | 219 |
| | | | 14SKEL24Z P6 | | | | |
| 1770504 | NM_022555.3 | HLA-DRB3 | Homo sapiens major histocompatibility complex, class II, DR beta 3 (HLA-DRB3), mRNA. | MGC117330; HLA-DR3B | 277.680203 | 3.411303809 | 247 |
| 1400053 | NM_001012513.1 | GRP | Homo sapiens gastrin-releasing peptide (GRP), transcript variant 3, mRNA. | proGRP; GRP-10; BN; preproGRP | 1422.990948 | 19.80285363 | 245 |
| 6940400 | NM_003924.2 | PHOX2B | Homo sapiens paired-like homeobox 2b (PHOX2B), mRNA. | PMX2B; NBPhox | 1270.518274 | 17.67224722 | 245 |
| 6420113 | NM_080723.3 | NRSN1 | Homo sapiens neurensin 1 (NRSN1), mRNA. | p24; VMP | 348.634687 | 4.628262173 | 245 |
| 2640068 | NM_002934.2 | RNASE2 | Homo sapiens ribonuclease, RNase A family, 2 (liver, eosinophil-derived neurotoxin) (RNASE2), mRNA. | EDN; RNS2 | 311.5109983 | 3.822915719 | 245 |

TABLE II-continued

| ProbeID | RefSeq_ID | Symbol | Definition | Synonyms | RFUs | Fold over Ave. | Filter Score |
|---|---|---|---|---|---|---|---|
| 670707 | NM_182532.1 | TMEM61 | Homo sapiens transmembrane protein 61 (TMEM61), mRNA. | | 230.0771574 | 2.701004249 | 245 |
| 1010097 | NM_021815.2 | SLC5A7 | Homo sapiens solute carrier family 5 (choline transporter), member 7 (SLC5A7), mRNA. | MGC126299; MGC126300; CHT1; hCHT; CHT | 381.1639594 | 5.549348396 | 244 |
| 2230088 | NM_213609.2 | FAM19A1 | Homo sapiens family with sequence similarity 19 (chemokine (C-C motif)-like), member A1 (FAM19A1), mRNA. | TAFA-1; TAFA1 | 797.6087986 | 11.01412578 | 243 |
| 4760626 | NM_002426.2 | MMP12 | Homo sapiens matrix metallopeptidase 12 (macrophage elastase) (MMP12), mRNA. | MGC138506; MME; HME | 677.6341794 | 10.48628525 | 243 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 664.0813875 | 8.518344803 | 243 |
| 160500 | NM_001012513.1 | GRP | Homo sapiens gastrin-releasing peptide (GRP), transcript variant 3, mRNA. | proGRP; GRP-10; BN; preproGRP | 4490.035702 | 49.15249384 | 242 |
| 6370315 | NM_002125.3 | HLA-DRB5 | Homo sapiens major histocompatibility complex, class II, DR beta 5 (HLA-DRB5), mRNA. | HLA-DRB1 | 837.2664975 | 6.387996646 | 242 |
| 1660152 | NM_001080534.1 | UNC13C | Homo sapiens unc-13 homolog C (C. elegans) (UNC13C), mRNA. | DKFZp547H074 | 326.5530457 | 4.285198161 | 242 |
| 1400392 | NM_006790.1 | MYOT | Homo sapiens myotilin (MYOT), mRNA. | LGMD1A; LGMD1; TTID | 364.8820643 | 4.444029014 | 241 |
| 4880138 | NM_000905.2 | NPY | Homo sapiens neuropeptide Y (NPY), mRNA. | PYY4 | 622.9119289 | 4.405649444 | 241 |
| 840017 | NM_206819.1 | MYBPC1 | Homo sapiens myosin binding protein C, slow type (MYBPC1), transcript variant 2, mRNA. | slow-type; MYBPCS; MYBPCC | 519.6189509 | 6.140464602 | 239 |
| 6270022 | NM_002110.2 | HCK | Homo sapiens hemopoietic cell kinase (HCK), mRNA. | JTK9 | 485.8601523 | 5.90851896 | 239 |
| 5910056 | NM_206821.1 | MYBPC1 | Homo sapiens myosin binding protein C, slow type (MYBPC1), transcript variant 4, mRNA. | slow-type; MYBPCS; MYBPCC | 364.4626058 | 4.056451585 | 239 |
| 1170048 | NM_001364.2 | DLG2 | Homo sapiens discs, large homolog 2, chapsyn-110 (Drosophila) (DLG2), mRNA. | PSD-93; DKFZp781E0954; FLJ37266; MGC131811; DKFZp781D1854 | 320.407868 | 3.885529634 | 239 |
| 7610441 | NM_002509.2 | NKX2-2 | Homo sapiens NK2 homeo-box 2 (NKX2-2), mRNA. | NKX2B; NKX2.2 | 3226.681387 | 18.16363746 | 238 |
| 6620369 | NM_015236.3 | LPHN3 | Homo sapiens latrophilin 3 (LPHN3), mRNA. | LEC3; CIRL3 | 337.6656514 | 4.17398182 | 238 |
| 6760725 | NM_172105.2 | EYA4 | Homo sapiens eyes absent homolog 4 (Drosophila) (EYA4), transcript variant 4, mRNA. | CMD1J; DFNA10 | 518.1888325 | 6.392146136 | 237 |
| 1190592 | NM_000827.2 | GRIA1 | Homo sapiens glutamate receptor, ionotropic, AMPA 1 (GRIA1), mRNA. | HBGR1; GLURA; GLUH1; GLUR1; MGC133252 | 251.2527919 | 2.615428092 | 237 |
| 1110564 | NM_006419.1 | CXCL13 | Homo sapiens chemokine (C—X—C motif) ligand 13 (B-cell chemoattractant) (CXCL13), mRNA. | SCYB13; ANGIE; BCA1; ANGIE2; BCA-1; BLR1L; BLC | 1223.904569 | 9.405833754 | 236 |
| 5870435 | NM_006043.1 | HS3ST2 | Homo sapiens heparan sulfate (glucosamine) 3-O-sulfotransferase 2 (HS3ST2), mRNA. | 3OST2; 3OST2 | 230.97022 | 2.353039027 | 236 |
| 7000176 | NM_152679.2 | SLC10A4 | Homo sapiens solute carrier family 10 (sodium/bile acid cotransporter family), member 4 (SLC10A4), mRNA. | MGC29802; P4 | 1430.703892 | 19.44818942 | 235 |

TABLE II-continued

| ProbeID | RefSeq_ID | Symbol | Definition | Synonyms | RFUs | Fold over Ave. | Filter Score |
|---|---|---|---|---|---|---|---|
| 2350139 | NM_004100.3 | EYA4 | Homo sapiens eyes absent homolog 4 (Drosophila) (EYA4), transcript variant 1, mRNA. | CMD1J; DFNA10 | 750.8103215 | 9.747239118 | 235 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 589.5439932 | 7.331651883 | 234 |
| 1260180 | NM_004100.3 | EYA4 | Homo sapiens eyes absent homolog 4 (Drosophila) (EYA4), transcript variant 1, mRNA. | CMD1J; DFNA10 | 1724.199831 | 15.97680418 | 233 |
| 3890332 | NM_001040002.1 | MEOX1 | Homo sapiens mesenchyme homeobox 1 (MEOX1), transcript variant 3, mRNA. | MOX1 | 406.2896785 | 5.733233367 | 233 |
| 4200725 | NR_001298.1 | HLA-DRB6 | Homo sapiens major histocompatibility complex, class II, DR beta 6 (pseudogene) (HLA-DRB6), non-coding RNA. | | 449.4566836 | 3.970459711 | 232 |
| 7320348 | NM_016511.2 | CLEC1A | Homo sapiens C-type lectin domain family 1, member A (CLEC1A), mRNA. | CLEC1; MGC34328 | 302.2972927 | 3.119318628 | 232 |
| 6400465 | NM_080548.3 | PTPN6 | Homo sapiens protein tyrosine phosphatase, non-receptor type 6 (PTPN6), transcript variant 2, mRNA. | SHP-1L; HCP; SH-PTP1; PTP- 1C; HCPH; SHP1; SHP-1; HPTP1C | 222.898308 | 2.054490235 | 232 |
| 4120408 | NM_003822.3 | NR5A2 | Homo sapiens nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 406.8490694 | 5.006329835 | 231 |
| 1990661 | NM_001010940.1 | C9orf135 | Homo sapiens chromosome 9 open reading frame 135 (C9orf135), mRNA. | | 7735.538579 | 45.39909909 | 230 |
| 1090561 | NM_145740.2 | GSTA1 | Homo sapiens glutathione S-transferase A1 (GSTA1), mRNA. | GTH1; GST2; MGC131939; GSTA1-1 | 514.3737733 | 5.273726533 | 229 |
| 3870246 | NM_001007097.1 | NTRK2 | Homo sapiens neurotrophic tyrosine kinase, receptor, type 2 (NTRK2), transcript variant b, mRNA. | GP145-TrkB; TRKB | 516.8939086 | 3.59507015 | 228 |
| 430102 | NM_001018065.1 | NTRK2 | Homo sapiens neurotrophic tyrosine kinase, receptor, type 2 (NTRK2), transcript variant d, mRNA. | GP145-TrkB; TRKB | 665.0204738 | 4.508254388 | 227 |
| 7210554 | NM_016300.4 | ARPP-21 | Homo sapiens cyclic AMP-regulated phosphoprotein, 21 kD (ARPP-21), transcript variant 1, mRNA. | FLJ32997 | 620.5603215 | 6.969776174 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 8934.08731 | 13.17814575 | 225 |
| 5260484 | NM_002124.1 | HLA-DRB1 | Homo sapiens major histocompatibility complex, class II, DR beta 1 (HLA-DRB1), mRNA. | HLA-DRB1*; HLA-DR1B; HLA DRB1; DRB1 | 1241.1511 | 8.89823738 | 225 |
| 7000181 | NM_001037317.1 | PAP2D | Homo sapiens phosphatidic acid phosphatase type 2 (PAP2D), transcript variant 1, mRNA. | PAP2 | 527.9923858 | 6.440833067 | 224 |
| 2850458 | NM_201572.1 | CACNB2 | Homo sapiens calcium channel, voltage-dependent, beta 2 subunit (CACNB2), transcript variant 8, mRNA. | CACNLB2; MYSB; FLJ23743 | 232.7450931 | 2.46588987 | 224 |

TABLE II-continued

| ProbeID | RefSeq_ID | Symbol | Definition | Synonyms | RFUs | Fold over Ave. | Filter Score |
|---|---|---|---|---|---|---|---|
| 6450746 | NR_002304.1 | POU5F1P1 | *Homo sapiens* POU class 5 homeobox 1 pseudogene 1 (POU5F1P1), non-coding RNA. | POU5FLC8; OTF3C; OTF3P1 | 10908.25076 | 18.0989943 | 223 |
| 6650477 | NM_006984.3 | CLDN10 | *Homo sapiens* claudin 10 (CLDN10), transcript variant 2, mRNA. | CPETRL3; OSP-L | 1775.710152 | 16.67476998 | 223 |
| 5290711 | NM_004143.2 | CITED1 | *Homo sapiens* Cbp/p300-interacting transactivator, with Glu/Asp-rich carboxy-terminal domain, 1 (CITED1), mRNA. | MSG1 | 245.1505922 | 2.003286952 | 222 |
| 2450307 | NM_000325.5 | PITX2 | *Homo sapiens* paired-like homeodomain 2 (PITX2), transcript variant 3, mRNA. | MGC111022; IGDS; RS; IDG2; RIEG; PTX2; IGDS2; Brx1; ARP1; RIEG1; IHG2; IRID2; RGS; Otlx2; MGC20144 | 311.378511 | 2.544517793 | 221 |
| 2760228 | NM_001001994.1 | GPM6B | *Homo sapiens* glycoprotein M6B (GPM6B), transcript variant 4, mRNA. | MGC54284; M6B; MGC17150 | 300.6131134 | 2.417812702 | 221 |
| | | | 14SKEL7X P6 | | | | |
| 5270619 | NM_033086.2 | FGD3 | *Homo sapiens* FYVE, RhoGEF and PH domain containing 3 (FGD3), transcript variant 2, mRNA. | MGC117260; FLJ00004; ZFYVE5 | 816.151692 | 11.03008908 | 247 |
| 2260471 | NM_032432.3 | ABLIM2 | *Homo sapiens* actin binding LIM protein family, member 2 (ABLIM2), mRNA. | KIAA1808; DKFZp761F129; MGC141918; FLJ39684 | 494.6637902 | 6.010679852 | 245 |
| 6940553 | NM_001098635.1 | SEZ6 | *Homo sapiens* seizure related 6 homolog (mouse) (SEZ6), transcript variant 2, mRNA. | | 2266.439594 | 29.92365216 | 244 |
| 3450544 | NM_138569.2 | C6orf142 | *Homo sapiens* chromosome 6 open reading frame 142 (C6orf142), mRNA. | MGC18257 | 296.6964467 | 4.081656423 | 243 |
| 1990333 | NM_004319.1 | ASTN1 | *Homo sapiens* astrotactin 1 (ASTN1), transcript variant 1, mRNA. | ASTN; KIAA1747; ASTN1 | 339.8981387 | 4.062577922 | 239 |
| 7610441 | NM_002509.2 | NKX2-2 | *Homo sapiens* NK2 homeobox 2 (NKX2-2), mRNA. | NKX2B; NKX2.2 | 5631.113706 | 32.44384171 | 238 |
| 6760725 | NM_172105.2 | EYA4 | *Homo sapiens* eyes absent homolog 4 (*Drosophila*) (EYA4), transcript variant 4, mRNA. | CMD1J; DFNA10 | 165.6005076 | 1.362349545 | 237 |
| 2350139 | NM_004100.3 | EYA4 | *Homo sapiens* eyes absent homolog 4 (*Drosophila*) (EYA4), transcript variant 1, mRNA. | CMD1J; DFNA10 | 272.2874788 | 2.897573808 | 235 |
| 1260180 | NM_004100.3 | EYA4 | *Homo sapiens* eyes absent homolog 4 (*Drosophila*) (EYA4), transcript variant 1, mRNA. | CMD1J; DFNA10 | 493.6221658 | 3.860299079 | 233 |
| 1070162 | NM_020116.2 | FSTL5 | *Homo sapiens* follistatin-like 5 (FSTL5), mRNA. | KIAA1263; DKFZp566D234 | 2549.290355 | 33.38394142 | 232 |
| 7320348 | NM_016511.2 | CLEC1A | *Homo sapiens* C-type lectin domain family 1, member A (CLEC1A), mRNA. | CLEC1; MGC34328 | 190.3830795 | 1.594295698 | 232 |
| 3120528 | NM_018557.2 | LRP1B | *Homo sapiens* low density lipoprotein-related protein 1B (deleted in tumors) (LRP1B), mRNA. | LRPDIT; LRP-DIT | 169.7130288 | 1.513481592 | 232 |
| 4120408 | NM_003822.3 | NR5A2 | *Homo sapiens* nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 186.4107445 | 1.751989621 | 231 |

TABLE II-continued

| ProbeID | RefSeq_ID | Symbol | Definition | Synonyms | RFUs | Fold over Ave. | Filter Score |
|---|---|---|---|---|---|---|---|
| 50626 | NM_015715.3 | PLA2G3 | Homo sapiens phospholipase A2, group III (PLA2G3), mRNA. | GIII-SPLA2; SPLA2III | 477.3011844 | 3.549175966 | 226 |
| 770615 | NM_002701.4 | POU5F1 | Homo sapiens POU class 5 homeobox 1 (POU5F1), transcript variant 1, mRNA. | OTF4; OCT3; OCT4; MGC22487; OTF3 | 3084.613029 | 3.89519428 | 225 |
| 6450746 | NR_002304.1 | POU5F1P1 | Homo sapiens POU class 5 homeobox 1 pseudogene 1 (POU5F1P1), non-coding RNA. | POU5FLC8; OTF3C; OTF3P1 | 3316.217936 | 4.806286347 | 223 |
| 1450358 | NM_000519.3 | HBD | Homo sapiens hemoglobin, delta (HBD), mRNA. | | 207.9585448 | 1.967937448 | 221 |
| 3450347 | NM_022161.2 | BIRC7 | Homo sapiens baculoviral IAP repeat-containing 7 (BIRC7), transcript variant 2, mRNA. | LIVIN; MLIAP; MLIAP; RNF50; KIAP | 184.8456853 | 1.428790724 | 221 |
| 6480593 | NM_020809.2 | ARHGAP20 | Homo sapiens Rho GTPase activating protein 20 (ARHGAP20), mRNA. | KIAA1391; RARHOGAP | 355.1510998 | 3.521700628 | 219 |
| 4180289 | NM_001538.2 | HSF4 | Homo sapiens heat shock transcription factor 4 (HSF4), transcript variant 1, mRNA. | CTM | 240.8184433 | 2.03194322 | 219 |
| 4890274 | NM_001040667.1 | HSF4 | Homo sapiens heat shock transcription factor 4 (HSF4), transcript variant 2, mRNA. | CTM | 191.5365482 | 1.378666317 | 219 |
| 7330639 | NM_003822.3 | NR5A2 | Homo sapiens nuclear receptor subfamily 5, group A, member 2 (NR5A2), transcript variant 2, mRNA. | FTF; B1F2; FTZ-F1beta; hB1F; hB1F-2; LRH-1; B1F; FTZ-F1; CPF | 263.0874788 | 2.409248407 | 217 |
| 5720075 | NM_003638.1 | ITGA8 | Homo sapiens integrin, alpha 8 (ITGA8), mRNA. | | 228.4329949 | 2.215645054 | 217 |
| 3440747 | NM_030820.2 | COL21A1 | Homo sapiens collagen, type XXI, alpha 1 (COL21A1), mRNA. | COLA1L; MGC26619; dJ708F5.1; DKFZp564B052; dJ682J15.1 | 223.3902707 | 1.402853959 | 214 |
| 5690301 | NM_001704.1 | BAI3 | Homo sapiens brain-specific angiogenesis inhibitor 3 (BAI3), mRNA. | KIAA0550; MGC133100 | 342.8615905 | 3.303694719 | 213 |
| 2260424 | NM_006727.2 | CDH10 | Homo sapiens cadherin 10, type 2 (T2-cadherin) (CDH10), mRNA. | | 284.0367174 | 1.820622674 | 213 |
| 3710243 | NM_024625.3 | ZC3HAV1 | Homo sapiens zinc finger CCCH-type, antiviral 1 (ZC3HAV1), transcript variant 2, mRNA. | FLJ13288; ZC3HDC2; FLB6421; ZAP; DKFZp686H1869; DKFZp686O19171; MGC48898; DKFZp686F2052; ZC3H2 | 321.5152284 | 2.67624495 | 212 |
| 5270544 | NM_006613.3 | GRAP | Homo sapiens GRB2-related adaptor protein (GRAP), mRNA. | MGC64880 | 196.3899323 | 1.471251846 | 212 |
| 3400307 | NM_015900.1 | PLA1A | Homo sapiens phospholipase A1 member A (PLA1A), mRNA. | PSPLA1; PS-PLA1 | 224.7513536 | 2.11003931 | 210 |
| 830348 | NM_001104.1 | ACTN3 | Homo sapiens actinin, alpha 3 (ACTN3), mRNA. | MGC117002; MGC117005 | 384.3610829 | 2.234935432 | 208 |
| 940639 | NM_152321.1 | ERP27 | Homo sapiens endoplasmic reticulum protein 27 kDa (ERP27), mRNA. | ERp27; FLJ32115; C12orf46 | 596.8041455 | 6.309864839 | 206 |
| 520673 | NM_152447.2 | LRFN5 | Homo sapiens leucine rich repeat and fibronectin type III domain containing 5 (LRFN5), mRNA. | C14orf146; DKFZp686G0210; FIGLER8; FLJ30803 | 447.0818105 | 3.88384487 | 205 |

TABLE II-continued

| ProbeID | RefSeq_ID | Symbol | Definition | Synonyms | RFUs | Fold over Ave. | Filter Score |
|---|---|---|---|---|---|---|---|
| 5490470 | NM_002463.1 | MX2 | Homo sapiens myxovirus (influenza virus) resistance 2 (mouse) (MX2), mRNA. | MXB | 326.8739425 | 1.564606019 | 205 |
| 2030170 | NM_052889.2 | COP1 | Homo sapiens caspase-1 dominant-negative inhibitor pseudo-ICE (COP1), transcript variant 2, mRNA. | PSEUDO-ICE; COP | 270.9976311 | 2.365305724 | 202 |
| 7050082 | NM_001611.2 | ACP5 | Homo sapiens acid phosphatase 5, tartrate resistant (ACP5), mRNA. | TRAP; MGC117378 | 285.5532995 | 1.732972465 | 200 |
| 7160102 | NM_017954.9 | CADPS2 | Homo sapiens Ca++-dependent secretion activator 2 (CADPS2), transcript variant 1, mRNA. | KIAA1591; FLJ40851 | 934.2084602 | 7.317902029 | 199 |
| 620112 | NM_001079691.1 | N4BP2L1 | Homo sapiens NEDD4 binding protein 2-like 1 (N4BP2L1), transcript variant 2, mRNA. | CG018 | 368.3773266 | 3.591762528 | 198 |
| 7380239 | NM_004114.2 | FGF13 | Homo sapiens fibroblast growth factor 13 (FGF13), transcript variant 1A, mRNA. | FGF2; FHF2 | 1373.698646 | 6.712119684 | 197 |
| 460575 | NM_080647.1 | TBX1 | Homo sapiens T-box 1 (TBX1), transcript variant C, mRNA. | VCFS; TGA; DORV; CTHM; TBX1C; DGS; CAFS; DGCR | 565.7820643 | 5.124850227 | 197 |
| 6550133 | NM_001079691.1 | N4BP2L1 | Homo sapiens NEDD4 binding protein 2-like 1 (N4BP2L1), transcript variant 2, mRNA. | CG018 | 380.0730964 | 3.76975768 | 196 |
| 430079 | NM_002310.3 | LIFR | Homo sapiens leukemia inhibitory factor receptor alpha (LIFR), mRNA. | CD118; STWS; SJS2; SWS | 279.1923858 | 1.662480673 | 196 |
| 2750092 | NM_005010.3 | NRCAM | Homo sapiens neuronal cell adhesion molecule (NRCAM), transcript variant 2, mRNA. | MGC138845; MGC138846; KIAA0343 | 853.3400169 | 4.537668221 | 194 |
| 4180707 | NM_001003683.1 | PDE1A | Homo sapiens phosphodiesterase 1A, calmodulin-dependent (PDE1A), transcript variant 2, mRNA. | HSPDE1A; MGC26303; HCAM1 | 544.2763959 | 2.241179844 | 193 |
| 5810678 | NM_002910.4 | RENBP | Homo sapiens renin binding protein (RENBP), mRNA. | RNBP; RBP | 1975.214721 | 9.912255749 | 192 |
| 6270372 | NM_182801.1 | EGFLAM | Homo sapiens EGF-like, fibronectin type III and laminin G domains (EGFLAM), transcript variant 4, mRNA. | AGRINL; AGRNL; FLJ39155 | 325.179357 | 1.635739588 | 192 |
| 6450661 | NM_032250.1 | ANKRD20A1 | Homo sapiens ankyrin repeat domain 20 family, member A1 (ANKRD20A1), mRNA. | ANKRD20A; DKFZp434A171 | 212.1874788 | 1.504584993 | 186 |
| 4250364 | NM_000860.3 | HPGD | Homo sapiens hydroxyprostaglandin dehydrogenase 15-(NAD) (HPGD), mRNA. | PGDH; 15-PGDH; PGDH1 | 703.4062606 | 2.505990181 | 184 |
| 3800017 | NM_001001924.1 | MTUS1 | Homo sapiens mitochondrial tumor suppressor 1 (MTUS1), nuclear gene encoding mitochondrial protein, transcript variant 1, mRNA. | MTSG1; MP44; DKFZp586D1519; ATIP; FLJ14295; KIAA1288; DKFZp686F20243 | 350.5238579 | 1.878143913 | 183 |
| | | | 14SMOO2X P6 | | | | |
| 7400356 | NM_173848.5 | RALYL | Homo sapiens RALY RNA binding protein-like (RALYL), transcript variant 3, mRNA. | HNRPCL3 | 712.1052453 | 13.05313107 | 251 |
| 6980543 | NM_002315.1 | LMO1 | Homo sapiens LIM domain only 1 (rhombotin 1) (LMO1), mRNA. | RBTN1; MGC116692; TTG1; RHOM1 | 566.7424704 | 8.156794155 | 250 |

TABLE II-continued

| ProbeID | RefSeq_ID | Symbol | Definition | Synonyms | RFUs | Fold over Ave. | Filter Score |
|---|---|---|---|---|---|---|---|
| 2490551 | NM_005604.2 | POU3F2 | Homo sapiens POU class 3 homeobox 2 (POU3F2), mRNA. | OTF7; OCT7; BRN2; POUF3 | 516.5646362 | 6.335929595 | 250 |
| 3890743 | NM_006789.2 | APOBEC2 | Homo sapiens apolipoprotein B mRNA editing enzyme, catalytic polypeptide-like 2 (APOBEC2), mRNA. | ARCD1; ARP1 | 308.3164129 | 4.080790747 | 250 |
| 1170274 | NM_003665.2 | FCN3 | Homo sapiens ficolin (collagen/fibrinogen domain containing) 3 (Hakata antigen) (FCN3), transcript variant 1, mRNA. | MGC22543; FCNH; HAKA1 | 587.9492386 | 8.195514874 | 247 |
| 6350682 | NM_016102.2 | TRIM17 | Homo sapiens tripartite motif-containing 17 (TRIM17), transcript variant 1, mRNA. | RBCC; terf; RNF16 | 363.9677665 | 5.105782345 | 247 |
| 4610692 | NM_004389.2 | CTNNA2 | Homo sapiens catenin (cadherin-associated protein), alpha 2 (CTNNA2), mRNA. | DKFZp686H02198; CAPR; CAP-R; CTNR | 276.3861252 | 3.283049351 | 247 |
| 6220750 | NM_000826.2 | GRIA2 | Homo sapiens glutamate receptor, ionotropic, AMPA 2 (GRIA2), mRNA. | HBGR2; GLURB; GLUR2 | 6419.420981 | 67.49112003 | 245 |
| 7650168 | NM_002942.2 | ROBO2 | Homo sapiens roundabout, axon guidance receptor, homolog 2 (Drosophila) (ROBO2), mRNA. | KIAA1568; SAX3 | 494.7444162 | 7.185399681 | 245 |
| 3360187 | NM_052836.1 | CDH23 | Homo sapiens cadherin-like 23 (CDH23), transcript variant 2, mRNA. | DKFZp434P2350; USH1H; KIAA1774; FLJ00233; MGC102761; FLJ36499; DFNB12; USH1D; KIAA1812 | 468.8033841 | 6.296863132 | 244 |
| 1770603 | NM_001062.3 | TCN1 | Homo sapiens transcobalamin I (vitamin B12 binding protein, R binder family) (TCN1), mRNA. | TCI; TC1 | 985.6319797 | 3.730333725 | 244 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 2764.305584 | 38.62106781 | 243 |
| 6860736 | NM_000260.2 | MYO7A | Homo sapiens myosin VIIA (MYO7A), mRNA. | USH1B; DFNA11; NSRD2; MYU7A; DFNB2 | 713.0751269 | 10.67926317 | 243 |
| 6220484 | NM_172081.1 | CAMK2B | Homo sapiens calcium/calmodulin-dependent protein kinase (CaM kinase) II beta (CAMK2B), transcript variant 5, mRNA. | CAMKB; CAM2; MGC29528; CAMK2 | 422.8152284 | 5.620626163 | 243 |
| 6660747 | NM_004826.1 | ECEL1 | Homo sapiens endothelin converting enzyme-like 1 (ECEL1), mRNA. | XCE; DINE; ECEX | 400.5661591 | 5.296765231 | 243 |
| 6510274 | NM_022124.3 | CDH23 | Homo sapiens cadherin-like 23 (CDH23), transcript variant 1, mRNA. | DKFZp434P2350; USH1H; KIAA1774; FLJ00233; MGC102761; FLJ36499; DFNB12; USH1D; KIAA1812 | 1654.861083 | 23.91892227 | 242 |
| 4040286 | NM_001184.2 | ATR | Homo sapiens ataxia telangiectasia and Rad3 related (ATR), mRNA. | SCKL1; MEC1; FRP1; SCKL | 645.500846 | 8.134952228 | 242 |
| 4810487 | NM_018712.2 | ELMOD1 | Homo sapiens ELMO/CED-12 domain containing 1 (ELMOD1), mRNA. | DKFZp547C176 | 456.806599 | 5.34751353 | 242 |

TABLE II-continued

| ProbeID | RefSeq_ID | Symbol | Definition | Synonyms | RFUs | Fold over Ave. | Filter Score |
|---|---|---|---|---|---|---|---|
| 6560487 | NM_001842.3 | CNTFR | Homo sapiens ciliary neurotrophic factor receptor (CNTFR), transcript variant 2, mRNA. | MGC1774 | 302.2123519 | 3.402590384 | 242 |
| 50176 | NM_020373.1 | TMEM16B | Homo sapiens transmembrane protein 16B (TMEM16B), mRNA. | DKFZp434P102; C12orf3 | 274.1839255 | 3.014927177 | 242 |
| 1580037 | NM_002152.2 | HRC | Homo sapiens histidine rich calcium binding protein (HRC), mRNA. | MGC133236 | 304.4183587 | 2.771181143 | 242 |
| 5860075 | NM_004345.3 | CAMP | Homo sapiens cathelicidin antimicrobial peptide (CAMP), mRNA. | HSD26; LL37; FALL39; FALL-39; CAP18 | 828.3456853 | 12.58918189 | 241 |
| 4920075 | NM_003245.2 | TGM3 | Homo sapiens transglutaminase 3 (E polypeptide, protein-glutamine-gamma-glutamyltransferase) (TGM3), mRNA. | MGC126249; TGE; MGC126250 | 3202.826142 | 33.87180029 | 240 |
| 2750563 | NM_006741.2 | PPP1R1A | Homo sapiens protein phosphatase 1, regulatory (inhibitor) subunit 1A (PPP1R1A), mRNA. | | 303.6515228 | 3.433098747 | 240 |
| 4890670 | NM_006365.1 | C1orf61 | Homo sapiens chromosome 1 open reading frame 61 (C1orf61), mRNA. | CROC4; RP11-139I14.3; FLJ38303 | 271.9483926 | 3.29450522 | 240 |
| 1710131 | NM_172078.1 | CAMK2B | Homo sapiens calcium/calmodulin-dependent protein kinase (CaM kinase) II beta (CAMK2B), transcript variant 2, mRNA. | CAMKB; CAM2; MGC29528; CAMK2 | 367.1896785 | 5.103733461 | 238 |
| 70086 | NM_198993.2 | STAC2 | Homo sapiens SH3 and cysteine rich domain 2 (STAC2), mRNA. | 24b2; 2462/STAC2; MGC129694 | 304.1529611 | 2.773641982 | 238 |
| 730093 | NM_020209.2 | SHD | Homo sapiens Src homology 2 domain containing transforming protein D (SHD), mRNA. | | 1929.630626 | 25.70944633 | 237 |
| 6380689 | NM_004842.2 | AKAP7 | Homo sapiens A kinase (PRKA) anchor protein 7 (AKAP7), transcript variant alpha, mRNA. | AKAP18 | 413.02978 | 5.244727373 | 237 |
| 5270520 | NM_005449.3 | FAIM3 | Homo sapiens Fas apoptotic inhibitory molecule 3 (FAIM3), mRNA. | TOSO | 345.6143824 | 3.989229652 | 237 |
| 7000176 | NM_152679.2 | SLC10A4 | Homo sapiens solute carrier family 10 (sodium/bile acid cotransporter family), member 4 (SLC10A4), mRNA. | MGC29802; P4 | 458.8385787 | 5.557903578 | 235 |
| 5550414 | NM_019845.2 | RPRM | Homo sapiens reprimo, TP53 dependent G2 arrest mediator candidate (RPRM), mRNA. | FLJ90327; REPRIMO | 3607.350423 | 25.2462122 | 234 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 326.4632826 | 3.613698815 | 234 |
| 580561 | NM_021116.1 | ADCY1 | Homo sapiens adenylate cyclase 1 (brain) (ADCY1), mRNA. | | 1862.033503 | 23.40775682 | 233 |
| 4890292 | NM_173485.4 | TSHZ2 | Homo sapiens teashirt zinc finger homeobox 2 (TSHZ2), mRNA. | C20orf17; OVC10-2; TSH2; ZNF218; FLJ33887; DKFZp686K2480; ZABC2 | 1285.017936 | 10.87318918 | 233 |
| 1230477 | NM_005853.4 | IRX5 | Homo sapiens iroquois homeobox protein 5 (IRX5), mRNA. | IRX-2a | 1015.143655 | 9.898813475 | 233 |
| 1990731 | NM_006157.2 | NELL1 | Homo sapiens NEL-like 1 (chicken) (NELL1), mRNA. | FLJ45906; IDH3GL; NRP1 | 602.1 | 6.291765482 | 233 |
| 1660386 | NM_030667.1 | PTPRO | Homo sapiens protein tyrosine phosphatase, | GLEPP1; PTP-U2; | 518.52022 | 6.07356951 | 233 |

TABLE II-continued

| ProbeID | RefSeq_ID | Symbol | Definition | Synonyms | RFUs | Fold over Ave. | Filter Score |
|---|---|---|---|---|---|---|---|
| 3190246 | NM_004067.2 | CHN2 | receptor type, O (PTPRO), transcript variant 1, mRNA. *Homo sapiens* chimerin (chimaerin) 2 (CHN2), transcript variant 2, mRNA. | PTPU2 BCH; ARHGAP3; RHOGAP3; MGC138360 | 356.2817259 | 4.305540154 | 233 |
| 7550358 | NM_006159.1 | NELL2 | *Homo sapiens* NEL-like 2 (chicken) (NELL2), mRNA. | NRP2 | 621.7490694 | 3.474177808 | 233 |
| 5050681 | NM_017899.2 | TESC | *Homo sapiens* tescalcin (TESC), mRNA. | TSC; FLJ20607 | 334.614044 | 3.076014713 | 232 |
| 5390575 | NM_006561.2 | CUGBP2 | *Homo sapiens* CUG triplet repeat, RNA binding protein 2 (CUGBP2), transcript variant 2, mRNA. | BRUNOL3; ETR-3; NAPOR | 341.5216582 | 3.850276727 | 230 |
| 360014 | NM_052836.1 | CDH23 | *Homo sapiens* cadherin-like 23 (CDH23), transcript variant 2, mRNA. | DKFZp434P2350; USH1H; KIAA1774; FLJ00233; MGC102761; FLJ36499; DFNB12; USH1D; KIAA1812 | 854.4878173 | 10.72476097 | 229 |
| 7200341 | NM_152721.3 | DOK6 | *Homo sapiens* docking protein 6 (DOK6), mRNA. | HsT3226; DOK5L; MGC20785 | 523.1500846 | 6.976167836 | 229 |
| 5390128 | NM_018176.2 | LGI2 | *Homo sapiens* leucine-rich repeat LGI family, member 2 (LGI2), mRNA. | KIAA1916; MGC126808; MGC126810; FLJ10675; LGIL2 | 332.0390017 | 2.972012889 | 229 |
| 2750154 | NM_014800.9 | ELMO1 | *Homo sapiens* engulfment and cell motility 1 (ELMO1), transcript variant 1, mRNA. | MGC126406; CED12; CED-12; KIAA0281; ELMO-1 | 578.9230964 | 7.197406463 | 228 |
| 3180615 | NM_001001552.3 | LEMD1 | *Homo sapiens* LEM domain containing 1 (LEMD1), mRNA. | LEMP-1 | 422.2824027 | 4.640235588 | 228 |
| 2350201 | NM_181670.2 | ANKS1B | *Homo sapiens* ankyrin repeat and sterile alpha motif domain containing 1B (ANKSIB), transcript variant 2, mRNA. 14SMOO8X P6 | MGC26087; EB-1; ANKS2; AIDA-1; AIDA; cajalin-2 | 814.623181 | 10.76509991 | 227 |
| 7400356 | NM_173848.5 | RALYL | *Homo sapiens* RALY RNA binding protein-like (RALYL), transcript variant 3, mRNA. | HNRPCL3 | 1350.184433 | 25.64538554 | 251 |
| 3990278 | NM_006998.3 | SCGN | *Homo sapiens* secretagogin, EF-hand calcium binding protein (SCGN), mRNA. | SEGN; DJ501N12.8; CALBL; setagin; SECRET | 310.5986464 | 4.222983258 | 251 |
| 6480575 | NM_052917.2 | GALNT13 | *Homo sapiens* UDP-N-acetyl-alpha-D-galactosamine:polypeptide N-acetylgalactosaminyltransferase 13 (GalNAc-T13) (GALNT13), mRNA. | FLJ16031; MGC119459; GalNAc-T13; MGC119461; WUGSC: H_NH0187G20.1; H_NH0187G20.1; FLJ41157; KIAA1918 | 268.8393401 | 3.761884681 | 251 |
| 6980543 | NM_002315.1 | LMO1 | *Homo sapiens* LIM domain only 1 (rhombotin 1) (LMO1), mRNA. | RBTN1; MGC116692; TTG1; RHOM1 | 534.0829103 | 7.629117327 | 250 |
| 2490551 | NM_005604.2 | POU3F2 | *Homo sapiens* POU class 3 homeobox 2 (POU3F2), mRNA. | OTF7; OCT7; BRN2; POUF3 | 584.7906937 | 7.304833618 | 250 |
| 4260471 | NM_005076.2 | CNTN2 | *Homo sapiens* contactin 2 (axonal) (CNTN2), mRNA. | TAG-1; TAX; DKFZp781D102; TAX1; MGC157722; FLJ42746; AXT | 387.7181049 | 5.843291823 | 250 |
| 840681 | NM_001037317.1 | PAP2D | *Homo sapiens* phosphatidic acid phosphatase type 2 (PAP2D), transcript variant 1, mRNA. | PAP2 | 280.1494924 | 4.318001407 | 249 |

TABLE II-continued

| ProbeID | RefSeq_ID | Symbol | Definition | Synonyms | RFUs | Fold over Ave. | Filter Score |
|---|---|---|---|---|---|---|---|
| 1010189 | NM_033225.3 | CSMD1 | Homo sapiens CUB and Sushi multiple domains 1 (CSMD1), mRNA. | KIAA1890 | 330.048308 | 5.58655547 | 248 |
| 1170274 | NM_003665.2 | FCN3 | Homo sapiens ficolin (collagen/fibrinogen domain containing) 3 (Hakata antigen) (FCN3), transcript variant 1, mRNA. | MGC22543; FCNH; HAKA1 | 573.0299492 | 7.962177473 | 247 |
| 3180068 | NM_013371.2 | IL19 | Homo sapiens interleukin 19 (IL19), transcript variant 2, mRNA. | NG.1; IL-10C; ZMDA1; MDA1 | 363.062775 | 5.930565585 | 247 |
| 6350682 | NM_016102.2 | TRIM17 | Homo sapiens tripartite motif-containing 17 (TRIM17), transcript variant 1, mRNA. | RBCC; terf; RNF16 | 352.8722504 | 4.919648262 | 247 |
| 6220750 | NM_000826.2 | GRIA2 | Homo sapiens glutamate receptor, ionotropic, AMPA 2 (GRIA2), mRNA. | HBGR2; GLURB; GLUR2 | 8741.622166 | 92.26752285 | 245 |
| 7650168 | NM_002942.2 | ROBO2 | Homo sapiens roundabout, axon guidance receptor, homolog 2 (Drosophila) (ROBO2), mRNA. | KIAA1568; SAX3 | 760.7395939 | 11.58621103 | 245 |
| 3360187 | NM_052836.1 | CDH23 | Homo sapiens cadherin-like 23 (CDH23), transcript variant 2, mRNA. | DKFZp434P2350; USH1H; KIAA1774; FLJ00233; MGC102761; FLJ36499; DFNB12; USH1D; KIAA1812 | 495.5326565 | 6.712900749 | 244 |
| 7160192 | NM_139319.1 | SLC17A8 | Homo sapiens solute carrier family 17 (sodium-dependent inorganic phosphate cotransporter), member 8 (SLC17A8), mRNA. | VGLUT3 | 234.1624365 | 3.283310633 | 244 |
| 7320471 | NM_003221.3 | TFAP2B | Homo sapiens transcription factor AP-2 beta (activating enhancer binding protein 2 beta) (TFAP2B), mRNA. | MGC21381; AP-2B; AP2-B | 1913.046193 | 26.41988201 | 243 |
| 6860736 | NM_000260.2 | MYO7A | Homo sapiens myosin VIIA (MYO7A), mRNA. | USH1B; DFNA11; NSRD2; MYU7A; DFNB2 | 618.9494078 | 9.137603664 | 243 |
| 6220484 | NM_172081.1 | CAMK2B | Homo sapiens calcium/calmodulin-dependent protein kinase (CaM kinase) II beta (CAMK2B), transcript variant 5, mRNA. | CAMKB; CAM2; MGC29528; CAMK2 | 575.7461929 | 8.015286233 | 243 |
| 6660747 | NM_004826.1 | ECEL1 | Homo sapiens endothelin converting enzyme-like 1 (ECEL1), mRNA. | XCE; DINE; ECEX | 491.9045685 | 6.732574293 | 243 |
| 3310068 | NM_004113.3 | FGF12 | Homo sapiens fibroblast growth factor 12 (FGF12), transcript variant 2, mRNA. | FHF1; FGF12B | 386.514467 | 5.033556556 | 243 |
| 5270102 | NM_001015887.1 | IGSF11 | Homo sapiens immunoglobulin superfamily, member 11 (IGSF11), transcript variant 2, mRNA. | VSIG3; Igsfl3; MGC35227; BT-IgSF; CXADRL1 | 325.0898477 | 3.411330596 | 243 |
| 2340438 | NM_001048209.1 | HNT | Homo sapiens neurotrimin (HNT), transcript variant 2, mRNA. | NTM; MGC60329 | 283.6207276 | 2.992407537 | 243 |
| 6510274 | NM_022124.3 | CDH23 | Homo sapiens cadherin-like 23 (CDH23), transcript variant 1, mRNA. | DKFZp434P2350; USH1H; KIAA1774; FLJ00233; MGC102761; FLJ36499; DFNB12; USH1D; KIAA1812 | 1603.834856 | 23.15056861 | 242 |

TABLE II-continued

| ProbeID | RefSeq_ID | Symbol | Definition | Synonyms | RFUs | Fold over Ave. | Filter Score |
|---|---|---|---|---|---|---|---|
| 4810487 | NM_018712.2 | ELMOD1 | Homo sapiens ELMO/CED-12 domain containing 1 (ELMOD1), mRNA. | DKFZp547C176 | 1255.341032 | 16.44347434 | 242 |
| 4040286 | NM_001184.2 | ATR | Homo sapiens ataxia telangiectasia and Rad3 related (ATR), mRNA. | SCKL1; MEC1; FRP1; SCKL | 480.6663283 | 5.802259011 | 242 |
| 6560487 | NM_001842.3 | CNTFR | Homo sapiens ciliary neurotrophic factor receptor (CNTFR), transcript variant 2, mRNA. | MGC1774 | 365.4590525 | 4.323960122 | 242 |
| 6660463 | NM_020140.2 | ANKS1B | Homo sapiens ankyrin repeat and sterile alpha motif domain containing 1B (ANKS1B), transcript variant 3, mRNA. | MGC26087; ANKS2; AIDA; cajalin-2; EB-1; AIDA-1 | 276.051692 | 3.070028549 | 242 |
| 1580037 | NM_002152.2 | HRC | Homo sapiens histidine rich calcium binding protein (HRC), mRNA. | MGC133236 | 325.0898477 | 3.027262707 | 242 |
| 5860075 | NM_004345.3 | CAMP | Homo sapiens cathelicidin antimicrobial peptide (CAMP), mRNA. | HSD26; LL37; FALL39; FALL-39; CAP18 | 389.4118443 | 5.38838166 | 241 |
| 4920075 | NM_003245.2 | TGM3 | Homo sapiens transglutaminase 3 (E polypeptide, protein-glutamine-gamma-glutamyltransferase) (TGM3), mRNA. | MGC126249; TGE; MGC126250 | 2657.075635 | 27.92976602 | 240 |
| 7550156 | NM_032880.2 | IGSF21 | Homo sapiens immunoglobin superfamily, member 21 (IGSF21), mRNA. | FLJ41177; RP11-121A23.1; MGC15730 | 639.0837563 | 7.139008159 | 240 |
| 2750563 | NM_006741.2 | PPP1R1A | Homo sapiens protein phosphatase 1, regulatory (inhibitor) subunit 1A (PPP1R1A), mRNA. | | 304.9199662 | 3.451617128 | 240 |
| 3180639 | NM_020783.2 | SYT4 | Homo sapiens synaptotagmin IV (SYT4), mRNA. | KIAA1342; HsT1192 | 272.0239425 | 2.947078494 | 239 |
| 1710131 | NM_172078.1 | CAMK2B | Homo sapiens calcium/calmodulin-dependent protein kinase (CaM kinase) II beta (CAMK2B), transcript variant 2, mRNA. | CAMKB; CAM2; MGC29528; CAMK2 | 554.2815567 | 8.213730893 | 238 |
| 730093 | NM_020209.2 | SHD | Homo sapiens Src homology 2 domain containing transforming protein D (SHD), mRNA. | | 1398.263452 | 18.35439981 | 237 |
| 6380689 | NM_004842.2 | AKAP7 | Homo sapiens A kinase (PRKA) anchor protein 7 (AKAP7), transcript variant alpha, mRNA. | AKAP18 | 606.8905245 | 8.175769047 | 237 |
| 5270520 | NM_005449.3 | FAIM3 | Homo sapiens Fas apoptotic inhibitory molecule 3 (FAIM3), mRNA. | TOSO | 573.0299492 | 7.272161577 | 237 |
| 7000176 | NM_152679.2 | SLC10A4 | Homo sapiens solute carrier family 10 (sodium/bile acid cotransporter family), member 4 (SLC10A4), mRNA. | MGC29802; P4 | 445.6170897 | 5.368936795 | 235 |
| 6330070 | NM_013371.2 | IL19 | Homo sapiens interleukin 19 (IL19), transcript variant 2, mRNA. | NG.1; IL-10C; ZMDA1; MDA1 | 290.8384095 | 2.929329671 | 235 |
| 5550414 | NM_019845.2 | RPRM | Homo sapiens reprimo, TP53 dependent G2 arrest mediator candidate (RPRM), mRNA. | FLJ90327; REPRIMO | 9603.588832 | 68.87339758 | 234 |
| 7160437 | NM_001025068.1 | ARPP-21 | Homo sapiens cyclic AMP-regulated phosphoprotein, 21 kD (ARPP-21), transcript variant 3, mRNA. | FLJ32997 | 362.5733503 | 4.124019532 | 234 |
| 580561 | NM_021116.1 | ADCY1 | Homo sapiens adenylate cyclase 1 (brain) (ADCY1), mRNA. | | 1274.147885 | 15.70168216 | 233 |

TABLE II-continued

| ProbeID | RefSeq_ID | Symbol | Definition | Synonyms | RFUs | Fold over Ave. | Filter Score |
|---|---|---|---|---|---|---|---|
| 1990731 | NM_006157.2 | NELL1 | Homo sapiens NEL-like 1 (chicken) (NELL1), mRNA. | FLJ45906; IDH3GL; NRP1 | 779.0571912 | 8.434815372 | 233 |
| 1660386 | NM_030667.1 | PTPRO | Homo sapiens protein tyrosine phosphatase, receptor type, O (PTPRO), transcript variant 1, mRNA. | GLEPP1; PTP-U2; PTPU2 | 685.3079526 | 8.348860955 | 233 |
| 4890292 | NM_173485.4 | TSHZ2 | Homo sapiens teashirt zinc finger homeobox 2 (TSHZ2), mRNA. | C20orf17; OVC10-2; TSH2; ZNF218; FLJ33887; DKFZp686K2480; ZABC2 | 980.7642978 | 8.061974719 | 233 |
| 3190246 | NM_004067.2 | CHN2 | Homo sapiens chimerin (chimaerin) 2 (CHN2), transcript variant 2, mRNA. | BCH; ARHGAP3; RHOGAP3; MGC138360 | 481.9829949 | 6.177410311 | 233 |
| 460010 | NM_004615.2 | TSPAN7 | Homo sapiens tetraspanin 7 (TSPAN7), mRNA. | TM4SF2; MRX58; MXS1; DXS1692E; CD231; CCG-B7; TALLA-1; A15; TM4SF2b | 583.9037225 | 5.651359668 | 233 |
| 1230477 | NM_005853.4 | IRX5 | Homo sapiens iroquois homeobox protein 5 (IRX5), mRNA. | IRX-2a | 586.184264 | 5.29340776 | 233 |

What is claimed is:

1. An isolated progenitor cell line, wherein said isolated progenitor cell line constitutively expresses OCT4 and a transcription factor selected from the group consisting of SIX1, FOXA1, SOX17, SIX2, SOX21, PAX6, MYOD1, MYOG, NEUROG1, NKX2.5, and combinations thereof, wherein the expression level of OCT4 is greater than the expression level of OCT4 in an iPS cell.

2. The isolated progenitor cell line of claim 1, wherein said progenitor cell line expresses LHX3.

3. An isolated progenitor cell line, wherein said progenitor cell line expresses the genes RESP18 and LHX3 simultaneously and is the in vitro progeny of a pluripotent stem cell.

4. An isolated progenitor cell line, wherein said isolated progenitor cell line constitutively expresses a transcription factor and is a differentiated cell line differentiated in vitro from a pluripotent stem cell.

5. The isolated progenitor cell line of claim 3, wherein the cell line expresses the gene ESR2.

* * * * *

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: synthetic peptide

<400> SEQUENCE: 1

Tyr Gly Arg Lys Lys Arg Arg Gln Arg Arg Arg
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Arg Lys Lys Arg Arg Gln Arg Arg Arg
 1               5

<210> SEQ ID NO 3
<211> LENGTH: 11
<212> TYPE: PRT
<213> ORGANISM: Artificial Sequence
<220> FEATURE:
<223> OTHER INFORMATION: synthetic peptide

<400> SEQUENCE: 3

Tyr Ala Arg Lys Ala Arg Arg Gln Ala Arg Arg
 1               5                  10

<210> SEQ ID NO 4
<211> LENGTH: 12
```

```
<212> TYPE: PRT
<213> ORGANISM: Artificial Sequence
<220> FEATURE:
<223> OTHER INFORMATION: synthetic peptide

<400> SEQUENCE: 4

Tyr Ala Arg Glx Leu Ala Ala Arg Gln Ala Arg Ala
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Tyr Ala Arg Ala Ala Arg Arg Ala Ala Arg Arg
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: synthetic peptide

<400> SEQUENCE: 6

Arg Ala Arg Ala Ala Arg Arg Ala Ala Arg Ala
 1               5                  10

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Arg Gln Ile Lys Ile Trp Phe Gln Asn Arg Arg Met Lys Trp Met
 1               5                  10                  15

<210> SEQ ID NO 8
<211> LENGTH: 34
<212> TYPE: PRT
<213> ORGANISM: Artificial Sequence
<220> FEATURE:
<223> OTHER INFORMATION: synthetic peptide

<400> SEQUENCE: 8

Asp Ala Ala Thr Ala Thr Arg Gly Arg Ser Ala Ala Ser Arg Pro Thr
 1               5                  10                  15

Glu Arg Pro Arg Ala Pro Ala Arg Ser Ala Ser Arg Pro Arg Arg Pro
                20                  25                  30

Val Glu

<210> SEQ ID NO 9
<211> LENGTH: 7
<212> TYPE: PRT
<213> ORGANISM: Artificial Sequence
<220> FEATURE:
<223> OTHER INFORMATION: synthetic peptide

<400> SEQUENCE: 9

Arg Arg Arg Arg Arg Arg Arg
 1               5
```

```
<210> SEQ ID NO 10
<211> LENGTH: 11
<212> TYPE: PRT
<213> ORGANISM: Artificial Sequence
<220> FEATURE:
<223> OTHER INFORMATION: synthetic peptide

<400> SEQUENCE: 10

Tyr Ala Arg Ala Ala Ala Arg Gln Ala Arg Ala
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: synthetic peptide

<400> SEQUENCE: 11

Tyr Ala Arg Ala Arg Ala Arg Gln Ala Arg Ala
 1               5                  10
```